US012758629B2

(12) United States Patent
Carson et al.

(10) Patent No.: US 12,758,629 B2
(45) Date of Patent: Oct. 13, 2026

(54) N-ARYL SULFONAMIDE DERIVATIVES AS VACCINE ADJUVANT

(71) Applicant: The Regents of the University of California, Oakland, CA (US)

(72) Inventors: Dennis A. Carson, La Jolla, CA (US); Tomoko Hayashi, San Diego, CA (US); Maripat Corr, San Diego, CA (US); Howard B. Cottam, Escondido, CA (US); Nikunj Shukla, San Diego, CA (US); Michael Chan, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1052 days.

(21) Appl. No.: 17/635,983

(22) PCT Filed: Aug. 15, 2020

(86) PCT No.: PCT/US2020/046568

§ 371 (c)(1),
(2) Date: Feb. 16, 2022

(87) PCT Pub. No.: WO2021/034729

PCT Pub. Date: Feb. 25, 2021

(65) Prior Publication Data

US 2022/0305121 A1 Sep. 29, 2022

Related U.S. Application Data

(60) Provisional application No. 62/887,843, filed on Aug. 16, 2019.

(51) Int. Cl.

| | |
|---|---|
| ***A61K 39/39*** | (2006.01) |
| ***A61K 31/63*** | (2006.01) |
| ***A61K 39/00*** | (2006.01) |
| ***C12N 7/00*** | (2006.01) |
| *A61K 31/18* | (2006.01) |
| *A61K 31/40* | (2006.01) |
| *A61K 31/52* | (2006.01) |
| *A61K 45/06* | (2006.01) |
| *A61K 47/54* | (2017.01) |
| *A61K 47/55* | (2017.01) |

(52) U.S. Cl.

CPC .............. *A61K 39/39* (2013.01); *A61K 31/63* (2013.01); *A61K 39/00* (2013.01); *C12N 7/00* (2013.01); *A61K 2039/55511* (2013.01)

(58) Field of Classification Search

CPC ........ A61K 39/39; A61K 31/63; A61K 39/00; A61K 2039/55511; A61K 31/18; A61K 31/40; A61K 31/52; A61K 45/06; A61K 47/544; A61K 47/55; A61K 2039/55572; C12N 7/00

See application file for complete search history.

(56) References Cited

U.S. PATENT DOCUMENTS

| | | | |
|---|---|---|---|
| 4,689,338 | A | 8/1987 | Gerster |
| 4,929,624 | A | 5/1990 | Gerster et al. |
| 4,938,949 | A | 7/1990 | Borch et al. |
| 5,037,986 | A | 8/1991 | Gerster |
| 5,175,296 | A | 12/1992 | Gerster |
| 5,238,944 | A | 8/1993 | Wick et al. |
| 5,352,784 | A | 10/1994 | Nikolaides et al. |
| 5,367,076 | A | 11/1994 | Gerster |
| 5,395,937 | A | 3/1995 | Nikolaides et al. |
| 5,444,065 | A | 8/1995 | Nikolaides et al. |
| 5,624,677 | A | 4/1997 | El-Rashidy et al. |
| 5,627,281 | A | 5/1997 | Nikolaides et al. |
| 5,648,516 | A | 7/1997 | Nikolaides et al. |
| 5,693,811 | A | 12/1997 | Lindstrom |
| 5,736,553 | A | 4/1998 | Wick et al. |
| 5,741,908 | A | 4/1998 | Gerster et al. |
| 5,998,619 | A | 12/1999 | Gerster et al. |
| 6,038,505 | A | 3/2000 | Probst et al. |
| 6,039,969 | A | 3/2000 | Tomai et al. |
| 6,083,505 | A | 7/2000 | Miller et al. |
| 6,150,523 | A | 11/2000 | Gerster et al. |
| 6,200,592 | B1 | 3/2001 | Tomai et al. |
| 6,245,776 | B1 | 6/2001 | Skwiercynski et al. |
| 6,329,381 | B1 | 12/2001 | Kurimoto et al. |
| 6,333,331 | B1 | 12/2001 | Moschel et al. |
| 6,372,725 | B1 | 4/2002 | Zilch et al. |
| 6,437,131 | B1 | 8/2002 | Gerster et al. |
| 6,486,168 | B1 | 11/2002 | Skwierczynski et al. |
| 6,534,654 | B2 | 3/2003 | Gerster et al. |
| 6,552,192 | B1 | 4/2003 | Hanus et al. |
| 6,610,319 | B2 | 8/2003 | Tomai et al. |
| 6,613,902 | B2 | 9/2003 | Gerster et al. |
| 6,624,305 | B2 | 9/2003 | Gerster |
| 6,696,076 | B2 | 2/2004 | Tomai et al. |
| 6,706,728 | B2 | 3/2004 | Hedenstrom et al. |

(Continued)

FOREIGN PATENT DOCUMENTS

| | | |
|---|---|---|
| AU | 2007257423 | 5/2012 |
| AU | 2006283524 B2 | 3/2013 |

(Continued)

OTHER PUBLICATIONS

Alexiou et al. A Diverse Series of Substituted Benzenesulfonamides as Aldose Reductase Inhibitors with Antioxidant Activity: Design, Synthesis, and in Vitro Activity, J. Med. Chem. 2010, 53, 7756-7766 (Year: 2010).*

(Continued)

*Primary Examiner* — Bruck Kifle
*Assistant Examiner* — Kevin S Martin
(74) *Attorney, Agent, or Firm* — SCHWEGMAN LUNDBERG & WOESSNER, P.A.

(57) ABSTRACT

Bis-aryl sulfonamide compounds and methods of using those compounds, e.g., in a method of enhancing or prolonging an immune response, are provided. For example, the compounds may be employed with a vaccine and optionally at least one other adjuvant and/or one or more TLR ligands, at least one MAP kinase inhibitor, or any combination thereof.

3 Claims, 8 Drawing Sheets

(56) References Cited

U.S. PATENT DOCUMENTS

| | | | |
|---|---|---|---|
| 6,716,840 | B2 | 4/2004 | Chu et al. |
| 6,733,764 | B2 | 5/2004 | Martin |
| 6,734,187 | B1 | 5/2004 | Tanaka et al. |
| 6,897,314 | B2 | 5/2005 | Gerster et al. |
| 6,960,582 | B2 | 11/2005 | Boyce et al. |
| 7,001,609 | B1 | 2/2006 | Matson et al. |
| 7,037,929 | B1 | 5/2006 | Pevarello et al. |
| 7,157,465 | B2 | 1/2007 | Isobe et al. |
| 7,189,727 | B2 | 3/2007 | Boyce |
| 7,238,700 | B2 | 7/2007 | Palle et al. |
| 7,241,890 | B2 | 7/2007 | Kasibhatla et al. |
| 7,521,454 | B2 | 4/2009 | Isobe et al. |
| 7,576,068 | B2 | 8/2009 | Averett |
| 7,754,728 | B2 | 7/2010 | Isobe et al. |
| 7,968,544 | B2 | 6/2011 | Graupe et al. |
| 8,211,863 | B2 | 7/2012 | Averett |
| 8,357,374 | B2 | 1/2013 | Carson et al. |
| 8,729,088 | B2 | 5/2014 | Carson et al. |
| 8,790,655 | B2 | 7/2014 | Carson |
| 8,846,697 | B2 | 9/2014 | Carson et al. |
| 9,034,857 | B2 | 5/2015 | Burhans et al. |
| 9,050,376 | B2 | 6/2015 | Carson et al. |
| 9,173,931 | B2 | 11/2015 | Jessouroun et al. |
| 9,359,360 | B2 | 6/2016 | Carson et al. |
| 9,505,768 | B2 | 11/2016 | Carson et al. |
| 2002/0127224 | A1 | 9/2002 | Chen |
| 2002/0193595 | A1 | 12/2002 | Chu et al. |
| 2003/0003505 | A1 | 1/2003 | Cook |
| 2003/0187261 | A1 | 10/2003 | Havlicek et al. |
| 2003/0191086 | A1 | 10/2003 | Hanus et al. |
| 2004/0023211 | A1 | 2/2004 | Groen et al. |
| 2004/0091491 | A1 | 5/2004 | Kedl et al. |
| 2004/0132748 | A1 | 7/2004 | Isobe et al. |
| 2004/0202663 | A1 | 10/2004 | Hu et al. |
| 2004/0209899 | A1 | 10/2004 | Palle et al. |
| 2004/0248895 | A1 | 12/2004 | Chu et al. |
| 2004/0265351 | A1 | 12/2004 | Miller et al. |
| 2005/0004038 | A1 | 1/2005 | Lyon et al. |
| 2005/0004144 | A1 | 1/2005 | Carson et al. |
| 2005/0038027 | A1 | 2/2005 | Boyce |
| 2005/0042272 | A1 | 2/2005 | Hou et al. |
| 2005/0049263 | A1 | 3/2005 | Kasibhatla et al. |
| 2005/0054590 | A1 | 3/2005 | Averett |
| 2005/0059613 | A1 | 3/2005 | Memarzadeh et al. |
| 2005/0158325 | A1 | 7/2005 | Hammerbeck et al. |
| 2005/0266067 | A1 | 12/2005 | Sengupta et al. |
| 2006/0052403 | A1 | 3/2006 | Isobe et al. |
| 2006/0110746 | A1 | 5/2006 | Andre et al. |
| 2007/0037832 | A1 | 2/2007 | Isobe et al. |
| 2007/0087009 | A1 | 4/2007 | Burdin |
| 2007/0100146 | A1 | 5/2007 | Dzwiniel |
| 2007/0161582 | A1 | 7/2007 | Mijikovic et al. |
| 2007/0173483 | A1 | 7/2007 | Kasibhatla et al. |
| 2007/0173530 | A1 | 7/2007 | Mitchell et al. |
| 2007/0190071 | A1 | 8/2007 | Kurimoto et al. |
| 2007/0292418 | A1 | 12/2007 | Fields et al. |
| 2008/0008682 | A1 | 1/2008 | Chong et al. |
| 2008/0125446 | A1 | 5/2008 | Kasibhatla et al. |
| 2008/0214580 | A1 | 9/2008 | Neagu et al. |
| 2009/0047249 | A1 | 2/2009 | Graupe et al. |
| 2009/0053186 | A1 | 2/2009 | Hu et al. |
| 2009/0069289 | A1 | 3/2009 | Neagu et al. |
| 2009/0099212 | A1 | 4/2009 | Zablocki et al. |
| 2009/0105212 | A1 | 4/2009 | Isobe et al. |
| 2009/0118263 | A1 | 5/2009 | Hashimoto et al. |
| 2009/0202484 | A1 | 8/2009 | Chong et al. |
| 2009/0202626 | A1 | 8/2009 | Carson et al. |
| 2009/0263470 | A1 | 10/2009 | Coller et al. |
| 2009/0324551 | A1 | 12/2009 | Carson et al. |
| 2010/0029585 | A1 | 2/2010 | Howbert et al. |
| 2010/0210598 | A1 | 8/2010 | Carson et al. |
| 2011/0098248 | A1 | 4/2011 | Halcomb et al. |
| 2011/0098294 | A1 | 4/2011 | Carson et al. |
| 2011/0150836 | A1 | 6/2011 | Halcomb et al. |
| 2011/0306671 | A1 | 12/2011 | Carson et al. |
| 2011/0319442 | A1 | 12/2011 | Leoni et al. |
| 2012/0003298 | A1 | 1/2012 | Barberis et al. |
| 2012/0009247 | A1 | 1/2012 | Maj et al. |
| 2012/0083473 | A1 | 4/2012 | Holldack et al. |
| 2012/0128715 | A1 | 5/2012 | Levy et al. |
| 2012/0148660 | A1 | 6/2012 | Carson et al. |
| 2012/0177681 | A1 | 7/2012 | Singh et al. |
| 2013/0156807 | A1 | 6/2013 | Carson et al. |
| 2013/0165455 | A1 | 6/2013 | Carson et al. |
| 2013/0190494 | A1 | 7/2013 | Carson et al. |
| 2014/0255368 | A1 | 9/2014 | Kim et al. |
| 2014/0302120 | A1 | 10/2014 | Carson et al. |
| 2015/0197527 | A1 | 7/2015 | Carson et al. |
| 2015/0203844 | A1 | 7/2015 | Marban et al. |
| 2015/0366962 | A1 | 12/2015 | Carson et al. |
| 2016/0031814 | A1 | 2/2016 | Minor, Jr. et al. |
| 2016/0193313 | A1 | 7/2016 | Kim et al. |
| 2016/0199499 | A1 | 7/2016 | Carson et al. |
| 2017/0165359 | A1 | 6/2017 | Berzofsky et al. |
| 2017/0342504 | A1 | 11/2017 | Barrett et al. |
| 2018/0110784 | A1 | 4/2018 | Carson et al. |
| 2020/0071668 | A1 | 3/2020 | Kim et al. |
| 2020/0087625 | A1 | 3/2020 | Carson et al. |
| 2020/0261562 | A1 | 8/2020 | Vinetz |
| 2021/0038742 | A1 | 2/2021 | Huang et al. |
| 2021/0187087 | A1 | 6/2021 | Mcneel et al. |
| 2021/0380546 | A1 | 12/2021 | Carson et al. |
| 2022/0152188 | A1 | 5/2022 | Carson et al. |
| 2023/0365570 | A1 | 11/2023 | Carson et al. |
| 2025/0281465 | A1 | 9/2025 | Carson et al. |

FOREIGN PATENT DOCUMENTS

| | | | |
|---|---|---|---|
| AU | 2008227128 | B2 | 3/2013 |
| AU | 2009210655 | B2 | 8/2013 |
| AU | 2010214112 | B2 | 4/2015 |
| AU | 2020236254 | A1 | 10/2021 |
| CA | 3132994 | A1 | 9/2020 |
| CN | 101304748 | A | 11/2008 |
| CN | 101790380 | B | 7/2013 |
| CN | 102439011 | B | 5/2016 |
| CN | 114401738 | A | 4/2022 |
| CN | 114401738 | B | 2/2025 |
| DE | 1810053 | | 2/1970 |
| EA | 019768 | B1 | 6/2014 |
| EP | 0145340 | A2 | 6/1985 |
| EP | 0310950 | A1 | 4/1989 |
| EP | 0389302 | A1 | 9/1990 |
| EP | 0394026 | A1 | 10/1990 |
| EP | 0553202 | A1 | 8/1993 |
| EP | 0575549 | A1 | 12/1993 |
| EP | 0636031 | A1 | 2/1995 |
| EP | 0681570 | A1 | 11/1995 |
| EP | 0708773 | A1 | 5/1996 |
| EP | 0912564 | A1 | 5/1999 |
| EP | 0912565 | A1 | 5/1999 |
| EP | 0938315 | A1 | 9/1999 |
| EP | 1035123 | A1 | 9/2000 |
| EP | 1035123 | B1 | 8/2003 |
| EP | 1386923 | A1 | 2/2004 |
| EP | 1550662 | A1 | 7/2005 |
| EP | 1939202 | A1 | 7/2008 |
| EP | 2396328 | | 12/2011 |
| EP | 1931352 | B1 | 4/2016 |
| EP | 3908316 | A1 | 11/2021 |
| EP | 3908316 | A4 | 3/2023 |
| HK | 1170226 | A | 2/2013 |
| HK | 1138767 | B | 5/2014 |
| HK | 1177886 | B | 7/2016 |
| IL | 286254 | B1 | 6/2025 |
| JP | 11193282 | A | 7/1999 |
| JP | 11269177 | A | 10/1999 |
| JP | 2004137157 | A | 5/2004 |
| JP | 2005046160 | A | 2/2005 |
| JP | 2005505504 | A | 2/2005 |
| JP | 200589334 | A | 4/2005 |
| JP | 2005089334 | A | 4/2005 |
| JP | 2005126374 | A | 5/2005 |
| JP | 2006519784 | A | 8/2006 |

(56) References Cited

FOREIGN PATENT DOCUMENTS

| | | | |
|---|---|---|---|
| JP | 2007504232 | A | 3/2007 |
| JP | 2009504803 | A | 2/2009 |
| JP | 2009510096 | A | 3/2009 |
| JP | 201051882 | A | 5/2010 |
| JP | 2012517428 | A | 8/2012 |
| JP | 2013525431 | A | 6/2013 |
| JP | 2014129425 | A | 7/2014 |
| JP | 7638528 | B2 | 2/2025 |
| KR | 1020220035870 | A | 3/2022 |
| WO | WO-9215581 | A1 | 9/1992 |
| WO | WO-9320847 | A1 | 10/1993 |
| WO | WO-9817279 | A1 | 4/1998 |
| WO | WO-9848805 | A1 | 11/1998 |
| WO | WO-9928321 | A1 | 6/1999 |
| WO | WO-1999028321 | A1 | 6/1999 |
| WO | WO-0043394 | A1 | 7/2000 |
| WO | WO-0144259 | A1 | 6/2001 |
| WO | WO-0144260 | A2 | 6/2001 |
| WO | WO-0149688 | A1 | 7/2001 |
| WO | WO-0224225 | A1 | 3/2002 |
| WO | WO-0230399 | A2 | 4/2002 |
| WO | WO-03077944 | A1 | 9/2003 |
| WO | WO-2004029054 | A1 | 4/2004 |
| WO | WO-2004066947 | A2 | 8/2004 |
| WO | WO-2005025583 | A2 | 3/2005 |
| WO | WO-2005060966 | A1 | 7/2005 |
| WO | WO-2005092892 | A1 | 10/2005 |
| WO | WO-2006062945 | A2 | 6/2006 |
| WO | WO-2006065234 | A1 | 6/2006 |
| WO | WO-2006100226 | A1 | 9/2006 |
| WO | WO-2006117670 | A1 | 11/2006 |
| WO | WO-2007024707 | A2 | 3/2007 |
| WO | WO-2007024707 | A3 | 3/2007 |
| WO | WO-2007034817 | A1 | 3/2007 |
| WO | WO-2007034917 | A1 | 3/2007 |
| WO | WO-2007038720 | A2 | 4/2007 |
| WO | WO-2007128158 | A1 | 11/2007 |
| WO | WO-2007142755 | A2 | 12/2007 |
| WO | WO-2007142755 | A3 | 12/2007 |
| WO | WO-2008005555 | A1 | 1/2008 |
| WO | WO-2008115319 | A2 | 9/2008 |
| WO | WO-2008115319 | A3 | 9/2008 |
| WO | WO-2009005687 | A1 | 1/2009 |
| WO | WO-2009099650 | A2 | 8/2009 |
| WO | WO-2009099650 | A3 | 8/2009 |
| WO | WO-2009099650 | A4 | 8/2009 |
| WO | WO-2009143457 | A2 | 11/2009 |
| WO | WO-2010033074 | A1 | 3/2010 |
| WO | WO-2010077310 | A2 | 7/2010 |
| WO | WO-2010093436 | A2 | 8/2010 |
| WO | WO-2010093436 | A3 | 8/2010 |
| WO | WO-2010077310 | A3 | 11/2010 |
| WO | WO-2011139348 | A3 | 9/2011 |
| WO | WO-2011134668 | A1 | 11/2011 |
| WO | WO-2011134669 | A1 | 11/2011 |
| WO | WO-2011139348 | A2 | 11/2011 |
| WO | WO-2011139348 | A9 | 11/2011 |
| WO | WO-2014052828 | A1 | 4/2014 |
| WO | WO-2015023858 | A2 | 2/2015 |
| WO | WO-2015023858 | A3 | 2/2015 |
| WO | WO-2016164640 | A1 | 10/2016 |
| WO | WO-2016168680 | A1 | 10/2016 |
| WO | WO-2018183930 | A1 | 10/2018 |
| WO | WO-2019212356 | A1 | 11/2019 |
| WO | WO-2020086625 | A1 | 4/2020 |
| WO | WO-2020186229 | A1 | 9/2020 |
| WO | WO-2021034729 | A1 | 2/2021 |
| WO | WO-2022076473 | A1 | 4/2022 |

OTHER PUBLICATIONS

Neeman et al. Substituted benzenesulfonanilides as synergists for DDT, Nature, vol. 177, 800-801, 1956 (Year: 1956).*

Afzal et al. Synthesis, spectral analysis and biological screening of some new N-(un)substituted N-(5-chloro-2-methoxyphenyl)-aryl sulfonamides, Journal of Pharmacy Research, 2013, 559-564 (Year: 2013).*

"U.S. Appl. No. 15/604,400, Notice of Allowance mailed Feb. 24, 2023", 5 pgs.

"European Application Serial No. 20770127.7, EP Search Report mailed Feb. 27, 2023.", 10 pgs.

Chan, Michael, "Structure-Activity Relationship Studies of Pyrimido[5,4- b]indoles as Selective Toll-Like Receptor 4 Ligands", J Med Chem. Nov. 22, 2017, 60(22) pp. 9142-9161, (May 8, 2018), 48 pgs.

Goff, Peter, "Synthetic Toll~Like Receptor 4 (TLR4) and TLR7 Ligands as Influenza Tirus Vaccine Adjuvants Induce Rapid, Sustained, and Broadly Protective Responses", Journal of Virology, vol. 89, No. 6, Mar. 2015., (Mar. 2015), 15 pgs.

Sato-Kaneko, F., "A Novel Synthetic Dual Agonistic Liposomal TLR4 7 Adjuvant Promotes Broad Immune Responses in an Influenza Vaccine With Minimal Reactogenicity", Frontiers in Immunology, vol. 11, Article 1207. Jun. 2020., (Jun. 19, 2020), 19 pgs.

Schmidt, Signe, "Liposome-Based Adjuvants for Subunit Vaccines: Formulation Strategies for Subunit Antigens and Immunostimulators", Researchgate, Pharmaceutics, 8,7, Mar. 2016, 23 pgs., (Mar. 2016), 23 pgs.

"International Application Serial No. PCT/US2021/053648, International Preliminary Report on Patentability mailed Apr. 20, 2023", 7 pgs.

"Israel Application Serial No. 286254, Office Action mailed Dec. 17, 2023", 6 pgs.

"Israel Application Serial No. 286254, Response filed Aug. 18, 2024 to Office Action mailed Dec. 17, 2023", w/ current English claims, 17 pgs.

Chan, M., et al., "Structure-Activity Relationship Studies of Pyrimido[5,4-b]indoles as Selective Toll-Like Receptor 4 Ligands", J. Med. Chem. 60, (2017), 20 pgs.

Goff, P. H., et al., "Synthetic Toll-like receptor 4 (TLR4) and ILR7 ligands as influenza virus vaccine adjuvants induce rapid, sustained, and broadly protective responses", Journal of Virology, vol. 89 No. 6, Mar. 2015. jvi.asm.org 3221, (Mar. 31, 2015), 15 pgs.

Schmidt, Tandrup Signe, et al., "Liposome-Based Adjuvants for Subunit Vaccines: Formulation Strategies for Subunit Antigens and Immunostimulators", Pharmaceutics, vol. 8, No. 1, 22 pgs.

U.S. Appl. No. 16/495,083, Final Office Action mailed Aug. 6, 2025, 8 pgs.

U.S. Appl. No. 16/495,083, Response filed Jul. 17, 2025 to Non Final Office Action mailed Jan. 17, 2025, 6 pgs.

U.S. Appl. No. 17/438,934, Non Final Office Action mailed Oct. 2, 2025, 16 pgs.

U.S. Appl. No. 17/438,934, Response filed Dec. 8, 2025 to Non Final Office Action mailed Oct. 2, 2025, 13 pgs.

U.S. Appl. No. 18/029,899, Examiner Interview Summary mailed Oct. 28, 2025, 2 pgs.

U.S. Appl. No. 18/029,899, Non Final Office Action mailed Nov. 21, 2025, 9 pgs.

U.S. Appl. No. 18/029,899, Response filed Oct. 27, 2025 to Restriction Requirement mailed Aug. 27, 2025, 8 pgs.

U.S. Appl. No. 18/029,899, Restriction Requirement mailed Aug. 27, 2025, 11 pgs.

U.S. Appl. No. 18/861,136, Preliminary Amendment filed Aug. 7, 2025, 69 pgs.

U.S. Appl. No. 18/861,136, Preliminary Amendment filed Oct. 23, 2025, 3 pgs.

Australian Application Serial No. 2020236254, First Examination Report mailed Oct. 14, 2025, 5 pgs.

Brazilian Application Serial No. PI 0807196-9, Office Action mailed Jun. 30, 2025, With English Machine Translation, 23 pgs.

Brazilian Application Serial No. PI 0807196-9, Response filed Sep. 5, 2025 to Office Action mailed Jun. 30, 2025, With English Machine Translation, 209 pgs.

Canadian Application Serial No. 3,132,994, Examiners Rule 86(2) Report mailed Jul. 15, 2025, 5 pgs.

Canadian Application Serial No. 3,132,994, Response filed Nov. 14, 2025 to Examiners Rule 86(2) Report mailed Jul. 15, 2025, 213 pgs.

(56) References Cited

OTHER PUBLICATIONS

Korean Application Serial No. 10-2021-7033212, Notice of Preliminary Rejection mailed Jun. 20, 2025, w/ English translation, 15 pgs.
Korean Application Serial No. 10-2021-7033212, Response filed Sep. 3, 2025 to Notice of Preliminary Rejection mailed Jun. 20, 2025, With English Machine Translation, 52 pgs.
Korean Application Serial No. 10-2021-7033212, Notice of Preliminary Rejection mailed Feb. 18, 2026, w/ English Translation, 9 pgs.
"8H-Purin-8-one, 6-amino-2-(butylthio)-7,9-dihydro-9-(phenylmethyl)-", CAS Registry No. 226906-70-3, (2012), 1 pg.
"U.S. Appl. No. 12/027,960, Amendment Under 37 C.F.R. Sec. 1.312 filed Nov. 1, 2012", 7 pgs.
"U.S. Appl. No. 12/027,960, Non Final Office Action mailed Apr. 10, 2012", 16 pgs.
"U.S. Appl. No. 12/027,960, Notice of Allowance mailed Aug. 1, 2012", 10 pgs.
"U.S. Appl. No. 12/027,960, Preliminary Amendment mailed Dec. 8, 2010", 21 pgs.
"U.S. Appl. No. 12/027,960, PTO Response to 312 Amendment mailed Nov. 14, 2012", 2 pgs.
"U.S. Appl. No. 12/027,960, Response filed Jul. 10, 2012 to Non Final Office Action mailed Apr. 10, 2012", 8 pgs.
"U.S. Appl. No. 12/027,960, Response filed Oct. 24, 2011 to Restriction Requirement mailed Sep. 23, 2011", 21 pgs.
"U.S. Appl. No. 12/027,960, Restriction Requirement mailed Sep. 23, 2011", 9 pgs.
"U.S. Appl. No. 12/064,529, Final Office Action mailed Sep. 20, 2012", 14 pgs.
"U.S. Appl. No. 12/064,529, Non Final Office Action mailed Apr. 9, 2012", 15 pgs.
"U.S. Appl. No. 12/064,529, Preliminary Amendment filed Feb. 22, 2008", 11 pgs.
"U.S. Appl. No. 12/064,529, Response filed Jul. 9, 2012 to Non Final Office Action mailed Apr. 9, 2012", 11 pgs.
"U.S. Appl. No. 12/064,529, Response filed Oct. 24, 2011 to Restriction Requirement mailed Aug. 24, 2011", 9 pgs.
"U.S. Appl. No. 12/064,529, Restriction Requirement mailed Aug. 24, 2011", 9 pgs.
"U.S. Appl. No. 12/302,738, Final Office Action mailed Oct. 3, 2013", 11 pgs.
"U.S. Appl. No. 12/302,738, Non Final Office Action mailed Jan. 2, 2013", 10 pgs.
"U.S. Appl. No. 12/302,738, Notice of Allowance mailed Apr. 22, 2014", 7 pgs.
"U.S. Appl. No. 12/302,738, Notice of Allowance mailed Dec. 27, 2013", Examiner Interview Summary, 9 pgs.
"U.S. Appl. No. 12/302,738, Preliminary Amendment filed Nov. 26, 2008", 8 pgs.
"U.S. Appl. No. 12/302,738, Response filed Jun. 26, 2013 to Non Final Office Action mailed Jan. 2, 2013", 10 pgs.
"U.S. Appl. No. 12/302,738, Response filed Nov. 19, 2012 to Restriction Requirement mailed Oct. 19, 2012", 7 pgs.
"U.S. Appl. No. 12/302,738, Response filed Dec. 3, 2013 to Final Office Action mailed Oct. 3, 2013", 8 pgs.
"U.S. Appl. No. 12/302,738, Restriction Requirement mailed Oct. 19, 2012", 7 pgs.
"U.S. Appl. No. 12/367,172, Final Office Action mailed Jan. 18, 2012", 15 pgs.
"U.S. Appl. No. 12/367,172, Final Office Action mailed Apr. 13, 2012", 21 pgs.
"U.S. Appl. No. 12/367,172, Final Office Action mailed Apr. 21, 2015", 19 pgs.
"U.S. Appl. No. 12/367,172, Non Final Office Action mailed May 27, 2011", 20 pgs.
"U.S. Appl. No. 12/367,172, Non Final Office Action mailed Jul. 1, 2014", 20 pgs.
"U.S. Appl. No. 12/367,172, Response filed Mar. 8, 2011 to Restriction Requirement mailed Dec. 8, 2010", 11 pgs.
"U.S. Appl. No. 12/367,172, Response filed Aug. 13, 2012 to Final Office Action mailed Apr. 13, 2012", 9 pgs.
"U.S. Appl. No. 12/367,172, Response filed Nov. 16, 2011 to Non Final Office Action mailed May 27, 2011", 6 pgs.
"U.S. Appl. No. 12/367,172, Response filed Dec. 29, 2014 to Non Final Office Action mailed Jul. 1, 2014", 7 pgs.
"U.S. Appl. No. 12/367,172, Restriction Requirement mailed Dec. 8, 2010", 6 pgs.
"U.S. Appl. No. 12/704,343, Advisory Action mailed Apr. 5, 2013", 3 pgs.
"U.S. Appl. No. 12/704,343, Examiner Interview Summary mailed Feb. 7, 2013", 3 pgs.
"U.S. Appl. No. 12/704,343, Examiner Interview Summary mailed Feb. 25, 2013", 3 pgs.
"U.S. Appl. No. 12/704,343, Final Office Action mailed May 10, 2013", 7 pgs.
"U.S. Appl. No. 12/704,343, Final Office Action mailed Dec. 7, 2012", 9 pgs.
"U.S. Appl. No. 12/704,343, Non Final Office Action mailed Jul. 16, 2012", 14 pgs.
"U.S. Appl. No. 12/704,343, Notice of Allowance mailed Jan. 3, 2014", 11 pgs.
"U.S. Appl. No. 12/704,343, Notice of Allowance mailed Aug. 2, 2013", 10 pgs.
"U.S. Appl. No. 12/704,343, Response filed Feb. 27, 2013 to Final Office Action mailed Dec. 7, 2012", 9 pgs.
"U.S. Appl. No. 12/704,343, Response filed Jun. 5, 2012 to Restriction Requirement mailed May 7, 2012", 7 pgs.
"U.S. Appl. No. 12/704,343, Response filed Jul. 10, 2013 to Final Office Action mailed May 10, 2013", 8 pgs.
"U.S. Appl. No. 12/704,343, Response filed Oct. 16, 2012 to Non Final Office Action mailed Jul. 16, 2012", 12 pgs.
"U.S. Appl. No. 12/704,343, Restriction Requirement mailed May 7, 2012", 7 pgs.
"U.S. Appl. No. 13/140,613, Restriction Requirement mailed Oct. 5, 2012", .10 pgs.
"U.S. Appl. No. 13/682,208, Advisory Action mailed Oct. 30, 2015", 10 pgs.
"U.S. Appl. No. 13/682,208, Advisory Action mailed Dec. 31, 2015", 8 pgs.
"U.S. Appl. No. 13/682,208, Examiner Interview Summary mailed Sep. 11, 2014", 4 pgs.
"U.S. Appl. No. 13/682,208, Final Office Action mailed May 23, 2014", 17 pgs.
"U.S. Appl. No. 13/682,208, Final Office Action mailed Aug. 4, 2015", 19 pgs.
"U.S. Appl. No. 13/682,208, Non Final Office Action mailed Nov. 5, 2014", 11 pgs.
"U.S. Appl. No. 13/682,208, Non Final Office Action mailed Nov. 7, 2013", 13 pgs.
"U.S. Appl. No. 13/682,208, Notice of Allowance mailed Jan. 29, 2016", 11 pgs.
"U.S. Appl. No. 13/682,208, Preliminary Amendment filed Nov. 20, 2012", 7 pgs.
"U.S. Appl. No. 13/682,208, PTO Response to Rule 312 Communication mailed May 13, 2016", 2 pgs.
"U.S. Appl. No. 13/682,208, Response filed Jan. 4, 2016 to Advisory Action mailed Dec. 31, 2015", 6 pgs.
"U.S. Appl. No. 13/682,208, Response filed Feb. 7, 2014 to Non Final Office Action mailed Nov. 7, 2013", 9 pgs.
"U.S. Appl. No. 13/682,208, Response filed May 5, 2015 to Non Final Office Action mailed Nov. 5, 2014", 9 pgs.
"U.S. Appl. No. 13/682,208, Response filed Aug. 7, 2013 to Restriction Requirement mailed Jun. 6, 2013", 8 pgs.
"U.S. Appl. No. 13/682,208, Response filed Sep. 23, 2014 to Final Office Action mailed May 23, 2014", 9 pgs.
"U.S. Appl. No. 13/682,208, Response filed Sep. 28, 2015 to Final Office Action mailed Aug. 4, 2015", 10 pgs.
"U.S. Appl. No. 13/682,208, Response filed Nov. 25, 2015 to Advisory Action mailed Oct. 30, 2015", 14 pgs.
"U.S. Appl. No. 13/682,208, Restriction Requirement mailed Jun. 6, 2013", 9 pgs.

(56) References Cited

OTHER PUBLICATIONS

"U.S. Appl. No. 13/695,385, Final Office Action mailed Oct. 28, 2014", 24 pgs.
"U.S. Appl. No. 13/695,385, Non Final Office Action mailed Feb. 4, 2014", 20 pgs.
"U.S. Appl. No. 13/695,385, Response filed May 5, 2014 to Non Final Office Action mailed Feb. 4, 2014", 8 pgs.
"U.S. Appl. No. 13/695,385, Response filed Sep. 24, 2013 to Restriction Requirement mailed Aug. 2, 2013", 7 pgs.
"U.S. Appl. No. 13/695,385, Restriction Requirement mailed Aug. 2, 2013", 7 pgs.
"U.S. Appl. No. 13/736,545, Notice of Allowance mailed Mar. 18, 2014", 6 pgs.
"U.S. Appl. No. 13/736,545, Notice of Allowance mailed Aug. 2, 2013", 9 pgs.
"U.S. Appl. No. 13/736,545, Preliminary Amendment filed Mar. 6, 2013", 3 pgs.
"U.S. Appl. No. 13/791,175, Examiner Interview Summary mailed Jun. 2, 2015", 2 pgs.
"U.S. Appl. No. 13/791,175, Final Office Action mailed Nov. 20, 2014", 12 pgs.
"U.S. Appl. No. 13/791,175, Final Office Action mailed Dec. 26, 2013", 12 pgs.
"U.S. Appl. No. 13/791,175, Non Final Office Action mailed Jun. 7, 2013", 10 pgs.
"U.S. Appl. No. 13/791,175, Non Final Office Action mailed Jul. 21, 2014", 11 pgs.
"U.S. Appl. No. 13/791,175, Preliminary Amendment filed Mar. 8, 2013", 4 pgs.
"U.S. Appl. No. 13/791,175, Response filed Jun. 26, 2014 to Final Office Action mailed Dec. 26, 2013", 9 pgs.
"U.S. Appl. No. 13/791,175, Response filed Oct. 21, 2014 to Non Final Office Action mailed Jul. 21, 2014", 7 pgs.
"U.S. Appl. No. 13/791,175, Response filed Nov. 1, 2013 to Non Final Office Action mailed Jun. 7, 2013", 8 pgs.
"U.S. Appl. No. 14/309,245, Notice of Allowance mailed Jan. 20, 2015", 12 pgs.
"U.S. Appl. No. 14/912,043, Non Final Office Action mailed Aug. 19, 2016", 12 pgs.
"U.S. Appl. No. 14/912,043, Preliminary Amendment filed Feb. 17, 2016", 6 pgs.
"U.S. Appl. No. 15/565,097, Advisory Action mailed Mar. 8, 2019", 3 pgs.
"U.S. Appl. No. 15/565,097, Final Office Action mailed Jan. 8, 2019", 10 pgs.
"U.S. Appl. No. 15/565,097, Non Final Office Action mailed Sep. 10, 2018", 9 pgs.
"U.S. Appl. No. 15/565,097, Non Final Office Action mailed Sep. 13, 2019", 8 pgs.
"U.S. Appl. No. 15/565,097, Preliminary Amendment filed Oct. 11, 2017", 11 pgs.
"U.S. Appl. No. 15/565,097, Response filed Feb. 28, 2019 to Final Office Action mailed Jan. 8, 2019", 11 pgs.
"U.S. Appl. No. 15/565,097, Response filed Apr. 8, 2019 to Advisory Action mailed Mar. 8, 2019", 15 pgs.
"U.S. Appl. No. 15/565,097, Response filed May 11, 2018 to Restriction Requirement mailed Apr. 20, 2018", 9 pgs.
"U.S. Appl. No. 15/565,097, Response filed Dec. 6, 2018 to Non Final Office Action mailed Sep. 10, 2018", 12 pgs.
"U.S. Appl. No. 15/565,097, Restriction Requirement mailed Apr. 20, 2018", 6 pgs.
"U.S. Appl. No. 15/604,400, Advisory Action mailed Jan. 12, 2021", 3 pgs.
"U.S. Appl. No. 15/604,400, Final Office Action mailed Jun. 2, 2022", 11 pgs.
"U.S. Appl. No. 15/604,400, Final Office Action mailed Oct. 28, 2020", 19 pgs.
"U.S. Appl. No. 15/604,400, Non Final Office Action mailed Mar. 20, 2020", 20 pgs.
"U.S. Appl. No. 15/604,400, Non Final Office Action mailed Sep. 2, 2021", 11 pgs.
"U.S. Appl. No. 15/604,400, Notice of Allowance mailed Oct. 28, 2022", 11 pgs.
"U.S. Appl. No. 15/604,400, Response filed Jan. 28, 2021 to Advisory Action mailed Jan. 12, 2021", 11 pgs.
"U.S. Appl. No. 15/604,400, Response filed Feb. 2, 2022 to Non Final Office Action mailed Sep. 2, 2021", 9 pgs.
"U.S. Appl. No. 15/604,400, Response Filed Jul. 2, 2019 to Restriction Requirement mailed Feb. 6, 2019", 7 pgs.
"U.S. Appl. No. 15/604,400, Response filed Jul. 20, 2020 to Non Final Office Action mailed Mar. 20, 2020", 9 pgs.
"U.S. Appl. No. 15/604,400, Response filed Oct. 4, 2022 to Final Office Action mailed Jun. 2, 2022", 10 pgs.
"U.S. Appl. No. 15/604,400, Response filed Dec. 16, 2019 to Restriction Requirement mailed Oct. 31, 2019", 6 pgs.
"U.S. Appl. No. 15/604,400, Response filed Dec. 28, 2020 to Final Office Action mailed Oct. 28, 2020", 10 pgs.
"U.S. Appl. No. 15/604,400, Restriction Requirement mailed Feb. 6, 2019", 8 pgs.
"U.S. Appl. No. 15/604,400, Restriction Requirement mailed Oct. 31, 2019", 6 pgs.
"U.S. Appl. No. 16/495,083, Advisory Action mailed Dec. 30, 2022", 3.pgs.
"U.S. Appl. No. 16/495,083, Final Office Action mailed Sep. 19, 2022", 6 pgs.
"U.S. Appl. No. 16/495,083, Non Final Office Action mailed Jun. 30, 2022", 7 pgs.
"U.S. Appl. No. 16/495,083, Response filed Jan. 19, 2023 to Advisory Action mailed Dec. 30, 2022", 8 pgs.
"U.S. Appl. No. 16/495,083, Response filed May 31, 2022 to Restriction Requirement mailed Apr. 1, 2022", 6 pgs.
"U.S. Appl. No. 16/495,083, Response filed Aug. 16, 2022 to Non Final Office Action mailed Jun. 30, 2022", 7 pgs.
"U.S. Appl. No. 16/495,083, Response filed Dec. 8, 2022 to Final Office Action mailed Sep. 19, 2022", 8 pgs.
"U.S. Appl. No. 16/495,083, Restriction Requirement mailed Apr. 1, 2022", 4 pgs.
"U.S. Appl. No. 13/695,385, Preliminary Amendment filed Oct. 30, 2012", 7 pgs.
"Aromatic Ions (Chemgapedia)", [online]. [retrieved on Dec. 3, 2012]. Retrieved From Internet: <URL: http://www.chemgapedia.de/vsengine/vlu/vsc/en/ch/12/oc/vlu_organik/aromaten/aromaten/aromaten_gesamt.vlu/Page/vsc/en/ch/12/oc/aromaten/aromaten/ar_ionen/ar_ionen.vscml.html>, (2012), 2 pgs.
"Australia Application Serial No. 2008227128, First Examiner Report mailed Jul. 6, 2012", 2 pgs.
"Australian Application Serial No. 2006283524, Office Action mailed Mar. 27, 2008", 1 pg.
"Australian Application Serial No. 2006283524, Office Action mailed Aug. 3, 2011", 4 pgs.
"Australian Application Serial No. 2006283524, Preliminary Amendment mailed Mar. 3, 20008", 18 pgs.
"Australian Application Serial No. 2006283524, Response filed May 19, 20008 to Office Action mailed Mar. 27, 20008", 10 pgs.
"Australian Application Serial No. 2006283524, Response filed Aug. 2, 2012 to Examiner Report mailed Aug. 3, 2011", 34 pgs.
"Australian Application Serial No. 2007257423, Office Action mailed Jun. 6, 2011", 2 pgs.
"Australian Application Serial No. 2007257423, Office Action mailed Sep. 22, 2010", 4 pgs.
"Australian Application Serial No. 2007257423, Office Action mailed Oct. 20, 2011", 2 pgs.
"Australian Application Serial No. 2007257423, Response filed May 31, 2011 to Office Action mailed Sep. 22, 2010", 16 pgs.
"Australian Application Serial No. 2007257423, Response filed Sep. 13, 2011 to Office Action mailed Jun. 6, 2011", 12 pgs.
"Australian Application Serial No. 2007257423, Response filed Dec. 19, 2011 to Office Action mailed Oct. 20, 2011", 5 pgs.
"Australian Application Serial No. 2008227128, Preliminary Amendment filed Sep. 7, 2009", 45 pgs.
"Australian Application Serial No. 2008227128, Secondary Amendment filed Jan. 9, 2012", 16 pgs.

(56) References Cited

OTHER PUBLICATIONS

"Australian Application Serial No. 2009210655, Office Action mailed Apr. 19, 2013", 3 pgs.
"Australian Application Serial No. 2009210655, Response filed Jul. 18, 2013 to First Examiner Report mailed Apr. 19, 2013", 19 pgs.
"Australian Application Serial No. 2010214112 Response filed Feb. 27, 2015 to First Examiner Report mailed May 23, 2014", 16 pgs.
"Australian Application Serial No. 2010214112, First Examiner Report mailed May 23, 2014", 6 pgs.
"Bioassay Record NCI Yeast Anticancer Drug Screen", PUBCHEM, Data for the sgs1 mgt1 strain, PubChem AID 161, <https://pubchem.ncbi.nlm.nih.gov/bioassay/16>, (Aug. 15, 2004), 8 pgs.
"Brazil Application Serial No. PI1008383-9, Office Action mailed Oct. 23, 2018", W/ English translation, 7 pgs.
"Brazilian Application Serial No. PI 0807196-9, Amendment filed Mar. 2, 2011", w/English Claims, 19 pgs.
"Brazilian Application Serial No. PI 0807196-9, Office Action mailed Jun. 11, 2019", w/ English Translation, 9 pgs.
"Brazilian Application Serial No. PI 0807196-9, Response filed Sep. 5, 2019 to Office Action mailed Jun. 11, 2019", w/ English Claims, 26 pgs.
"Brazilian Application Serial No. PI0807196-9, Office Action mailed Apr. 8, 2021", w/ English translation, 11 pgs.
"Brazilian Patent Application Serial No. P10907907, Amendment filed Dec. 27, 2011", w/ English Claims, 11 pgs.
"Canadian Application Serial No. 2,620,182, Office Action mailed Aug. 24, 2012", 5 pgs.
"Canadian Application Serial No. 2,653,941, Office Action May 10, 2011", 3 pgs.
"Canadian Application Serial No. 2,653,941, Office Action mailed Feb. 8, 2012", 2 pgs.
"Canadian Application Serial No. 2,653,941, Office Action mailed Aug. 23, 2010", 5 pgs.
"Canadian Application Serial No. 2,653,941, Response filed Feb. 23, 2011 to Office Action mailed Aug. 23, 2010", 20 pgs.
"Canadian Application Serial No. 2,653,941, Response filed Aug. 2, 2012 to Office Action mailed Feb. 8, 2012", 7 pgs.
"Canadian Application Serial No. 2,653,941, Response filed Nov. 9, 2011 to Office Action mailed May 10, 2011", 15 pgs.
"Canadian Application Serial No. 2,677,733 Response filed Feb. 16, 2015 to Office Action mailed Aug. 25, 2014", 6 pgs.
"Canadian Application Serial No. 2,677,733, Office Action mailed Jan. 6, 2016", 3 pgs.
"Canadian Application Serial No. 2,677,733, Office Action mailed Aug. 25, 2014", 2 pgs.
"Canadian Application Serial No. 2,677,733, Voluntary Amendment filed Aug. 7, 2009", 45 pgs.
"Canadian Application Serial No. 2,713,438, Office Action mailed Feb. 3, 2015", 5 pgs.
"Canadian Application Serial No. 2,752,074, Office Action mailed Jan. 5, 2016", 5 pgs.
"Chinese Application Serial No. 200680038761.X, Office Action mailed Mar. 22, 2012", (w/ English Translation), 9 pgs.
"Chinese Application Serial No. 200680038761.X, Office Action mailed Apr. 14, 2010", with English translation, 9 pgs.
"Chinese Application Serial No. 200680038761.X, Office Action mailed Jun. 23, 2011", (w/ English Translation), 9 pgs.
"Chinese Application Serial No. 200680038761.X, Response filed Sep. 7, 2011 to Office Action mailed Jun. 23, 2011", (w/ English Translation of Amended Claims), 19 pgs.
"Chinese Application Serial No. 200680038761.X, Response filed Oct. 29, 2010 to Office Action mailed Apr. 14, 2010", (w/ English Translation of Amended Claims), 22 pgs.
"Chinese Application Serial No. 200680038761.X, Response filed Jul. 6, 2012 to Action mailed Mar. 22, 2012", (w/ English Translation), 9 pgs.
"Chinese Application Serial No. 200880011525.8, Office Action mailed Jan. 30, 2012", English Translation Only, 9 pgs.
"Chinese Application Serial No. 200880011525.8, Office Action mailed Jul. 5, 2012", (w/ English Translation), 14 pgs.
"Chinese Application Serial No. 200880011525.8, Office Action mailed Oct. 16, 2012", (w/ English Translation), 13 pgs.
"Chinese Application Serial No. 200880011525.8, Response filed Feb. 27, 2013 to Office Action mailed Oct. 16, 2012", (w/ English Translation of Amended Claims), 10 pgs.
"Chinese Application Serial No. 200880011525.8, Response filed Jun. 13, 2012 to Office Action mailed Jan. 30, 2012", (w/ English Translation of Claims), 14 pgs.
"Chinese Application Serial No. 200880011525.8, Response filed Sep. 20, 2012 to Office Action mailed Jul. 5, 2012", (w/ English Translation of Claims), 12 pgs.
"Chinese Application Serial No. 200880011525.8, Voluntary Amendment filed Dec. 2, 2010", (w/ English Translation of Claims), 12 pgs.
"Chinese Application Serial No. 200980112411.7, Office Action mailed Nov. 5, 2012", (w/ English Translation), 15 pgs.
"Chinese Application Serial No. 200980112411.7, Office Action mailed Nov. 5, 2012", (English Translation), 8 pgs.
"Chinese Application Serial No. 200980112411.7, Rejection Decision mailed Jul. 23, 2013", (w/ English Translation), 14 pgs.
"Chinese Application Serial No. 200980112411.7, Response filed Mar. 19, 2013 to Office Action mailed Nov. 5, 2012", (w/ English Translation), 4 pgs.
"Chinese Application Serial No. 200980112411.7, Response filed Aug. 15, 2012 to Office Action mailed Feb. 2, 2012", (w/ English Translation of Amended Claims), 70 pgs.
"Chinese Application Serial No. 200980112411.7, Voluntary Amendment filed Jan. 31, 2011", (w/ English Translation of Claims), 74 pgs.
"Chinese Application Serial No. 201080016320.6, Office Action mailed Mar. 20, 2014", w/English translation, 14 pgs.
"Chinese Application Serial No. 201080016320.6, Office Action mailed Jun. 10, 2015", w/English Translation, 10 pgs.
"Chinese Application Serial No. 201080016320.6, Office Action mailed Jul. 8, 2013", (w/ English Translation), 16 pgs.
"Chinese Application Serial No. 201080016320.6, Office Action mailed Oct. 21, 2014", W/ English Translation, 12 pgs.
"Chinese Application Serial No. 201080016320.6, Response filed Mar. 5, 2015 to Office Action mailed Oct. 21, 2014", (w/ English Translation of Amended Claims), 10 pgs.
"Chinese Application Serial No. 201080016320.6, Response filed Aug. 4, 2014 to Office Action mailed Mar. 20, 2014", w/ English translation, 7 pgs.
"Chinese Application Serial No. 201080016320.6, Response filed Nov. 25, 2013 to Office Action mailed Jul. 8, 2013", (w/ English Translation of Claims), 12 pgs.
"Chinese Application Serial No. 201180033022.2 Response filed Jan. 6, 2015 to Non-Final Office Action mailed Sep. 30, 2014", With the English claims, 7 pgs.
"Chinese Application Serial No. 201180033022.2, Office Action mailed Jan. 13, 2014", w/English translation, 12 pgs.
"Chinese Application Serial No. 201180033022.2, Office Action mailed Apr. 28, 2015", w/English Translation, 14 pgs.
"Chinese Application Serial No. 201180033022.2, Office Action mailed Aug. 22, 2014", w/English Translation, 18 pgs.
"Chinese Application Serial No. 201180033022.2, Response filed May 28, 2014 to Office Action mailed Jan. 13, 2014", w/English claims, 9 pgs.
"Chinese Application Serial No. 201180033022.2, Voluntary Amendment filed Sep. 12, 2013", w/English translation, 13 pgs.
"Chinese Application Serial No. 200980112411.7, Office Action Mailed Feb. 2, 2012", w/ English Translation, 9 pgs.
"Definition: Micelle", Merriam-Webster, [Online]. Retrieved from the Internet: <URL:http://www.merriam-webster.com/dictionary/micelle>, (Accessed on Jun. 25, 2014), 1 pg.
"Eurasian Application Serial No. 201001264, Office Action mailed Sep. 12, 2012", (w/ English Summary), 2 pgs.
"Eurasian Application Serial No. 201101165, Office Action mailed Dec. 12, 2012", (w/ English Translation), 7 pgs.
"Eurasian Application Serial No. 200901078, Office Action mailed Jan. 29, 2013", (w/ English Translation), 4 pgs.
"Eurasian Application Serial No. 200901078, Office Action mailed Apr. 2, 2012", w/English Translation, 3 pgs.

(56) References Cited

OTHER PUBLICATIONS

"Eurasian Application Serial No. 200901078, Office Action mailed May 26, 2011", (w/ English Translation), 5 pgs.
"Eurasian Application Serial No. 200901078, Office Action mailed Sep. 18, 2012", (w/ English Translation), 4 pgs.
"Eurasian Application Serial No. 200901078, Office Action mailed Sep. 21, 2011", (w/ English Translation), 4 pgs.
"Eurasian Application Serial No. 200901078, Response filed Jan. 16, 2013 to Office Action mailed Sep. 18, 2012", (w/ English Translation of Claims), 68 pgs.
"Eurasian Application Serial No. 200901078, Response filed Jul. 29, 2013 to Office Action mailed Jan. 29, 2013", (w/ English Translation of Claims), 138 pgs.
"Eurasian Application Serial No. 200901078, Response filed Sep. 13, 2011 to Office Action mailed May 11, 2011", (w/ English Translation of Claims), 13 pgs.
"Eurasian Application Serial No. 201001264, Office Action mailed Mar. 20, 2013", (w/ English Translation), 3 pgs.
"Eurasian Application Serial No. 201001264, Office Action mailed Jul. 10, 2014", w/English Claims, 3 pgs.
"Eurasian Application Serial No. 201001264, Office Action mailed Sep. 26, 2013", (w/ English Translation), 3 pgs.
"Eurasian Application Serial No. 201001264, Response filed Apr. 24, 2014 to Office Action mailed Sep. 26, 2013", w/English claims, 4 pgs.
"Eurasian Application Serial No. 201001264, Response filed Jun. 5, 2013 to Office Action mailed Mar. 20, 2013", (w/ English Translation of Amended Claims), 11 pgs.
"Eurasian Application Serial No. 201001264, Response filed Dec. 19, 2012 to Office Action mailed Sep. 12, 2012", (w/ English Translation of Amended Claims), 16 pgs.
"Eurasian Application Serial No. 201101165, Office Action mailed Jun. 28, 2013", (w/ English Translation), 3 pgs.
"Eurasian Application Serial No. 201101165, Response filed Apr. 9, 2013 to Office Action mailed Dec. 12, 2012", (w/ English Translation), 11 pgs.
"Eurasian Application Serial No. 201101165, Response filed Oct. 28, 2013 to Office Action mailed Jun. 28, 2013", (w/ English Translation of Amended Claims), 10 pgs,.
"Eurasian Patent Application Serial No. 200901078, Response filed Mar. 21, 2012 to Office Action mailed Sep. 21, 2011", (w/ English Translation of Claims), 8 pgs.
"Eurasian Patent Application Serial No. 200901078, Response filed Aug. 2, 2012 to Office Action mailed Apr. 2, 2012", (w/ English Translation of Claims), 4 pgs.
"European Application Serial No. 12004181.9, European Search Report mailed Sep. 13, 2012", 8 pgs.
"European Application Serial No. 06813535.9, Examination Notification Art. 94(3) mailed Sep. 24, 2013", 4 pgs.
"European Application Serial No. 06813535.9, Extended Search Report mailed Oct. 24, 2011", l6 pgs.
"European Application Serial No. 06813535.9, Response filed Apr. 4, 2014 to Examination Notification Art. 94(3) mailed Sep. 24, 2013", 70 pgs.
"European Application Serial No. 06813535.9, Response filed May 14, 2012 to Extended Search Report mailed Oct. 24, 2011", 18 pgs.
"European Application Serial No. 06813535.9, Voluntary Amendment filed Apr. 22, 2008", 9 pgs.
"European Application Serial No. 07755916.9, Examination Notification Art. 94(3) mailed Aug. 15, 2013", 4 pgs.
"European Application Serial No. 07755916.9, Office Action mailed Mar. 25, 2014", 1 pg.
"European Application Serial No. 07755916.9, Office Action mailed Nov. 11, 2011", 1 pg.
"European Application Serial No. 07755916.9, Response filed May 18, 2012 to Extended Search Report mailed Oct. 25, 2011", 11 pgs.
"European Application Serial No. 07755916.9, Response filed May 23, 2014 to Examination Notification Art. 94(3) mailed Aug. 15, 2013", 13 pgs.
"European Application Serial No. 07755916.9, Response filed May 23, 2014 to Office Action mailed Mar. 25, 2014", 10 pgs.
"European Application Serial No. 07755916.9, Supplemental Search Report mailed Oct. 25, 2011", 9 pgs.
"European Application Serial No. 08799591.6, Office Action mailed May 21, 2012", 4 pgs.
"European Application Serial No. 08799591.6, Office Action mailed Jun. 4, 2010", 4 pgs.
"European Application Serial No. 08799591.6, Response filed Sep. 20, 2012 to Office Action mailed May 21, 2012", 31 pgs.
"European Application Serial No. 08799591.6, Response filed Nov. 22, 2011 to Office Action mailed May 17, 2011", 26 pgs.
"European Application Serial No. 08799591.6, Response filed Dec. 2, 2010 to Office Action mailed Jun. 4, 2010", 20 pgs.
"European Application Serial No. 09709019.5, Examination Notification Art. 94(3) mailed Apr. 22, 2015", 6 pgs.
"European Application Serial No. 09709019.5, Examination Notification Art. 94(3) mailed Oct. 9, 2013", 6 pgs.
"European Application Serial No. 09709019.5, Extended European Search Report mailed Feb. 15, 2011", 8 pgs.
"European Application Serial No. 09709019.5, Extended European Search Report mailed Feb. 15, 2011", 7 pgs.
"European Application Serial No. 09709019.5, Notification of Loss of Rights mailed Oct. 21, 2011", 2 pgs.
"European Application Serial No. 09709019.5, Office Action mailed Mar. 19, 2013", 5 pgs.
"European Application Serial No. 09709019.5, Response filed Sep. 25, 2013 to Examination Notification Art. 94(3) mailed Mar. 19, 2013", 25 pgs.
"European Application Serial No. 09709019.5, Response filed Dec. 7, 2011 to Communication pursuant to 70(2) and 70a(2) EPC and the Notification of Loss of Rights mailed Oct. 21, 2011", 41 pgs.
"European Application Serial No. 10706399.2, Communication pursuant to Rules 16(1) and 162 EPC mailed Sep. 27, 2011", 2 pgs.
"European Application Serial No. 10706399.2, Examination Notification Art. 94(3) mailed Jun. 11, 2015", 6 pgs.
"European Application Serial No. 10706399.2, Examination Notification mailed Apr. 17, 2013", 4 pgs.
"European Application Serial No. 10706399.2, Examination Notification mailed Oct. 2, 2012", 6 pgs.
"European Application Serial No. 10706399.2, Response filed Mar. 21, 2013 to Examination Notification mailed Oct. 2, 2012", 11 pgs.
"European Application Serial No. 10706399.2, Response filed Aug. 13, 2013 to Examination Notification Art. 94(3) mailed Apr. 17, 2013", 12 pgs.
"European Application Serial No. 11777689.8, Amendment filed Mar. 12, 2014", 11 pgs.
"European Application Serial No. 11777689.8, Communication pursuant to Rules 70(2) and 70a(2) EPC mailed Nov. 6, 2013", 1 pg.
"European Application Serial No. 11777689.8, Examination Notification Art. 94(3) mailed Oct. 8, 2014", 6 pgs.
"European Application Serial No. 11777689.8, Response filed Mar. 12, 2014 to Communication pursuant to Rules 70(2) and 70a(2) EPC mailed Nov. 6, 2013", 11 pgs.
"European Application Serial No. 11777689.8, Supplementary European Search Report mailed Oct. 18, 2013", 5 pgs.
"European Application Serial No. 12004181.9 Response Filed Dec. 15, 2014 to Non-Final Office Action Mailed Jul. 18, 2014", 138 pgs.
"European Application Serial No. 12004181.9, Communication mailed Oct. 22, 2012", 2 pgs.
"European Application Serial No. 12004181.9, Communication pursuant to Rule 112(1) EPC mailed May 31, 2013", 1 pg.
"European Application Serial No. 12004181.9, Examination Notification Art. 94(3) mailed Jul. 18, 2014", 4 pgs.
"European Application Serial No. 12004181.9, Examination Notification Art. 94(3) mailed Sep. 2, 2013", 5 pgs.
"European Application Serial No. 12004181.9, Response filed Mar. 7, 2014 to Examination Notification Art. 94(3) mailed Sep. 2, 2013", 10 pgs.
"European Application Serial No. 12004181.9, Response filed Jul. 31, 2013 to Communication pursuant to Rule 112(1) EPC mailed May 31, 2013 and Communication mailed Oct. 22, 2012", 9 pgs.

(56) References Cited

OTHER PUBLICATIONS

"European Application Serial No. 13001458.2, Communication Pursuant to Article 94(3) EPC mailed Mar. 22, 2016", 5 pgs.
"European Application Serial No. 13001458.2, Communication pursuant to Rules 70(2) and 70a(2) EPC mailed Jul. 1, 2013", 1 pg.
"European Application Serial No. 13001458.2, Examination Notification Art. 94(3) mailed Apr. 14, 2014", 5 pgs.
"European Application Serial No. 13001458.2, Extended European Search Report mailed Apr. 22, 2013", 5 pgs.
"European Application Serial No. 13001458.2, Response filed Oct. 20, 2014 to Examination Notification Art. 94(3) mailed Apr. 14, 2014", 28 pgs.
"European Application Serial No. 13001458.2, Response filed Dec. 16, 2013 to Communication pursuant to Rules 70(2) and 70a(2) EPC mailed Jul. 1, 2013", 8 pgs.
"European Application Serial No. 13001957.3, Extended European Search Report mailed Jan. 28, 2014", 17 pgs.
"European Application Serial No. 13001957.3, Office Action mailed Mar. 3, 2014", 2 pgs.
"European Application Serial No. 13001957.3, Response filed Aug. 20, 2014 Extended European Search Report mailed Jan. 28, 2014", Includes Response Office Action mailed Mar. 3, 2014, 7 pgs.
"European Application Serial No. 20770127.7, Response to Communication pursuant to Rules 161(2) and 162 EPC filed Mar. 8, 2022", 22 pgs.
"European Application Serial No. 08799591.6, Examination Notification Art. 94(3) mailed May 17, 2011", 5 pgs.
"I. Pharmaceutical Importance of Crystallin Hydrates", [online]. [retrieved on May 30, 2008]. Retrieved from the Internet: <URL: http://www.netlibrary.com/nireader.dll?bookid=12783&filename=Page_126.html>, (2008), 126-127.
"Indian Application Serial No. 10156/DELNP/2012, Amendment filed Dec. 26, 2012", 14 pgs.
"Indian Application Serial No. 10156/DELNP/2012, First Examination Report mailed Oct. 25, 2017", (W/ English Translation), 5 pgs.
"Indian Application Serial No. 2064/DELNP/2008, Examination Report mailed Aug. 21, 2012", 5 pgs.
"Indian Application Serial No. 5675/DELNP/2009 Response filed Mar. 18, 2015 to First Examination Report mailed Sep. 11, 2014", 6 pgs.
"Indian Application Serial No. 5675/DELNP/2009, First Examiner Report mailed Sep. 11, 2014", 2 pgs.
"Indian Application Serial No. 5675/DELNP/2009, Voluntary Amendment filed Feb. 18, 2011", 7 pgs.
"Indian Application Serial No. 6293/DELNP/2010, First Examiner Report mailed Dec. 22, 2016", 18 pgs.
"Indian Application Serial No. 6531-DELNP-2011, First Examiner Report mailed on Jun. 23, 2017", 7 pgs.
"Indian Application Serial No. 6531-DELNP-2011, Response filed Feb. 6, 2020 to Hearing of Jan. 28, 2020", 34 pgs.
"Indian Application Serial No. 6531-DELNP-2011, Response Filed Sep. 8, 2017 to First Examiner Report mailed on Jun. 23, 2017", (W/ English Claims), 19 pgs.
"International Application Serial No. PCT/US06/32371, International Preliminary Report on Patentability mailed Mar. 6, 2008", 6 pgs.
"International Application Serial No. PCT/US06/32371, International Search Report mailed Jul. 23, 2007", 3 pgs.
"International Application Serial No. PCT/US06/32371, Written Opinion mailed Jul. 23, 2007", 6 pgs.
"International Application Serial No. PCT/US2007/009840, International Preliminary Report On Patentability mailed Dec. 18, 2008", 9 pgs.
"International Application Serial No. PCT/US2007/009840, International Search Report mailed Aug. 5, 2008", 4 pgs.
"International Application Serial No. PCT/US2007/009840, Written Opinion mailed Aug. 5, 2008", 7 pgs.
"International Application Serial No. PCT/US2008/001631, International Preliminary Examination Report mailed Aug. 20, 2009", 12 pgs.
"International Application Serial No. PCT/US2008/001631, International Search Report mailed Jan. 21, 2009", 6 pgs.
"International Application Serial No. PCT/US2008/001631, Written Opinion mailed Jan. 21, 2009", 9 pgs.
"International Application Serial No. PCT/US2009/000771, International Preliminary Report on Patentability mailed Aug. 19, 2010", 8 pgs.
"International Application Serial No. PCT/US2009/000771, International Search Report mailed Aug. 28, 2009", 4 pgs.
"International Application Serial No. PCT/US2009/000771, Written Opinion mailed Aug. 28, 2009", 5 pgs.
"International Application Serial No. PCT/US2009/006584, International Preliminary Report on Patentability mailed Jun. 30, 2011", 8 pgs.
"International Application Serial No. PCT/US2009/006584, Search Report mailed Sep. 8, 2010", 5 pgs.
"International Application Serial No. PCT/US2009/006584, Written Opinion mailed Sep. 8, 2010", 6 pgs.
"International Application Serial No. PCT/US2010/000369, International Preliminary Report on Patentability dated Jun. 28, 2011", 13 pgs.
"International Application Serial No. PCT/US2010/000369, International Search Report mailed Sep. 21, 2010", 6 pgs.
"International Application Serial No. PCT/US2010/000369, Partial International Search Report mailed Jul. 5, 2010", 6 pgs.
"International Application Serial No. PCT/US2010/000369, Response filed Dec. 21, 2010 to Written Opinion mailed Sep. 21, 2010", 8 pgs.
"International Application Serial No. PCT/US2010/000369, Written Opinion mailed Feb. 11, 2010", 9 pgs.
"International Application Serial No. PCT/US2010/000369, Written Opinion mailed Sep. 21, 2010", 9 pgs.
"International Application Serial No. PCT/US2011/000757, International Preliminary Report on Patentability, mailed Nov. 15, 2012", 7 pgs.
"International Application Serial No. PCT/US2011/000757, International Search Report mailed Dec. 21, 2011", 5 pgs.
"International Application Serial No. PCT/US2011/000757, Written Opinion mailed Dec. 21, 2011", 6 pgs.
"International Application Serial No. PCT/US2014/051090, International Preliminary Report on Patentability mailed Feb. 25, 2016", 6 pgs.
"International Application Serial No. PCT/US2014/051090, International Search Report mailed Nov. 14, 2014", 4 pgs.
"International Application Serial No. PCT/US2014/051090, Written Opinion mailed Nov. 14, 2014", 4 pgs.
"International Application Serial No. PCT/US2016/026522, International Preliminary Report on Patentability mailed Oct. 19, 2017", 9 pgs.
"International Application Serial No. PCT/US2016/026522, International Search Report mailed Jun. 20, 2016", 5 pgs.
"International Application Serial No. PCT/US2016/026522, Written Opinion mailed Jun. 20, 2016", 7 pgs.
"International Application Serial No. PCT/US2018/025522, International Preliminary Report on Patentability mailed Oct. 10, 2019", 8 pgs.
"International Application Serial No. PCT/US2018/025522, International Search Report mailed Jun. 18, 2018", 3 pgs.
"International Application Serial No. PCT/US2018/025522, Written Opinion mailed Jun. 18, 2018", 6 pgs.
"International Application Serial No. PCT/US2019/056284, International Preliminary Report on Patentability mailed May 6, 2021", 9 pgs.
"International Application Serial No. PCT/US2019/057496, International Search Report mailed Feb. 27, 2020", 4 pgs.
"International Application Serial No. PCT/US2019/057496, Invitation to Pay Add'l Fees and Partial Search Report mailed Jan. 9, 2020", 2 pgs.
"International Application Serial No. PCT/US2019/057496, Written Opinion mailed Feb. 27, 2020", 7 pgs.

(56) References Cited

OTHER PUBLICATIONS

"International Application Serial No. PCT/US2020/022786, International Preliminary Report on Patentability mailed Sep. 23, 2021", 7 pgs.
"International Application Serial No. PCT/US2020/022786, International Search Report mailed Jun. 16, 2020", 3 pgs.
"International Application Serial No. PCT/US2020/022786, Written Opinion mailed Jun. 16, 2020", 5 pgs.
"International Application Serial No. PCT/US2020/046568, International Preliminary Report on Patentability mailed Mar. 3, 2022", 8 pgs.
"International Application Serial No. PCT/US2020/046568, International Search Report mailed Jan. 12, 2021", 4 pgs.
"International Application Serial No. PCT/US2020/046568, Invitation to Pay Additional Fees and Partial Search Report mailed Oct. 27, 2020", 2 pgs.
"International Application Serial No. PCT/US2020/046568, Written Opinion mailed Jan. 12, 2021", 6 pgs.
"International Application Serial No. PCT/US2021/053648, International Search Report mailed Mar. 9, 2022", 5 pgs.
"International Application Serial No. PCT/US2021/053648, Invitation to Pay Additional Fees mailed Dec. 9, 2021", 3 pgs.
"International Application Serial No. PCT/US2021/053648, Written Opinion mailed Mar. 9, 2022", 5 pgs.
"Isolation/Modification/Labeling Product Sheet", Interchim Inc, (Jan. 15, 2000), 1-23.
"Israel Application Serial No. 207246, Office Action mailed May 27, 2014", 2 pgs.
"Israel Application Serial No. 207246, Office Action mailed Feb. 10, 2013", (English Translation), 2 pgs.
"Israel Application Serial No. 207246, Response filed Jun. 10, 2013 to Office Action mailed Feb. 10, 2013", (w/ English Translation of Claims), 7 pgs.
"Israeli Application Serial No. 200240, Examiner Report mailed Aug. 5, 2013", (English Translation), 3 pgs.
"Israeli Application Serial No. 200240, Examiner Report mailed Aug. 28, 2012", (English Translation), 4 pgs.
"Israeli Application Serial No. 200240, Response filed Nov. 25, 2013 to Examiner Report mailed Aug. 5, 2013", w/ English translation, 8 pgs.
"Israeli Application Serial No. 200240, Response filed Dec. 17, 2012", 5 pgs.
"Israeli Application Serial No. 200240, Response filed Dec. 17, 2012 to Examiner Report mailed Aug. 28, 2012", (w/ English Translation of Claims), 4 pgs.
"Israeli Application Serial No. 207246, Office Action mailed Jun. 29, 2015", 3 pgs.
"Israeli Application Serial No. 214572, Office Action mailed Jan. 2, 2014", (English Translation), 2 pgs.
"Israeli Application Serial No. 214572, Office Action mailed Feb. 7, 2014", 2 pgs.
"Israeli Application Serial No. 214572, Office Action mailed Jul. 9, 2013", (English Translation), 3 pgs.
"Israeli Application Serial No. 214572, Office Action mailed Nov. 13, 2012", EN Office Action only, 2 pgs.
"Israeli Application Serial No. 214572, Response filed Apr. 28, 2014 to Office Action mailed Jan. 2, 2014", English claims, 10 pgs.
"Israeli Application Serial No. 214572, Response filed Nov. 3, 2013 to Office Action mailed Jul. 9, 2013", (English Translation of Claims), 5 pgs.
"Israeli Application Serial No. 214572, Response filed Dec. 30, 2014 to Office Action mailed Jul. 3, 2014", 4 pgs.
"Israeli Application Serial No. 214572, Response filed Dec. 30, 2014 to Office Action mailed Jul. 9, 2013", English claims only, 4 pgs.
"Japanese Application Serial No. 2008-528017, Office Action mailed May 22, 2012", (w/ English Transation), 7 pgs.
"Japanese Application Serial No. 2008-528017, Preliminary Amendment filed Aug. 12, 2009", w/English Claims, 26 pgs.
"Japanese Application Serial No. 2008-528017, Response filed Nov. 20, 2012 to Office Action mailed May 22, 2012", (w/ English Translation of Amended Claims), 19 pgs.
"Japanese Application Serial No. 2009-549102, Office Action mailed May 29, 2013", (w/ English Translation), 5 pgs.
"Japanese Application Serial No. 2009-549102, Office Action mailed Oct. 16, 2012", (w/ English Translation), 10 pgs.
"Japanese Application Serial No. 2009-549102, Response filed Mar. 22, 2013 to Office Action mailed Oct. 16, 2012", (w/ English Translation of Amended Claims), 7 pgs.
"Japanese Application Serial No. 2009-549102, Response filed Aug. 20, 2013 to Office Action mailed May 29, 2013", (w/ English Translation of Amended Claims), 5 pgs.
"Japanese Application Serial No. 2009-549102, Voluntary Amendment filed Feb. 7, 2011", (w/ English Translation of Amended Claims), 24 pgs.
"Japanese Application Serial No. 2010-545884, Amendment filed Jan. 23, 2012", (English Translation), 7 pgs.
"Japanese Application Serial No. 2010-545884, Examiners Decision of Final Refusal mailed Aug. 20, 2014", 6 pgs.
"Japanese Application Serial No. 2010-545884, Office Action mailed Oct. 9, 2013", (w/ English Translation), 5 pgs.
"Japanese Application Serial No. 2010-545884, Response filed Apr. 8, 2014 to Office Action mailed Oct. 9, 2013", w/English claims, 49 pgs.
"Japanese Application Serial No. 2010-545884, Voluntary Amendment filed Oct. 7, 2010", (w/ English Translation), 65 pgs.
"Japanese Application Serial No. 2011-549168, Amendment Filed Dec. 27, 2012", (English Translation of Claims), 6 pgs.
"Japanese Application Serial No. 2011-549168, Office Action mailed Apr. 17, 2015", w/English translation, 5 pgs.
"Japanese Application Serial No. 2011-549168, Office Action mailed Jun. 2, 2014", w/English translation, 13 pgs.
"Japanese Application Serial No. 2011-549168, Response filed Dec. 1, 2014 to Office Action mailed Jun. 2, 2014", W/ English Translation, 19 pgs.
"Japanese Application Serial No. 2011-549168, Response filed Dec. 1, 2014 to Office Action mailed Jun. 2, 2014", w/ English Translation of Amended Claims), 19 pgs.
"Japanese Application Serial No. 2013-507951, Office Action mailed Mar. 6, 2015", 4 pgs.
"Japanese Application Serial No. 2013-507951, Voluntary Amendment filed Mar. 19, 2014", 13 pgs.
"Japanese Application Serial No. 2013-59721, Office Action mailed May 30, 2014", w/English translation, 10 pgs.
"Japanese Application Serial No. 2014-79326, Office Action mailed Mar. 31, 2015", 2 pgs.
"Japanese Patent Application Serial No. 2008-528017, Office Action mailed May 22, 2012", (English Translation), 4 pgs.
"Korean Application Serial No. 10-2009-7018499, Office Action mailed Sep. 17, 2014", 8 pgs.
"Korean Application Serial No. 10-2011-7021190, Office Action mailed Aug. 18, 2016", 11pgs.
"Korean Application Serial No. 10-2010-7019944, Amendment filed Jan. 10, 2014", w/English claims, 31 pgs.
"Mexican Application Serial No. MX/a/2010/008697 , Response filed Mar. 28, 2012 to Office Action mailed Nov. 28, 2011", (w/ English Translation of Claims), 22 pgs.
"Mexican Application Serial No. MX/a/2010/008697, Office Action mailed Nov. 28, 2011", (w/ English Translation), 7 pgs.
"Mexican Application Serial No. MX/a/2010/008697, Response filed Jul. 10, 2012 to Office Action mailed May 4, 2012", (w/ English Translation of Claims), 6 pgs.
"Mexican Application Serial No. MX/a/2010/8697, Office Action mailed May 10, 2012", (English Translation), 3 pgs.
"Mexican Application Serial No. MX/a/2011/008500, Office Action mailed Jun. 14, 2013", (English Translation), 1 pg.
"Mexican Application Serial No. MX/a/2011/008500, Response filed Oct. 24, 2013 to Office Action mailed Jun. 14, 2013", (w/ English Translation of Claims), 17 pgs.
"Modulation of cytokine production and enhancement of cell viability byTLR7 and TLR9 ligands during anthrax infection of macrophages", FEMS Immunol. Med. Microbiol., 2006, vol. 47, No. 3, 369-379.

(56) References Cited

OTHER PUBLICATIONS

"PubChem CID 100446926", [Online] Retrieved from the Internet: <URL: https://pubchem.ncbi.nlm.nih.gov/compound/100446926>, [Accessed Dec. 8, 2020], (Dec. 11, 2015), 7 pgs.
"PubChem-CID-4371238", (Sep. 14, 2005), 11 pages.
"Singapore Application Serial No. 201005638-0, Response filed Aug. 22, 2012 to Office Action mailed Jun. 27, 2012", 2 pgs.
"Singapore Application Serial No. 201005638-0, Examination Report mailed Dec. 6, 2012", (English Translation), 6 pgs.
"Singapore Application Serial No. 201005638-0, Office Action mailed Jun. 27, 2012", 7 pgs.
"Singapore Application Serial No. 201005638-0, Office Action mailed Nov. 9, 2011", 16 pgs.
"Singapore Application Serial No. 201005638-0, Search Report mailed Oct. 27, 2011", 7 pgs.
"Singapore Application Serial No. 201005638-0, Written Opinion mailed Oct. 27, 2011", 8 pgs.
"Singapore Application Serial No. 201005638-0, Office Action Response filed Mar. 29, 2012 to Office Action mailed Nov. 9, 2011", (English Translation), 91 pgs.
"Substance Record for SID 384153951", PUBCHEM, <https://pubchem.ncbi.nlm.nih.gov/6Ubstance/384153951>, (May 15, 2019), 5 pgs.
"Substance Record for SID 458963136", PUBCHEM, <https://pubchem.ncbi.nlm.nih.gov/substance/458963136>, (Dec. 15, 2021), 6 pgs.
"Synthesis and Immunological Characterization of Tull-Like Receptor 7 Agonistic Conjugates", Bioconjug. Chem., 2009, vol. 20, No. 6, 1194-1200.
"Turkey Application Serial No. 120041819, Office Action mailed Apr. 29, 2016", w/ English translation, 6 pgs.
Admyre, et al., Europ. J of Immunology, v.36, (2006), 1772-1781.
Anders, H.-J., et al., "Molecular mechanisms of autoimmunity triggered by microbial infection", Arthritis Research & Therapy, 7(5), (2005), 215-224.
Ang, W. H, et al., "Organometallic ruthenium inhibitors of glutathione-S-transferase P1-1 as anticancer drugs.", ChemMedChem, 2(12), (Dec., 2007), 1799-806.
Baenziger, S., et al., "Triggering TLR7 in mice induces immune activation and lymphoid system disruption, resembling HIV-mediated pathology", Blood, 113(2), (Jan. 8, 2009), 377-388.
Barrett, et al., "Systematic transcriptome analysis reveals tumor-specific isoforms for ovarian cancer diagnosis and therapy", PNAS, (May 26, 2015), E3050-E3057.
Bhunia, Debabrata, et al., "Design, Synthesis, and Evaluation of Novel 1,2,3-Triazole-Tethered Glycolipids as Vaccine Adjuvants", Arch. Pharm. Chem. Life Sci. vol. 348, (2015), 15 pages.
Brown, Gordon, "Dectin-1: a signalling non-TLR pattern-recognition receptor", Nature Reviews Immunology, (2006), 33-43.
Bryan, G. T., et al., "Interferon (IFN) and IFN Inducers Protect Mouse Bladder Urothelium Against Carcinogenicity by FANFT", Journal of Cancer Research and Clinical Oncology, 116(Suppl. Part 1), (Abstract A3.106.36), (15th International Cancer Congress, Hamburg, Aug. 16-22, 1990), (1990), p. 308.
Butler, Roslyn S, et al., "Highly fluorescent donor acceptor purines", J. Mater. Chem, 17(19), (2007), 1863-1865.
Carson, D. A., et al., "TLR Agonists", U.S. Appl. No. 60/710,337, filed Aug. 22, 2005, 52 pgs.
Chan, et al., "Structure-Activity Relationship Studies To Identify Affinity Probes in Bis-aryl Sulfonamides That Prolong Immune Stimuli", Journal of Medicinal Chemistry vol. 62, (Oct. 11, 2019), 9521-9540.
Chan, M., et al., "Identification of Substituted Pyrimido[5,4-b]indoles as Selective Toll-Like Receptor 4 Ligands", J. Med. Chem., 56, (2013), 4206-4223.
Chan, M., et al., "Synthesis and Characterization of PEGylated Toll Like Receptor 7 Ligands", Bioconjugate Chem., 22, (2011), 445-454.
Chan, Michael, et al., "Identification of Biologically Active Pyrimido[5,4-b]indoles That Prolong NF-kappa-B Activation without Intrinsic Activity", ACS Comb Sci. vol. 19(8), (2017), 26 pages.
Chan, Michael, et al., "Synthesis and Immunological Characterization of Toll-Lke Receptor 7 Agonistic Conjugates", Bioconjugate Chem., 20(6), (2009), 1194-1200.
Colombo, R., et al., "Combination of intravesical chemotherapy and hyperthermia for the treatment of superficial bladder cancer: preliminary clinical experience", Crit Rev Oncol Hematol., 47(2), (Aug. 2003), 127-39.
David, Charles J, et al., "Alternative pre-mRNA splicing regulation in cancer: pathways and programs unhinged", Genes and Development, vol. 24, [Online] Retrieved from the Internet: <URL: http://www.genesdev.org/cgi/doi/10.1101/gad.1973010>, (2010), 2343-2364.
Dolan, M. E, et al., "Metabolism of O6-benzylguanine, an inactivator of O6-alkylguanine-DNA alkyltransferase.", Cancer Res., 54(19), (Oct. 1, 1994), 5123-30.
Fox, et al., "A nanoliposome delivery system to synergistically trigger TLR4 and TLR7", Journal of Nanobiotechnology vol. 12, (Apr. 26, 2014), 1-9.
Goff, P.H., et al., "Synthetic Toll-Like Receptor 4 (TLR4) and TLR7 Ligands and Influenza Virus Vaccine Adjuvants Induce Rapid, Sustained, and Broadly Protective Responses", Journal of Virology, 89, (Mar. 2015), 3221-3235.
Greenwald, R B, et al., "Poly(Ethylene Glycol) Conjugated Drugs and Prodrugs: A Comprehensive review", Critical reviews in therapeutic drug carrier systems vol. 17, No. 2, (Jan. 1, 2000), 101-161.
Hayashi, T., et al., "Mast cell-dependent anorexia and hypothermia induced by mucosal activation of Toll-like receptor 7", Am J Physiol Regul Integr Comp Physiol., 295(1), (2008), R123-32.
Hayashi, T., et al., "Novel Synthetic Toll-Like Receptor 4/MD2 Ligands Attenuate Sterile Inflammation", J. Pharmacol.Exp. Ther., 350, (Aug. 2014), 330-340.
Hemler, Martin E, "Tetraspanin proteins promote multiple cancer stages", Nature Reviews Cancer, vol. 14, (Jan. 2014), 49-60.
Horner, et al., "Optimized conjugation ratios lead to allergen immunostimulatory oligodeoxynucleotide conjugates with retained Immunogenicity and minimal anaphylactogenicity", J Allergy Clin Immunol 110, (2002), 413-42 0.
Hwang, Jae Ryoung, et al., "Upregulation of CD9 in ovarian cancer is related to the induction of TNF-alpha gene expression and constitutive NF-kappa Beta activation", Carcinogenesis Advance Access, (Nov. 16, 2011), 7 pgs.
Jacobson, Kenneth A, et al., "Adenosine analogs with covalently attached lipids have enhanced potency at AI-adenosine receptors", FEBS Letters, 225(1-2), (1987), 97-102.
Jin, G., et al., "Synthesis and immunostimulatory activity of 8-substituted amino 9-benzyladenines as potent Toll-like receptor 7 agonists.", Bioorg Med Chem Lett., 16(17), (Sep. 1, 2006), 4559-4563.
Johnson, John W, et al., "Binding of Liposomes to Human Bladder Tumor Epithelial Cell Lines: Implications for an Intravesical Drug Delivery System for the Treatment of Bladder Cancer", Selective Cancer Therapeutics vol. 5, No. 4, 1989, [Online]. Retrieved from the Internet: <http://online.liebertpub.com/doi/pdf/10.1089/sct.1989.5.147>, (1989), 9 pgs.
Julien, R. M., "Chapter 2: Pharmacodynamics: How Drugs Act", A Primer of Drug Action (Ninth Edition); Worth Publishers, (2001), 37-57.
Kaeppler, U., et al., "A new lead for nonpeptidic active-site-directed inhibitors of the severe acute respiratory syndrome coronavirus main protease discovered by a combination of screening and docking methods.", J Med Chem., 48(22), (Nov. 3, 2005), 6832-42.
Kobayashi, H., et al., "Prepriming: a novel approach to DNA-based vaccination and immunomodulation", Springer Seminars in Immunopathology, 22(Nos. 1-2), (2000), 85-96.
Krawitt, "Autoimmune hepatitis", N Engl J Med. Jan. 5, 2006;354(1):, (2006), 54-66.
Kulikov, V. I, et al., "Lipid derivatives of prostaglandins and nonsteroidal antiinflammatory drugs (a review)", Pharmaceutical Chemistry Journal, 31(4), (1997), 173-177.

(56) References Cited

OTHER PUBLICATIONS

Kurimoto, A., et al., "Prodrugs of 9-benzyl-8-hydroxy-2-(2-hydroxyethylthio)adenine: potent interferon inducing agents in monkeys", Chem. Pharm. Bull. 52(4), Retrieved from the Internet: <URL: https://www.jstage.jst.go.jp/article/cpb/52/4/52_4_466/_pdf/-char/ja>, (2004), 466-469.
Kurimoto, A., et al., "Synthesis and evaluation of 2-substituted 8-hydroxyadenines as potent interferon inducers with improved oral bioavailabilities", Bioorg Med Chem., 12(5), (Mar. 1, 2004), 1091-1099.
Kurimoto, A., et al., "Synthesis and structure-activity relationships of 2-amino-8-hydroxyadenines as orally active interferon inducing agents", Bioorg Med Chem., 11(24), (Dec. 1, 2003), 5501-8.
Lam, Andy KY, et al., "FOXM1b, which is present at elevated levels in cancer cells, has a greater transforming potential than FOXM1c", Frontiers in Oncology, 3(11), (Jan. 2012), 5 pgs.
Lee, J., et al., "Molecular basis for the immunostimulatory activity of guanine nucleoside analogs: Activation of Toll-like receptor 7", Proc. Natl. Acad. Sci., 100(11), (2003), 6646-6651.
Leth-Larsen, Rikke, et al., "Functional Heterogeneity within the CD44 High Human Breast Cancer Stem Cell-Like Compartment Reveals a Gene Signature Predictive of Distant Metastasis", Molecular Medicine, vol. 18, (2012), 1109-21.
Lippard, Stephen J, "The Art of chemistry", Nature, 416, (2002), 587.
Liu, H., et al., "Tumour growth inhibition by an imidazoquinoline is associated with c-Myc down-regulation in urothelial cell carcinoma", BJU International, 101(7), (Apr. 2008), 894-901.
Maeda, D. Y, et al., "Bivalent inhibitors of glutathione S-transferase: the effect of spacer length on isozyme selectivity.", Bioorg Med Chem Lett., 16(14), (Jul. 15, 2006), 3780-3.
Mahajan, S. S, et al., "Optimization of bivalent glutathione S-transferase inhibitors by combinatorial linker design.", J Am Chem Soc., 128(26), (Jul. 5, 2006), 8615-25.
Mayer, R., et al., "A randomized controlled trial of intravesical bacillus calmette-guerin for treatment refractory interstitial cystitis", Journal of Urology, 173(4), (Apr. 2005), 1186-1191.
Metzler, David E, "Biosynthesis of triglycerides and phospholipids", Biochemistry: The Chemical Reactions of Living Cells, (1977), 708.
Miller, R L, et al., "Imiquimod applied topically: a novel immune response modifier and new class of drug", Int J Immunopharmacol., 21(1), (Jan. 1999), 1-14.
Moroishi, et al., "The Hippo Pathway Kinases LATS1/2 Suppress Cancer Immunity' Cell", vol. 167, No. 6, (Dec. 1, 2016), 1525-1539.
Mosmann, T. R., et al., "TH1 and TH2 cells: different patterns of lymphokine secretion lead to different functional properties", Annual Review Immunology, 7, (1989), 145-173.
Rafi, et al., BioImpact, v.5, (2015), 117-122.
Reeves, David, et al., "The Contribution of Social Networks to the Health and Self-Management of Patients with Long-Term Conditions: A Longitudinal Study", PLOS One, 9(6): e98340, (Jun. 2014), 12 pgs.
Roh YS, Seki E, "Toll-like receptors in alcoholic liver disease, non-alcoholic steatohepatitis and carcinogenesis", J Gastroenterol Hepatol Suppl 1, (2013), 38-42.
Rohn, S., et al., "Antioxidant activity of protein-bound quercetin", J Agric Food Chem., 52(15), (Jul. 28, 2004), 4725-9.
Schon, M., et al., "Tumor-Selective Induction of Apoptosis and the Small-Molecule Immune Response Modifier Imiquimod", J Natl Cancer Inst, 95(15), (2003), 1138-1149.
Shi, B, et al., "Discovery of glutathione S-transferase inhibitors using dynamic combinatorial chemistry.", J Am Chem Soc., 128(26), (Jul. 5, 2006), 8459-67.
Sidky, Y. A., et al., "Curative effectiveness of the interferon inducing imiquimod as a signal agent in mouse bladder tumors", Proceedings, Eighty-Fourth Meeting of the American Association for Cancer Research, vol. 34, (Abstract 2789) (May 19-22, 1993, Orlando, FL), (Mar. 1993), 467.
Sidky, Y. A, et al., "Effects of Treatment with an Oral Interferon Inducer, Imidazoquinolinamine (R-837), on the Growth of Mouse Bladder Carcinoma FCB", Journal of Interferon Research, 10(Supp 1), (Abstract 116-12) (Annual Meeting of the ISIR, San Francisco, CA, Nov. 14-18, 1990), (Nov. 1990), S123.
Sidky, Y. A., et al., "Effects of treatment with the oral interferon inducer, R-837, on the growth of mouse colon carcinoma, MC-26", Proceedings, 81st Annual Meeting of the American Association for Cancer Research, vol. 31, (Abstract 2574), (Mar. 1990), p. 433.
Sidky, Y. A, et al., "Inhibition of murine tumor growth by an interferon-inducing imidazoquinolinamine", Cancer Research, 52(13), (Jul. 1, 1992), 3528-33.
Sidky, Y. A., et al., "Inhibition of tumor-induced angiogenesis by the interferon inducer Imiquimod", Proceedings, Eighty-Third Annual Meeting of the American Association of Cancer Research, vol. 33, (Abstract 458) (May 20-23, 1992, San Diego, CA), (Mar. 1992), p. 77.
Simons, M. P., et al., "Identification of the Mycobacterial Subcomponents Involved in the Release of Tumor Necrosis Factor-Related Apoptosis-Inducing Ligand from Human Neutrophils", Infection and Immunity, 75(3), (2007), 1265-1271.
Smith, E. B, et al., "Effects of Imiquimod, a toll-like receptor-7 agonist, on cell proliferation and cytokine production in bladder cancer in vitro and in vivo", Journal of Urology, 173(4, Suppl. S), (Apr. 2005), 158.
Smith, Eric B., et al., "Antitumor Effects of Imidazoquinolines in Urothelial Cell Carcinoma of the Bladder", The Journal of Urology, 177(6), (Jun. 2007), 2347-2351.
Spohn, R., et al., "Synthetic lipopeptide adjuvants and Toll-like receptor 2-structure-activity relationships", Vaccine, 22(19), (Jun. 23, 2004), 2494-9.
Staros, E. B., et al., "New Approaches to Understanding Its Clinical Significance", Am. J. Clin. Pathol., 123(2), (2005), 305-312.
Takeda, K., et al., "Toll-like receptors", Annu Rev Immunol., 21, (2003), 335-76.
Takeda, K., et al., "Toll-like receptors in innate immunity", International Immunology, 17(1), (2005), 1-14.
Tyagi, P., et al., "Local drug delivery to bladder using technology innovations", Urol Clin North Am., 33(4), (Nov. 2006), 519-530.
Venables, Julian P, et al., "Cancer-associated regulation of alternative splicing", Nature Structural and Molecular Biology, 16(6):670-6, (May 2009), 8 pgs.
Veronese, F. M., et al., "The impact of PEGylation on biological therapies", BioDrugs, 22(5), (2008), 315-329.
Wille-Reece, U., et al., "HIV Gag protein conjugated to a Toll-like receptor 7/8 agonist improves the magnitude and quality of Th1 and CD8+ T cell responses in nonhuman primates", Proc. Natl. Acad. Sci. USA, 102(42), (Oct. 18, 2005), 15190-15194.
Wu, Christina C. N., et al., "Immunotherapeutic activity of a conjugate of a Toll-like receptor 7 ligand", Proc Natl Acad Sci USA., 104(10), (Mar. 6, 2007), 3990-3995.
Yang, Victor C., et al., "Bioconjugates for Effective Drug Targeting", Advanced Drug Delivery Reviews 55 (2003), (2002), 169-170.
Yoo, Euna, "Exploration of Toll-like Receptor 7 and 8 Agonists as Potential Vaccine Adjuvants", PhD Diss., University of Kansas, [Online] Retrieved from the Internet: <URL: https://kuscholarworks.ku.edu/handle/1808/23923?show=full>, (May 7, 2017), 281 pgs.
Zaks, K, et al., "Efficient Immunization and Cross-Priming by Vaccine Adjuvants Containing TLR3 or TLR9 Agoinst Complexed to Cationic Liposomes", Journal of Immunology, 176(12), (Jun. 15, 2006), 7335-7345.
Zaks, Karen, et al., "Efficient immunization and cross-priming by vaccine adjuvants containing TLR3 or TLR9 agonists complexed to cationic liposomes", J Immunol., 176(12), (Jun. 15, 2006), 7335-45.
"Australian Application Serial No. 2020236254, Response filed Apr. 23, 2026 to First Examination Report mailed Oct. 14, 2025", 19 pgs.
"Korean Application Serial No. 10-2021-7033212, Response filed Apr. 22, 2026 to Notice of Preliminary Rejection mailed Feb. 18, 2026", With English Machine Translation, 15 pgs.
"Australian Application Serial No. 2020236254, Subsequent Examination Report mailed May 5, 2026", 5 pgs.

(56) References Cited

OTHER PUBLICATIONS

"European Application Serial No. 23797227.8, Communication pursuant to Rule 1641 EPC mailed May 18, 2026", 3 pgs.
"U.S. Appl. No. 17438,934, Supplemental Amendment filed Apr. 14, 2026", 3 pgs.
"U.S. Appl. No. 17438,934, Notice of Allowance mailed May 5, 2026", 10 pgs.

* cited by examiner

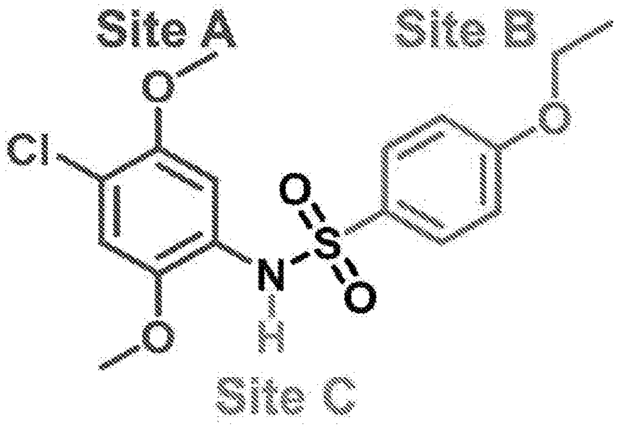
Figure 1. Structure of compound 1 and sites of modification on the scaffold. SAR studies on the bis-aryl sulfonamide compound 1 were approached by modifying one site at a time.

Figure 2. Differential activity profile for terminal alkane v/s terminal alkyne bearing derivatives of
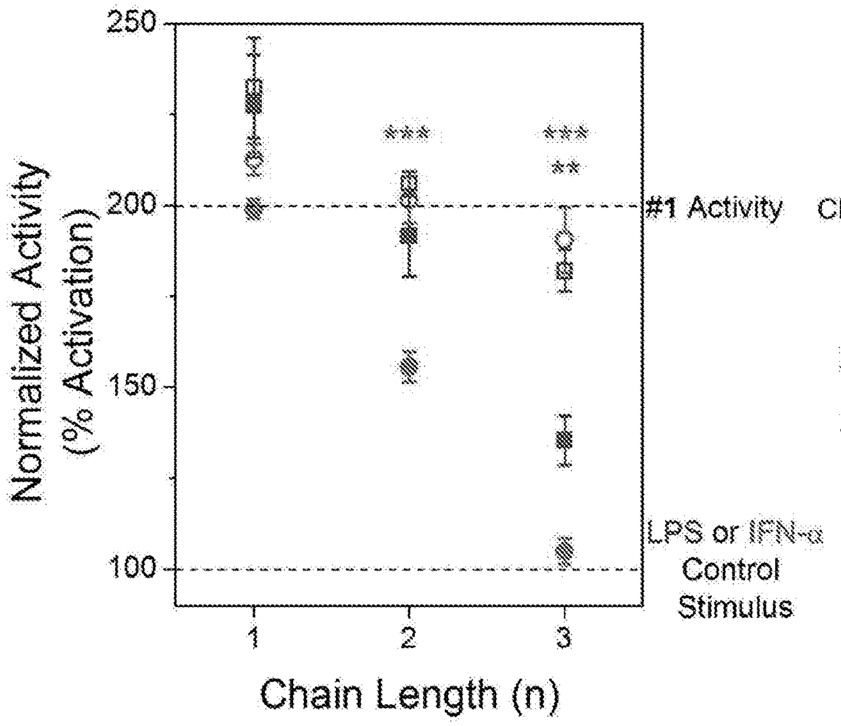
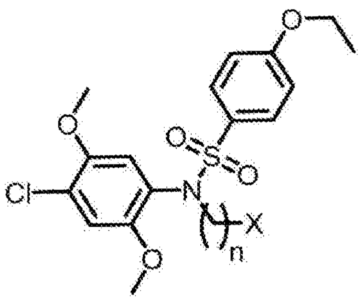
X = $-CH_2-CH_3$, alkanes
(closed symbols)
X = $-C \equiv CH$, alkynes
(open symbols)

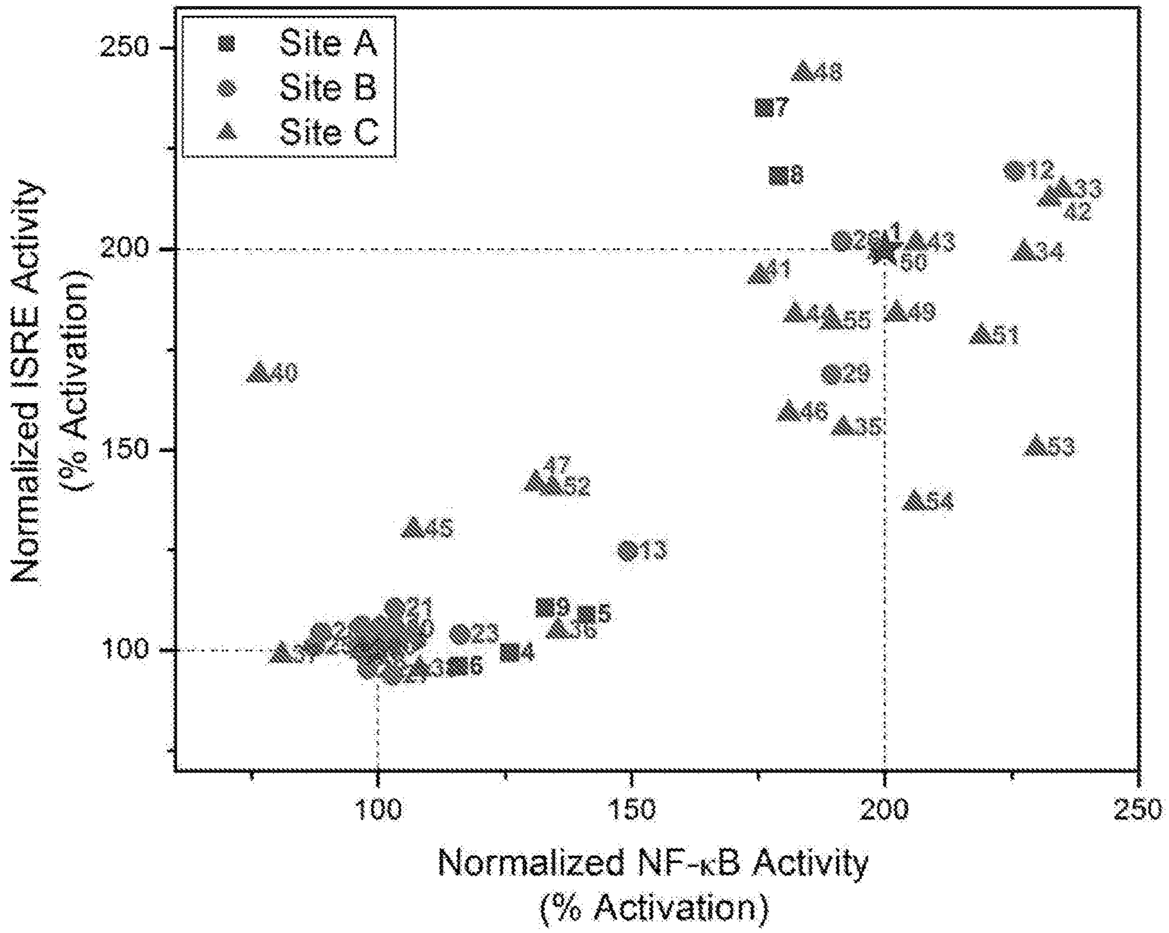

Figure 3. Bioactivity analysis for synthesized bis-aryl sulfonamide analogs. Scatter plot showing the ISRE activity on the Y-axis for cells treated with each compound and IFN-α and NF-κB activity on X-axis for cells treated with compound and LPS. Data are shown as a two-point normalization between the active hit compound 1 as 200% (purple star) and vehicle (0.1% LPS or IFN-α) as 100%. Site A, B, and C modified analogs are designated as blue, red, and green squares, circles and triangles, respectively. Pearson two-tailed correlation was significant (P<0.0001) for the two activities for all these compounds.

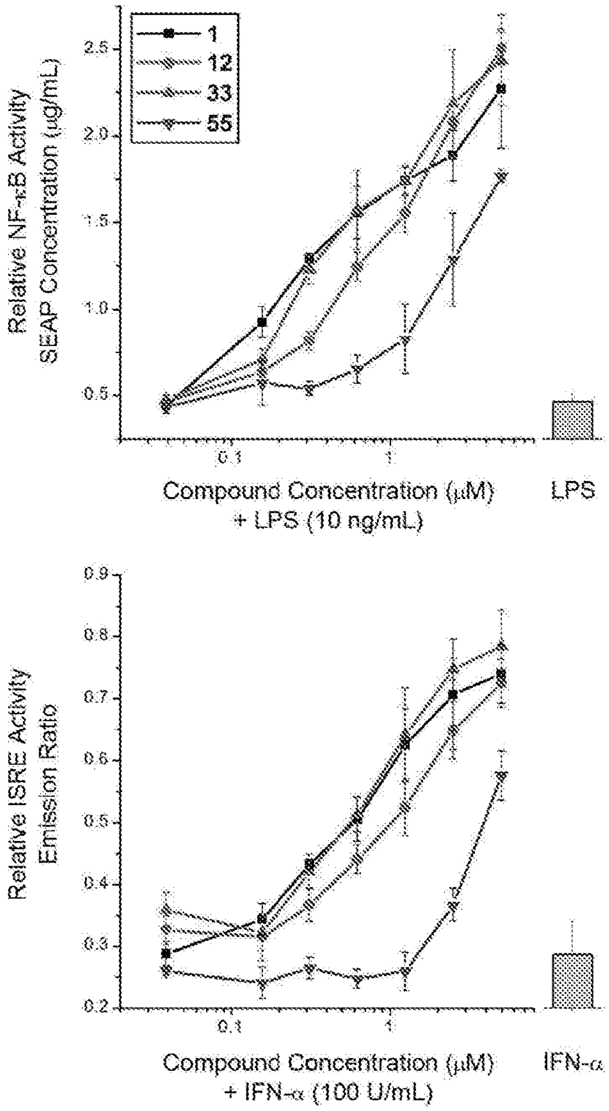

Figure 4. Dose response curves for selected active analogs. Compounds 1, 12, 33, and 55 were evaluated for enhancement of NF-κB and ISRE signaling at graded concentrations. Compound 33 was equipotent as compound 1 while chemically reactive handle (amino) bearing compound 55 retained activity even though slightly attenuated. The activity of stimulus alone is shown as grey bar. Data are presented as mean ± SEM. The NF-κB activity is measured as amount of SEAP induced, while ISRE activity is measured as emission ratio for the FRET based assay.

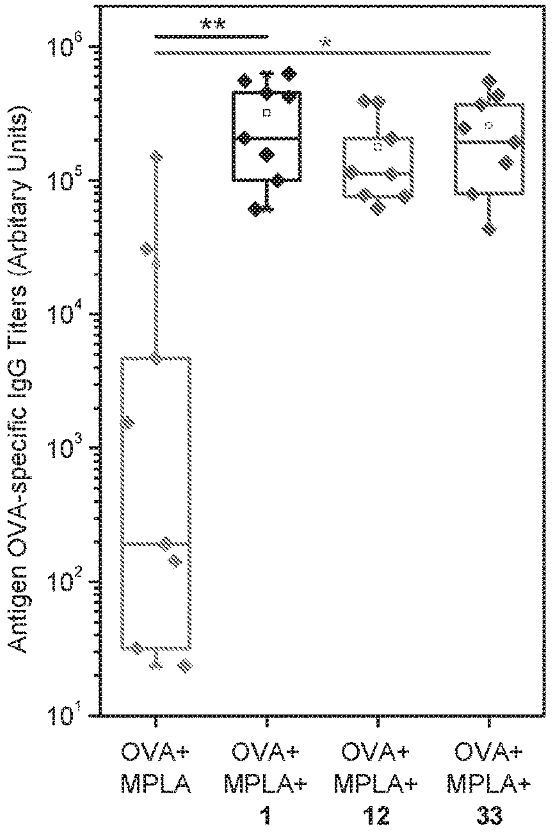

Figure 5. Co-adjuvanticity of potent bis-aryl sulfonamide compounds with MPLA. Mice (n=8 per group) were immunized on day 0 and day 21 with antigen (ovalbumin, 20 μg/animal), MPLA (10 μg/animal) and compound 1, 12 or 33 (100 nmol/animal). The immunized mice were bled on day 21 and OVA-specific IgG titers were measured using ELISA. Note, that the potent compounds 1 and 33 showed significant enhancement of antibody titers when co-adjuvanted with MPLA compared to MPLA alone. **$p<0.01$ and *$p<0.05$ compared to MPLA group using one-way ANOVA followed by Dunnett's post hoc testing.

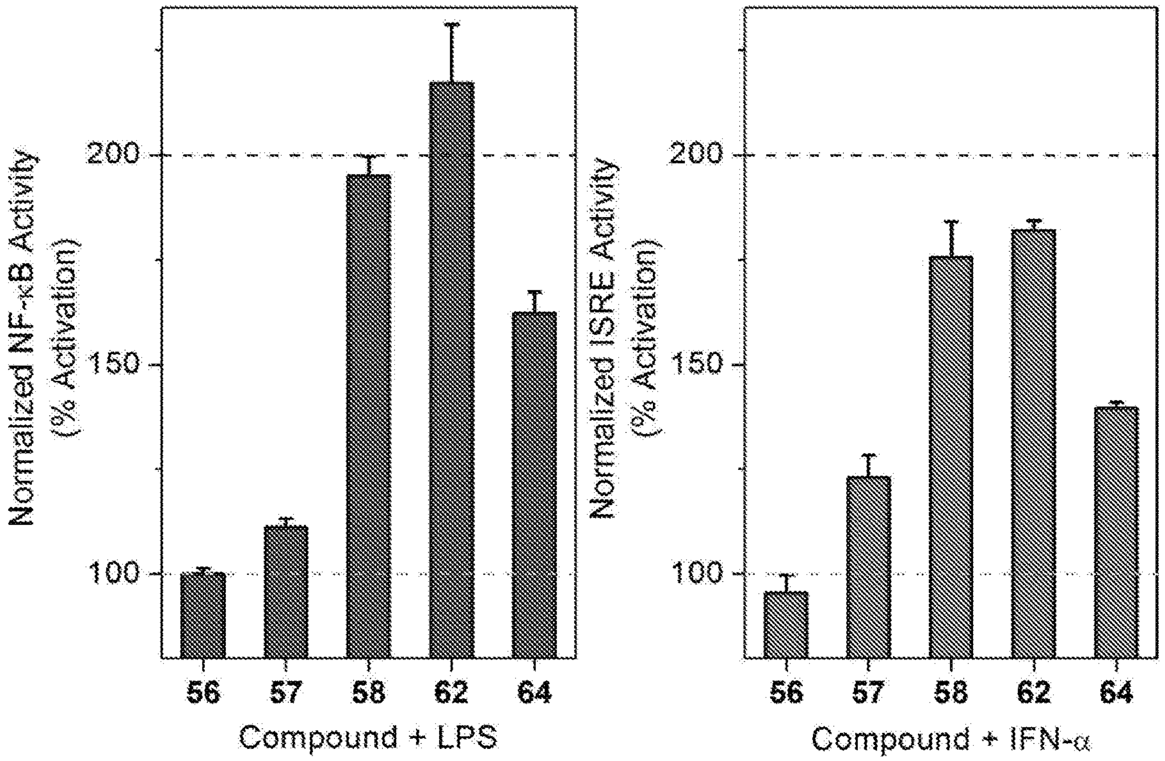

Figure 6. Bioactivities of different affinity probes for compound 1. NF-κB activity of affinity probes in presence of LPS is shown by blue bars (left) while ISRE activity in presence of IFN-α is shown by red bars (right). Reporter cells for NF-κB and ISRE activation were treated with LPS or IFN-α respectively with 5μM compounds 56, 57, 58, 62, and 64, in addition to compound 1 and respective vehicle (LPS of IFN-α) as controls. Data are presented as mean ± SEM after normalized to the activity of vehicle (100%, grey dotted lines) and compound 1 (200%, black dotted lines), respectively.

| Affinity Probe | X | Y |
|---|---|---|
| **Biotin** | Cl | Biotin |
| **Fluorescent** | Cl | Rhodamine |
| **Photoaffinity** | $N_3$ | Biotin |
| **Photoaffinity** | $N_3$ | Alkyne |

Supporting Information Figure S1
Activity data for bis-aryl sulfonamides in the NF-κB and ISRE HTS screens[a]

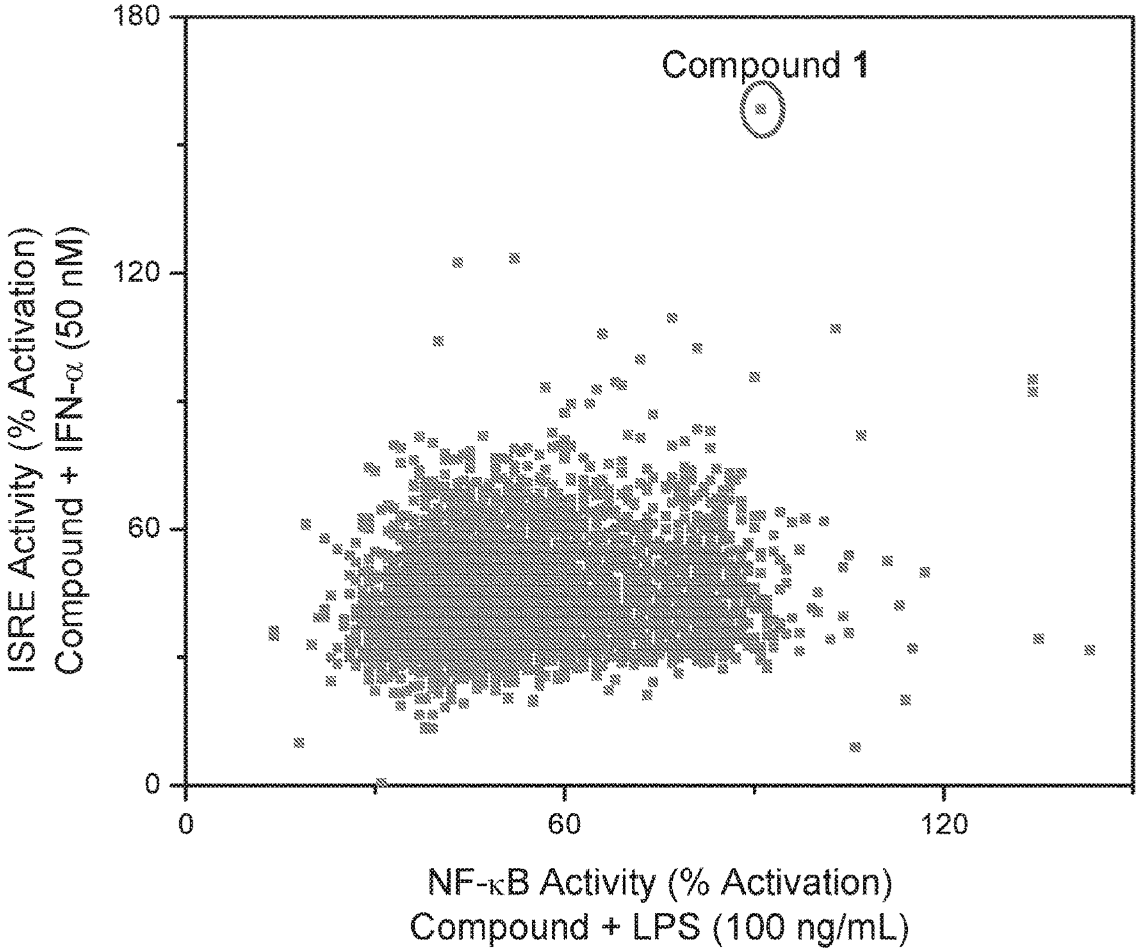

[a] Scatter plot showing activation data for all the bis-aryl sulfonamides screened in the two HTS. The NF-κB activity for compounds treated with LPS (100 ng/mL) is shown on X-axis, while the ISRE activity for compounds treated with IFN-α (50 nM) is shown on Y-axis. The most potent compound that exhibited immune prolongation activity in both NF-κB and ISRE pathways was compound 1, marked by red circle.

Figure 8

N-ARYL SULFONAMIDE DERIVATIVES AS VACCINE ADJUVANT

CROSS-REFERENCE TO RELATED APPLICATIONS

This application claims the benefit of the filing date of U.S. application No. 62/887,843, field on Aug. 16, 2019, the disclosure of which is incorporated by reference herein

STATEMENT OF GOVERNMENT RIGHTS

This application is a U.S. National Stage Filing under 35 U.S.C. 371 from International Application No. PCT/US2020/046568, filed on Aug. 15, 2020, and published as WO 2021/034729 A1 on February 25. 2021, which claims the benefit of the filing date of U.S. application No. 62/887,843, field on Aug. 16, 2019, the disclosure of each of which is incorporated by reference herein.

BACKGROUND

Vaccines consisting of antigen and adjuvant rely primarily on adjuvants for enhancement of immune stimuli (Shukla et al., 2018a). These adjuvants include ligands for pattern recognition receptors (PRRs) such as Toll-like receptors (TLR) 2, 4, 7, 8, and 9, nucleotide-binding oligomerization domain-like receptors (NLRB), RIG-I-like receptors (RLRs), and cytokines such as interferon-α (IFN-α), IFN-γ, and IL-12 (Reed et al., 2013; Shukla et al, 2012; Vasilakos et al., 2013; Maisonneuve et al., 2014; Basto & Leitao, 2014; Wheeler et al., 2016; Ho et al., 2002; Pavot et al., 2016; Probst et al., 1964-1971; Tovey & Lallernand, 2010; Chan et al., 2013). Some of these adjuvants have been approved for human use by the U.S. Food and Drug Administration (FDA) including the TLR-4 agonist rnonophosphoryl lipid A (MPLA) (Alving et al., 2012), the TLR-9 agonist CpG 1018 (Hyer et al., 2018), and other adjuvants with different mechanisms of action such as alum and squalene based adjuvants, Despite the availability of approved adjuvants, the need for coadjuvants is evident since single adjuvant vaccines often do not generate long lasting protective immunity (Fraser et al., 2007). Alum has been used as an effective single adjuvant for decades primarily due to its safety record and induction of increased humoral immunity (Brady et al., 2009; Mori et al., 2012); however it induces only weak cellular immunity and predominantly a T helper (Th) type 2 associate response, whereas in some cases a T helper type 1 response would be more effective for protection. In addition, it is not always sufficient for vaccinating immunocompromised and elderly populations (Brady et al., 2009; Campbell, 2017). A coadjuvant is a substance that may or may not be an adjuvant by itself but can work with a known adjuvant to offer synergistic effects such as enhanced antibody response. For example, IL-2 has been shown to be a coadjuvant with alum-adsorbed hepatitis B vaccine (Gurser & Gregoriadis, 1995). Similarly, combination adjuvants can be obtained using a PRR or NLR ligand, an immunogenic protein, a delivery system, or another adjuvant with a complementary mechanism of action (Fraser et al., 2007). One such combination AS04 (adjuvant system 04), consisting of MPLA and alum, has been FDA approved in a hepatitis B vaccine Fendrix and human papillomavirus vaccine Cervarix (Reran, 2008; Fabrizi et al., 2019; Lin et al., 2018; Schwarz et al., 2015). Alternative combinations involving approved adjuvants, TLR agonists, NOD agonists, and delivery systems are being explored (Mutwiri et al., 2011; Ebensen et al., 2019; Ignacio et al., 2018; Levast et al., 2014).

SUMMARY

Agents that safely induce, enhance, or sustain multiple innate immune signaling pathways could be developed as potent vaccine adjuvants or coadjuvants. Using high-throughput screens (HTS) with cell-based nuclear factor κB (NF-κB) and interferon stimulating response element (ISRE) reporter assays, a bis-aryl sulfonamide bearing compound 1 was identified that demonstrated sustained NF-κB and ISRE activation after a primary stimulus with lipopolysaccharide or interferon-α, respectively.

Compounds described in this disclosure are useful for enhancing and/or prolonging an immune response, such as, in a vaccine as a co-adjuvant. The compounds combined with other adjuvants to broaden, enhance, and/or prolong the immune stimulation should make the vaccine more effective as there are no approved co-adjuvants used at the present time, and only a few non-approved co-adjuvants have been reported. The sulfonamide derivatives disclosed herein appear to be quite potent. One example of the N-aryl sulfonamides is called compound 81, which may enhance NFkB activation and cytokine production, and that compound or other N-aryl sulfonamides such as those disclosed herein, when combined with one or more TLR ligands, one or more MAP kinase inhibitors, other anti-cancer agents, and/or immune stimulators such as another adjuvant, e.g., LPS, in any combination. In one embodiment, the MAK kinase inhibitor comprises SB203580, BIRB796, Trolox, ginsenoside Rg1, MW181, icariin, apigenin, astaxanthin, 4-o-methyhonokiool, L-theanine, 3,4-dihydroxyphenylethanol, linalool, pinocembrin, pueranin, tanshinone IIA, PD169316, triptolide, esculentiside A, NOSH-aspirin, floridoside, alpha-iso-cubebene, glaucocalyxin B, obovstol, MW01-2-069A-SRM, or SB239063.

Specifically, a systematic structure-activity relationship (SAR) study on the two phenyl rings and amide nitrogen of the sulfonamide group of compound 1 (identified in the screen) focused toward identification of affinity probes. The murine vaccination studies showed that compounds 1 and 33 when used as coadjuvants with monophosphoryl lipid A (MPLA) showed significant enhancement in antigen ovalbumin-specific immunoglobulin responses compared to MPLA alone. SAR studies pointed to the sites on the scaffold that can tolerate the introduction of aryl azide, biotin, and fluorescent rhodamine substituents to obtain several affinity and photoaffinity probes which will be utilized in concert for future target identification and mechanism of action studies.

In one embodiment, a sulfonamide derivative comprises a compound of formula (II):

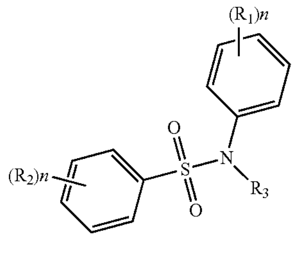

The present disclosure provides bis-aryl sulfonamide compounds, derivatives thereof, analogues thereof, and pharmaceutically acceptable salts thereof, and methods of making and using such compounds, in some embodiments of the bi-aryl sulfonamides, the compound has Formula II, wherein n is an integer from 1 to 4;

wherein $R_1$ and $R_2$ are independently hydrogen, halogen, nitro, azide, hydroxyl, amino, alkylamino, —$CF_3$, carboxylic acid, —OR', or —COXR', and wherein $R_3$ is $C_1$-$C_{14}$ saturated or unsaturated alkyl, saturated or unsaturated cycloalkyl, saturated or unsaturated heterocycloalkyl, aryl car heteroaryl, substituted or unsubstituted aralkyl, or —$(CH_2)_m$—Y, where m is an integer from 1 to 10 and Y is —NHR', OR', COXR', wherein X is O or NH, wherein R' is a $C_1$-$C_6$ alkyl, cycloalkyl, heterocycloalkyl, aryl, heteroaryl, isothiocyanate, —COR", wherein R" is, for example, biotin, fluorescent molecules such as Rhodamine B or Fluorescein, or N-hydroxy succinimide; or wherein $R_3$ is H, $C_1$-$C_{14}$ saturated or unsaturated alkyl, saturated or unsaturated cycloalkyl, saturated or unsaturated heterocycloalkyl, aryl or heteroaryl, substituted or unsubstituted aralkyl, or —$(CH_2)_m$—Y, or comprises an antigen, where m is an integer from 1 to 10 and Y is —NHR', OR', COXR', wherein X is O or NH, wherein R' is a $C_1$-$C_6$ alkyl, cycloalkyl, heterocycloalkyl, aryl, heteroaryl, isothiocyanate, —COR", wherein R" is, for example, biotin, fluorescent molecules, such as Rhodamine B or Fluorescein, or N-hydroxy succinimide, and L1 is a divalent linker comprising one or more alkylene, arylene, heteroarylene, alkylamine, alkylamide, alkylether, alkylester, alkylthio, acyl, diacyl, diester, diamine, diamide, cycloalkyl, and G is a protein-reactive electrophilic functional group, an immune potentiator, or an enzyme-cleavable group; or L1 is a divalent linker comprising one or more alkylene, arylene, heteroarylene, alkylamine, alkylamide, alkylether, alkylester, alkylthio, acyl, diacyl, diester, diamine, diamide, cycloalkyl, oxy, carbonyl, amino, thio, sulfinyl, or sulfonyl, each which is independently substituted or unsubstituted, or a bond, and G is a protein-interactive functional group, an immune potentiator, or an enzyme-cleavable group; or G is a click chemistry substrate or other terminal reactive group useful for linking chemical moieties, for example, an ester, carboxylic acid, amide, alcohol, thiol, amine, azide, halide, isocyanate, or isothiocyanate and optionally L1 is absent;

or a salt, ester, or prodrug thereof.

In one embodiment, formula (II) does not include 4-chloro-2,5-dimethoxy and 4-ethoxy substituted phenyl group connected by a sulfonamide group (compound 1 herein).

The disclosure provides a method of enhancing or prolonging an immune response, comprising: administering to a mammal in need thereof a vaccine, an effective amount of at least two adjuvants, at least one adjuvant and one or more TLR ligands, or at least one adjuvant and at least one MAP kinase inhibitor, other anti-cancer agents, or other immune stimulators such as another adjuvant, wherein at least one adjuvant comprises a sulfonamide derivative, e.g., a N-aryl sulfonamide. In one embodiment, the mammal is a human. In one embodiment, one of the adjuvants comprises LPS or MPLA. In one embodiment, at least one of the TLR ligands comprises a compound of formula (I). In one embodiment, at least two adjuvants are administered. In one embodiment, at least one adjuvant and one or more TLR ligands are administered. In one embodiment, at least one adjuvant and at least one MAP kinase inhibitor, other anti-cancer agent, other immune stimulator, e.g., that is not an adjuvant, or another adjuvant are administered.

Further provided is a method of enhancing or prolonging an immune response, comprising: administering to a mammal in need thereof an effective amount of at least one adjuvant and at least one MAP kinase inhibitor, wherein at least one adjuvant comprises a sulfonamide derivative, e.g., a N-aryl sulfonamide. Also provided is a method of enhancing or prolonging an immune response, comprising: administering to a mammal in need thereof an effective amount of at least two adjuvants, wherein at least one adjuvant comprises a sulfonamide derivative. In addition, a method of enhancing or prolonging an immune response, comprising: administering to a mammal in need thereof an effective amount of at least one adjuvant and one or more TLR ligands, wherein at least one adjuvant comprises a sulfonamide derivative. In one embodiment, the vaccine and the sulfonamide derivative and at least one other agent are administered concurrently. In one embodiment, the vaccine and the sulfonamide derivative and at least one other agent are subcutaneously, dermally or orally administered The disclosure also provides a method of enhancing or prolonging an immune response, comprising: administering to a mammal in need thereof an effective amount of a composition comprising at least one adjuvant and at least one MAP kinase inhibitor, wherein at least one adjuvant comprises a sulfonamide derivative. Further provided is a method of enhancing or prolonging an immune response, comprising: administering to a mammal in need thereof an effective amount of a composition comprising at least two adjuvants, wherein at least one adjuvant comprises a sulfonamide derivative. Also provided is a method of enhancing or prolonging an immune response, comprising: administering to a mammal in need thereof an effective amount of a composition comprising at least one adjuvant and one or more TLR ligands, wherein at least one adjuvant comprises a sulfonamide derivative.

In one embodiment, of formula (II), n is an integer from 1 to 3.

In one embodiment, $R_1$ is hydrogen, halogen, nitro, azido, hydroxyl, —$CF_3$, carboxylic acid, —OR', or —COXR'.

In one embodiment, $R_2$ is hydrogen, halogen, nitro, azido, hydroxyl, —$CF_3$, carboxylic acid, —OR', —COXR'.

In one embodiment, $R_1$ is nitro, azido, hydroxyl, —$CF_3$, carboxylic acid, —OR', or —COXR'.

In one embodiment, $R_2$ is nitro, azido, hydroxyl, —$CF_3$, carboxylic acid, —OR', or —COXR'.

In one embodiment, $R_3$ is $C_2$-$C_{10}$ saturated or unsaturated alkyl, saturated or unsaturated cycloalkyl, saturated or unsaturated heterocycloalkyl, aryl, heteroaryl, substituted or unsubstituted aralkyl, —$(CH_2)_m$—Y, where m is an integer from 1 to 10 and Y is —NHR', OR', COXR', where X is O or NH, R' is a $C_1$-$C_6$ alkyl, cycloalkyl, heterocycloalkyl, aryl, heteroaryl, isothiocyanate, —COR", R" is a marker, e.g., biotin, a fluorescent molecule or N-hydroxy succinimide.

In one embodiment, $R_3$ is H, -L1-G, $C_1$-$C_{14}$ saturated or unsaturated alkyl, saturated or unsaturated cycloalkyl, saturated or unsaturated heterocycloalkyl, aryl or heteroaryl, substituted or unsubstituted aralkyl, or —$(CH_2)_m$—Y, where m is an integer from 1 to 10 and Y is —NHR', OR', COXR', wherein X is O or NH, wherein R' is a $C_1$-$C_6$ alkyl, cycloalkyl, heterocycloalkyl, aryl, heteroaryl, isothiocyanate, —COR", wherein R" is, for example, biotin, fluorescent molecules such as Rhodamine B or Fluorescein, or N-hydroxy succinimide, L1 is a divalent linker comprising one or more alkylene, arylene, heteroarylene, alkylamine, alkylamide, alkylether, alkylester, alkylthio, acyl, diacyl, diester, diamine, diamide, cycloalkyl, and G is a protein-reactive electrophilic functional group, an immune potentiator, or an enzyme-cleavable group.

In one embodiment, R3 comprises an antigen, e.g., a self-adjuvanting molecule.

In one embodiment, a compound of formula (II) is covalently linked to a compound of formula (I).

In one embodiment, a composition comprising at least one adjuvant and at least one MAP kinase inhibitor, wherein at least one adjuvant comprises a bis-aryl sulfonamide derivative, is provided. In one embodiment, a composition comprising at least two adjuvants, wherein at least one adjuvant comprises a bis-aryl sulfonamide derivative, is provided. In one embodiment, the two adjuvants are covalently linked. In one embodiment, a composition comprising at least one adjuvant and one or more TLR ligands is provided, wherein at least one adjuvant comprises a bis-aryl sulfonamide derivative. In one embodiment, a composition is provided wherein a bis-aryl sulfonamide derivative is covalently linked to an antigen.

BRIEF DESCRIPTION OF FIGURES

FIG. 1. Structure of compound 1 and sites of modification on the scaffold, SAR studies on the bis-aryl sulfonamide compound 1 were approached by modifying one site at a time.

FIG. 2. Differential activity profile for terminal alkane vs terminal alkyne bearing derivatives of compound 1. Chain length (n) dependent reduction in activity was observed for site C modified terminal alkane (closed symbols) and terminal alkyne (open symbols) bearing compounds. The % activation values in NF-κB and ISRE induction assays were two point normalized between compound 1 as 200% (gray dotted line) and LPS (10 ng/mL) for NF-κB or IFN-α (100 U/mL) for ISRE as 100% (gray dotted line). The relative reduction in the activity for terminal alkane compounds was significantly greater than the terminal alkynes for the same chain length suggesting involvement of π-π interactions. NF-κB activity is shown in blue squares, and ISRE activity is shown in red circles. Structures of the compounds are shown to the right with variable chain length "n" varying from 1 to 3. Data are presented as the mean±SEM: $^{}p<0.01$ and $^{*}p<0.001$ for alkyne bearing compounds compared to alkane bearing compounds for the same chain length using two-way ANOVA followed by Bonferroni post hoc analysis.

FIG. 3. Bioactivity analysis for synthesized bis-aryl sulfonamide analogs. Scatter plot showing the ISRE activity on the Y-axis for cells treated with each compound and IFN-α and NF-κB activity on X-axis for cells treated with compound and LPS. Data are shown as a two-point normalization between the active hit compound 1 as 200% (purple star) and vehicle (0.1% LPS or IFN-α) as 100%. Sites A, B, and C modified analogs are designated as blue squares, red circles, and green triangles, respectively. Pearson two-tailed correlation was significant (P<0.0001) for the two activities for all these compounds.

FIG. 4. Dose-response curves for selected active analogs. Compounds 1, 12, 33, and 55 were evaluated for enhancement of NF-κB and ISRE signaling at graded concentrations. Compound 33 was equipotent as compound 1, while chemically reactive handle (amino) bearing compound 55 retained activity even though slightly attenuated. The activity of stimulus alone is shown as gray bar. Data are presented as the mean±SEM. The NF-κB activity is measured as amount of SEAP induced, while ISRE activity is measured as emission ratio for the FRET based assay.

FIG. 5. Coadjuvanticity of potent bis-aryl sulfonamide compounds with MPLA. Mice (n=8 per group) were immunized on day 0 and day 21 with antigen (ovalbumin, 20 μg/animal), MPLA (10 μg/animal), and compound 1, 12, or 33 (100 nmol/animal). The immunized mice were bled on day 21 and OVA-specific IgG titers were measured using ELISA. Note that the potent compounds 1 and 33 showed significant enhancement of antibody titers when coadjuvanted with MPLA compared to MPLA alone. $^{**}p<0.01$ and $^{*}p<0.05$ compared to MPLA group using one-way ANOVA followed by Dunnett's post hoc testing.

FIG. 6. Bioactivities of different affinity probes for compound 1. NF-κB activity of affinity probes in the presence of LPS is shown by blue bars (left), while ISRE activity in the presence of IFN-α is shown by red bars (right). Reporter cells for NF-κB and ISRE activation were treated with LPS and IFN-α, respectively, with 5 μM compounds 56, 57, 58, 62, and 64, in addition to compound 1 and respective vehicle (LPS of IFN-α) as controls. Data are presented as the mean±SEM after normalization to the activity of vehicle (100%, gray dotted lines) and compound 1 (200%, black dotted lines).

FIG. 8. Scatter plot.

DETAILED DESCRIPTION

Figure 7:
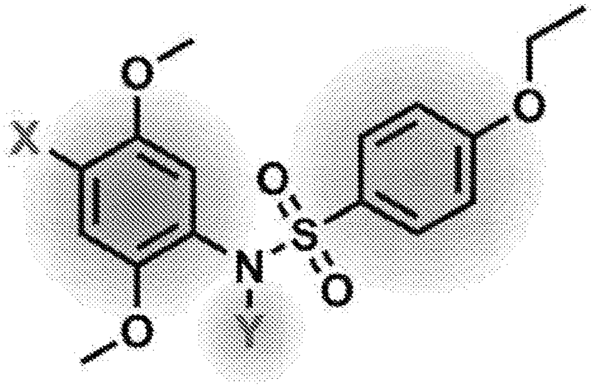
FIG. 7. Schematic of affinity probes.

Agents that safely induce, enhance, or sustain multiple innate immune signaling pathways could be developed as potent vaccine adjuvants or co-adjuvants. Using high-throughput screens with cell-based nuclear factor kappa B (NF-κB) and interferon stimulating response element (ISRE) reporter assays, we identified a bis-aryl sulfonamide bearing compound 1 that demonstrated sustained NF-κB and ISRE activation after a primary stimulus with lipopolysaccharide or interferon-α, respectively. Here, we present systematic structure-activity relationship studies on the two phenyl rings and amide nitrogen of the sulfonamide group of compound 1 which led to identification of several potent compounds. The murine vaccination studies showed that compounds 1 and 33 when used as co-adjuvants with monophosphoryl lipid A (MPLA) showed significant enhancement in antigen ovalbumin-specific immunoglobulin responses compared to MPLA alone. Structure-activity relationship studies pointed to the sites on the scaffold that can tolerate the introduction of aryl azide, biotin and fluorescent rhodamine substituents to obtain affinity and photoaffinity probes which will be utilized in concert for future target identification and mechanism of action studies.

Vaccines consisting of antigen and adjuvant rely primarily on adjuvants for enhancement of immune stimuli (Shukla et al., 2018a). These adjuvants include ligands for pattern recognition receptors (PRRs) such as Toll-like receptors (TLR)-2, -4, -7, -8, and -9, nucleotide-binding oligomerization domain-like receptors (NLRs), RIG-I-like receptors (RLRs) and cytokines such as interferon-α (IFN-α), IFN-γ and IL-12 (Reed et al., 2013; Shukla et al., 2012; Vasilakos & Tamai, 2013; Maisonneuve et al., 2014; Basto & Leitao, 2014; Wheeler et al., 2016; Ho et al., 2018; Proietti et al., 2002; Pavot et al., 2016; Probst et al., 2017; Tovey * Lallemand, 2010; Chan et al., 2013). Some of these adjuvants have been approved for human use by the U.S. Food and Drug Administration (FDA) including the TLR-4 agonist monophosphoryl Lipid A (MPLA) (Alving et al., 2012), the TLR-9 agonist CpG 1018 (Hyer & Janssen, 2018), and other adjuvants with different mechanisms of action such as alum and squalene based adjuvants. Despite the availability of approved adjuvants, the need for co-adjuvants is evident since single adjuvant vaccines often do not generate protective immunity (Fraser et al., 2007). A co-adjuvant is a substance that can work with a known adjuvant to offer synergistic effects. Such combinations with an approved adjuvant can be obtained using a PRR or NLR ligand, an immunogenic protein, a delivery system or another adjuvant with a complementary mechanism of action (Fraser et al., 2007). One such combination AS04 (Adjuvant System 04), consisting of MPLA and alum, has been FDA approved in a hepatitis B vaccine Fendrix® and human papillomavirus vaccine Cervarix® (Beran, 2008; Fabrizi et al., 2019; Lin et al., 2018; Schwarz et al., 2015). Alternative combinations involving approved adjuvants, TLR agonists, NOD agonists, and delivery systems are being explored (Mutwiri et al., 2011; Ebensen et al., 2019; Ignacio et al., 2018; Levast et al., 2014).

Definitions

A composition is comprised of "substantially all" of a particular compound, or a particular form a compound (e.g., an isomer) when a composition comprises at least about 90%, and at least about 95%, 99%, and 99.9%, of the particular composition on a weight basis. A composition comprises a "mixture" of compounds, or forms of the same compound, when each compound (e.g., isomer) represents at least about 10% of the composition on a weight basis. A TLR7 agonist, or a conjugate thereof, can be prepared as an acid salt or as a base salt, as well as in free acid or free base forms. In solution, certain of the compounds may exist as zwitterions, wherein counter ions are provided by the solvent molecules themselves, or from other ions dissolved or suspended in the solvent.

As used herein, the term "isolated" refers to in vitro preparation, isolation and/or purification of a nucleic acid molecule, a peptide or protein, or other molecule so that it is not associated with in vivo substances or is present in a form that is different than is found in nature. Thus, the term "isolated" when used in relation to a nucleic acid, as in "isolated oligonucleotide" or "isolated polynucleotide" refers to a nucleic acid sequence that is identified and separated from at least one contaminant with which it is ordinarily associated in its source. An isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. Hence, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. The isolated nucleic acid molecule may be present in single-stranded or double-stranded form. When a nucleic acid molecule is to be utilized to express a protein, the nucleic acid contains at a minimum, the sense or coding strand (i.e., the nucleic acid may be single-stranded), but may contain both the sense and anti-sense strands (i.e., the nucleic acid may be double-stranded).

The term "amino acid" as used herein, comprises the residues of the natural amino acids (e.g., Ala, Arg, Asn, Asp, Cys, Glu, Gin, Gly, His, Hyl, Hyp, He, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine, ornithine, citruline, -methyl-alanine, parabenzoylphenylalanine, phenylglycine, propargylglycine, sarcosine, and tert-butylglycine). The term also comprises natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an -methylbenzyl amide). Other suitable amino and carboxy protecting groups are known to those skilled in the art (see for example, T. W, Greene, *Protecting Groups In Organic Synthesis*; Wiley: New York, 1981, and references cited therein). For instance, an amino acid can be linked to the remainder of a compound of formula I through the carboxy terminus, the amino terminus, or through any other convenient point of attachment, such as, for example, through the sulfur of cysteine.

The term "toll-like receptor agonist" (TLR agonist) refers to a molecule that binds to a TLR. Synthetic TLR agonists are chemical compounds that are designed to bind to a TLR and activate the receptor.

The term "nucleic acid" as used herein, refers to DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 7-position purine modifications, 8-position purine modifications, 9-position purine modifications, modifications at exocyclic amines, substitution of 4-thiouridine, substitution of 5-bromo or 5-iodo-uracil, backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a BHQ, a fluorophore or another moiety.

A "phospholipid" or analog thereof as the term is used herein refers to a glycerol mono- or diester or diether bearing a phosphate group bonded to a glycerol hydroxyl group with an alkanolamine group being bonded as an ester to the phosphate group, of the general formula

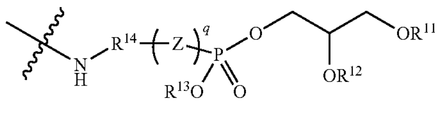

wherein $R^{11}$ and $R^{12}$ are each independently a hydrogen, a $C_8$-$C_{25}$ alkyl group or a $C_8$-$C_{25}$ acyl group, provided that at least one of $R^{11}$ and $R^{12}$ is an alkyl or an acyl group; $R^{13}$ is a negative charge or a hydrogen, and $R^{14}$ is a $C_1$-$C_8$ n-alkyl or branched alkyl group which can be substituted or unsubstituted, wherein optionally one of the carbon atoms of the $R^{14}$ alkyl group may be replaced by NH, S, or O; Z is O, S, or NH, and q is 0 or 1; wherein a wavy line indicates a position of bonding, wherein an absolute configuration at the carbon atom bearing $OR^{12}$ is R, S, or any mixture thereof.

$R^{13}$ is a negative charge or a hydrogen, depending upon pH. When $R_{13}$ is a negative charge, a suitable counterion, such as a sodium ion, can be present. In one embodiment, $R^{14}$ is substituted or unsubstituted $C_1$-$C_7$ alkyl chain wherein one of the carbons may be substituted with a heteroatom selected from N or S. For example, the alkanolamine moiety can be an ethanolamine moiety, such that m=1. It is also understood that the NH group can be protonated and positively charged, or unprotonated and neutral, depending upon pH. For example, the phospholipid can exist as a zwitterion with a negatively charged phosphate oxy anion and a positively charged protonated nitrogen atom. The carbon atom bearing $OR^{12}$ is a chiral carbon atom, so the molecule can exist as an R isomer, an S isomer, or any mixture thereof. When there are equal amounts of R and S isomers in a sample of the compound of formula (I), the sample is referred to as a "racemate." For example in the commercially available product 1,2-dioleoyl-sn-glycero-3-phosphoethanolamine, as used in Example I below, the $R^3$ group is of the chiral structure

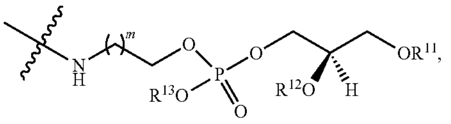

which is of the R absolute configuration (where m is absent or is a $C_1$-$C_8$ n-alkyl or branched alkyl group which can be substituted or unsubstituted, wherein optionally one of the carbon atoms of the $R^{14}$ alkyl group may be replaced by NH or S but optionally does not form a NH—NH group with the amine).

A phospholipid can be either a free molecule, or covalently linked to another group for example as shown

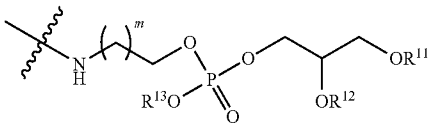

wherein a wavy line indicates point of bonding (where m is absent or is a $C_1$-$C_8$ n-alkyl or branched alkyl group which can be substituted or unsubstituted, wherein optionally one of the carbon atoms of the $R^{14}$ alkyl group may be replaced by NH or S but does not form a NH—NH group with the amine).

Accordingly, when a substituent group, such as $R^3$ of the compound of formula (I) herein, is stated to be a phospholipid or analog thereof what is meant that a phospholipid or phospholipid analog group is bonded as specified by the structure to another group, such as to an N-benzyl heterocyclic ring system as disclosed herein. The point of attachment of the phospholipid group can be at any chemically feasible position unless specified otherwise, such as by a structural depiction. For example, in the phospholipid structure shown above, the point of attachment to another chemical moiety can be via the ethanolamine nitrogen atom, for example as an amide group by bonding to a carbonyl group of the other chemical moiety, for example

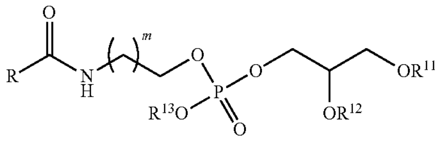

wherein R represents the other chemical moiety to which the phospholipid is bonded. In this bonded, amide derivative, the $R^{13}$ group can be a proton or can be a negative charge associated with a counterion, such as a sodium ion. The acylated nitrogen atom of the alkanolamine group is no longer a basic amine, but a neutral amide, and as such is not protonated at physiological pH.

An "acyl" group as the term is used herein refers to an organic structure bearing a carbonyl group through which the structure is bonded, e.g., to glycerol hydroxyl groups of a phospholipid, forming a "carboxylic ester" group. Examples of acyl groups include fatty acid groups such as oleoyl groups, that thus form fatty (e.g., oleoyl) esters with the glycerol hydroxyl groups. Accordingly, when $R^{11}$ or $R^{12}$, but not both, are acyl groups, the phospholipid shown above is a mono-carboxylic ester, and when both $R^{11}$ and $R^{12}$ are acyl groups, the phospholipid shown above is a di-carboxylic ester.

An "alkyl" group includes straight or branched $C_{8-24}$ alkyl groups which may be substituted. An alkyl group, when bonded to the glyceryl moiety, forms a glyceryl ether. In various embodiments, the compound of formula (I) can be a glyceryl mono- or di-ester. When the compound is a mono-ester, one of $R^{11}$ and $R^{12}$ is an acyl and the other is hydrogen. In other embodiments, the compound of formula (I) can be a glyceryl mono- or di-ether. When the compound is a mono-ether, one of $R^{11}$ and $R^{12}$ is an alkyl and the other is hydrogen. In other embodiments, the compound of formula (I) can be a mixed glyceryl ester-ether, where one of $R^{11}$ and $R^{12}$ is an acyl and the other is an alkyl group.

It is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that any tautomeric form is encompassed, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

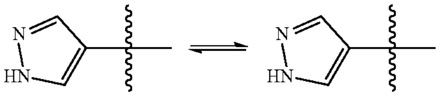 [SMILES: *c1cn[nH]c1 ; *c1cn[nH]c1]

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

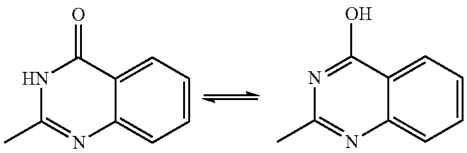

is an example of tautomerism. Accordingly, a structure depicted herein as one tautomer is intended to also include the other tautomer.

Optical Isomerism

It will be understood that when compounds described herein contain one or more chiral centers, the compounds may exist in, and may be isolated as pure enantiomeric or diastereomeric forms or as racemic mixtures. Included is any possible enantiomers, diastereomers, racemates or mixtures thereof of the compounds described herein.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

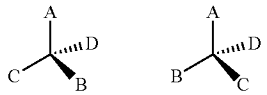

(R) configuration (S) configuration

Diastereomers as well as their racemic and resolved, diastereomerically and enantiomerically pure forms and salts thereof are meant to be encompassed. Diastereomeric pairs may be resolved by known separation techniques including normal and reverse phase chromatography, and crystallization.

"Isolated optical isomer" means a compound which has been substantially purified from the corresponding optical isomer(s) of the same formula. In some embodiments, the isolated isomer is at least about 80%, e.g., at least 90%, 98% or 99% pure, by weight.

Isolated optical isomers may be purified from racemic mixtures by well-known chiral separation techniques. According to one such method, a racemic mixture of a compound, or a chiral intermediate thereof, is separated into 99% wt. % pure optical isomers by HPLC using a suitable chiral column, such as a member of the series of DAICEL' CHIRALPAK® ' family of columns (Daicel Chemical Industries, Ltd., Tokyo; Japan). The column is operated according to the manufacturer's instructions.

As used herein, "pharmaceutically acceptable salts" refer to derivatives of the disclosed compounds where the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, behenic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds described herein can be synthesized from the parent compound, which contains a basic or acidic moiety, by conventional chemical methods, Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile may be employed, Lists of suitable salts are found in *Remington's Pharmaceutical Sciences,* 17th ed., Mack Publishing Company, Easton, Pa., p, 1418 (1985), the disclosure of which is hereby incorporated by reference.

The compounds of the formulas described herein can be solvates, and in some embodiments, hydrates. The term "solvate" refers to a solid compound that has one or more solvent molecules associated with its solid structure. Solvates can form when a compound is crystallized from a solvent. A solvate forms when one or more solvent molecules become an integral part of the solid crystalline matrix upon solidification. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. Hydrates can form when a compound is solidified or crystallized in water, where one or more water molecules become an integral part of the solid crystalline matrix.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Het can be heteroaryl, which encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a bent-derivative or one derived by fusing a propylene, trimethylene, or tetramethylene diradical thereto.

It will be appreciated by those skilled in the art that compounds described herein having a chiral center may exist in and be isolated in optically active and racemic forms. Some compounds may exhibit polymorphism. It is to be understood that any racemic, optically-active, polymorphic, or stereoisomeric form, or mixtures thereof, of a compound described herein, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine agonist activity using the standard tests described herein, or using other similar tests which are well known in the art. It is also understood by those of skill in the art that the compounds described herein include their various tautomers, which can exist in various states of equilibrium with each other.

The terms "treat" and "treating" as used herein refer to (i) preventing a pathologic condition from occurring (e.g., prophylaxis); (ii) inhibiting the pathologic condition or arresting its development; (iii) relieving the pathologic condition; and/or (iv) ameliorating, alleviating, lessening, and removing one or more symptoms of a condition. A candidate molecule or compound described herein may be in an amount in a formulation or medicament, which is an amount that can lead to a biological effect, or lead to protection from, ameliorating, alleviating, lessening, relieving, diminishing or a disease condition, e.g., infection, for example. These terms also are applicable to reducing a titre of a microorganism (microbe) or infectious agent in a system (e.g., cell, tissue, or subject) infected with a microbe, reducing the rate of microbial propagation, reducing the duration of infection of an infectious agent, delaying or attenuating an infection by an infectious agent, reducing the number of symptoms or an effect of a symptom associated with the microbial infection, and/or removing detectable amounts of the microbe from the system. Examples of symptoms include but are not limited weight loss, fever, malaise, weakness, dehydration, failure or diminished organ or organ system function (e.g., pulmonary function). Examples of microbes include but are not limited to viruses, bacteria and fungi.

The term "therapeutically effective amount" as used herein refers to an amount of a compound, or an amount of a combination of compounds, to treat or prevent a disease or disorder or a microbial infection, or to treat or prevent a symptom of the disease or disorder or microbial infection, in a subject. As used herein, the terms "subject" and "patient" generally refers to an individual who will receive or who has received treatment (e.g., administration of a compound) according to a method described herein.

The term "immunocompromised" as used herein refers to a subject having an immune system or portion thereof that is impaired or destroyed such that the ability to prevent, control, or alleviate infection by an infectious agent or mitigate symptoms of such infection is reduced relative to that of an immune system of a comparable (e.g., sex, age, weight, ethnicity, etc.) healthy individual. The subject may be immunocompromised, for example, due to illness or because of receiving treatment (e.g., radiation therapy, chemotherapy or bone marrow transplantation).

The term "elderly" as used herein refers to a subject that is typically 65 years old or greater, Elderly may in include a subject that is at least 50 years old or at least 55 years old, or at least 60 years old, Elderly as used herein refers to any subject that is more prone to infection by an infectious agent and/or has a reduced capacity to prevent, control or alleviate an infection by an infectious agent due in whole or part to aging.

The term "young child" as used herein refers to a subject that is typically under the age of 5 years.

The term "lethal dose" as used herein is meant a dose of infectious agent (e.g., number of infectious units or concentration of infectious agent in air or other medium to which a subject is exposed) that results in an infection that causes death. The lethal dose for human can be extrapolated from data obtained from related species challenged by the infectious agent, Lethal doses are usually expressed as median lethal dose (LD50), the point where 50% of test subjects exposed would die. For example, the median lethal dose for humans for anthrax is approximately 2,500 to 55,000 anthrax spores.

The term "sub-lethal dose" as used herein is meant a dose of an infectious agent that is not lethal but which may result in an infection of a subject who may manifest symptoms caused by the infection.

"Stable compound" and "stable structure" are meant to indicate a compound that is sufficiently robust to survive isolation to a useful degree of purity from a reaction mixture, and formulation into an efficacious therapeutic agent. Only stable compounds are contemplated.

Identification of Compounds Useful as an Adjuvant

Compounds were identified in an HTS that could enhance and prolong the immune response after an immune stimulus was administered, such as LPS or type 1 interferon. These positive compounds were found to be of a chemotype that contained a specific functional group, namely, N-aryl sulfonamides. These sulfonamides were found to be active in vitro as well as in vivo studies. They were able to prolong and enhance the antigen specific antibody production upon immunization of animals with antigen and compound. Thus, these compounds could be used as co-adjuvants with adjuvants in vaccine compositions, e.g., two separate adjuvants or two adjuvants that are covalently linked. In addition to the active compounds identified, special probes in this chemotype were prepared in order to help determine the target of this series of co-adjuvants.

The approach towards identifying co-adjuvants focused on small molecules that modulate the TLR signaling pathway but do not interact directly with TLRs. The rationale behind the approach is as follows: Upon vaccine administration, local antigen presenting cells (APCs) at the site of injection, such as dendritic cells and Langerhans cells, are activated by adjuvant and these APCs engulf antigen and travel to local draining lymph nodes where the antigen is presented to T cells. The activation levels of APCs induced by these adjuvants, peaks at 2-6 hours and then decay due to negative feedback mechanisms. It takes approximately 12-24 hours for an APC to become activated and travel to the lymph node after vaccination, arriving during the decay phase of the immune activation, Thus, prolonging or sustaining the activation of APCs induced by an adjuvant for 12-24 hours may lead to presentation of antigen to the T cells which would enhance the initial immune response and potentially allow for a longer lasting response. stimulus was administered, such as LPS or type I interferon.

In particular, the approach towards identifying coadjuvants focused on small molecules that may not lead to immune activation by themselves but may enhance the primary immune activation such as nuclear factor κB (NF-κB) or IFN stimulating response element (ISRE) activation induced by a TLR-4 agonist (LPS or MPLA), The rationale behind the approach is as follows: Upon vaccine administration, local antigen presenting cells (APCs) at the site of injection, such as dendritic cells and Langerhans cells, are activated by the TLR-4 agonist. These APCs engulf antigen and travel to local draining lymph nodes where the antigen is presented to T cells (Forster et al., 2012). The activation levels of APCs induced by a TLR-4 agonist peak at 2-6 hours and then decay due to negative feedback mechanisms (Qian et al., 2013; Turnis et al., 2010; Yuk et al., 2011; Ho et al., 2012; Liu et al., 2010; Ma et al., 2010; An et al., 2006; Kondo et al., 2012). Because it takes approximately 12-24 hours for an APC to travel to the lymph node after vaccination (Marin-Fontecha et al., 2009), APCs are arriving during the decay phase of the activation. This rationale is well supported from a report that showed that the absence of interleukin-1 receptor associated kinase M (IRAK-M, a negative regulator of TLR signaling) (Kobayashi et al., 2002) increases NF-κB activation and improves migration of dendritic cells (QCs) to lymph nodes thereby increasing the lifespan of the activated DCs and secretion of Th1-skewed cytokines and chemokines (Turnis et al., 2010). Thus, it was hypothesized that prolonging or sustaining the activation of APCs induced by the TLR-4 agonist for 12-24 hours leads to optimal presentation of antigen to the T cells which would enhance the initial immune response and potentially allow for a longer lasting response. The hypothesis is supported by reports that enhanced responses to vaccinations were observed in mice with genetic disruption either of IRAKM, an inhibitor of the NF-κB pathway (Turnis et al., 2010), or of UBP43, a negative regulator of type 1 IFN signaling (Kim et al., 2005). Thus, to address this issue, HTS methods directed toward identification of coadjuvants that prolonged activation of an immune response induced by a primary stimulus (Chan et al., 2017; Skukla et al., 2018b) were employed.

These cell based HTS tested protraction of a TLR-4 agonist lipopolysaccharide (LPS) stimulus through the NF-κB pathway (Chan et al., 2017) or of IFN-α signaling via the interferon stimulating response element (ISRE) (Shukla et al., 2018b) pathway. Compounds that prolonged LPS induced NF-κB signaling included a distinct set of pyrimido[5,4-b]indoles that were also found to be effective coadjuvants with MPLA, an FDA approved adjuvant, in murine vaccination studies (Chan et al., 2017). In parallel, compounds that prolonged IFN-α induced ISRE signaling in vitro were also evaluated as coadjuvants in vivo (Shukla et al., 2018b) which led to identification of a potent bis-aryl sulfonamide compound 1 (FIG. 1) bearing 4-chloro-2,5-dimethoxy and 4-ethoxy substituted phenyl groups connected by a sulfonamide functional group. Compound 1 possessed little if any NF-κB or ISRE activity when tested alone, but it enhanced their activation when tested in the presence of LPS or IFN-α, respectively, compared to the stimulus alone. The further drug development of such hits identified through cell-based phenotypic assays and involved in cell signaling pathways is hampered without the knowledge of the target receptor or the compound's mechanism of action (Schenone et al., 2013).

This necessitated SAR studies focused toward identification of affinity probes which involved evaluation of structural variations for compound 1 that were unexplored in the HTS with an aim to identify positions on the scaffold that can tolerate the introduction of small functional groups such as aryl azide or diazirine to make photoreactive probes or large substituents such as biotin and fluorescence moieties to generate affinity and fluorescent probes, respectively (Pan et al. 2016; Smith & Collins, 2015; Sumranjit & Chung, 2013; Kan et al., 2007; Ban et al., 2016; Kawada et al., 1989; Shukla et al., 2010). Exploration of several different functional groups and substituents will allow us to systematically identify the position and size of the affinity probe as well as the reactive handle to be used for introducing these probes. These chemical probes would then be useful tools for future mechanistic and functional receptor studies. In addition, the chemical handle would allow one to covalently conjugate the small molecule to peptides or protein antigens to make self-adjuvanting vaccine constructs which are widely explored in vaccine development (Shukla et al., 2011; Fagan et al, 2017; Gential et al., 2019; Li & Guo, 2018; Liao et al., 2019; Nevagi et al., 2019).

TLR7 Agonists and Uses Thereof

In various embodiments are provided methods which employ a compound of formula (II) and a TLR7 agonist in combination with an antigen, e.g., of an infectious agent, to prevent or inhibit infection by the infectious agent in a mammal. Thus, the methods include administering to a mammal in need thereof an effective amount of a composition comprising an amount of a compound of Formula (I):

(I)

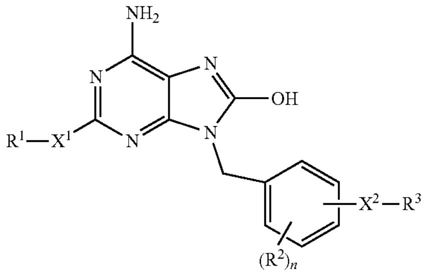

wherein $X^1$ is —O—, —S—, or —$NR^c$—;

$R^1$ is hydrogen, $(C_1\text{-}C_{10})$alkyl, substituted $(C_1\text{-}C_{10})$alkyl, $C_{6\text{-}10}$aryl, or substituted $C_{6\text{-}10}$aryl, $C_{5\text{-}9}$ heterocyclic, substituted $C_{5\text{-}9}$ heterocyclic;

$R^c$ is hydrogen, $C_{1\text{-}10}$alkyl, or substituted $C_{1\text{-}10}$alkyl; or $R^c$ and $R^1$ taken together with the nitrogen to which they are attached form a heterocyclic ring or a substituted heterocyclic ring;

each $R^2$ is independently —OH, $(C_1\text{-}C_6)$alkyl, substituted $(C_1\text{-}C_6)$alkyl, $(C_1\text{-}C_6)$alkoxy, substituted $(C_1\text{-}C_6)$alkoxy, —C(O)—$(C_1\text{-}C_6)$alkyl (alkanoyl), substituted —C(O)—$(C_1\text{-}C_6)$alkyl, —C(O)—$(C_6\text{-}C_{10})$aryl (aroyl), substituted —C(O)—$(C_6\text{-}C_{10})$aryl, —C(O)OH (carboxyl), —C(O)O$(C_1\text{-}C_6)$alkyl (alkoxycarbonyl), substituted —C(O)O$(C_1\text{-}C_6)$alkyl, —$NR^aR^b$, C(O)$NR^aR^b$ (carbamoyl), halo, nitro, or cyano, or $R^2$ is absent;

each $R^a$ and $R^b$ is independently hydrogen, $(C_1\text{-}C_6)$alkyl, substituted $(C_1\text{-}C_6)$alkyl, $(C_3\text{-}C_8)$cycloalkyl, substituted ($C_3$-$C_8$)cycloalkyl, ($C_1$-$C_6$)alkoxy, substituted ($C_1$-$C_6$) alkoxy, ($C_1$-$C_6$)alkanoyl, substituted ($C_1$-$C_6$)alkanoyl, aryl, aryl($C_1$-$C_6$)alkyl, Het, Het ($C_1$-$C_6$)alkyl, or ($C_1$-$C_6$)alkoxy-carbonyl;

wherein the substituents on any alkyl, aryl or heterocyclic groups are hydroxy, $C_{1-6}$alkyl, hydroxy$C_{1-6}$alkylene, $C_{1-6}$alkoxy, $C_{3-6}$cycloalkyl, $C_{1-6}$alkoxy$C_{1-6}$alkylene, amino, cyano, halo, or aryl;

n is 0, 1, 2, 3 or 4;

$X^2$ is a bond or a linking group; and $R^3$ is a phospholipid, or analog thereof comprising one or two alkyl ethers or carboxylic esters of the glyceryl moiety;

or a tautomer thereof;

or a pharmaceutically acceptable salt or solvate thereof.

For example, $R^3$ can comprise a group of formula

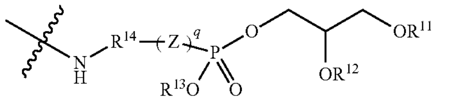

wherein $R^{11}$ and $R^{12}$ are each independently a hydrogen, a $C_8$-$C_{25}$ alkyl group or a $C_8$-$C_{25}$ acyl group, provided that at least one of $R^{11}$ and $R^{12}$ is an alkyl or an acyl group; $R^{13}$ is a negative charge or a hydrogen, and $R^{14}$ is a $C_1$-$C_8$ n-alkyl or branched alkyl group which can be substituted or unsubstituted, wherein optionally one of the carbon atoms of the alkyl group is replaced by NH, S, or O; Z is O, S, or NH, and q is 0 or 1;

wherein a wavy line indicates a position of bonding, wherein an absolute configuration at the carbon atom bearing $OR^{12}$ is R, S, or any mixture thereof.

An absolute configuration at the carbon atom bearing $OR^{12}$ is R, S, or any mixture thereof. In one embodiment, $R^{14}$ is substituted or unsubstituted $C_1$-$C_7$ alkyl chain wherein one of the carbons may be substituted with a heteroatom selected from N or S.

or

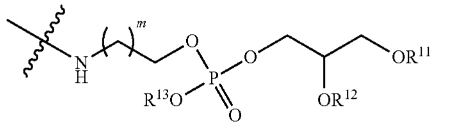

wherein $R^{11}$ and $R^{12}$ are each independently a hydrogen, an alkyl group or an acyl group, $R^{13}$ is a negative charge or a hydrogen, and m is 0 to 8, wherein a wavy line indicates a position of bonding, wherein an absolute configuration at the carbon atom bearing $OR^{12}$ is R, S, or any mixture thereof. In one embodiment, m is absent. In one embodiment, m is a $C_1$-$C_8$ n-alkyl or branched alkyl group which can be substituted or unsubstituted, wherein optionally one of the carbon atoms of the $R^{14}$ alkyl group may be replaced by NH or S.

For example, m can be 1, providing a glycerophosphatidylethanolamine. More specifically, $R^{11}$ and $R^{12}$ can each be oleoyl groups.

In various embodiments, the phospholipid of $R^3$ can comprise two carboxylic esters and each carboxylic ester includes one, two, three or four sites of unsaturation, epoxidation, hydroxylation, or a combination thereof.

In various embodiments, the phospholipid of $R^3$ can comprise two alkyl ethers which may include one, two, three or four sites of unsaturation, epoxidation, hydroxylation, or a combination thereof, or is saturated. In various embodiments, the phospholipid analog of $R^3$ can comprise two glyceryl alkyl ether groups, and the alkyl ethers may be the same or different. More specifically, each ether of the phospholipid analog can be a C17 or C19 saturated alkyl. Alternatively, each ether of the phospholipid analog can be a C18 saturated alkyl.

In various embodiments, the phospholipid of $R^3$ can comprise two carboxylic esters and the carboxylic esters of are the same or different. More specifically, each carboxylic ester of the phospholipid can be a C17 carboxylic ester with a site of unsaturation at C8-C9. Alternatively, each carboxylic ester of the phospholipid can be a C18 carboxylic ester with a site of unsaturation at C9-C10.

In various embodiments, $X^2$ can be a bond or a chain having one to about 10 atoms in a chain wherein the atoms of the chain are selected from the group consisting of carbon, nitrogen, sulfur, and oxygen, wherein any carbon atom can be substituted with oxo, and wherein any sulfur atom can be substituted with one or two oxo groups. The chain can be interspersed with one or more cycloalkyl, aryl, heterocyclyl, or heteroaryl rings.

In various embodiments, $X^2$ can be carbonyl (e.g., C(O)), or can be

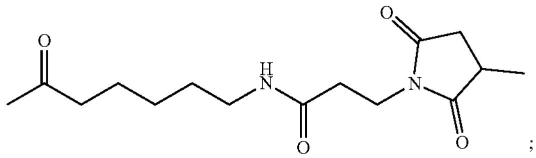

;

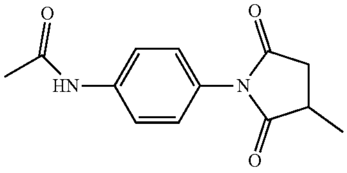

; or

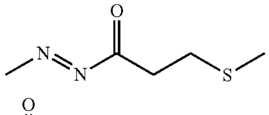

;

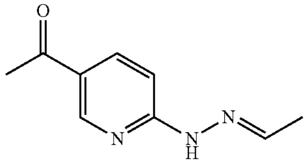

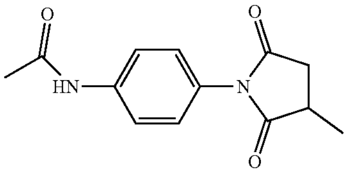

; or

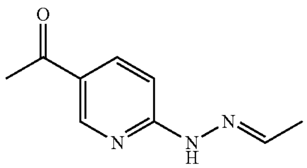

In various embodiments, $X^2$ can be

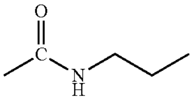
,
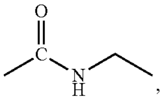
,
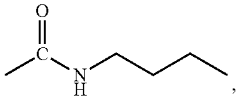
,
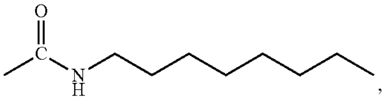
,
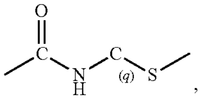
,
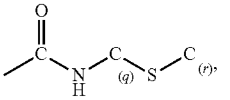
,
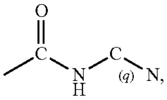
or
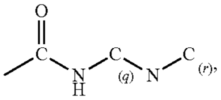
, where q=0 to 8 in various embodiments.

In various embodiments, $R^3$ can be dioleoylphosphatidyl ethanolamine (DOPE). In various embodiments $R^3$ is not DOPE.

In various embodiments, $R^3$ can be 1,2-dioleoyl-sn-glycero-3-phospho ethanolamine and $X^2$ can be C(O).

In various embodiments, $X^1$ can be oxygen.

In various embodiments, $X^1$ can be sulfur, or can be —$NR^c$— where $R^c$ is hydrogen, $C_{1-6}$ alkyl or substituted $C_{1-6}$ alkyl, where the alkyl substituents are hydroxy, $C_{3-6}$cycloalkyl, $C_{1-6}$alkoxy, amino, cyano, or aryl. More specifically, $X^1$ can be —NH—.

In various embodiments, $R^1$ and $R^c$ taken together can form a heterocyclic ring or a substituted heterocyclic ring. More specifically, $R^1$ and $R^c$ taken together can form a substituted or unsubstituted morpholino, piperidine, pyrrolidino, or piperazine ring.

In various embodiments $R^1$ can be a C1-C10 alkyl substituted with C1-6 alkoxy.

In various embodiments, $R^1$ can be hydrogen, $C_{1-4}$ alkyl, or substituted $C_{1-4}$alkyl. More specifically, $R^1$ can be hydrogen, methyl, ethyl, propyl, butyl, hydroxyCiAalkylene, or $C_{1-4}$alkoxy$C_{1-4}$ alkylene. Even more specifically, $R^1$ can be hydrogen, methyl, ethyl, methoxyethyl, or ethoxyethyl.

In various embodiments, $R^2$ can be absent, or $R^2$ can be halogen or $C_{1-4}$ alkyl. More specifically, $R^2$ can be chloro, bromo, methyl, or ethyl.

In various embodiments, $X^1$ can be O, $R^1$ can be $C_{1-4}$ alkoxy-ethyl, n can be 1, $R^2$ can be hydrogen, $X^2$ can be carbonyl, and $R^3$ can be 1,2-dioleoylphosphatidyl ethanolamine (DOPE).

In various embodiments, the compound of Formula (I) can be:

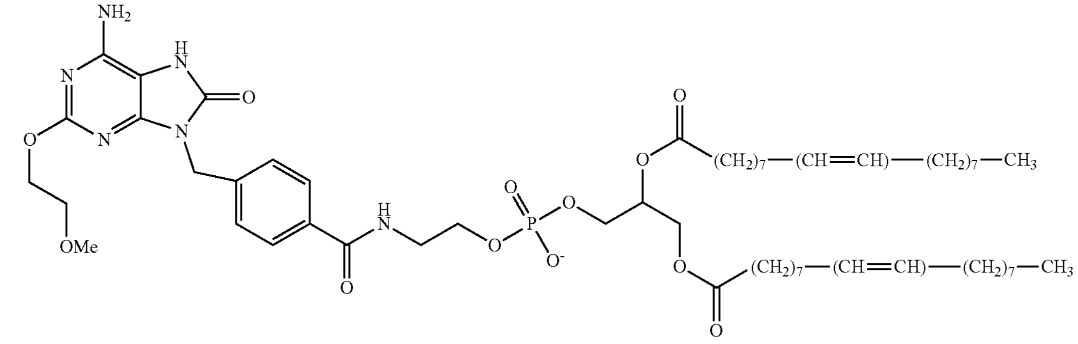

In various embodiments, the compound of formula (I) can be the R-enantiomer of the above structure:

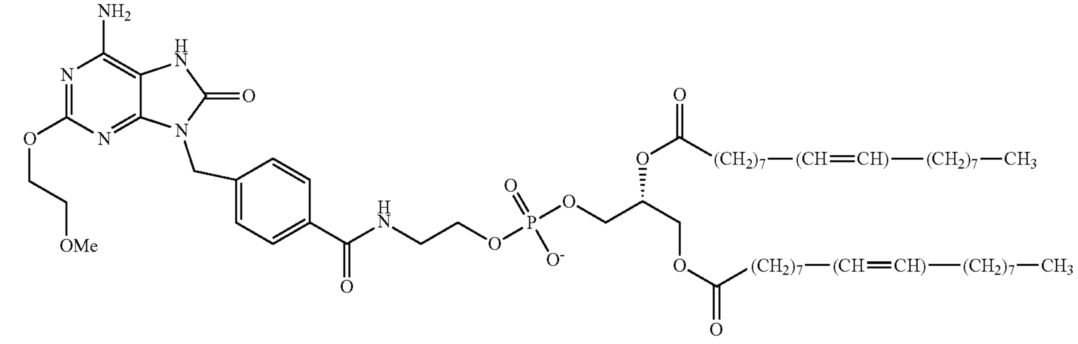

In various embodiments, the compound of formula (I) can be the phospholipid

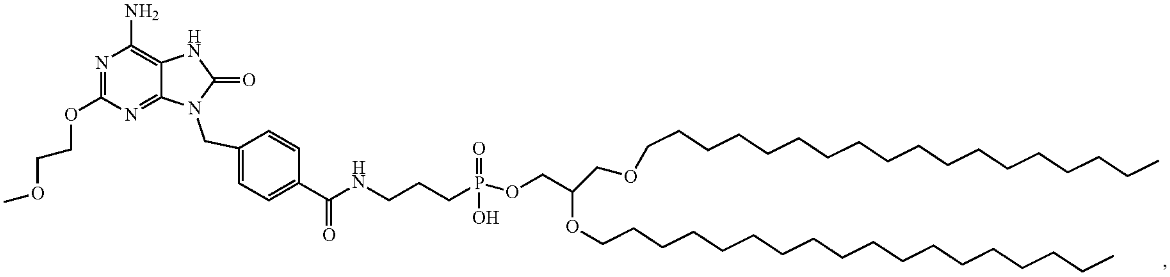 [SMILES: CCCCCCCCCCCCCCCCCCOCC(COP(=O)(O)CCCNC(=O)c1ccc(Cn2c(=O)[nH]c3c(N)nc(OCCOC)nc32)cc1)OCCCCCCCCCCCCCCCCCC]

, wherein a phosphonate analog of a phospholipid, having a glyceryl diether group bonded thereto, is conjugated to the benzyladenine moiety via an carboxamide group.

In some embodiments, the composition comprises nanoparticles comprising a compound of formula (I). In various embodiments, a phospholipid conjugate such as 1V270 can be incorporated into a nanoparticle such as those described in WO 2010/083337, the disclosure of which is incorporated by reference herein.

As used herein, a nanoparticle has a diameter of about 30 nm to about 600 nm, or a range with any integer between 30 and 600, e.g., about 40 nm to about 250 nm, including about 40 to about 80 or about 100 nm to about 150 nm in diameter. The nanoparticles may be formed by mixing a compound of formula (I), which may spontaneously form nanoparticles, or by mixing a compound of formula (I) with a preparation of lipids, such as phospholipids including but not limited to phosphatidylcholine, phosphatidylserine or cholesterol, thereby forming a nanoliposome. In certain embodiments, a composition forms particles of about 10 nanometers to about 1000 nanometers, and sometimes, a composition forms particles with a mean, average or nominal size of about 100 nanometers to about 400 nanometers.

In various embodiments, a phospholipid conjugate such as 1V270 can be prepared in the form of a nanoparticulate suspension of the phospholipid conjugate in combination with a lipid and/or a phospholipid in an aqueous medium (e.g., a nanoliposome). A nanoliposome is a submicron bilayer lipid vesicle (see Chapter 2 by Mozafari in: Liposomes, Methods in Molecular Biology, vol. 605, V, Weissing (ed.), Humana Press, the disclosure of which is incorporated by reference herein). Nanoliposomes provide more surface area and may increase solubility, bioavailability and targeting.

Optionally, a compound of formula (I), a lipid preparation and a glycol such as propylene glycol are combined.

Lipids are fatty acid derivatives with various head group moieties, Triglycerides are lipids made from three fatty acids and a glycerol molecule (a three-carbon alcohol with a hydroxyl group [OH] on each carbon atom). Mono- and diglycerides are glyceryl mono- and di-esters of fatty acids, Phospholipids are similar to triglycerides except that the first hydroxyl of the glycerol molecule has a polar phosphate-containing group in place of the fatty acid. Phospholipids are amphiphilic, possessing both hydrophilic (water soluble) and hydrophobic (lipid soluble) groups. The head group of a phospholipid is hydrophilic and its fatty acid tail (acyl chain) is hydrophobic. The phosphate moiety of the head group is negatively charged.

In addition to lipid and/or phospholipid molecules, nanoliposomes may contain other molecules such as sterols in their structure. Sterols are important components of most natural membranes, and incorporation of sterols into nanoliposome bilayers can bring about major changes in the properties of these vesicles. The most widely used sterol in the manufacture of the lipid vesicles is cholesterol (Choi), Cholesterol does not by itself form bilayer structures, but it can be incorporated into phospholipid membranes in very high concentrations, for example up to 1:1 or even 2:1 molar ratios of cholesterol to a phospholipid such as phosphatidylcholine (PC) (11). Cholesterol is used in nanoliposome structures in order to increase the stability of the vesicles by modulating the fluidity of the lipid bilayer. In general, cholesterol modulates fluidity of phospholipid membranes by preventing crystallization of the acyl chains of phospholipids and providing steric hindrance to their movement. This contributes to the stability of nanoliposomes and reduces the permeability of the lipid membrane to solutes.

Physicochemical properties of nanoliposomes depend on several factors including pH, ionic strength and temperature. Generally, lipid vesicles show low permeability to the entrapped material. However, at elevated temperatures, they undergo a phase transition that alters their permeability. Phospholipid ingredients of nanoliposomes have an important thermal characteristic, i.e., they can undergo a phase transition (Tc) at temperatures lower than their final melting point (Tm). Also known as gel to liquid crystalline transition temperature, Tc is a temperature at which the lipidic bilayer loses much of its ordered packing while its fluidity increases. Phase transition temperature of phospholipid compounds and lipid bilayers depends on the following parameters: polar head group; acyl chain length; degree of saturation of the hydrocarbon chains; and nature and ionic strength of the suspension medium. In general, Tc is lowered by decreased chain length, by unsaturation of the acyl chains, as well as presence of branched chains and bulky head groups (e.g. cyclopropane rings).

Hydrated phospholipid molecules arrange themselves in the form of bilayer structures via Van-der Waals and hydrophilic/hydrophobic interactions. In this process, the hydrophilic head groups of the phospholipid molecules face the water phase while the hydrophobic region of each of the monolayers faces each other in the middle of the membrane. It should be noted that formation of liposomes and nanoliposomes is not a spontaneous process and sufficient energy must be put into the system to overcome an energy barrier. In other words, lipid vesicles are formed when phospholipids such as lecithin are placed in water and consequently form bilayer structures, once adequate amount of energy is supplied. Input of energy (e.g. in the form of sonication, homogenisation, heating, etc.) results in the arrangement of the lipid molecules, in the form of bilayer vesicles, to achieve a thermodynamic equilibrium in the aqueous phase.

For example, a composition comprising a compound such as 1V270 as a mixture with a lipid such as cholesterol or a phospholipid such as phosphatidylcholine can be dispersed into a nanoparticulate form where lipid or phospholipid nanoparticles contain the TLR7 ligand conjugate associated therewith.

For example, a nanoparticulate/nanoliposome composition can be prepared using 1V270 and the phophatidylcholine preparation Phosal 50 PG®. 1V270 can be dissolved in Phosal 50 PG (Phospholipid Gmbh, Cologne, Germany) to make a 20× concentrated solution. The Phosal 50 PG-1V270 mixture can be further diluted (1:19) with nanopure water to make a 5% Phosal 50 PG:water suspension. The suspension can be vortexed vigorously and sonicated in a sonicating bath for 10 minutes. The suspension can be further sonicated with a probe sonicater (Branson Sonifier Cell Disrupter 185) at 30% power for a total of 30 seconds at 10 second intervals with 10 seconds rest between so as to not overheat the suspension. Finally, the suspension can be passed through a 100 nm filter with syringe extruder a total of 10 times back and forth. The final nanoparticles can be analyzed with a Malvern Zetasizer to check size distribution. The resulting particles may be referred to as nanoliposomes (a submicron bilayer lipid vesicle) (see Chapter 2 by Mozafari in: Liposomes, Methods in Molecular Biology, vol. 605, V. Weissing (ed.), Humana Press, the disclosure of which is incorporated by reference herein). Nanoliposomes provide more surface area and may increase solubility, bioavailability and targeting.

Nanoparticles are generally stable over time. The particle size of UV-1V270 in PBS is relatively constant with an average of about 110 nm regardless of concentration.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Alkyl includes straight or branched $C_{1-10}$ alkyl groups, e.g., methyl, ethyl, propyl, butyl, pentyl, isopropyl, isobutyl, 1-methylpropyl, 3-methylbutyl, hexyl, and the like.

Lower alkyl includes straight or branched $C_{1-6}$ alkyl groups, e.g., methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, and the like.

The term "alkylene" refers to a divalent straight or branched hydrocarbon chain (e.g., ethylene: $—CH_2—CH_2—$).

$C_{3-7}$ Cycloalkyl includes groups such as, cyclopropyl, cyclopentyl, cyclohexyl, cycloheptyl, and the like, and alkyl-substituted $C_{3-7}$ cycloalkyl group, e.g., straight or branched $C_{1-6}$ alkyl group such as methyl, ethyl, propyl, butyl or pentyl, and $C_{5-7}$ cycloalkyl group such as, cyclopentyl or cyclohexyl, and the like.

Lower alkoxy includes $C_{1-6}$ alkoxy groups, such as methoxy, ethoxy or propoxy, and the like.

Lower alkanoyl includes $C_{1-6}$ alkanoyl groups, such as formyl, acetyl, propanoyl, butanoyl, pentanoyl or hexanoyl, and the like.

$C_{7-11}$ aroyl, includes groups such as benzoyl or naphthoyl;

Lower alkoxycarbonyl includes $C_{2-7}$ alkoxycarbonyl groups, such as methoxycarbonyl, ethoxycarbonyl or propoxycarbonyl, and the like.

Lower alkylamino group means amino group substituted by $C_{1-6}$ alkyl group, such as, methylamino, ethylamino, propylamino, butylamino, and the like.

Di(lower alkyl)amino group means amino group substituted by the same or different and $C_{1-6}$ alkyl group (e.g., dimethylamino, diethylamino, ethylmethylamino).

Lower alkylcarbamoyl group means carbamoyl group substituted by $C_{1-6}$ alkyl group (e.g., methylcarbamoyl, ethylcarbamoyl, propylcarbamoyl, butylcarbamoyl).

Di(lower alkyl)carbamoyl group means carbamoyl group substituted by the same or different and $C_{1-6}$ alkyl group (e.g., dimethylcarbamoyl, diethylcarbamoyl, ethylmethylcarbamoyl).

Halogen atom means halogen atom such as fluorine atom, chlorine atom, bromine atom or iodine atom.

Aryl refers to a $C_{6-10}$ monocyclic or fused cyclic aryl group, such as phenyl, indenyl, or naphthyl, and the like.

Heterocyclic or heterocycle refers to monocyclic saturated heterocyclic groups, or unsaturated monocyclic, or fused heterocyclic group containing at least one heteroatom, e.g., 0-3 nitrogen atoms $NR^c$, 0-1 oxygen atom (—O—), and 0-1 sulfur atom (—S—), Non-limiting examples of saturated monocyclic heterocyclic group includes 5 or 6 membered saturated heterocyclic group, such as tetrahydrofuranyl, pyrrolidinyl, morpholinyl, piperidyl, piperazinyl or pyrazolidinyl. Non-limiting examples of unsaturated monocyclic, heterocyclic group includes 5 or 6 membered unsaturated heterocyclic group, such as furyl, pyrrolyl, pyrazolyl, imidazolyl, thiazolyl, thienyl, pyridyl or pyrimidinyl. Non-limiting examples of unsaturated fused heterocyclic groups includes unsaturated bicyclic heterocyclic group, such as indolyl, isoindolyl, quinolyl, benzothizolyl, chromanyl, benzofuranyl, and the like. A Het group can be a saturated heterocyclic group or an unsaturated heterocyclic group, such as a heteroaryl group.

Routes of Administration and Dosages

Administration of compositions described herein can be via any of suitable route of administration. In one embodiment, intramuscular administration is employed.

One non-limiting example of a route of administration is to the respiratory system. The respiratory system includes the nasal cavity and associated sinuses, the nasopharynx, oropharynx, larynx, trachea, bronchi, bronchioles, respiratory bronchioles, alveolar ducts and alveolar sacs. In specific embodiments the compounds described herein are administered to the lungs or the nasal cavity.

Pulmomary administration can be used for delivery to the lungs and other regions of the respiratory system. Pulmonary administration includes, but is not limited to, aerosol inhalation via nasal (intranasal) or oral routes and intratracheal instillation.

Aerosol inhalation is by any means by which an aerosol can be introduced into the respiratory system, including, but not limited to, pressurized metered dose inhalers, dry power inhalers and nebulisers (e.g., liquid spray and suspension spray) for oral route or any device suitable for intranasal administration.

In addition, in some embodiments, are provided various dosage formulations for inhalation delivery. For example, formulations may be designed for aerosol use in devices such as metered-dose inhalers, dry powder inhalers and nebulizers.

Intratracheal instillation can be carried out by delivering a solution into the lungs via a device, such as a syringe.

Intranasal administration which can be employed to effect pulmonary administration can be used specifically for administration to the nasal cavity and sinuses. Devises for intranasal administration include, but are not limited to liquid drop devices, spray devices, dry powder devices and aerosol devices. Intranasal administration can also be by nasal gel or insuffulations.

Formulation of the compounds described herein as aerosols (solid or liquid particles), liquids, powders, gels, nanoparticles may be obtained using standard procedures well known in the art.

The compositions may also be administered parenterally, for example, intravenously, intra-arterially, intraperitoneally, intrathecally, intraventricularly, intraurethrally, intrasternally, intracranially, intramuscularly, or subcutaneously. Such administration may be as a single bolus injection, multiple injections, or as a short- or long-duration infusion. Implantable devices (e.g., implantable infusion pumps) may also be employed for the periodic parenteral delivery over time of equivalent or varying dosages of the particular formulation. For such parenteral administration, the compounds may be formulated as a sterile solution in water or another suitable solvent or mixture of solvents. The solution may contain other substances such as salts, sugars (particularly glucose or mannitol), to make the solution isotonic with blood, buffering agents such as acetic, critric, and/or phosphoric acids and their sodium salts, and preservatives.

The compositions can be formulated as pharmaceutical compositions and administered to a mammalian host, such as a human patient in a variety of forms adapted to the chosen route of administration, e.g., by pulmonary routes, orally or parenterally, by intravenous, intramuscular, topical or subcutaneous routes.

Thus; the present compositions may be systemically administered, e.g., orally; in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compositions may be combined with one or more excipients and used in the form of ingestible tablets, buccal tablets, troches, capsules, elixirs; suspensions, syrups; wafers, and the like. Such compositions and preparations should contain at least 0.1% of active compound. The percentage of the compositions and preparations may, of course, be varied and may conveniently be between about 2 to about 60% of the weight of a given unit dosage form. The amount of adjuvants in such useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the adjuvants or other agents may be incorporated into sustained-release preparations and devices.

The compositions may also be administered intravenously or intraperitoneally by infusion or injection, Solutions of the compositions can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms during storage can be brought about by various antibacterial and antifungal agents, for example, parabens, chlorobutanol, phenol, sorbic acid, thimerosal, and the like. In many cases, it may be useful to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating compound(s) in the required amount in the appropriate solvent with various of the other ingredients enumerated above, as required, followed by filter sterilization. In the case of sterile powders for the preparation of sterile injectable solutions, one method of preparation includes vacuum drying and the freeze drying techniques, which yield a powder of the active ingredient plus any additional desired ingredient present in the previously sterile-filtered solutions.

For topical administration, the compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages can be determined by comparing their in vitro activity, and in vivo activity in animal models. Methods for the extrapolation of effective dosages in mice, and other animals, to humans are known to the art; for example, see U.S. Pat. No. 4,938,949. The ability of a compound to act as a TLR agonist may be determined using pharmacological models which are well known to the art, including the procedures disclosed by Lee et al., *Proc. Natl. Acad. Sci. USA,* 100: 6646 (2003).

Generally, the concentration of the active compound in a liquid composition, such as a lotion, will be from about 0.1-25 wt-%, e.g., from about 0.5-10 wt-%. The concentration in a semi-solid or solid composition such as a gel or a powder will be about 0.1-5 wt-%, e.g., about 0.5-2.5 wt-%.

The active ingredient may be administered to achieve peak plasma concentrations of the active compound of from about 0.5 to about 75 μM, e.g., about 1 to 50 μM, such as about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The amount of the active compound, or an active salt or derivative thereof, required for use in treatment, e.g., in conjunction with a vaccine, will vary not only with the particular salt selected but also with the route of administration, the nature of the condition being treated and the age and condition of the patient and will be ultimately at the discretion of the attendant physician or clinician. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, for instance in the range of 6 to 90 mg/kg/day, e.g., in the range of 15 to 60 mg/kg/day, More than one dose (e.g., 2, 3, 4, 5, 6, 7, 8, 9, 10, 11, 12, 13, 14, 15, 16, 17, 18, 19, 20, 21, 22, 23, 24, 25, 26, 27, or 28, or, for example, 35, 42, 49, 56, 63, or 70) may be determined by a physician or clinician to be required. Doses of formula (I), formula (II), or vaccine, or any combination thereof, may be administered before, after, or before and after exposure to the infectious agent as determined by a physician or clinician based on the above discussed factors and other relevant factors. Scheduling of administration of doses (e.g., consecutive days, alternate days, multiple doses in one day) can also be determined by a physician or clinician based on the above discussed factors and other relevant factors.

The duration of treatment can be for a predetermined period of time. For example, 1, 2, 3, 4, 5, 6, 7 or more days, one week, two weeks, three weeks, four weeks or more. Alternatively, the duration of treatment can be for a period of time until the infectious agent is no longer detectable in the subject or the infectious agent is present at a level that does not result in symptoms or until there is an elimination or reduction in the number or severity of symptoms typically exhibited by a subject infected with a specific infectious agent. The duration of treatment can be determined by a physician or clinician based on the above discussed factors and other relevant factors.

The active compounds may be conveniently administered in unit dosage form; for example, containing 5 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. The dose, and perhaps the dose frequency, will also vary according to the age, body weight, condition, and response of the individual patient. In general, the total daily dose range for an active agent for the conditions described herein, may be from about 50 mg to about 5000 mg, in single or divided doses. In some embodiments, a dose range should be about 100 mg to about 4000 mg, e.g., about 1000-3000 mg, in single or divided doses, e.g., 750 mg every 6 hr of orally administered compound. This can achieve plasma levels of about 500-750 uM, which can be effective to kill cancer cells. In managing the patient, the therapy should be initiated at a lower dose and increased depending on the patient's global response.

In some embodiments the compound is not administered with a solvent or preservative such as DMSO or ethanol, which may have toxic effects, e.g., in humans.

EXEMPLARY EMBODIMENTS

In one embodiment, a method of enhancing or prolonging an immune response is provided. The method includes administering to a mammal in need thereof a vaccine, and an effective amount of at least two adjuvants, at least one adjuvant and one or more TLR ligands, at least one adjuvant and at least one MAP kinase inhibitor, or a combination thereof, wherein at least one adjuvant comprises a bis-aryl sulfonamide. In one embodiment, the bis-aryl sulfonamide derivative comprises formula (II):

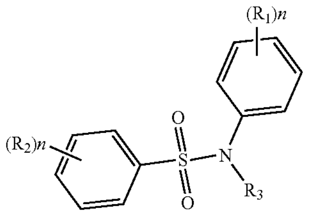

wherein n is an integer from 1 to 4;

wherein $R_1$ and $R_2$ are independently hydrogen, halogen, nitro, azido, hydroxyl; amino, alkylamino, —$CF_3$, carboxylic acid, —OR', or —COXR'; and wherein is $C_1$-$C_{14}$ saturated or unsaturated alkyl, saturated or unsaturated cycloalkyl, saturated or unsaturated heterocycloalkyl, aryl or heteroaryl, substituted or unsubstituted aralkyl, or —$(CH_2)_m$—Y, where m is an integer from 1 to 10 and Y is —NHR', OR', COXR', wherein X is O or NH, wherein R' is a $C_1$-$C_6$ alkyl, cycloalkyl, heterocycloalkyl, aryl, heteroaryl, isothiocyanate, —COR", wherein R" is, for example, biotin, fluorescent molecules such as Rhodamine B or Fluorescein, or N-hydroxy succinimide; or wherein $R^3$ is H, -L1-G, $C_1$-$C_{14}$ saturated or unsaturated alkyl, saturated or unsaturated cycloalkyl, saturated or unsaturated heterocycloalkyl, aryl or heteroaryl, substituted or unsubstituted aralkyl, or —$(CH_2)_m$—Y, or comprises an antigen or an adjuvant, where m is an integer from 1 to 10 and Y is —NHR', OR', COXR', wherein X is O or NH, wherein R' is a $C_1$-$C_6$ alkyl, cycloalkyl, heterocycloalkyl, aryl, heteroaryl, isothiocyanate, COR", wherein R" is, for example, biotin, fluorescent molecules such as Rhodamine B or Fluorescein, or N-hydroxy succinimide, and L1 is a divalent linker comprising one or more alkylene, arylene, heteroarylene, alkylamine, alkylamide, alkylether, alkylester, alkylthio, acyl, diacyl, diester, diamine, diamide, cycloalkyl, and G is a protein-reactive electrophilic functional group, an immune potentiator, or an enzyme-cleavable group;

or

L1 is a divalent linker comprising one or more alkylene, arylene, heteroarylene, alkylamine, alkylamide, alkylether, alkylester, alkylthio, acyl, diacyl, diester, diamine, diamide, cycloalkyl, oxy, carbonyl, amino, thio, sulfinyl, or sulfonyl, each which is independently substituted or unsubstituted, or a bond, and G is a protein-interactive functional group, an immune potentiator, or an enzyme-cleavable group;

or a salt, ester, or prodrug thereof.

In one embodiment, the mammal is a human. In one embodiment, one of the adjuvants comprises LPS or MPLA. In one embodiment, the TLR ligand is a TLR4 or TLR7 ligand. In one embodiment, the TLR ligand comprises 1V270. In one embodiment, at least two adjuvants are administered. In one embodiment, at least one adjuvant and one or more TLR ligands are administered. In one embodiment, at least one adjuvant and at least one MAP kinase inhibitor are administered.

Also provided is a method of enhancing or prolonging an immune response, that includes administering to a mammal in need thereof an effective amount of at least one adjuvant and at least one MAP kinase inhibitor, wherein at least one adjuvant comprises a bis-aryl sulfonamide.

Further provided is a method of enhancing or prolonging an immune response, that includes administering to a mammal in need thereof an effective amount of at least two adjuvants, wherein at least one adjuvant comprises a bis-aryl sulfonamide.

In one embodiment, the bis-aryl sulfonamide comprises a compound of formula (II). In one embodiment, $R^3$ is H, -L1-G, $C_1$-$C_{14}$ saturated or unsaturated alkyl, saturated or unsaturated cycloalkyl, saturated or unsaturated heterocycloalkyl, aryl or heteroaryl, substituted or unsubstituted aralkyl, or —$(CH_2)_m$—Y, or comprises an antigen or an adjuvant, where m is an integer from 1 to 10 and Y is —NHR', OR', COXR', wherein X is O or NH, wherein R' is a $C_1$-$C_6$ alkyl, cycloalkyl, heterocycloalkyl, aryl, heteroaryl, isothiocyanate, COR", wherein R" is, for example, biotin, fluorescent molecules such as Rhodamine B or Fluorescein, or N-hydroxy succinimide, L1 is a divalent linker comprising one or more alkylene, arylene, heteroarylene, alkylamine, alkylamide, alkylether, alkylester, alkylthio, acyl, diacyl, diester, diamine, diamide, cycloalkyl, and G is a protein-reactive electrophilic functional group, an immune potentiator, or an enzyme-cleavable group. In one embodiment, $R^3$ is H. In one embodiment, R3 is -L1-G, L1 is a divalent linker comprising one or more alkylene, arylene, heteroarylene, alkylamine, oxy, amino, thio, oxo, sulfinyl, sulfonyl, alkylamide, alkylether, alkylester, alkylthio, acyl, diacyl, diester, diamine, diamide, or cycloalkyl, or a bond, and G is a protein-reactive electrophilic functional group, an immune potentiator, or an enzyme-cleavable group. In one embodiment, G is an isocyanate, an isothiocyanate, alkyl, alkenyl, alkynyl, aryl, aralkyl, alkyloxycarbonyl, alkenyloxycarbonyl, alkynyloxycarbonyl, aryloxycarbonyl, aralkyloxycarbonyl, alkylcarbonyl, alkenylcarbonyl, alkynylcarbonyl, arylcarbonyl, aralkylcarbonyl, carboxylic acid, carboxylate, amino, ammonium, N-succinimidyl, N-maleimidyl, N-succinimidyloxy, N-maleimidyloxy, N-succinimidyloxycarbonyl, and N-maleimidyloxycarbonyl, each of which is independently substituted or unsubstituted. In one embodiment, G is aryl, heteroaryl, or heterocyclyl. In one embodiment, G is succinimide, maleimide, or n-hydroxysuccinirnide or wherein G is phenyl, benzyl, N-succinimidyl, N-maleimidyl, N-succinimidyloxy, N-maleimidyloxy, N-succinimidyloxycarbonyl, and N-maleimidyloxycarbonyl, each of which is unsubstituted. In one embodiment, G is 8-oxoadenine or a derivative thereof. In one embodiment, G is a TLR-7 agonist. In one embodiment, L1 comprises a product of click chemistry. In one embodiment, L1 comprises an enzyme-hydrolysable bond. In one embodiment, L1 comprises a carbamate, an amide, or both. In one embodiment, L1 comprises a substituted or unsubstituted benzyl, a substituted or unsubstituted dimethylenephenylene, or any combination thereof. In one embodiment, L1 comprises a substituted or unsubstituted benzamide, a substituted or unsubstituted benzoyl, or any combination thereof. In one embodiment, L1 comprises a 1,3-diamino, 1,3-diacyl, 1,3-diester, a 1,3-diamide, or any combination thereof. In one embodiment, L1 comprises a $C_1$-$C_{10}$ alkylene linkage, an $C_6$-arylene, a $C_2$-$C_8$-heteroarylene, a $C_3$-C-cycloalkyl, a $C_2$-$C_{10}$alkylene, $C_1$-$C_{10}$ acyl, $C_2$-$C_{10}$ diacyl, oxy, amino, or thio. In one embodiment, L1 comprises 1,3-diaminopropyl, 1,4-diaminobutyl, propanyl, butanoyl, malonyl, succinyl, malonate, acetoacyl, acetoacetate, benzyl, m-dimethylenephenylene, benzyl, benzoyl, amino, or oxy. In one embodiment, G and L1, taken together, is benzyl, benzylamide, benzylcarbamate, benzylester, benzoyl, or benzamide. In one embodiment, G and L1 taken together, is p-aminomethylbenzyl, m-aminomethylbenzyl, or N-protected forms thereof, or wherein G and L1, taken together, is alkylcarbamate.

In one embodiment, a compound of formula (II) which is not compound 1 herein is provided. In one embodiment, $R^3$ comprises an adjuvant or an antigen. In one embodiment, $R_3$ is H, $C_1$-$C_{14}$ saturated or unsaturated alkyl, saturated or unsaturated cycloalkyl, saturated or unsaturated heterocycloalkyl, aryl or heteroaryl, substituted or unsubstituted aralkyl, or —$(CH_2)_m$—Y, where m is an integer from 1 to 10 and Y is —NHR', OR', COXR', wherein X is O or NH, wherein R' is a $C_1$-$C_6$ cycloalkyl, heterocycloalkyl, aryl, heteroaryl, isothiocyanate, —COR", wherein R" is, for example, biotin, fluorescent molecules such as Rhodamine B or Fluorescein, or N-hydroxy succinimide, L1 is a divalent linker comprising one or more alkylene, arylene, heteroarylene, alkylamine, alkylamide, alkylether, alkylester, alkylthio, acyl, diacyl, diester, diamine, diamide, cycloalkyl, and G is a protein-reactive electrophilic functional group, an immune potentiator, or an enzyme-cleavable group. In one embodiment, $R^3$ is H. In one embodiment, R3 is -L1-G, L1 is a divalent linker comprising one or more alkylene, arylene, heteroarylene, alkylamine, oxy, amino, thio, oxo, sulfinyl, sulfonyl, alkylamide, alkylether, alkylester, alkylthio, acyl, diacyl, diester, diamine, diamide, or cycloalkyl, or a bond, and G is a protein-reactive electrophilic functional group, an immune potentiator, or an enzyme-cleavable group. In one embodiment, G is an isocyanate, an isothiocyanate, alkyl, alkenyl, alkynyl, aryl, aralkyl, alkyloxycarbonyl, alkenyloxycarbonyl, alkynyloxycarbonyl, aryloxycarbonyl, aralkyloxycarbonyl, alkylcarbonyl, alkenylcarbonyl, alkynylcarbonyl; arylcarbonyl; aralkylcarbonyl, carboxylic acid, carboxylate, amino, ammonium, N-succinimidyl, N-maleimidyl, N-succinimidyloxy, N-maleimidyloxy, N-succinimidyloxycarbonyl, and N-maleimidyloxycarbonyl, each of which is independently substituted or unsubstituted. In one embodiment, G is aryl, heteroaryl, or heterocyclyl. In one embodiment, G is succinimide, maleimide, or n-hydroxysuccinimide or wherein G is phenyl; benzyl, N-succinimidyl, N-maleimidyl, N-succinimidyloxy, N-maleimidyloxy; N-succinimidyloxycarbonyl, and N-maleimidyloxycarbonyl, each of which is unsubstituted. In one embodiment, G is 8-oxoadenine or a derivative thereof. In one embodiment, G is a TLR-7 agonist. In one embodiment, L1 comprises a product of click chemistry. In one embodiment, L1 comprises an enzyme-hydrolysable bond. In one embodiment, L1 comprises a carbamate, an amide, or both. In one embodiment, L1 comprises a benzyl, a dimethylenephenylene, or both. In one embodiment, L1 comprises a benzamide, a benzoyl, or both. In one embodiment, L1 comprises a 1,3-diamino, 1,3-diester; a 1,3-diamide; or any combination thereof. In one embodiment, L1 comprises a $C_1$-$C_{10}$ alkylene linkage, an $C_6$-arylene, a $C_2$-$C_8$-heteroarylene, a $C_3$-C-cycloalkyl; a $C_2$-$C_{10}$ alkylene; acyl, $C_2$-$C_{10}$ diacyl, oxy, amino, or thio. In one embodiment, L1 comprises 1,3-diaminopropyl, 1,4-diaminobutyl, propanoyl, butanoyl, malonyl, succinyl, malonate, acetoacyl, acetoacetate, benzyl, m-dimethylenephenylene, benzyl, benzoyl, amino, or oxy. In one embodiment, G and L1, taken together, is benzyl, benzylamide, benzylcarbamate, benzylester, benzoyl, or benzamide. In one embodiment, G and L1, taken together, is p aminomethylbenzyl, m-aminomethylbenzyl, or N-protected forms thereof, or wherein G and L1, taken together, is alkylcarbamate. In one embodiment, the compound is

65

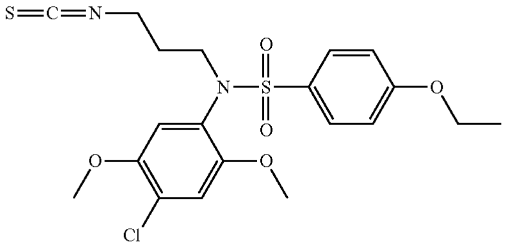

-continued

66

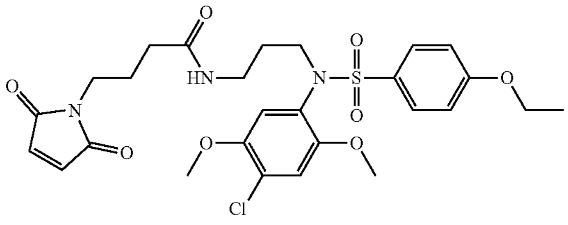

67

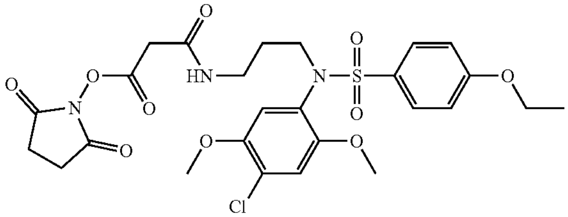

68

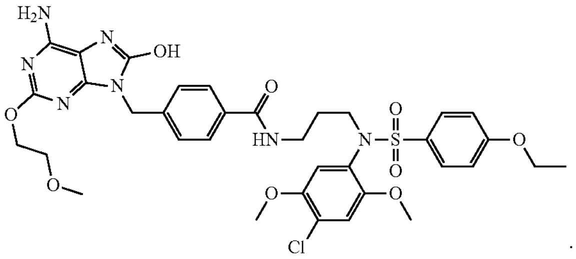

.

69

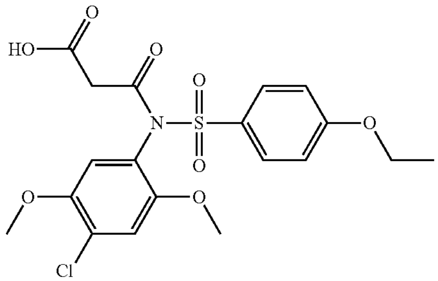

70

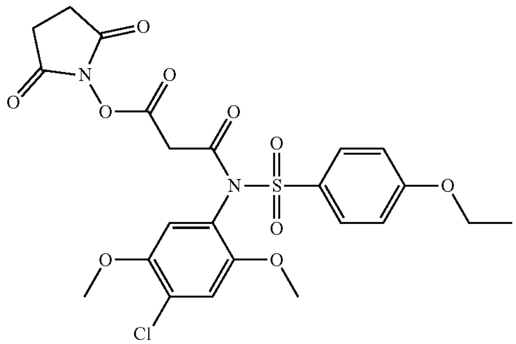

-continued

71

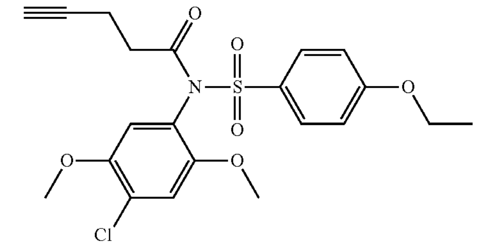

72

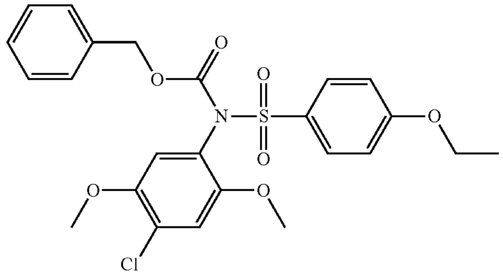

73

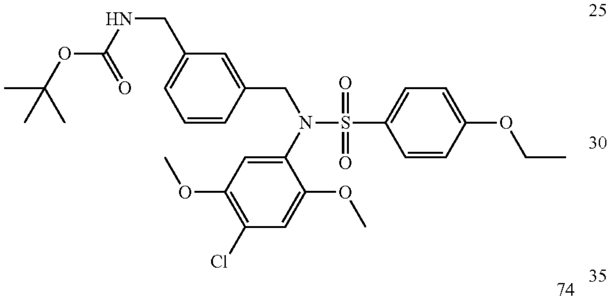

74

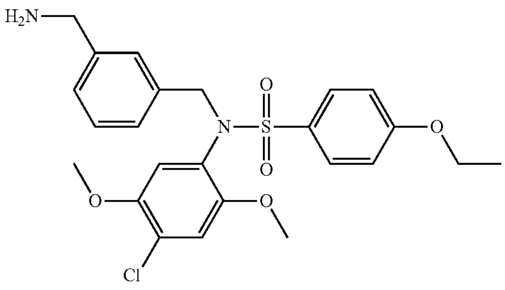

75

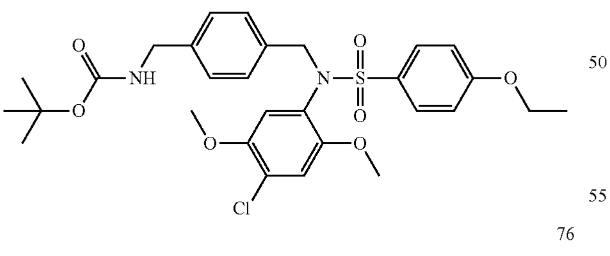

76

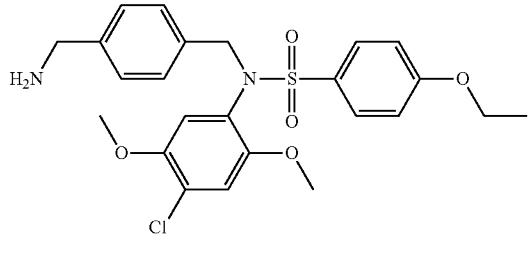

or

-continued

55

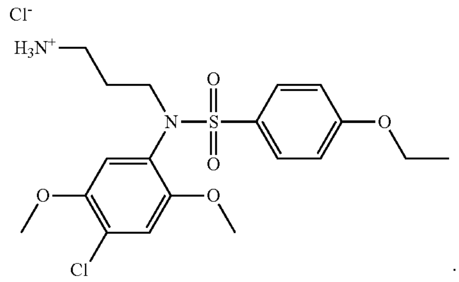

.

In one embodiment, the compound is in salt, prodrug, or ester form.

Further provided is a self-adjuvating vaccine construct comprising a compound of formula (II).

Also provided is a pharmaceutical composition comprising the compound of formula (II). In one embodiment, the composition further comprised an antigen. In one embodiment, the composition further comprises an adjuvant.

The invention will be further described by the following non-limiting examples.

Example 1

The approach towards identifying novel co-adjuvants focused on small molecules that sustain the activation of a primary adjuvant. The rationale behind the approach is as follows: Upon vaccine administration, local antigen presenting cells (APCs) at the site of injection, such as dendritic cells and Langerhans cells, are activated by adjuvant. These APCs engulf antigen and travel to local draining lymph nodes where the antigen is presented to T cells (Forster et al., 2012). The activation levels of APCs induced by these adjuvants, peaks at 2-6 hours and then decays due to negative feedback mechanisms (Qian et al., 2013; Turnis et al., 2010; Yuk et al., 2011; Ho et al., 2012; Liu et al., 2010; Ma et al., 2010; An et al., 2006; Kondo et al., 2012). Because it takes approximately 12-24 hours for an APC to travel to the lymph node after vaccination (Martin-Fontecha et al., 2009), APCs are arriving during the decay phase of the activation. Thus, we hypothesize that prolonging or sustaining the activation of APCs induced by an adjuvant for 12-24 hours will lead to optimal presentation of antigen to the T cells which would enhance the initial immune response and potentially allow for a longer lasting response. Our hypothesis is supported by reports that enhanced responses to vaccinations were observed in mice with genetic disruption of either interleukin-1 receptor-associated kinase-M (IRAK-M), an inhibitor of the nuclear factor kappa B (NF-κB) pathway (Trunis et al., 2010), or of UBP43, a negative regulator of type 1 IFN signaling (Kim et al., 2005). Thus, to address this issue, we sought HTS methods directed towards identification of co-adjuvants that prolonged activation of an immune response induced by a primary stimulus (Chan et al., 2017; Shukla et al., 2018b).

These cell based HTS campaigns tested protraction of a TLR-4 agonist lipopolysaccharide (LPS) stimulus through the NF-κB pathway (Chan et al., 2017) or IFN-α signaling via the interferon stimulating response element (ISRE) (Shukla et al., 2018b) pathway. Compounds that prolonged LPS induced NF-κB signaling included a distinct set of pyrimido[5,4-b]indoles that were also found to be effective co-adjuvants with MPLA, an FDA approved adjuvant, in murine vaccination studies (Chan et al., 2017). In parallel, compounds that prolonged IFN-α induced ISRE signaling in vitro were also evaluated as co-adjuvants in vivo (Shukla et al., 2018b) which led to identification of a potent bis-aryl sulfonamide compound 1 bearing 4-chloro-2,5-dimethoxy and 4-ethoxy substituted phenyl groups connected by a sulfonamide functional group. The further drug development of such hits identified through cell-based phenotypic assays and involved in cell signaling pathways is hampered without the knowledge of the target receptor or the compound's mechanism of action (Schenone et al., 2013).

This necessitated evaluation of structural variations for compound 1 that were unexplored in the HTS with an aim to identify positions on the scaffold that can tolerate the introduction of small functional groups such as aryl azide or diazirine to make photoreactive probes or large substituents such as biotin and fluorescence moieties to generate affinity and fluorescent probes, respectively (Pan et al., 2016; Smith et al., 2015; Sumranjit & Chung, 2013; Kan et al., 2007; Ban et al., 2016; Kawada et al., 1989; Shukla et al., 2010). These chemical probes would then be useful tools for future mechanistic and functional receptor studies. In addition, the chemical handle would allow one to covalently conjugate the small molecule to peptides or protein antigens to make self-adjuvanting vaccine constructs which are widely explored in vaccine development (Shukla et al., 2011; Fagan et al., 2017; Gential et al., 2019; Li et al., 2018; Liao et al., 2019; Nevagi et al., 2019).

Results and Discussion: Approximately 3400 differently substituted bis-aryl sulfonamide compounds were screened in the original HTS libraries and a scatter plot showing activation data for these compounds in both cell-based NF-κB and ISRE assays prepared. These results provided preliminary SAR analysis indicating the substituents on the two aryl rings necessary for activity and pointed to compound 1 as an advanced lead, Hence, further SAR studies on compound 1 were conducted by first identifying three areas (sites A, B and C) of potential modification. To standardize the reaction, we began with synthesis of compound 1 by reaction of 4-ethoxysulfonyl chloride (3a) and 4-chloro-2,5-dimethoxy aniline (2a) in the presence of an organic base (Scheme 1). However, the reaction not only provided the desired compound 1, but also formed the bissulfonamide side-product in high yields. This undesired side-product was formed in situ by further reaction of compound 1 with another equivalent of 4-ethoxysulfonyl chloride (3a). This bis-sulfonamide side-product was isolated but was somewhat unstable. Limited hydrolysis by lithium hydroxide facilitated the complete conversion of this bissulfonamide side-product to compound 1 without further hydrolysis of the mono-sulfonamide bond thereby improving reaction yields for compound 1 (Scheme 1). This reaction strategy was utilized for synthesis of several site A and site B modified compounds for SAR analysis.

SAR studies were initiated by modifying the substituents at site A. These compounds were synthesized according to Scheme 1 using different anilines (2a-h). The removal of one aryl substituent at a time was investigated, leading to compounds 4, 5, and 6 lacking the 2-methoxy, 3-methoxy and 4-chloro substituent, respectively. Replacement of 4-chloro by a 4-bromo substituent gave compound 7 and migration of the 2-methoxy substituent to the 3-position gave compound 8. These compounds were evaluated for sustained activation of both NF-κB and ISRE pathways using LPS and IFN-ca as primary stimuli, respectively. The SAR studies pointed to the importance of the methoxy substituents at the 2 and 5 positions of the aryl ring, because either removal of any one of the substituents as in compound 4 and 5 or its displacement to another position on the ring as in 8 led to complete loss of activity. Removal of the 4-chloro as in compound 6 or its replacement with a spatially larger bromo substituent as in compound 7 retained activity (Table 1). Thus, to further explore position 4 on the phenyl ring, analogs were synthesized with 4-nitro (9) substitution and its 4-amino (10) derivative. However, both these analogs were inactive suggesting that only hydrophobic substituents at this site are tolerated (Table 1).

Next, site B was altered as shown in FIG. 1. The compounds were synthesized as discussed earlier (Scheme 1) using different aryl sulfonyl chlorides (3a-p) and 4-chloro-2,5-dimethoxy aniline (2a). Some of the aryl sulfonyl chlorides were commercially available, while the others were synthesized. The homologous series of 4-O-alkylated compounds were prepared starting with 4-hydroxy analog 11, 4-methoxy analog 12, 4-propoxy analog 13 and 4-butoxy analog 14 compared to 4-ethoxy analog compound 1. Bioactivity evaluation of these compounds showed that only the smaller homolog as in 4-methoxy compound 12 was tolerated while the hydrophilic interaction with hydroxy group of 11 without any hydrophobic alkyl group was not tolerated. The higher 4-alkoxy chains showed gradual loss of activity (Table 2), While the 4-propoxy substituted compound was weakly active, the 4-propargyloxy compound 15, designed to use the alkyne as a handle for click chemistry reaction, was found to be inactive. Removal of the ether oxygen to obtain 4-propyl substituted compound 16 also led to loss of activity suggesting a crucial role of hydrogen bond interaction by the ether oxygen. Other functional groups that could be involved in such hydrogen bond interactions led to the syntheses of 4-nitro analog 17 and its amine bearing derivative 18 (Scheme 2) obtained by reduction of the nitro group. Also, the 4-nitrile analog 19, N-Boc methylamine derivative 20 obtained by in situ N-Boc protection during the reduction of the nitrile group and its free methylamine derivative 21 (Scheme 2) were synthesized. All these compounds were also evaluated but found to be either weakly active or completely inactive. A prior report indicated that analogs bearing a 4-O-phenyl substitution exhibited ubiquitin ligase inhibition activity (Ramesh et al., 2005), so the 4-O-phenyl analog 22 was synthesized, but this compound was inactive. Encouraged by the activity of 4-methoxy substituted analog 12, 3-methoxy and 2-methoxy substituted compounds 23 and 24, respectively, were synthesized. However, none of these molecules was active. In order to find an additional handle for modification, bromine was introduced to obtain a 3-bromo-4-methoxy substituted compound 25, which was also found to be inactive. Learning from the requirement of a hydrogen bonding functional group at site B for activity, we probed the addition of another oxo-containing group to obtain the 4-methylester analog 26 and an amide analog 27. Ester hydrolysis of compound 26 yielded the 4-carboxyl derivative 28 (Scheme 2). While the methyl ester bearing analog 26 was active, the hydrolyzed carboxylic acid analog 28 and the amide linked compound 27 lost activity (Table 2). Hypothesizing that the lack of hydrophobic alkyl group interaction could be a cause for the loss of activity, compound 28 was further derivatized to obtain the ethyl ester analog 29, and the Nmethylamide analog 30 (Scheme 2). While analog 29 retained partial activity, compound 30 was completely inactive suggesting that only hydrogen bond accepting substituents were tolerated (Table 2). An additional analog (compound 31, Scheme 1) was synthesized by inversing the sulfonamide bond obtained by reaction of 2-ethoxyaniline and 4-chloro-2,5-dimethoxybenzenesulfonyl chloride, but the inactivity of this analog suggested that the positioning of the sulfonamide functional group was also critical for activity.

Moving forward, the expansion at site C on the nitrogen of the sulfonamide function of compound 1 was investigated. These compounds were synthesized by derivatization of compound 1 as shown in Scheme 3. The first extensive series of compounds were the N-alkylated derivatives including N-methyl (33). N-propyl (34), N-butyl (35), N-pentyl (36), N-hexyl (37). N-heptyl (38), and N-dodecyl (39). A clear correlation of bioactivity with the alkyl chain length was observed with potency gradually decreasing with increased alkyl chain length and compounds bearing alkyl chain length greater than N-pentyl were completely inactive (Table 3). The effect of steric bulk around the core structure was investigated by synthesizing N-isopropyl (40) and N-isobutyl (41) derivatives. Steric bulk closer to the core structure, as in compound 40, eliminated the NF-κB activity while retaining ISRE activity. In contrast, spacing the isopropyl group away by one methylene unit as in compound 41 regained the activity in both the NF-κB and ISRE assays. Encouraged by these results, alkyne bearing compounds were synthesized with an additional aim to utilize the functional group as a biorthogonal reactive site. A homologous series of alkyne bearing molecules including N-propargyl (42), N-butynyl (43), and N-pentynyl (44) were synthesized (Scheme 3). Activity data showed that while N-alkyl derivatization with increasing alkyl chain length led to dramatic loss of activity, the corresponding N-alkynyl derivatives retained activity almost equivalent to that of compound 1 (Table 3) for the corresponding alkyl chain length.

The retention of activity for the N-alkynyl compounds compared to loss in activity for the analogous N-alkyl derivatives for the same carbon unit chain length suggested the possible involvement of π-π interactions in near proximity with the target receptor(s). A triethyleneglycol linked alkyne derivative (45) was evaluated to conveniently place the reactive functional group distant from the core. However, the 12-atom chain length equivalent to N-dodecyl compound 39 was too long to retain activity.

These results for the alkyne bearing compounds led to making compounds where substituents can form enhanced π-π interactions. Thus N-benzyl (46) and N-phenethyl (47) derivatives were synthesized and were also found to be potent analogs (Table 3). Since the Nisopropyl analog 40 was inactive, it was determined if steric bulk was the only reason for its inactivity and if that could be mitigated by some hydrogen bonding functional group such as acetyl. Thus, the N-acetyl derivative (48) was synthesized and the bioactivity assays showed that the compound was active. However, before proceeding with syntheses of additional acylated analogs, its stability in stock solutions was evaluated since during the assay this compound could behave as a prodrug by undergoing deacetylation to release active compound 1. While the stock of compound 48 in DMSO was stable, incubation of compound with assay media showed release of compound 1 (data not shown), suggesting that the bioactivity could be due to a prodrug effect and not true interaction with the receptor. Thus, syntheses of additional acylated analogs were not pursued.

Since the hydrophobic alkyl and alkynyl groups were well tolerated at site C, it was examined if incorporating a hydrophilic group that could serve as a handle for further chemical modification would be acceptable for activity. A pair of compounds bearing a precursor to a reactive handle such as carboxylic esters were synthesized by alkylation of compound 1 to obtain the N-ethyl glycinate (49) and N-ethyl butanoate (50) analogs (Scheme 3). Attempts to make a stable propionate analog failed after several attempts likely due to retro Michael type reaction, and despite isolating a few milligrams of the tert-butyl propionate ester derivative, activity studies were not pursued due to stability concerns. Both the ethyl ester substituted compounds 49 and 50 retained dual NF-κB and ISRE activities (Table 3). To avoid additional substitution closer to the core sulfonamide pharmacophore, we chose propylene spacer for further analogs. A terminal hydroxy bearing analog as in N-propan-3-ol (51) and the N-Boc protected aminopropane analog (52) were then synthesized. The ethyl ester of compound 50 was de-esterified using lithium hydroxide to obtain its carboxylic acid analog 53, which was converted to the ethyl amide analog 54 (Scheme 4). Similarly, a free amine bearing molecule was obtained by N-Boc deprotection of 52 to obtain compound 55. Biological evaluation showed that the terminal hydroxy analog 51 retained activity in both the assays while the N-Boc protected compound 52 showed reduction in activity, which was recovered when the N-Boc group was removed as in compound 55, Both the free carboxylic acid and ethyl amide derivatives retained activity, which was more skewed towards the NF-κB pathway (Table 3).

All these compounds were evaluated for toxicity using 3-(4,5-dimethylthiazol-2-yl)-2,5-diphenyltetrazolium bromide (MTT) assays. All the active compounds showed viability between 69% and 81%. Some of the inactive compounds were completely non-toxic. Compound 47 with the N-phenethyl substitution was an exception showing somewhat higher toxicity (% viability=44%) suggesting that an aryl group connected by an ethylene unit near the core sulfonamide structure may lead to toxicity (Tables 1-3).

The bioactivity data from both the assays for all the compounds were plotted to verify the correlation between the chemical structure and bioactivity. Most of the compounds were active in both NF-κB and ISRE bioassays and showed a good correlation (Pearson two-tailed, $R^2$=0.6812, P<0.0001). The SAR trends however varied depending on the site of modification. Site A modifications involving removal of the methoxy substituent (compounds 4 and 5) led to significant loss of activity. On the other hand, nonpolar modifications at position 4 of site A (compounds 7 and 8) showed slightly skewed ISRE activity compared to compound 1, while hydrogen bond forming substituents at this position led to loss of activity (compounds 9 and 10). Most of the site B modified compounds were inactive suggesting restricted SAR tolerance due to limited spatial availability in the target receptor. Only short alkyl groups connected via ether-linkage as in compounds 1, 12 and 13 or carboxyl (ester)-linkage as in compounds 26 and 29 retained activity. A good correlation was seen, however, between the two assays for these compounds. In contrast, most of the site C modified compounds were active in both the bioassays suggesting that only a part of the substituent may be involved in receptor interaction and the rest of the group subtends out of the target receptor(s). A notable variation was observed in sterically hindered bulky groups close to the core structure as in compound 40 which led to a loss of NF-κB activity, while still retaining ISRE activity. On the other hand, another subset of compounds bearing a reactive handle such as carboxylic acid analog 53 and its amidated derivative 54, showed reduction in ISRE activity while retaining the NF-κB activity. This suggested that a negative charge on the compound may be a deterrent for ISRE activity.

Continuing with the focus on compounds that retain dual NF-κB and ISRE activity similar to original hit compound 1, site B modified compound 12, site C modified compound 33 and an aliphatic amine bearing compound 55 were selected for dose response experiments and $EC_{50}$ determination as these compounds are nearly equipotent in both the assays when evaluated at 5 μM concentration. Both compounds 12 and 33 showed relatively higher NF-κB activity at 5 μM concentration, but the activity of compound 12 decreased faster at lower concentrations which led to $EC_{50}$ value of 1.85 μM. Compound 1 and 33 were almost equipotent with $EC_{50}$ values of 0.60 μM and 0.69 μM, respectively. Compound 55 was relatively weaker with $EC_{50}$ of 3.32 μM. The potency trends for these compounds remained the same in ISRE activity with compounds 1, 12 and 33 exhibiting $EC_{50}$ of 0.66 μM, 1.4 μM, and 0.84 μM, respectively, and compound 55 with $EC_{50}$=3.04 μM. Even though the activity of compound 55 was slightly attenuated, the amine handle can be utilized for derivatization to obtain affinity probes.

The adjuvanticity of select compounds was assessed to verify if prolongation of immune stimulus by this chemotype leads to enhancement of in vivo antibody responses and if prolonged activation of the innate immune system could lead to systemic inflammation that may be harmful to the host (Cooks et al., 2012; Perez et al., 2015). All the compounds administered to mice had low toxicity in the MTT assays. Since these vaccine co-adjuvants are designed to be administered locally (mostly intramuscularly) and show negligible toxicity (based on MTT data), an excessive systemic inflammatory response was not expected. LPS is a widely recognized activator of the innate immune system and well characterized TLR-4 ligand to screen over 160,000 compounds for their ability to enhance APC activation (Chan et al., 2017; Shukla et al., 2018b). However, to test these compounds for potency as co-adjuvants, MPLA (a TLR4 ligand) was selected for in vivo evaluation. Immunization experiments in mice (8 mice/group) were performed to evaluate the coadjuvanticity of the lead compounds 1, 12 or 33 using ovalbumin (OVA) as a model antigen and MPLA as an adjuvant. Amine handle bearing compound 55 was not selected for immunization since it was designed for further derivatization as an intermediate to make probes as discussed below. Examination of OVA-specific IgG antibodies showed that co immunization of MPLA with compounds 1 and 33 induced statistically significant increases in antigen-specific antibody titers when compared to mice immunized with MPLA alone, without demonstrable systemic toxicity, as indicated by behavior change or weight loss. These results verified the approach that selected bis-aryl sulfonamide compounds that prolong immune stimulation could enhance the adjuvanticity of MPLA.

After confirming the in vitro and in vivo potency of selected active compounds, SAR studies were conducted for designing affinity probes. The activity data guided us to utilize site C for the introduction of an identifiable tag by derivatizing compound 55. Although compound 55 was less potent than compound 1, the changes in the hydrophobic interaction after amine derivatization may improve the potency. Compound 55 was derivatized to obtain fluorescein labeled compound 56, rhodamine labeled compound 57 and biotin labeled compound 58 (Scheme 5). In primary screens, the biotin labeled compound 58 was equipotent to compound 1 and thus could serve as the affinity probe (Table 4). The rhodamine analog 57 showed reduced activity compared to compound 1 in both the NF-κB and ISRE assays likely due to the presence of a fixed charge on the molecule similar to the amine bearing compound 55. In contrast, the fluorescein analog 56 was completely inactive in both the assays (Table 4).

Having validated specific site C modifications that tolerated the introduction of a trackable tag, it was investigated if there was a position where a photoreactive group such as aryl azide could be introduced to make photoaffinity probes. This prompted derivatization of compounds 10 and 25, even though these were inactive but surmising that a change in the hydrogen bonding properties may have an opposite effect. The aromatic amine on position 4 at site A of compound 10 was converted to aryl azide using diazotization reaction to obtain compound 59 (Scheme 6). In parallel, the 3-bromo substitution at site B of compound 25 was reacted with sodium azide using copper catalyzed reaction. However, the major product of this reaction was aromatic amine analog 60, which was further converted to azide using the earlier described diazotization chemistry to obtain compound 61 (Scheme 6). The photoreactive aryl azide bearing compounds 59 and 61 and the aromatic amine analog 60 were then evaluated in the primary screens. While compound 61 was inactive just like its precursor bromo analog 25, the reversal of hydrogen bonding capacity in compound 60 led to resurgence of activity in both the assays possibly due to hydrophilic interaction with the aromatic amine (Table 4). In contrast, the reversal of hydrogen bonding capacity of compound 10 led us to a potent aryl azide bearing analog 59 which was then utilized for making photoaffinity probes (Table 4).

Using the methods utilized earlier, compound 59 was derivatized to obtain an alkyne analog 62, and a biotin analog 64 was obtained via an aliphatic amine derivative 63 (Scheme 6). Evaluation of these compounds in the primary screens showed that the alkyne probe 62 was very potent while the biotin probe 64 showed relatively weak activity in both the NF-κB and ISRE assays (Table 4). Also, all the affinity probes had viability in the same range as the potent compounds in this series making them ideal candidates for future studies.

The systematic SAR studies on bis-aryl sulfonamides that sustain NF-κB and ISRE activation have led to the identification of not only rhodamine labeled affinity fluorescent probe 57 and biotin-tagged affinity probe 58, but also alkyne and biotin labeled photoaffinity probes 62 and 64, respectively. These affinity probes will be utilized in concert for target identification and cell trafficking experiments.

In addition, the amine bearing handle was further utilized to introduce chemically reactive electrophilic functional groups to obtain derivatives that can react with proteins and peptides to form self-adjuvanting vaccine constructs. This includes isothiocyanate bearing analog 65 and NHS ester 67 as shown in Scheme 7. These compounds are used to make protein conjugates with ovalbumin to evaluate the self-adjuvanting constructs.

Conclusions

Compound 1 was identified from HTS campaigns, that screened for agents, that prolonged immune signaling, and was shown to be a potent co-adjuvant with MPLA in vivo. Here, systematic SAR studies are presented consisting of design, syntheses and evaluation of analogs of compound 1 to identify sites on the scaffold that can tolerate modification while still retaining dual NF-κB and ISRE enhancing activities. SAR studies pointed to key substitutions at site B and site C that retain potency in vitro and in vivo, while site A allowed the introduction of photoreactive aryl azide functionality. In addition, observed SAR trends at site C allowed the introduction of trackable tags such as rhodamine or biotin. This led to syntheses of several affinity probes which will be utilized to determine the mechanism of action and receptor target for this bis-aryl sulfonamide series of compounds that sustain NF-κB and ISRE activation.

Experimental Section:

Chemistry

Materials. Reagents were purchased as at least reagent grade from commercial vendors unless otherwise specified and used without further purification. Solvents were purchased from Fischer Scientific (Pittsburgh, Pa.) and were either used as purchased or redistilled with an appropriate drying agent. All the reagents 2a-g and 3g-o were purchased from commercially available vendors while reagents 3a-f were synthesized from commercially available reagents. Compounds used for structure-activity studies were synthesized according to methods described below and all the compounds were identified to be least 95% pure using HPLC.

Instrumentation. Analytical TLC was performed using precoated TLC silica gel 60 F254 aluminum sheets purchased from EMD (Gibbstown, N.J.) and visualized using UV light. Flash chromatography was carried out using with a Biotage Isolera One (Charlotte, N.C.) system using the specified solvent. Microwave reaction was performed using Biotage Initiator+ (Charlotte, N.C.). Reaction monitoring and purity analysis were done using an Agilent 1260 LC/6420 Triple Quad mass spectrometer (Santa Clara, Calif.) with Onyx Monolithic C18 (Phenomenex, Torrance, Calif.) column. Purity of all final compounds was above 95%. All final compounds were analyzed by high resolution MS (HRMS) using an Agilent 6230 ESI-TOFMS (Santa Clara, Calif.), $^{1}$H and $^{13}$C NMR spectra were obtained on a Varian 500 with XSens probe (Varian, Inc., Palo Alto, Calif.), The chemical shifts are expressed in parts per million (ppm) using suitable deuterated NMR solvents.

General procedure A for the syntheses of select site A and site B modified compounds. To a solution of a substituted phenyl sulfonyl chloride (reagent 3, 1 eq.) in anhydrous $CH_2Cl_2$ were added, triethylamine (2 eq.) and a solution of substituted aniline (reagent 2, 2 eq.) in $CH_2Cl_2$. The reaction mixture was stirred at room temperature overnight and then poured into water and acidified with 3N HCl followed by extraction with EtOAc. The EtOAc fraction was then dried over $MgSO_4$, and solvent was removed under vacuum. The resultant residue was dissolved in MeOH and THF, followed by the addition of lithium hydroxide monohydrate (15 eq.) in water and stirred at room temperature until bis-sulfonamide side product is converted to the desired product. The solvent was then removed, dissolved in EtOAc, washed with water and brine, dried under vacuum to obtain the residue which was purified by column chromatography to obtain the final product.

Compound 1 and site A modified compounds 4-9 were synthesized using general procedure. A described above.

N-(4-chloro-2,5-dimethoxyphenyl)-4-ethoxybenzenesulfonamide (1). Compound 1 was synthesized using 4-chloro-2,5-dimethoxyaniline (2a, 1.7 g, 5.3 mmol) and 4-ethoxybenzenesulfonyl chloride (3a, 1 g, 4.5 mmol) after recrystallization in EtOH as pink crystals (1.2 g, yield=71%). $^{1}$H NMR (500 MHz, CHLOROFORM-d) δ 7.66 (d, J=8.80 Hz, 2H), 7.24 (s, 1H), 6.91 (s, 1H), 6.86 (d, J=8.80 Hz, 2H), 6.77 (s, 1H), 4.04 (q, J=6.93 Hz, 2H), 3.87 (s, 3H), 3.60 (s, 3H), 1.42 (t, J=6.97 Hz, 3H). $^{13}$C NMR (126 MHz, CHLOROFORM-d) δ 162.6, 149.2, 143.6, 130.0, 129.4, 125.2, 117.8, 114.4, 113.1, 106.3, 64.0, 56.8, 56.4, 14.6. HRMS for $C_{16}H_{17}ClNO_5S$ [M−H$^-$] calculated 370.0521, found 370.0523.

N-(4-chloro-3-methoxyphenyl)-4-ethoxybenzenesulfonamide (4), Compound 4 was synthesized using 4-chloro-3-methoxyaniline (2b, 142.84 mg, 0.92 mmol) and 4-ethoxybenzenesulfonyl chloride (3a, 100 mg, 0.46 mmol) as off-white solid (83 mg, yield=54%). $^{1}$H NMR (500 MHz, CHLOROFORM-d) δ 7.70 (d, J=8.80 Hz, 2H), 7.17 (d, J=8.56 Hz, 1H), 7.01 (br. s., 1H), 6.89 (d, J=9.05 Hz, 2H), 6.80 (d, J=2.20 Hz, 1H), 6.51 (dd, J=2.20, 8.56 Hz, 1H), 4.05 (q, J=7.09 Hz, 2H), 3.83 (5, 3H), 1.42 (t, J=6.97 Hz, 3H). $^{13}$C NMR (126 MHz, CHLOROFORM-d) δ 162.7, 155.3, 136.3, 130.4, 129.6, 129.4, 119.0, 114.6, 113.9, 105.8, 64.0, 56.2, 14.6. HRMS for $C_{15}H_{15}ClNO_4S$ [M−H]$^-$ calculated 340.0416, found 340.0416.

N-(4-chloro-2-methoxyphenyl)-4-ethoxybenzenesulfonamide (5). Compound 5 was synthesized using 4-chloro-2-methoxyaniline (2c, 142.84 mg, 0.92 mmol) and 4-ethoxybenzenesulfonyl chloride (3a, 100 mg, 0.46 mmol) as tan solid (100 mg, yield=64%). $^{1}$H NMR (500 MHz, CHLOROFORM-d) δ 7.66 (d, J=8.80 Hz, 2H), 7.45 (d, J=8.56 Hz, 1H), 6.83-6.91 (m, 2H), 6.85 (d, J=8.80 Hz, 2H), 6.72 (d, J=1.96 Hz, 1H), 4.04 (q, J=7.09 Hz, 2H), 3.65 (s, 3H), 1.41 (t, J=6.97 Hz, 3H). $^{13}$C NMR (126 MHz, CHLOROFORM-d) δ 162.5, 150.0, 130.4, 130.2, 129.4, 124.8, 121.9, 121.0, 114.3, 111.3, 63.9, 55.9, 14.6, HRMS for $C_{15}H_{16}ClNO_4SNa$ [M+Na$^+$] calculated 364.0381, found 364.0382.

N-(2,5-dimethoxyphenyl)-4-ethoxybenzenesulfonamide (6). Compound 6 was synthesized using 2,5-dimethoxyaniline (2d, 138.8 mg, 0.92 mmol) and 4-ethoxybenzenesulfonyl chloride (3a, 100 mg, 0.46 mmol) as off-white solid (117 mg, yield=76%). $^{1}$H NMR (500 MHz, CHLOROFORM-d) δ 7.70 (d, J=8.80 Hz, 2H), 7.14 (d, J=2.93 Hz, 1H), 7.01 (s, 1H), 6.85 (d, J=8.80 Hz, 2H), 6.65 (d, J=8.80 Hz, 1H), 6.53 (dd, J=2.93, 9.05 Hz, 1H), 4.03 (q, J=6.85 Hz, 2H), 3.75 (s, 3H), 3.62 (s, 3H), 1.40 (t, J=7.09 Hz, 3H). $^{13}$C NMR (126 MHz, CHLOROFORM-d) δ 162.4, 153.8, 143.4, 130.4, 129.4, 126.8, 114.3, 111.4, 109.5, 106.8, 63.9, 56.2, 55.8, 14.6. HRMS for $C_{16}H_{19}NO_5SNa$ [M+Na$^+$] calculated 360.0876, found 360.0877.

N-(4-bromo-2,5-dimethoxyphenyl)-4-ethoxybenzenesulfonamide (7). Compound 7 was synthesized using 4-bromo-2,5-dimethoxyaniline (2e, 105.2 mg, 0.45 mmol) and 4-ethoxybenzenesulfonyl chloride (3a, 50 mg, 0.23 mmol) as purple solid (59 mg, yield=62%). $^{1}$H NMR (500 MHz, CHLOROFORM-d) δ 7.67 (d, J=8.80 Hz, 2H), 7.21 (s, 1H), 6.93 (5, 1H), 6.92 (5, 1H), 6.85 (d, J=9.05 Hz, 2H), 4.04 (q, J=7.09 Hz, 2H), 3.86 (s, 3H), 3.61 (5, 3H), 1.41 (t, J=6.97 Hz, 3H). $^{13}$C NMR (126 MHz, CHLOROFORM-d) δ 162.6, 150.2, 143.7, 130.0, 129.4, 126.0, 115.8, 114.4, 106.2, 105.8, 64.0, 56.9, 56.4, 14.6. HRMS for $C_{16}H_{18}BrNO_5SNa$ [M+Na$^+$] calculated 437.9981, found 437.9979.

N-(4-chloro-3,5-dimethoxyphenyl)-4-ethoxybenzenesulfonamide (8). Compound 8 was synthesized using 4-chloro-3,5-dimethoxyaniline (2f, 50 mg, 0.27 mmol) and 4-ethoxybenzenesulfonyl chloride (3a, 29 mg, 0.13 mmol) as white solid (30 mg, yield=61%). $^{1}$H NMR (500 MHz, CHLOROFORM-d) δ 7.71 (d, J=8.80 Hz, 2H), 6.89 (d, J=9.05 Hz, 2H), 6.76 (br. s., 1H), 6.35 (s, 2H), 4.06 (q, J=7.01 Hz, 2H), 3.80 (s, 6H), 1.43 (t, J=6.97 Hz, 3H). $^{13}$C NMR (126 MHz, CHLOROFORM-d) δ 162.8, 156.3, 136.1, 1291, 1295, 114.6, 107.2, 98.2, 64.0, 56.4, 14.6. HRMS for $C_{16}H_{17}ClNO_5S$ [M−H]− calculated 370.0521, found 370.0519.

N-(2,5-dimethoxy-4-nitrophenyl)-4-ethoxybenzenesulfonamide (9). Compound 9 was synthesized using 3,5-dimethoxy-4-nitroaniline (2 g, 50 mg, 0.27 mmol) and 4-ethoxybenzenesulfonyl chloride (3a, 29 mg, 0.13 mmol) as yellow solid (30 mg, yield=61%). $^{1}$H NMR (500 MHz, CHLOROFORM-d) δ 7.69-7.86 (m, J=8.80 Hz, 2H), 7.44 (s, 1H), 7.40 (s, 1H), 7.31 (s, 1H), 6.90-6.95 (m, 2H), 4.07 (q, J=6.93 Hz, 2H), 3.93 (s, 3H), 3.82 (s, 3H), 1.43 (t, J=6.97 Hz, 3H), $^{13}$C NMR (126 MHz, CHLOROFORM-d) δ 163.1, 149.4, 140.9, 133.1, 132.8, 129.5, 129.4, 114.8, 108.3, 103.2, 64.1, 57.0, 56.5, 14.5, HRMS for $C_{16}H_{19}N_2O_7S$ [M+H$^+$] calculated 383.0907, found 383.091.

N-(4-amino-2,5-dimethoxyphenyl)-4-ethoxybenzenesulfonamide (10). To a solution of compound 9 (128 mg, 0.33 mmol) in EtOAc were added, a catalytic amount of palladium on carbon and some sodium sulfate. The reaction was subjected to Parr hydrogenation apparatus using hydrogen gas at 50 psi pressure for 6 hours. The solvent was then removed, and the residue was purified using silica gel column chromatography (5% MeOH/$CH_2Cl_2$) to obtain 84 mg of compound 10 as tan solid (yield=72%). $^{1}$H NMR (500 MHz, METHANOL-$d_4$) δ 7.55 (d, J=8.80 Hz, 2H), 6.91 (d, J=8.80 Hz, 2H), 6.87 (s, 1H), 6.26 (s, 1H), 4.06 (q, J=7.01 Hz, 2H), 3.78 (s, 3H), 3.33 (s, 3H), 1.38 (t, J=6.97 Hz, 3H), $^{13}$C NMR (126 MHz, METHANOL-$d_4$) δ 162.2, 147.8, 140.9, 135.9, 131.2, 129.2, 114.4, 113.5, 110.3, 99.0, 63.6, 55.2, 54.7, 13.5. HRMS for $C_{16}H_{20}N_2O_5SNa$ [M+Na$^+$] calculated 375.0985, found 375.0988.

Site B modified compounds 11-17, 19, 22-27 were synthesized using general procedure A described above.

N-(4-chloro-2,5-dimethoxyphenyl)-4-hydroxybenzenesulfonamide (11). Compound 11 was synthesized using 4-chloro-2,5-dimethoxyaniline (2a, 383 mg, 2.03 mmol) and 4-hydroxybenzenesulfonyl chloride (3b, 195 mg, 1.02 mmol) as dark brown solid (237 mg, yield=68%). $^{1}$H NMR (500 MHz, DMSO-$d_6$) δ 10.44 (5, 1H), 9.39 (s, 1H), 7.54 (d, J=8.80 Hz, 2H), 7.02 (s, 1H), 6.97 (s, 1H), 6.83 (d, J=8.80 Hz, 2H), 3.66-3.78 (m, 3H), 3.48 (s, 3H). $^{13}$C NMR (126 MHz, DMSO-d6) δ 161.2, 148.1, 146.0, 129.9, 129.2, 125.5, 117.3, 115.3, 113.9, 109.2, 56.5, 56.4. HRMS for $C_{14}H_{13}ClNO_5S$ [M−H]− calculated 342.0208, found 342.0205.

N-(4-chloro-2,5-dimethoxyphenyl)-4-methoxybenzenesulfonamide (12). Compound 11 was synthesized using 4-chloro-2,5-dimethoxyaniline (2a, 450 mg, 2.40 mmol) and 4-methoxybenzenesulfonyl chloride (3c, 248 mg, 1.20 mmol) as light brown solid (189 mg, yield=44%). $^{1}$H NMR (500 MHz, CHLOROFORM-d) δ 7.68 (d, J=8.80 Hz, 2H), 7.24 (s, 1H), 6.92 (s, 1H), 6.88 (d, J=9.05 Hz, 2H), 6.77 (s, 1H), 3.87 (s, 3H), 3.83 (s, 3H), 3.61 (s, 3H). $^{13}$C NMR (126 MHz, CHLOROFORM-d) δ 163.1, 149.2, 143.6, 130.3, 129.4, 125.2, 117.9, 114.0, 113.1, 106.3, 56.8, 56.4, 55.6. HRMS for $C_{15}H_{16}ClNO_5SNa$ [M+Na$^+$] calculated 380.033, found 380.0326.

N-(4-chloro-2,5-dimethoxyphenyl)-4-propoxybenzenesulfonamide (13). Compound 13 was synthesized using 4-chloro-2,5-dimethoxyaniline (2a, 106 mg, 0.57 mmol) and 4-propoxybenzenesulfonyl chloride (3d, 66 mg, 0.28 mmol) as off-white solid (65 mg, yield=59%). $^{1}$H NMR (500 MHz, CHLOROFORM-d) δ 7.66 (d, J=8.80 Hz, 2H), 7.23 (5, 1H), 6.92 (5, 1H), 6.86 (d, J=9.05 Hz, 2H), 6.76 (s, 1H), 3.92 (t, J=6.60 Hz, 2H), 3.87 (s, 3H), 3.60 (s, 3H), 1.76-1.85 (m, 2H), 1.02 (t, J=7.46 Hz, 3H), $^{13}$C NMR (126 MHz, CHLOROFORM-d) δ 162.8, 149.2, 143.5, 130.0, 129.3, 125.2, 117.8, 114.4, 113.1, 106.2, 69.9, 56.8, 56.4, 22.3, 10.4. HRMS for $C_{17}H_{20}ClNO_5SNa$ [M+Na$^+$] calculated 408.0643, found 408.0641.

4-Butoxy-N-(4-chloro-2,5-dimethoxyphenyl)benzenesulfonamide (14). Compound 14 was synthesized using 4-chloro-2,5-dimethoxyaniline (2a, 191 mg, 1.02 mmol) and 4-butoxybenzenesulfonyl chloride (3e, 127 mg, 0.51 mmol) as off-white solid (95 mg, yield=47%). $^{1}$H NMR (500 MHz, CHLOROFORM-d) δ 7.66 (d, J=8.80 Hz, 2H), 7.23 (s, 1H), 6.91 (s, 1H), 6.85 (d, J=8.80 Hz, 2H), 6.76 (s, 1H), 3.96 (t, J=6.48 Hz, 2H), 3.87 (s, 3H), 3.60 (s, 3H), 1.76 (quin, J=7.20 Hz, 2H), 1.47 (sxt, J=7.40 Hz, 2H), 0.97 (t, J=7.46 Hz, 3H). $^{13}$C NMR (126 MHz, CHLOROFORM-d) δ 162.8, 149.2, 143.5, 130.0, 129.3, 125.3, 117.8, 114.4, 113.1, 106.2, 68.1, 56.8, 56.4, 31.0, 19.1, 13.8. HRMS for $C_{18}H_{22}ClNO_5SNa$ [M+Na$^+$] calculated 422.0799, found 422.0802.

N-(4-chloro-2,5-dimethoxyphenyl)-4-(prop-2-yn-1-yloxy)benzenesulfonamide (15). Compound 15 was synthesized using 4-chloro-2,5-dimethoxyaniline (2a, 66 mg, 0.35 mmol) and 4-(prop-2-yn-1-yloxy)benzenesulfonyl chloride (3f, 40.7 mg, 0.18 mmol) as off-white solid (24 mg, yield=32%). $^{1}$H NMR (500 MHz, CHLOROFORM-d) δ 7.69 (d, J=9.05 Hz, 2H), 7.23 (s, 1H), 6.96 (d, J=8.80 Hz, 2H), 6.90 (s, 1H), 6.76 (s, 1H), 4.72 (d, J=2.20 Hz, 2H), 3.87 (s, 3H), 3.59 (s, 3H), 2.55 (t, J=2.45 Hz, 1H). $^{13}$C NMR (126 MHz, DMSO-$d_6$) δ 160.2, 148.1, 146.4, 132.5, 128.9, 125.1, 117.7, 114.9, 113.9, 109.9, 78.8, 78.5, 56.4, 55.8. HRMS for $C_{17}H_{15}ClNO_5S$ [M−H]$^-$ calculated 380.0365, found 380.0365.

N-(4-chloro-2,5-dimethoxyphenyl)-4-propylbenzenesulfonamide (16). Compound 11 was synthesized using 4-chloro-2,5-dimethoxyaniline (2a, 210 mg, 1.12 mmol) and 4-propylbenzenesulfonyl chloride (3 g, 100 μL, 0.56 mmol) as white solid (121 mg, yield=59%). $^{1}$H NMR (500 MHz, CHLOROFORM-d) δ 7.64 (d, J=8.31 Hz, 2H), 7.23 (s, 1H), 7.21 (d, J=8.31 Hz, 2H), 6.92 (s, 1H), 6.76 (s, 1H), 3.87 (s, 3H), 3.53-3.58 (m, 3H), 2.60 (t, J=7.70 Hz, 2H), 1.61 (sxt, J=7.60 Hz, 2H), 0.91 (t, J=7.34 Hz, 3H). $^{13}$C NMR (126 MHz, CHLOROFORM-d) δ 149.2, 148.6, 143.6, 136.0, 128.9, 127.2, 125.1, 117.9, 113.1, 106.4, 56.8, 56.3, 37.8, 24.1, 13.7. HRMS for $C_{17}H_{20}ClNO_4SNa$ [M+Na$^+$] calculated 392.0694, found 392.0695.

N-(4-chloro-2,5-dimethoxyphenyl)-4-nitrobenzenesulfonamide (17). Compound 17 was synthesized using 4-chloro-2,5-dimethoxyaniline (2a, 847 mg, 4.51 mmol) and 4-nitrobenzenesulfonyl chloride (3h, 500 mg, 2.25 mmol) as yellow solid (182 mg, yield=22%). $^{1}$H NMR (500 MHz, DMSO-d6) δ 10.15 (s, 1H), 8.37 (d, J=8.80 Hz, 2H), 7.93 (d, J=8.80 Hz, 2H), 7.04 (s, 1H), 7.01 (s, 1H), 3.76 (s, 3H), 3.35 (s, 3H). $^{13}$C NMR (126 MHz, CHLOROFORM-d) δ 150.2, 149.4, 144.5, 144.0, 128.4, 124.1, 123.5, 119.6, 113.2, 107.4, 56.9, 56.3. HRMS for $C_{14}H_{12}ClN_2O_6S$ [M−H]$^-$ calculated 371.011, found 371.0104.

4-Amino-N-(4-chloro-2,5-dimethoxyphenyl)benzenesulfonamide (18). To a solution of compound 17 (150 mg, 0.4 mmol) in EtOAc were added, a catalytic amount of palladium on carbon and some sodium sulfate. The reaction was subjected to hydrogenation on Parr hydrogenation apparatus using hydrogen gas at 50 psi pressure for 6 hours. The solvent was then removed, and the residue was purified using silica gel column chromatography (9% MeOH/$CH_2Cl_2$) to obtain 86 mg of compound 10 as tan solid (yield=58%). $^{1}$H NMR (500 MHz, DMSO-d6) δ 9.07 (5, 1H), 7.31-7.41 (m, J=8.56 Hz, 2H), 6.97 (s, 1H), 7.01 (s, 1H), 6.47-6.56 (m, J=8.80 Hz, 2H), 5.98 (s, 2H), 3.70 (s, 3H), 3.54 (s, 3H). $^{13}$C NMR (126 MHz, DMSO-d6) δ 152.9, 148.1, 145.5, 128.9, 126.1, 124.6, 116.4, 113.9, 112.4, 108.0, 56.6, 56.4. HRMS for $C_{14}H_{15}ClN_2O_4SNa$ [M+Na$^+$] calculated 365.0333, found 365.0335.

N-(4-chloro-2,5-dimethoxyphenyl)-4-cyanobenzenesulfonamide (19). Compound 19 was synthesized using 4-chloro-2,5-dimethoxyaniline (2a, 372 mg, 1.98 mmol) and 4-cyanobenzenesulfonyl chloride (3i, 100 mg, 0.50 mmol) as white solid (40 mg, yield=23%). $^{1}$H NMR (500 MHz, CHLOROFORM-d) δ 7.83 (d, J=8.56 Hz, 2H), 7.73 (d, J=8.31 Hz, 2H), 7.25 (s, 1H), 6.92 (s, 1H), 6.79 (s, 1H), 3.90 (s, 3H), 3.57 (s, 3H). $^{13}C$ NMR (126 MHz, CHLOROFORM-d) δ 149.4, 144.0, 142.9, 132.6, 127.8, 123.5, 119.5, 117.1, 116.7, 113.1, 107.4, 56.8, 56.2. HRMS for $C_{15}H_{12}ClN_2O_4S$ $[M-H]^-$ calculated 351.0212, found 351.021.

tert-butyl (4-(N-(4-chloro-2,5-dimethoxyphenyl)sulfamoyl)benzyl) carbamate (20). To a crude solution of compound 19 (280 mg, 0.75 mmol) in methanol was added, a catalytic amount of palladium on carbon and di-tertbutyl dicarbonate (326 mg, 1.5 mmol). The reaction was subjected to hydrogenation on Parr hydrogenation apparatus using hydrogen gas at 50 psi pressure overnight. The solvent was then removed, and the residue was purified using silica gel column chromatography (9% $MeOH/CH_2Cl_2$) to obtain 86 mg of compound 10 as white solid (yield=58%). $^1H$ NMR (500 MHz, CHLOROFORM-d) δ 7.70 (d, J=8.07 Hz, 2H), 7.33 (d, J=8.07 Hz, 2H), 7.25 (s, 1H), 6.93 (br. s., 1H), 6.76 (s, 1H), 4.94 (br. s., 1H), 4.34 (d, J=5.87 Hz, 2H), 3.87 (s, 3H), 3.57 (s, 3H), 1.46 (s, 9H). $^{13}C$ NMR (126 MHz, CHLOROFORM-d) δ 155.8, 149.3, 144.9, 143.7, 137.5, 127.5, 127.5, 124.8, 118.2, 113.1, 106.5, 80.0, 56.8, 56.3, 44.0, 28.3 HRMS for $C_{20}H_{25}ClN_2O_6SNa$ $[M+Na^+]$ calculated 479.1014, found 479.1018.

4-(aminomethyl)-N-(4-chloro-2,5-dimethoxyphenyl)benzenesulfonamide (21). Compound 20 (11 mg, mmol) was stirred in a solution of 4N HCl in dioxane for 1 hour. The solvent was then removed to obtain compound 21 in quantitative yield as hydrochloride salt (grey solid). $^1H$ NMR (500 MHz, METHANOL-$d_4$) δ 7.71-7.88 (m, J=8.31 Hz, 2H), 7.51-7.67 (m, J=8.31 Hz, 2H), 7.23 (s, 1H), 6.87 (s, 1H), 4.17 (5, 2H), 3.82 (s, 3H), 3.51 (s, 3H). $^{13}C$ NMR (126 MHz, METHANOL-d4) δ 150.5, 147.2, 142.1, 139.5, 130.5, 129.3, 126.3, 120.3, 114.7, 110.4, 57.3, 57.0, 43.7. HRMS for $C_{15}H_{18}ClN_2O_4S$ $[M+H^+]$ calculated 357.067, found 357.0674.

N-(4-chloro-2,5-dimethoxyphenyl)-4-phenoxybenzenesulfonamide (22). Compound 22 was synthesized using 4-chloro-2,5-dimethoxyaniline (2a, 140 mg, 0.74 mmol) and 4-phenoxybenzenesulfonyl chloride (3j, 100 mg, 0.37 mmol) as light yellow solid (51 mg, yield=33%), $^1H$ NMR (500 MHz, CHLOROFORM-d) δ 7.69 (d, J=8.80 Hz, 1H), 7.41 (t, J=7.95 Hz, 1H), 7.25 (s, 2H), 7.23 (t, J=7.60 Hz, 2H), 7.03 (d, J=7.58 Hz, 2H), 6.95 (s, 1H), 6.94 (d, J=8.80 Hz, 2H), 6.80 (s, 1H), 3.87 (s, 3H), 3.64 (s, 3H), $^{13}C$ NMR (126 MHz, CHLOROFORM-d) δ 161.9, 154.8, 1493, 143.6, 132.2, 130.2, 129.4, 125.1, 125.0, 120.3, 118.0, 117.2, 113.1, 106.3, 56.8, 56.4. HRMS for $C_{20}H_{18}ClNO_5SNa$ $[M+Na^+]$ calculated 442.0486, found 442.0489.

N-(4-chloro-2,5-dimethoxyphenyl)-3-methoxybenzenesulfonamide (23). Compound 23 was synthesized using 4-chloro-2,5-dimethoxyaniline (2a, 182 mg, 0.97 mmol) and 3-methoxybenzenesulfonyl chloride (3k, 100 mg, 0.48 mmol) as brown solid (189 mg, yield=54%). $^1H$ NMR (500 MHz, CHLOROFORM-d) δ 7.29-7.35 (m, 2H), 7.21-7.26 (m, 2H), 7.00-7.09 (m, 1H), 6.94 (s, 1H), 6.78 (s, 1H), 3.87 (s, 3H), 3.77 (s, 3H), 3.58 (s, 3H). $^{13}C$ NMR (126 MHz, CHLOROFORM-d) δ 159.6, 149.3, 143.7, 139.8, 129.9, 124.9, 119.5, 119.3, 118.2, 113.1, 111.7, 106.5, 56.8, 56.4, 55.6. HRMS for $C_{15}H_{16}ClNO_5SNa$ $[M+Na^+]$ calculated 380.033, found 380.0329.

N-(4-chloro-2,5-dimethoxyphenyl)-2-methoxybenzenesulfonamide (24). Compound 24 was synthesized using 4-chloro-2,5-dimethoxyaniline (2a, 182 mg, 0.97 mmol) and 2-methoxybenzenesulfonyl chloride (3l, 100 mg, 0.48 mmol) as tan solid (121 mg, yield=70%). $^1H$ NMR (500 MHz, CHLOROFORM-d) δ 7.87 (td, J=1.70, 7.70 Hz, 1H), 7.58 (5, 1H), 7.49 (tt, J=1.50, 7.70 Hz, 1H), 7.22 (5, 1H), 6.99 (t, J=7.70 Hz, 1H), 6.95 (d, J=8.31 Hz, 1H), 6.78 (s, 1H), 3.95 (s, 3H), 3.80 (5, 3H), 3.73 (5, 3H). $^{13}C$ NMR (126 MHz, CHLOROFORM-d) δ 156.4, 149.2, 142.9, 135.1, 130.9, 126.1, 125.7, 120.3, 116.8, 113.0, 111.8, 104.9, 56.7, 56.6, 56.1. HRMS for $C_{15}H_{16}ClNO_5SNa$ $[M+Na^+]$ calculated 380.033, found 380.0329.

3-Bromo-N-(4-chloro-2,5-dimethoxyphenyl)-4-ethoxybenzenesulfonamide (25). Compound 25 was synthesized using 4-chloro-2,5-dimethoxyaniline (2a, 180 mg, 0.70 mmol) and 3-bromo-4-methoxybenzenesulfonyl chloride (3m, 100 mg, 0.35 mmol) as brown solid (68 mg, yield=58%). $^1H$ NMR (500 MHz, CHLOROFORM-d) δ 7.99 (d, J=2.20 Hz, 1H), 7.64 (dd, J=1.96, 8.56 Hz, 1H), 7.22 (s, 1H), 6.93 (s, 1H), 6.85 (d, J=8.56 Hz, 1H), 6.79 (s, 1H), 3.93 (s, 3H), 3.89 (s, 3H), 3.65 (s, 3H). $^{13}C$ NMR (126 MHz, CHLOROFORM-d) δ 159.4, 149.3, 143.7, 132.4, 131.4, 128.5, 124.6, 118.4, 113.1, 112.0, 111.0, 106.6, 56.8, 56.6, 56.4. HRMS for $C_{15}H_{14}BrClNO_5S$ $[M-H]^-$ calculated 433.947, found 433.9469.

Methyl 4-(N-(4-chloro-2,5-dimethoxyphenyl)sulfamoyl) benzoate (26). Compound 26 was synthesized using 4-chloro-2,5-dimethoxyaniline (2a, 80 mg, 0.42 mmol) and of methyl 4-(chlorosulfonyl)benzoate (3n, 50 mg, 021 mmol) as tan solid (31 mg, yield=38%). $^1H$ NMR (500 MHz, CHLOROFORM-d) δ 8.08 (d, J=8.31 Hz, 2H), 7.80 (d, J=8.31 Hz, 2H), 7.25 (s, 1H), 6.94 (s, 1H), 6.76 (s, 1H), 3.94 (s, 3H), 3.89 (s, 3H), 1.55 (s, 3H). $^{13}C$ NMR (126 MHz, CHLOROFORM-d) δ 165.5, 149.3, 143.8, 142.5, 134.1, 130.9, 127.2, 124.1, 118.9, 113.1, 107.0, 56.8, 56.2, 52.7. HRMS for $C_{16}H_{15}ClNO_6S$ $[M-H]^-$ calculated 384.0314, found 384.0308.

4-(N-(4-chloro-2,5-dimethoxyphenyl)sulfamoyl)benzamide (27). Compound 27 was synthesized using 4-chloro-2,5-dimethoxyaniline (2a, 171 mg, 0.77 mmol) and 4-carbamoylbenzenesulfonyl chloride (3o, 100 mg, 0.46 mmol) as white solid (14 mg, yield=8%), $^1H$ NMR (500 MHz, DMSO-$d_6$) δ 9.83 (br, s., 1H), 8.13 (br. s., 1H), 7.96 (d, J=8.31 Hz, 2H), 7.76 (d, J=8.31 Hz, 2H), 7.60 (br, s., 1H), 7.02 (s, 1H), 6.99 (s, 1H), 3.74 (s, 3H), 3.38 (br. s 3H), $^{13}C$ NMR (126 MHz, DMSO-$d_6$) δ 166.7, 148.2, 146.7, 142.4, 138.0, 128.0, 126.7, 124.5, 118.3, 114.0, 110.7, 56.5, 56.3. HRMS for $C_{15}H_{14}ClN_2O_5S$ $[M-H]^-$ calculated 369.0317, found 369.0315.

4-(N-(4-chloro-2,5-dimethoxyphenyl)sulfamoyl)benzoic acid (28). To a solution of compound 26 (25.0 mg, 0.06 mmol) in MeOH and THF was added a solution of LiOH (40.1 mg, 0.97 mmol) in water. The reaction was stirred overnight and the solvent was then removed under vacuum. The residue was mixed with acidified water (3N aq. HCl) extracted with EtOAc, dried over $MgSO_4$ and concentrated to dryness under vacuum to obtain compounds 28 as white solid (21 mg, yield=87%). $^1H$ NMR (500 MHz, DMSO-$d_6$) δ 10.44 (s, 1H), 9.39 (s, 1H), 7.54 (d, J=8.80 Hz, 2H), 7.02 (s, 1H), 6.97 (s, 1H), 6.83 (d, J=8.80 Hz, 2H), 3.66-3.78 (m, 3H), 3.48 (s, 3H). $^{13}C$ NMR (126 MHz, DMSO-$d_6$) δ 166.4, 148.3, 147.0, 143.9, 134.5, 129.9, 127.1, 124.4, 118.7, 114.0, 111.1, 56.6, 56.3. HRMS for $C_{15}H_{13}ClNO_6S$ $[M-H]^-$ calculated 370.0158, found 370.0152.

Ethyl 4-(N-(4-chloro-2,5-dimethoxyphenyl)sulfamoyl) benzoate (29). To a solution of compound 28 (20 mg, 0.05 mmol) in anhydrous EtOH was added trimethylsilyl chloride (68.3 μL, 0.54 mmol) and the reaction was stirred at room temperature until completion. The reaction mixture was poured into water and extracted with EtOAc. The organic layer was dried over $MgSO_4$ and concentrated under vacuum to obtain the residue which was purified by silica gel column chromatography (25% EtOAc/hexanes) to obtain compound 29 as white solid. (17.6 mg, yield=82%). $^1$H NMR (500 MHz, CHLOROFORM-d) δ 8.09 (d, J=8.31 Hz, 2H), 7.80 (d, J=8.31 Hz, 2H), 7.26 (s, 1H), 6.95 (s, 1H), 6.76 (s, 1H), 4.39 (q, J=7.17 Hz, 2H), 3.89 (s, 3H), 3.56 (s, 3H), 1.40 (t, J=7.09 Hz, 3H). $^{13}$C NMR (126 MHz, CHLOROFORM-d) δ 165.0, 149.3, 143.8, 142.4, 134.5, 130.0, 127.2, 124.2, 118.8, 113.1, 106.9, 61.8, 56.8, 56.3, 14.2. HRMS for $C_{17}H_{17}ClNO_6S$ [M−H]$^-$ calculated 398.0471, found 398.0467.

4-(N-(4-chloro-2,5-dimethoxyphenyl)sulfamoyl)-N-methylbenzamide (30). To a solution of compound 23 (25 mg, 0.07 mmol) in anhydrous DMF were added, 2M methyl amine solution in THF (67 μL, 0.13 mmol), triethylamine (38 μL, 0.27 mmol) and HATU (31 mg, 0.08 mmol). The reaction was stirred at room temperature until completion. The reaction mixture was poured into water and extracted with EtOAc. The organic layer was dried over $MgSO_4$ and concentrated under vacuum to obtain the residue which was purified by reverse-phase C18 column chromatography (56% MeOH/$H_2O$ with 0.1% $CF_3CO_2H$) to yield compound 30 as white solid (3 mg, yield=12%). $^1$H NMR (500 MHz, CHLOROFORM-d) δ 7.79 (s, 4H), 7.26 (s, 1H), 6.94 (s, 1H), 6.76 (s, 1H), 6.14 (s, 1H), 3.89 (s, 3H), 3.56 (s, 3H), 3.03 (d, J=4.89 Hz, 3H), $^{13}$C NMR (126 MHz, CHLOROFORM-d) δ 166.4, 149.3, 143.8, 141.2, 138.8, 127.5, 127.4, 124.2, 118.8, 113.1, 106.9, 56.8, 56.3, 27.0. HRMS for $C_{16}H_{15}ClN_2O_5S$ [M−H]$^-$ calculated 383.0474, found 383.0468.

4-Chloro-N-(4-ethoxyphenyl)-2,5-dimethoxybenzene-sulfonamide (31). Compound 31 was synthesized using the general procedure A using p-phenetidine (2h, 166.04 μL, 1.21 mmol) and 4-Cl-2,5-dimethoxybenzenesulfonyl chloride (3p, 100 mg, 0.61 mmol) as brown solid (98 mg, yield=43.6%). $^1$H NMR (500 MHz, DMSO-$d_6$) δ 9.74 (br. s., 1H), 7.35 (s, 1H), 7.28 (s, 1H), 6.97 (d, J=8.80 Hz, 2H), 6.75 (d, J=9.05 Hz, 2H), 3.88 (q, J=7.10 Hz, 2H), 3.86 (s, 3H), 3.77 (s, 3H), 1.24 (t, J=6.85 Hz, 3H). $^{13}$C NMR (126 MHz, CHLOROFORM-d) δ 157.5, 149.7, 149.0, 128.4, 128.4, 125.4, 125.1, 114.9, 114.9, 113.7, 63.6, 57.3, 56.8, 14.8. HRMS for $C_{16}H_{18}ClNO_5SNa$ [M+Na$^+$] calculated 394.0486, found 394.0489.

General procedure B for the syntheses of site C modified compounds 33-47 and 49-52. To a solution of compound 1 (1 eq.) in anhydrous DMF were added, potassium carbonate (2 eq.), and reagent 32 (1.1 eq.). The reaction was then heated at 45° C. with stirring until completion. The suspension was extracted with EtOAc and brine. Then the organic layer was isolated, dried over $MgSO_4$ and concentrated in vacuo. The crude material was purified by chromatography to obtain the final compounds.

N-(4-chloro-2,5-dimethoxyphenyl)-4-ethoxy-N-methyl-benzenesulfonamide (33). Compound 33 was synthesized using compound 1 (10 mg, 0.03 mmol) and iodomethane (32a, 1.85 μL, 0.03 mmol) as white solid (10 mg, yield=95%). $^1$H NMR (500 MHz, CHLOROFORM-d) δ 7.61 (d, J=8.80 Hz, 2H), 6.96 (s, 1H), 6.92 (d, J=8.80 Hz, 2H), 6.83 (s, 1H), 4.09 (d, J=6.85 Hz, 2H), 3.85 (s, 3H), 3.39 (s, 3H), 3.19 (s, 3H), 1.45 (t, J=6.97 Hz, 3H). $^{13}$C NMR (126 MHz, dichloroethane) δ 162.1, 150.4, 148.6, 130.6, 129.7, 128.0, 122.5, 116.1, 114.0, 113.8, 63.9, 56.7, 55.6, 37.8, 14.6. HRMS for $C_{17}H_{20}ClNO_5SNa$ [M+Na$^+$] calculated 408.0643, found 408.0641.

N-(4-chloro-2,5-dimethoxyphenyl)-4-ethoxy-N-propyl-benzenesulfonamide (34). Compound 34 was synthesized using compound 1 (10 mg, 0.03 mmol) and 1-iodopropane (32b, 2.9 μL, 0.03 mmol) as tan solid (11 mg, yield=96%). $^1$H NMR (500 MHz, CHLOROFORM-d) δ 7.59 (d, J=8.80 Hz, 2H), 6.86-6.92 (m, 3H), 6.81 (s, 1H), 4.07 (q, J=7.09 Hz, 2H), 3.84 (s, 3H), 3.51 (br. s., 2H), 3.36 (s, 3H), 1.44 (sxt, J=7.30 Hz, 5H), 0.89 (t, J=7.34 Hz, 3H). $^{13}$C NMR (126 MHz, CHLOROFORM-d) δ 162.0, 150.7, 148.6, 131.7, 129.6, 125.7, 122.6, 117.4, 113.9, 113.7, 63.9, 56.8, 55.6, 51.4, 22.2, 14.6, 11.2. HRMS for $C_{19}H_{24}ClNO_5SNa$ [M+Na$^+$] calculated 436.0956, found 436.0954.

N-(4-chloro-2,5-dimethoxyphenyl)-4-ethoxy-N-butyl-benzenesulfonamide (35). Compound 35 was synthesized using compound 1 (10 mg, 0.03 mmol) and 1-iodobutane (32c, 2.9 μL, 0.03 mmol) as white solid (11 mg, yield=96%), $^1$H NMR (500 MHz, CHLOROFORM-d) δ 7.60 (d, J=8.80 Hz, 2H), 6.87-6.93 (m, 3H), 6.82 (s, 1H), 4.08 (q, J=6.93 Hz, 2H), 3.85 (s, 3H), 3.48-3.61 (m, 2H), 3.37 (s, 3H), 1.45 (t, J=6.85 Hz, 3H), 1.39 (dd, J=7.46, 14.79 Hz, 2H), 1.29-1.35 (m, 2H), 0.87 (t, J=7.09 Hz, 3H), $^{13}$C NMR (126 MHz, CHLOROFORM-d) δ 162.0, 150.8, 148.6, 131.7, 129.6, 125.6, 122.6, 117.4, 113.9, 113.7, 63.9, 56.8, 55.6, 49.4, 31.0, 19.8, 14.6, 13.7. HRMS for $C_{20}H_{26}ClNO_5SNa$ [M+Na$^+$] calculated 450.1112, found 450.1106.

N-(4-chloro-2,5-dimethoxyphenyl)-4-ethoxy-N-pentyl-benzenesulfonamide (36). Compound 36 was synthesized using compound 1 (10 mg, 0.03 mmol) and 1-iodopentane (32d, 3.9 μL, 0.03 mmol) as off-white solid (12 mg, yield=98%). $^1$H NMR (500 MHz, CHLOROFORM-d) δ 7.59 (d, J=8.80 Hz, 2H), 6.87-6.92 (m, 3H), 6.82 (s, 1H), 4.08 (q, J=7.09 Hz, 2H), 3.85 (s, 3H), 3.54 (br. s., 2H), 3.36 (s, 3H), 1.45 (t, J=6.97 Hz, 3H), 1.37-1.42 (m, 2H), 1.26-1.30 (m, J=3.70 Hz, 4H), 0.85 (t, J=6.85 Hz, 3H). $^{13}$C NMR (126 MHz, CHLOROFORM-d) δ 162.0, 150.8, 148.6, 131.7, 129.6, 125.6, 122.6, 117.4, 113.9, 113.7, 63.9, 56.8, 55.5, 49.7, 28.7, 28.5, 22.3, 14.6, 14.0. HRMS for $C_{21}H_{28}ClNO_5SNa$ [M+Na$^+$] calculated 464.1269, found 464.1265.

N-(4-chloro-2,5-dimethoxyphenyl)-4-ethoxy-N-hexyl-benzenesulfonamide (37). Compound 37 was synthesized using compound 1 (10 mg, 0.03 mmol) and 1-iodohexane (32e, 4.4 μL, 0.03 mmol) as off-white solid (8 mg, yield=65%). $^1$H NMR (500 MHz, CHLOROFORM-d) δ 7.59 (d, J=8.80 Hz, 2H), 6.86-6.91 (m, 3H), 6.81 (s, 1H), 4.07 (q, J=7.09 Hz, 2H), 3.84 (s, 3H), 3.47-3.62 (m, 2H), 3.36 (s, 3H), 1.44 (t, J=7.10 Hz, 3H), 1.39 (quin, J=7.60 Hz, 2H), 1.16-1.34 (m, 6H), 0.85 (t, J=6.85 Hz, 3H). $^{13}$C NMR (126 MHz, CHLOROFORM-d) δ 162.0, 150.8, 148.6, 131.7, 129.6, 125.6, 122.6, 117.4, 113.9, 113.7, 63.9, 56.8, 55.5, 49.7, 31.4, 28.8, 26.2, 22.6, 14.6, 14.0. HRMS for $C_{22}H_{30}ClNO_5SNa$ [M+Na$^+$] calculated 478.1425, found 478.1422.

N-(4-chloro-2,5-dimethoxyphenyl)-4-ethoxy-N-heptyl-benzenesulfonamide (38). Compound 38 was synthesized using compound 1 (10 mg, 0.03 mmol) and 1-iodoheptane (32f, 4.9 μL, 0.03 mmol) as white solid (12 mg, yield=95%). $^1$H NMR (500 MHz, CHLOROFORM-d) δ 7.59 (d, J=8.80 Hz, 2H), 6.87-6.91 (m, 3H), 6.81 (s, 1H), 4.07 (q, J=6.85 Hz, 2H), 3.84 (5, 3H), 3.45-3.63 (m, 2H), 3.36 (5, 3H), 1.44 (t, J=7.10 Hz, 6H), 1.39 (quin, J=7.40 Hz, 1H), 1.14-1.33 (m, 10H), 0.85 (t, J=6.97 Hz, 3H). $^{13}$C NMR (126 MHz. CHLOROFORM-d) δ 161.9, 150.7, 148.5, 131.6, 129.5, 125.6, 122.6, 117.3, 113.9, 113.6, 63.9, 56.7, 55.5, 49.6, 31.7, 28.9, 28.9, 26.5, 22.6, 14.6, 14.1. HRMS for $C_{23}H_{32}ClNO_5SNa$ [M+Na$^+$] calculated 492.1582, found 492.1578.

N-(4-chloro-2,5-dimethoxyphenyl)-4-ethoxy-N-dodecyl-benzenesulfonamide (39). Compound 39 was synthesized using compound 1 (10 mg, 0.03 mmol) and 1-bromododecane (32g, 7.1 µL, 0.03 mmol) as white solid (14 mg, yield=96%). $^1$H NMR (500 MHz. CHLOROFORM-d) δ 7.59 (d, J=8.80 Hz, 2H), 6.86-6.92 (m, 3H), 6.81 (s, 1H), 4.07 (q, J=7.09 Hz, 2H), 3.84 (s, 3H), 3.45-3.63 (m, 2H), 3.36 (s, 3H), 1.44 (t, J=6.97 Hz, 3H), 1.38 (quin, J=7.30 Hz, 2H), 1.23-1.30 (m, 10H), 0.88 (t, J=6.97 Hz, 3H). $^{13}$C NMR (126 MHz, CHLOROFORM-d) δ 161.9, 150.7, 148.5, 131.6, 129.6, 125.6, 122.6, 117.3, 113.9, 113.6, 63.9, 56.7, 55.5, 49.7, 31.9, 29.7, 29.6, 29.6, 29.6, 29.4, 29.2, 28.9, 26.6, 22.7, 14.6, 14.1. HRMS for $C_{28}H_{43}ClNO_5S$ [M+H$^+$] calculated 540.2545, found 540.2549.

N-(4-chloro-2,5-dimethoxyphenyl)-4-ethoxy-N-isopropylbenzenesulfonamide (40). Compound 40 was synthesized using compound 1 (10 mg, 0.03 mmol) and 2-iodopropane (32h, 2.96 µL, 0.03 mmol) as white solid (5 mg, yield=48%). $^1$H NMR (500 MHz, CHLOROFORM-d) δ 7.76 (d, J=8.80 Hz, 2H), 6.94 (s, 1H), 6.92 (d, J=8.80 Hz, 2H), 6.70 (s, 1H), 4.39 (spt, J=6.70 Hz, 1H), 4.09 (q, J=7.09 Hz, 2H), 3.81 (s, 3H), 3.61 (s, 3H), 1.46 (t, J=6.97 Hz, 3H), 1.13 (d, J=6.60 Hz, 3H), 0.99 (d, J=6.60 Hz, 3H). $^{13}$C NMR (126 MHz, CHLOROFORM-d) δ 161.9, 152.9, 148.3, 132.9, 129.8, 123.3, 122.6, 118.5, 114.0, 113.9, 63.9, 56.8, 55.8, 51.9, 22.2, 20.9, 14.6. HRMS for $C_{19}H_{24}ClNO_5SNa$ [M+Na$^+$] calculated 436.0956, found 436.0957.

N-(4-chloro-2,5-dimethoxyphenyl)-4-ethoxy-N-isobutylbenzenesulfonamide (41). Compound 41 was synthesized using compound 1 (10 mg, 0.03 mmol) and 1-iodo-2-methylpropane (32i, 3.4 µL, 0.03 mmol) as white solid (9 mg, yield=77%). $^1$H NMR (500 MHz, CHLOROFORM-d) δ 7.56 (d, J=8.80 Hz, 2H), 6.92 (s, 1H), 6.89 (d, J=8.80 Hz, 2H), 6.80 (5, 1H), 4.07 (q, J=7.09 Hz, 2H), 3.85 (5, 3H), 3.29-3.51 (m, 2H), 3.33 (s, 3H), 1.59 (spt, J=7.00 Hz, 2H), 1.44 (t, J=6.97 Hz, 3H), 0.91 (br. s., 6H). $^{13}$C NMR (126 MHz, CHLOROFORM-d) δ 161.9, 150.6, 148.5, 131.5, 129.6, 126.0, 122.5, 117.2, 113.9, 113.7, 63.9, 57.1, 56.8, 55.5, 27.6, 20.1, 14.6. HRMS for $C_{20}H_{26}ClNO_5SNa$ [M+Na$^+$] calculated 450.1112, found 450.1109.

N-(4-chloro-2,5-dimethoxyphenyl)-4-ethoxy-N-(prop-2-yn-1-yl) benzenesulfonamide (42). Compound 42 was synthesized using compound 1 (10 mg, 0.03 mmol) and propargyl bromide solution in toluene (32j, 2.8 µL, 0.03 mmol) as white solid (9 mg, yield=81%). $^1$H NMR (500 MHz, CHLOROFORM-d) δ 7.62 (d, J=8.80 Hz, 2H), 6.96 (s, 1H), 6.90 (d, J=8.80 Hz, 2H), 6.85 (s, 1H), 4.44 (br. s., 2H), 4.08 (q, J=7.09 Hz, 2H), 3.82 (s, 3H), 3.44 (s, 3H), 2.12-2.23 (m, 1H), 1.45 (t, J=6.85 Hz, 3H). $^{13}$C NMR (126 MHz, CHLOROFORM-d) δ 162.3, 150.5, 148.6, 131.1, 129.8, 125.0, 123.1, 117.2, 114.1, 113.7, 78.4, 73.2, 64.0, 56.7, 55.8, 39.6, 14.6. HRMS for $C_{19}H_{20}ClNO_5SNa$ [M+Na$^+$] calculated 432.0643, found 432.0639.

N-(but-3-yn-1-yl)-N-(4-chloro-2,5-dimethoxyphenyl)-4-ethoxybenzenesulfonamide (43). Compound 43 was synthesized using compound 1 (40 mg, 0.11 mmol) and 4-bromo-1-butyne (32k, 11.1 µL, 0.11 mmol) as white solid (3 mg, yield=7%). $^1$H NMR (500 MHz, CHLOROFORM-d) δ 7.59 (d, J=8.80 Hz, 2H), 6.98 (s, 1H), 6.90 (d, J=8.80 Hz, 2H), 6.81 (s, 1H), 4.08 (q, J=7.09 Hz, 2H), 3.85 (s, 3H), 3.72 (br. s., 2H), 3.35 (s, 3H), 2.42 (dt, J=2.57, 7.40 Hz, 2H), 1.95 (t, J=2.57 Hz, 1H), 1.45 (t, J=6.97 Hz, 3H). $^{13}$C NMR (126 MHz, CHLOROFORM-d) δ 162.1, 150.3, 148.6, 131.4, 129.6, 125.2, 123.0, 117.6, 114.0, 113.6, 81.0, 70.0, 63.9, 56.7, 55.5, 48.6, 19.7, 14.6. HRMS for $C_{20}H_{22}ClNO_5SNa$ [M+Na$^+$] calculated 446.0799, found 446.0798.

N-(4-chloro-2,5-dimethoxyphenyl)-4-ethoxy-N-(pent-4-yn-1-yl) benzenesulfonamide (44). Compound 44 was synthesized using compound 1 (40 mg, 0.11 mmol) and 5-iodopent-1-yne (32l, 13.5 µL, 0.12 mmol) as off-white solid (40 mg, yield=84%). $^1$H NMR (500 MHz, CHLOROFORM-d) δ 7.59 (d, J=8.80 Hz, 2H), 6.90 (d, J=8.80 Hz, 2H), 6.87 (s, 1H), 6.83 (s, 1H), 4.08 (q, J=7.09 Hz, 2H), 3.84 (s, 3H), 3.64 (br, s., 2H), 3.38 (s, 3H), 2.26 (dt, J=2.45, 7.21 Hz, 2H), 1.91 (t, J=2.57 Hz, 1H), 1.67 (quip, J=7.09 Hz, 2H), 1.44 (t, J=6.97 Hz, 3H). $^{13}$C NMR (126 MHz, CHLOROFORM-d) δ 162.1, 150.7, 148.6, 131.3, 129.6, 125.5, 122.8, 117.0, 114.0, 113.7, 83.4, 68.7, 63.9, 56.8, 55.6, 48.9, 27.8, 15.8, 14.6. HRMS for $C_{21}H_{24}ClNO_5SNa$ [M+Na$^+$] calculated 460.0956, found 460.0954.

N-(4-chloro-2,5-dimethoxyphenyl)-4-ethoxy-N-(2-(2-(2-(prop-2-yn-1-yloxy)ethoxy)ethoxy)ethyl)benzenesulfonamide (45). Compound 45 was synthesized using compound 1 (40 mg, 0.11 mmol) and propargyl-PEG3-bromide (32m, 29.7 µL, 0.12 mmol) as clear oil (48 mg, yield=82%). $^1$H NMR (500 MHz, METHANOL-$d_4$) δ 7.59 (d, J=8.80 Hz, 2H), 7.02 (d, J=8.80 Hz, 2H), 6.97 (s, 1H), 6.96 (s, 1H), 4.16 (d, J=2.20 Hz, 2H), 4.11 (q, J=7.09 Hz, 2H), 3.72-3.85 (m, 5H), 3.61-3.65 (m, 2H), 3.57-3.60 (m, 2H), 3.48-3.54 (m, 6H), 3.38 (s, 3H), 2.85 (t, J=2.32 Hz, 1H), 1.41 (t, J=6.97 Hz, 3H). $^{13}$C NMR (126 MHz, METHANOL-$d_4$) δ 164.0, 152.4, 150.1, 132.9, 131.0, 127.1, 124.3, 119.1, 115.5, 115.0, 80.7, 76.1, 71.7, 71.5, 71.3, 70.5, 70.2, 65.3, 59.2, 57.4, 56.4, 50.4, 15.1. HRMS for $C_{25}H_{32}ClNO_8SNa$ [M+Na$^+$] calculated 564.1429, found 564.1431.

N-benzyl-N-(4-chloro-2,5-dimethoxyphenyl)-4-ethoxybenzenesulfonamide (46). Compound 46 was synthesized using compound 1 (10 mg, 0.03 mmol) and benzyl chloride (32n, 3.4 µL, 0.03 mmol) as white solid (12 mg, yield=94%). $^1$H NMR (500 MHz, CHLOROFORM-d) δ 7.65 (d, J=8.80 Hz, 2H), 7.10-7.25 (m, 5H), 6.92 (d, J=8.80 Hz, 2H), 6.75 (5, 1H), 6.63 (5, 1H), 4.74 (br. s., 2H), 4.09 (q, J=6.85 Hz, 2H), 3.67 (5, 3H), 3.35 (5, 3H), 1.46 (t, J=6.85 Hz, 3H). $^{13}$C NMR (126 MHz, CHLOROFORM-d) δ 162.1, 150.5, 148.4, 136.5, 131.7, 129.6, 128.8, 128.2, 127.6, 125.1, 122.6, 117.9, 114.0, 113.5, 63.9, 56.6, 55.5, 53.4, 14.6. HRMS for $C_{23}H_{24}ClNO_5SNa$ [M+Na$^+$] calculated 484.0956, found 484.0952.

N-(4-chloro-2,5-dimethoxyphenyl)-4-ethoxy-N-phenethylbenzenesulfonamide (47). Compound 47 was synthesized using compound 1 (10 mg, 0.03 mmol) and (2-iodoethyl) benzene (32o, 3.4 µL, 0.03 mmol) as off-white solid (12 mg, yield=95%). $^1$H NMR (500 MHz, CHLOROFORM-d) δ 7.45-7.52 (m, 2H), 7.18 (d, J=7.60 Hz, 2H), 7.12 (t. J=7.30 Hz, 1H), 7.06 (d, J=7.60 Hz, 2H), 6.76-6.83 (m, J=8.80 Hz, 2H), 6.72 (5, 1H), 6.66 (s, 1H), 3.99 (q, J=6.85 Hz, 2H), 3.61-3.85 (m, 5H), 3.25 (5, 3H), 2.74 (t, J=7.70 Hz, 2H), 1.37 (t, J=6.97 Hz, 3H). $^{13}$C NMR (126 MHz, CHLOROFORM-d) δ 162.0, 150.4, 148.5, 138.4, 131.4, 129.5, 128.9, 128.3, 126.4, 125.6, 122.6, 117.5, 113.9, 113.4, 63.9, 56.6, 55.5, 51.2, 35.8, 14.6. HRMS for $C_{24}H_{26}ClNO_5SNa$ [M+Na$^+$] calculated 498.1112, found 498.111.

N-(4-chloro-2,5-dimethoxyphenyl)-N-((4-ethoxyphenyl) sulfonyl)acetamide (48). To a solution of compound 1 (10 mg, 0.03 mmol) in anhydrous $CH_2Cl_2$ were added, acetyl chloride (32p, 3.8 µL, 0.03 mmol) and triethylamine (15 µL, 0.12 mmol) and the reaction was heated at 45° C. with stirring for 20 hours upon which more acetyl chloride (3.8 µL, 0.03 mmol) was added to drive the reaction to completion. The solvent was then removed, and the residue was dissolved in EtOAc, washed with water and brine, dried over $MgSO_4$ and concentrated under vacuum to obtain the residue which was purified by silica gel column chromatography (30% EtOAc/hexanes) to obtain compound 48 as white solid (5 mg, yield=45%). $^1$H NMR (500 MHz, CHLOROFORM-d) δ 7.98 (d, J=8.80 Hz, 2H), 7.05 (s, 1H), 6.85-7.01 (m, 3H), 4.12 (q, J=7.10 Hz, 2H), 3.91 (s, 3H), 3.67-3.76 (m, 3H), 1.86 (s, 3H), 1.46 (t, J=6.97 Hz, 3H). $^{13}C$ NMR (126 MHz, CHLOROFORM-d) δ 170.1, 163.2, 149.8, 149.3, 131.8, 130.0, 124.9, 123.9, 115.7, 114.1, 113.8, 64.0, 56.9, 56.0, 24.0, 14.6. HRMS for $C_{18}H_{20}ClNO_6SNa$ [M+Na$^+$] calculated 436.0592, found 436.0592.

Ethyl N-(4-chloro-2,5-dimethoxyphenyl)-N-((4-ethoxyphenyl)sulfonyl)glycinate (49). Compound 49 was synthesized using compound 1 (10 mg, 0.03 mmol) and ethylbromoacetate (32q, 3.3 μL, 0.03 mmol) as off-white solid (12 mg, yield=97%). $^1H$ NMR (500 MHz, CHLOROFORM-d) δ 7.60 (d, J=8.80 Hz, 2H), 7.18 (5, 1H), 6.89 (d, J=8.80 Hz, 2H), 6.80 (s, 1H), 4.38 (5, 2H), 4.16 (d, J=7.09 Hz, 2H), 4.07 (d, J=7.09 Hz, 2H), 3.83 (s, 3H), 3.39 (s, 3H), 1.44 (t, J=6.97 Hz, 3H), 1.25 (t, J=7.09 Hz, 3H). $^{13}C$ NMR (126 MHz, CHLOROFORM-d) δ 169.4, 162.3, 149.8, 148.6, 131.3, 129.7, 125.6, 123.0, 117.8, 114.0, 113.5, 63.9, 61.3, 56.7, 55.7, 51.0, 14.6, 14.2. HRMS for $C_{20}H_{25}ClNO_7S$ [M+H$^+$] calculated 458.1035, found 458.1035.

Ethyl 4-((N-(4-chloro-2,5-dimethoxyphenyl)-4-ethoxyphenyl) sulfonamido)butanoate (50). Compound 50 was synthesized using compound 1 (40 mg, 0.11 mmol) and ethyl-4-bromobutyrate (32r, 16.9 μL, 0.12 mmol) as white solid (47 mg, yield=91%). $^1H$ NMR (500 MHz, CHLOROFORM-d) δ 7.58 (d, J=8.80 Hz, 2H), 6.89 (d, J=8.80 Hz, 2H), 6.87 (s, 1H), 6.82 (s, 1H), 4.09 (q, J=7.20 Hz, 2H), 4.07 (q, J=7.00 Hz, 2H), 3.84 (s, 3H), 3.60 (br. s., 2H), 3.37 (s, 3H), 2.41 (t, J=7.46 Hz, 2H), 1.74 (quin, J=7.09 Hz, 2H), 1.44 (t, J=6.97 Hz, 3H), 1.23 (t, J=7.21 Hz, 3H). $^{13}C$ NMR (126 MHz, CHLOROFORM-d) δ 173.1, 162.1, 150.7, 148.6, 131.3, 129.6, 125.3, 122.9, 117.0, 114.0, 113.7, 63.9, 60.4, 56.8, 55.6, 49.0, 31.1, 24.1, 14.6, 14.2. HRMS for $C_{22}H_{28}ClNO_7SNa$ [M+Na$^+$] calculated 508.1167, found 508.117.

N-(4-chloro-2,5-dimethoxyphenyl)-4-ethoxy-N-(3-hydroxypropyl) benzenesulfonamide (51). Compound 51 was synthesized using compound 1 (10 mg, 0.03 mmol) and 3-bromo-1-propanol (32s, 2.7 μL, 0.03 mmol) as off-white solid (5 mg, yield=42%). $^1H$ NMR (500 MHz, DMSO-d$_6$) δ 7.55 (d, J=8.80 Hz, 2H), 7.14 (s, 1H), 7.08 (d, J=8.80 Hz, 2H), 6.76 (s, 1H), 4.43 (t, J=4.89 Hz, 1H), 4.11 (q, J=6.85 Hz, 2H), 3.72 (s, 3H), 3.50 (br. s., 2H), 3.42 (s, 3H), 3.33-3.36 (m, 2H), 1.46 (quin, J=6.80 Hz, 2H), 1.34 (t, J=6.85 Hz, 3H), $^{13}C$ NMR (126 MHz, DMSO-d6) δ 161.8, 151.1, 147.9, 130.8, 129.5, 125.9, 121.5, 116.4, 114.5, 114.3, 63.8, 58.1, 56.5, 56.1, 47.0, 31.7, 14.5. HRMS for $C_{19}H_{24}ClNO_6SNa$ [M+Na$^+$] calculated 452.0905, found 452.0907.

tert-Butyl (3-ON-(4-chloro-2,5-dimethoxyphenyl)-4-ethoxyphenyl) sulfonamido)propyl)carbamate (52). Compound 52 was synthesized using compound 1 (50 mg, 0.13 mmol) and tert-butyl (3-bromopropyl)carbamate (32t, 35.2 μL, 0.15 mmol) as off-white solid (60 mg, yield=84%). $^1H$ NMR (500 MHz, CHLOROFORM-d) δ 7.59 (d, J=8.80 Hz, 2H), 6.91 (d, J=8.80 Hz, 2H), 6.84 (s, 1H), 6.84 (s, 1H), 5.00 (br. s., 1H), 4.08 (q, J=6.85 Hz, 2H), 3.84 (s, 3H), 3.61 (br. s., 2H), 3.38 (s, 3H), 3.27 (br. s., 2H), 1.56 (quin, J=6.40 Hz, 2H), 1.40-1.50 (n, 12H). $^{13}C$ NMR (126 MHz, CHLOROFORM-d) δ 162.1, 156.0, 150.7, 148.7, 131.2, 129.6, 125.2, 123.0, 117.0, 114.0, 113.8, 79.1, 63.9, 56.8, 55.6, 47.0, 37.1, 28.8, 28.4, 14.6. HRMS for $C_{24}H_{33}ClN_2O_7SNa$ [M+Na$^+$] calculated 551.1589, found 551.1587.

4-((N-(4-chloro-2,5-dimethoxyphenyl)-4-ethoxyphenyl) sulfonamido)butanoic acid (53). To a solution of compound 50 (38 mg, 0.08 mmol) in MeOH (0.5 mL) was added a solution of lithium hydroxide monohydrate (16.4 mg, 0.39 mmol) in water (0.5 mL) and the reaction was stirred overnight. The solvent was then removed and the residue was dissolved in acidified water (3N aq. HCl) and extracted with EtOAc. The organic layer was dried over $MgSO_4$ and concentrated under vacuum to obtain the residue which was purified by silica gel column chromatography (8% MeOH/$CH_2Cl_2$) to obtain compounds 53 as white solid (26 mg, yield=73%). $^1H$ NMR (500 MHz, DMSO-d$_6$) δ 11.74-12.24 (m, 1H), 7.54 (d, J=9.05 Hz, 2H), 7.14 (s, 1H), 7.07 (d, J=9.05 Hz, 2H), 6.75 (s, 1H), 4.11 (q, J=7.09 Hz, 2H), 3.70 (s, 3H), 3.45-3.47 (m, 2H), 3.41 (s, 3H), 2.26 (t, J=7.34 Hz, 2H), 1.50 (quin, J=7.03 Hz, 2H), 1.34 (t, J=6.85 Hz, 3H). $^{13}C$ NMR (126 MHz, DMSO-d6) δ 174.1, 161.8, 151.1, 148.0, 130.7, 129.5, 125.8, 121.6, 116.2, 114.5, 114.3, 63.8, 56.5, 56.1, 48.9, 30.4, 23.5, 14.5. HRMS for $C_{20}H_{23}ClNO_7S$ [M−H]$^-$ calculated 456.0889, found 456.0889.

4-((N-(4-chloro-2,5-dimethoxyphenyl)-4-ethoxyphenyl) sulfonamido)-N-ethylbutanamide (54). To a solution of compound 53 (7 mg, 0.02 mmol) in anhydrous DMF were added, HATE) (6.4 mg, 0.02), 2M ethyl amine solution in THF (8.36 μL, 0.02 mmol), and triethylamine (4.3 μL, 0.03 mmol) and the reaction was stirred until completion. The solvent was then removed under vacuum and the residue was purified by silica gel column chromatography (5% MeOH/$CH_2Cl_2$) to obtain compound 54 as white solid (6 mg, yield=81%). $^1H$ NMR (500 MHz, CHLOROFORM-d) δ 7.56 (d, J=8.80 Hz, 2H), 6.91 (d, J=8.80 Hz, 2H), 6.85 (s, 1H), 6.79 (s, 1H), 5.90 (br. s., 1H), 4.08 (q, J=7.09 Hz, 2H), 3.83 (s, 3H), 3.58 (br. s., 2H), 3.40 (s, 3H), 3.32 (quin, J=6.85 Hz, 2H), 2.33 (t, J=6.85 Hz, 2H), 1.73 (quin, J=6.48 Hz, 2H), 1.45 (t, J=6.97 Hz, 3H), 1.18 (t, J=7.34 Hz, 3H). $^{13}C$ NMR (126 MHz. CHLOROFORM-d) δ 172.3, 162.2, 150.7, 148.7, 131.1, 129.6, 125.2, 123.1, 116.8, 114.1, 114.0, 63.9, 56.8, 55.7, 48.9, 34.4, 33.3, 24.6, 14.8, 14.6. HRMS for $C_{22}H_{30}ClN_2O_6S$ [M+H$^+$] calculated 485.1508, found 485.1511.

N-(3-aminopropyl)-N-(4-chloro-2,5-dimethoxyphenyl)-4-ethoxybenzenesulfonamide hydrochloride (55). Compound 52 (48 mg, 0.09 mmol) was dissolved in 4N HCl solution in dioxane (1 mL) and stirred at room temperature for 20 hours. Solvent was then removed under vacuum, reside was suspended in $CH_2Cl_2$ followed by removal of the solvent under vacuum to obtain compound 55 as white solid (37.1 mg, yield=95%). $^1H$ NMR (500 MHz, DMSO-d$_6$) δ 7.85 (br. s., 3H), 7.56 (d, J=8.80 Hz, 2H), 7.17 (s, 1H), 7.09 (d, J=8.80 Hz, 2H), 6.78 (s, 1H), 4.11 (q, J=6.85 Hz, 2H), 3.71-3.75 (m, 3H), 3.53 (br. s., 2H), 3.42 (5, 3H), 2.83 (t, J=8.10 Hz, 2H), 1.61 (td, J=7.00, 14.61 Hz, 2H), 1.34 (t, J=6.97 Hz, 3H). $^{13}C$ NMR (126 MHz, DMSO-d$_6$) δ 161.9, 151.0, 148.0, 130.5, 129.5, 125.5, 121.8, 116.3, 114.6, 114.4, 63.8, 56.6, 56.2, 47.1, 36.6, 26.4, 14.5. HRMS for $C_{19}H_{26}ClN_2O_5S$ [M+H$^+$] calculated 429.1245, found 429.1246.

N-(6-((3-((N-(4-chloro-2,5-dimethoxyphenyl)-4-ethoxyphenyl) sulfonamido)propyl)amino)-6-oxohexyl)-3',6'-dihydroxy-3-oxo-3H-spiro[isobenzofuran-1,9'-xanthene]-5-carboxamide (56). To a solution of compound 55 (4 mg, 0.01 mmol) in anhydrous DMF were added, triethylamine (3.6 μL, 0.03 mmol) and fluorescein-5(6)-carboxamidocaproic acid N-succinimidyl ester (5(6)-SFX SE, Chemodex, #F0044) (5 mg, 0.01 mmol). After completion of the reaction, solvent was removed, and the residue was purified using silica gel column chromatography (10% MeOH/$CH_2Cl_2$) to obtain compound 56 as bright yellow solid (5.4 mg, yield=70%). $^1H$ NMR (500 MHz, METHANOL-d$_4$) δ 8.12 (d, J=8.07 Hz, 1H), 8.06 (d, J=8.10 Hz, 1H), 7.60 (s, 1H), 7.55 (d, J=8.80 Hz, 2H), 6.99-7.03 (m, 2H), 6.97 (s, 1H), 6.87 (s, 1H), 6.65-6.73 (m, 2H), 6.60 (br. s., 2H), 6.54 (s, 2H), 4.10 (q, J=7.09 Hz, 2H), 3.78 (s, 3H), 3.54-3.64 (m, 2H), 3.35-3.37 (m, 3H), 3.12-3.28 (m, 4H), 2.12 (s, 2H), 1.48-1.69 (m, 8H), 1.40 (t, J=6.97 Hz, 3H). HRMS for $C_{46}H_{47}ClN_3O_{12}S$ [M+H$^+$] calculated 900.2563, found 900.2563.

N-(9-(2-carboxy-44(34(N-(4-chloro-2,5-dimethoxyphenyl)-4-ethoxyphenyl)sulfonamido)propyl)carbamoyl)phenyl)-6-(diethylamino)-3H-xanthen-3-ylidene)-N-ethylethanaminium (57). To a solution of compound 55 (5 mg, 0.01 mmol) in anhydrous DMF were added, triethylamine (4.5 μL, 0.03 mmol) and 5(6)-carboxytetramethylrhodamine succinimidyl ester (NHS-Rhodamine, 6 mg, 0.01 mmol). After completion of the reaction, solvent was removed, and the residue was purified using silica gel column chromatography (20% MeOH/$CH_2Cl_2$) to obtain compound 57 as dark purple solid (8.5 mg, yield=94%), $^1$H NMR (500 MHz, acetone) δ 8.38 (s, 1H), 7.99-8.27 (m, 2H), 7.58-7.73 (m, 2H), 7.55 (d, J=8.80 Hz, 1H), 7.33 (d, J=7.83 Hz, 1H), 6.93-7.11 (m, 4H), 6.52-6.69 Om 5H), 4.11-4.19 (m, 2H), 3.86 (s, 2H), 3.68-3.83 (m, 3H), 3.59 (s, 2H), 3.47 (s, 2H), 3.37 (s, 1H), 2.97-3.12 (m, 12H), 1.78 (quip, J=6.80 Hz, 1H), 1.59-1.68 Om J=6.85, 6.85, 6.85, 6.85 Hz, 1H), 1.37-1.42 (m, 3H). HRMS for $C_{44}H_{46}ClN_4O_9S$ [M+] calculated 841.2669, found 841.2659.

N-(3-((N-(4-chloro-2,5-dimethoxyphenyl)-4-ethoxyphenyl) sulfonamido)propyl)-5-((3aR,4R,6aS)-2-oxohexahydro-1H-thieno[3,4-d]imidazol-4-yl)pentanamide (58). To a solution of compound 55 (10 mg, 0.02 mmol) in anhydrous DMF were added, HATU (14.9 mg, 0.04 mmol), biotin (5.8 mg, 0.02 mmol) and triethylamine (11 μL, 0.08 mmol). After stirring overnight, the solvent was removed and the residue was purified using silica gel column chromatography (10% MeOH/$CH_2Cl_2$) to obtain compound 58 as off-white solid (14 mg, quantitative yield). $^1$H NMR (500 MHz, METHANOL-$d_4$) δ 7.57 (d, J=8.80 Hz, 2H), 7.03 (d, J=8.80 Hz, 2H), 6.99 (s, 1H), 6.89 (s, 1H), 4.48 (dd, J=4.89, 7.83 Hz, 1H), 4.30 (dd, J=4.40, 7.83 Hz, 1H), 4.12 (q, J=7.09 Hz, 2H), 3.80 (s, 3H), 3.63 (br. s., 2H), 3.39 (s, 3H), 3.17-3.29 (m, 3H), 2.92 (dd, J=4.89, 12.72 Hz, 1H), 2.70 (d, J=12.72 Hz, 1H), 2.17 (t, J=7.34 Hz, 2H), 1.57-1.75 (m, 6H), 1.36-1.48 (n, 5H). $^{13}$C NMR (126 MHz, METHANOL-$d_4$) δ 176.2, 166.3, 164.1, 152.6, 150.2, 132.4, 131.0, 126.8, 124.4, 118.5, 115.5, 115.2, 65.3, 63.5, 61.8, 57.3, 57.1, 56.5, 41.2, 37.8, 37.0, 29.9, 29.8, 29.6, 27.1, 15.1. HRMS for $C_{29}H_{40}ClN_4O_7S_2$ [M+H$^+$] calculated 655.2021, found 655.2025.

N-(4-azido-2,5-dimethoxyphenyl)-4-ethoxybenzenesulfonamide (59). To a solution of compound 10 (84 mg, 0.24 mmol) in anhydrous acetonitrile were added, tert-butyl nitrite (37 mg, 0.36 mmol) and azidotrimethylsilane (33 mg, 0.29 mmol) and the reaction was heated at 45° C. for 1 hour. The solvent was then removed, and the residue was purified using silica gel column chromatography (20% EtOAc/hexanes) under low-light conditions to obtain compound 59 as white solid (52 mg, yield=57%). $^1$H NMR (500 MHz, CHLOROFORM-d) δ 7.64 (d, J=8.80 Hz, 2H), 7.19 (s, 1H), 6.81-6.89 (m, 3H), 6.36 (s, 1H), 4.04 (q, J=6.85 Hz, 2H), 3.86 (s, 3H), 3.56 (s, 3H), 1.42 (t, J=6.97 Hz, 3H). $^{13}$C NMR (126 MHz, CHLOROFORM-d) δ 162.5, 146.3, 144.2, 130.1, 129.3, 124.7, 122.9, 114.3, 107.3, 103.8, 63.9, 56.7, 56.3, 14.6. HRMS for $C_{16}H_{18}N_4O_5SNa$ [M+Na$^+$] calculated 401.089, found 401.0894.

3-Amino-N-(4-chloro-2,5-dimethoxyphenyl)-4-methoxybenzenesulfonamide (60). Combine 1,2-dimethylethylenediamine (7.2 μL, 0.069 mmol), CuI (9.2 mg, 0.057 mmol) and sodium ascorbate (8.7 mg, 0.057 mmol) in a microwave reaction vial. Seal and evacuate the vial and add $H_2O$ (300 Separately combine compound 25 (50 mg, 0.11 mmol) and $NaN_3$ (41.6 mg, 0.23 mmol) in EtOH (350 μL) and DMF (350 μL) and add to the reaction vial. Fill vial with argon gas and irradiate reaction using microwave at 100° C. for 1 hour, Water was poured into the reaction mixture and extracted with EtOAc. The organic layer was collected, solvent was removed to obtain the residue which was purified using silica gel column chromatography (30% EtOAc/hexanes) to obtain compound 60 as a tan solid (28 mg, yield=63%). $^1$H NMR (500 MHz, METHANOL-$d_4$) δ 7.16 (s, 1H), 7.02-7.10 (m, 2H), 6.89 (s, 1H), 6.84 (d, J=8.56 Hz, 1H), 3.86 (s, 3H), 3.80 (s, 3H), 3.55 (s, 3H). $^{13}$C NMR (126 MHz, METHANOL-$d_4$) δ 152.1, 150.5, 147.1, 138.9, 132.7, 127.1, 119.6, 119.0, 114.7, 113.7, 110.4, 109.8, 57.2, 57.2, 56.4. HRMS for $C_{15}H_{18}ClN_2O_5S$ [M+H$^+$] calculated 373.0619, found 373.062.

3-Azido-N-(4-chloro-2,5-dimethoxyphenyl)-4-methoxybenzenesulfonamide (61). To a solution of compound 60 (23 mg, 0.06 mmol) in anhydrous acetonitrile were added, tert-butyl nitrite (10 mg, 0.09 mmol) and azidotrimethylsilane (9 mg, 0.07 mmol) and the reaction was heated at 45° C. for 1 hour. The solvent was then removed, and the residue was purified using silica gel column chromatography (25% EtOAc/hexanes) under low-light conditions to obtain compound 61 as light yellow solid (22 mg, yield=88%), $^1$H NMR (500 MHz, CHLOROFORM-d) δ 7.49 (dd, J=1.96, 8.56 Hz, 1H), 7.38 (d, J=1.71 Hz, 1H), 7.24 (s, 1H), 6.95 (s, 1H), 6.85 (d, J=8.56 Hz, 1H), 6.80 (s, 1H), 3.91 (s, 3H), 3.88 (s, 3H), 3.66 (s, 3H). $^{13}$C NMR (126 MHz, CHLOROFORM-d) δ 155.4, 149.3, 143.5, 131.2, 129.2, 125.4, 124.8, 119.2, 118.2, 113.1, 111.2, 106.2, 56.8, 56.4, 56.3. HRMS for $C_{15}H_{15}ClN_4O_5SNa$ [M+Na$^+$] calculated 421.0344, found 421.0348.

N-(4-azido-2,5-dimethoxyphenyl)-4-ethoxy-N-(prop-2-yn-1-yl) benzenesulfonamide (62). To a solution of compound 61 (10 mg, 0.03 mmol) in anhydrous DMF were added, potassium carbonate (7.0 mg, 0.06 mmol) and propargyl bromide solution in toluene (32j, 3.23 μL, 0.03 mmol). The reaction was heated at 45° C. for 2 hours, followed by removal of the solvent. The residue was then dissolved in EtOAc and washed by water and brine, dried over sodium sulfate, concentrated under vacuum to obtain the residue which was purified by silica gel column chromatography (28% EtOAc/hexanes) to obtain compound 62 as off-white solid (10 mg, yield=89%). $^1$H NMR (500 MHz, CHLOROFORM-d) δ 7.62 (d, J=8.80 Hz, 2H), 6.81-6.97 (m, 3H), 6.41 (s, 1H), 4.43 (br. s., 2H), 4.08 (q, J=7.10 Hz, 2H), 3.80 (s, 3H), 3.42 (s, 3H), 2.17 (t, J=2.40 Hz, 1H), 1.44 (t, J=6.97 Hz, 3H). $^{13}$C NMR (126 MHz, CHLOROFORM-d) δ 162.3, 151.0, 145.6, 131.2, 129.8, 129.2, 122.6, 117.4, 114.1, 104.2, 78.6, 73.1, 63.9, 56.6, 55.7, 39.7, 14.6. HRMS for $C_{19}H_{20}N_4O_5SNa$ [M+Na$^+$] calculated 439.1047, found 439.105.

N-(3-aminopropyl)-N-(4-azido-2,5-dimethoxyphenyl)-4-ethoxybenzenesulfonamide (63). To a solution of compound 61 (27 mg, 0.07 mmol) in anhydrous DMF were added, potassium carbonate (19.5 mg, 0.14 mmol) and tert-butyl (3-bromopropyl)carbamate (32t, 22 mg, 0.09 mmol). The reaction was heated at 45° C. for 2 hours, followed by removal of the solvent. The residue was then dissolved in EtOAc and washed by water and brine, dried over sodium sulfate, concentrated under vacuum to obtain the residue which was purified by silica gel column chromatography (35% EtOAc/hexanes) to obtain N-Boc protected intermediate (14 mg) which was stirred in a solution of 4N HCl in dioxane for 1 hour. The solvent was then removed to obtain the compound 63 as tan solid (12 mg, yield=36%). $^1$H NMR (500 MHz, METHANOL-$d_4$) δ 7.58 (d, J=8.80 Hz, 2H), 7.04 (d, J=8.80 Hz, 2H), 6.79 (s, 1H), 6.56 (s, 1H), 4.12 (q, J=7.09 Hz, 2H), 3.79 (s, 3H), 3.67-3.72 (m, 2H), 3.40 (s, 3H), 3.13 (t, J=7.58 Hz, 2H), 1.77 (quin, J=7.00 Hz, 2H), 1.42 (t, J=6.97 Hz, 3H). 13C NMR (126 MHz, METHANOL-$d_4$) δ 164.3, 153.1, 147.8, 132.1, 131.2, 131.0, 124.2, 118.3, 115.6, 106.5, 65.3, 57.5, 56.4, 38.6, 28.0, 15.1. HRMS for $C_{19}H_{26}N_5O_5S$ [M+H$^+$] calculated 436.1649, found 436.1652.

N-(3-((N-(4-azido-2,5-dimethoxyphenyl)-4-ethoxyphenyl)sulfonamido) propyl)-5-((3aR,4R,6aS)-2-oxohexahydro-1H-thieno[3,4-d]imidazol-4-yl) pentanamide (64). To a solution of compound 63 (9 mg, 0.02 mmol) in anhydrous DMF were added, HATU (8.6 mg, 0.02 mmol), biotin (4.3 mg, 0.02 mmol), and triethylamine (6.6 μL, 0.05 mrnol). The reaction was stirred overnight, followed by removal of the solvent to obtain the residue which was purified using silica gel column chromatography (10% $MeOH/CH_2Cl_2$) to obtain compound 64 as offwhite solid (8.4 mg, 67%). $^1H$ NMR (500 MHz, METHANOL-$d_4$) δ 7.91 (br, s., 1H), 7.57 (d, J=8.80 Hz, 2H), 7.02 (d, J=8.80 Hz, 2H), 6.84 (s, 1H), 6.51 (s, 1H), 4.48 (dd, J=5, 01, 7.70 Hz, 1H), 4.30 (dd, J=4.40, 7.83 Hz, 1H), 4.12 (q, J=6.85 Hz, 2H), 3.80 (s, 3H), 3.61 (br, s., 2H), 3.36 (s, 3H), 3.16-3.29 (m, 3H), 2.92 (dd, J=5.14, 12.72 Hz, 1H), 2.70 (d, J=12.72 Hz, 1H), 2.17 (t, J=7.34 Hz, 2H), 1.51-1.80 (m, 6H), 1.36-1.49 (m, 5H). 13C NMR (126 MHz, METHANOL-$d_4$) δ 176.3, 176.2, 166.3, 164.1, 153.0, 147.6, 132.5, 131.0, 130.7, 124.3, 118.8, 115.5, 106.2, 65.3, 63.5, 61.8, 57.5, 57.1, 56.3, 41.2, 37.8, 37.0, 29.9, 29.7, 29.6, 27.1, 15.1. HRMS for $C_{29}H_{39}N_7O_7S_2Na$ [$M+Na^+$] calculated 684.2245, found 684.2241.

Biology: Cell Lines and Reagents

The THP1-Blue™ NF-κB cell line was purchased from Invivogen (San Diego, Calif.) which contains a stably integrated NF-κB-inducible secreted embryonic alkaline phosphatase (SEAP). ISRE-bla THP-1 cell line was generated by us as described earlier.37 QuantiBlue was purchased from Invivogen, MTT (3-[4,5-dimethylthiazol-2-yl]-2,5-diphenyl tetrazolium bromide) was purchased from Acros Organics, LPS (lps-eb) from Invivogen, and IFN-α from R&D Systems (#11200-2).

Measurement of NF-κB Activation Using THP1-Blue™ NF-κB Cells

THP1-Blue™ NF-κB cells were plated in 96-well plates at $10^5$ cells/well in 100 μl RPMI supplemented with 10% fetal bovine serum (FBS, Omega Scientific, Inc., Tarzana, Calif.), 100 U/mL penicillin, 100 μg/ml streptomycin (Thermo Fisher Scientific) and Normocin (Invivogen). LPS was prepared in assay medium at a concentration of 20 μg/mL. Tested compounds were dissolved in DMSO at 1 mM as a stock solution and were further diluted in the LPS solution to a final concentration of 10 μM. 100 μL of this solution was then transferred to the plated cells to obtain a final concentration of LPS at 10 μg/mL and compound at 5 μM (0.05% DMSO). The culture supernatants were harvested after a 20 hour incubation period, SEAP activity in the culture supernatants was determined by a colorimetric assay using QuantiBlue (Invivogen). Plate absorbance was read at 630 nm using a Tecan Infinite M200 plate reader (Männedorf, Switzerland). The SEAP concentration was directly proportional to NF-κB activity, which was 2-point normalized to yield activity of compound 1+LPS as 200% and activity for LPS as 100%.

Measurement of ISRE Activity in ISRE-Bla THP-1 Cells

ISRE-bla THP-1 cells were plated in 96-well plates at $5\times10^4$ cells/well in 50 μl RPMI supplemented with 10% dialyzed FBS (Atlanta Biologicals, Inc., GA), 0.1 mM nonessential amino acids, 1 mM sodium pyruvate, 100 U/mL penicillin and 100 μg/ml streptomycin. Type I IFN-α (R&D Systems, #11200-2) solution was prepared in assay medium at a concentration of 200 U/mL Tested compounds were dissolved in DMSO at 1 mM and were further diluted in the IFN-α solution to a final concentration of 10 μM. 50 μL of this solution was then transferred to the plated cells to obtain a final concentration of IFN-α at 100 U/mL and compound at 5 μM (0.05% DMSO), The cells were incubated for 16 hours, after which 20 μL of 6×LiveBLAzer™ FRET B/G Substrate (CCF4-AM) mixture (prepared according to the manufacturer's instructions) was added to each well, Plates were incubated at room temperature in the dark for 3 hours. Fluorescence was measured on a Tecan Infinite M200 plate reader at an excitation wavelength of 405 nm, and emission wavelengths of 465 nm and 535 nm. Background values (cell free wells at the same fluorescence wavelength) were subtracted from the raw fluorescence intensity values and the emission ratios were calculated as the ratio of background subtracted fluorescence intensities at 465 nm to background subtracted fluorescence intensities at 535 nm. The ISRE activity values for these compounds were 2-point normalized to yield activity of compound 1+IFN-α as 200% and activity for IFN-α as 100%.

Cell Viability Assay

THP-1 cells were plated in 96-well plates ($10^5$ cells/well) in 100 μL RPMI supplemented with 10% FBS, 100 U/mL penicillin and 100 μg/ml streptomycin. Compounds were dissolved in DMSO at 1 mM stock solution and were further diluted to 10 μM in the assay medium. 100 μL of this solution was added to the cells to obtain a final compound concentration of 5 μM (0.05% DMSO). After 18 hours incubation, a solution of MTT in assay media (0.5 mg/mL) was added to each well and further incubated for 4 to 6 hours, followed by addition of cell lysis buffer (15% w/v SDS and 0.12% v/v 12N HCl aqueous solution), incubated overnight, and then absorbance measured at 570 nm using 650 nm as reference using Tecan Infinite M200 plate reader.

Animals

Seven to nine-week-old C57BL/6 (wild-type, WT) mice were purchased from The Jackson Laboratories (Bar Harbor, Mass.). All animal experiments received prior approval from the UCSD Institutional Animal Care and Use Committee, In Vivo Adjuvant Activity Study WT mice (n=8 per group) were immunized in the gastronemius muscle with ovalbumin (20 μg/animal) mixed with MPLA (10 ng/animal) and compound 1 or 12 or 33 (50 nmol/animal) on days 0 and 21. On day 28, immunized mice were bled and OVA-specific IgG titers were measured by ELISA as previously described (Chan et al., 2009).

Statistical Analysis

Data are represented as mean±standard error of the mean (SEM). Origin 7 (Origin Lab, Northampton, Mass.) graphing software was used for figure preparation while Prism 4 (GraphPad, San Diego, Calif.) software was used for statistical calculations.

Example 2

Results and Discussion

Approximately 3400 differently substituted bis-aryl sulfonamide compounds were screened in the original HIS libraries, and a scatter plot showing activation data for these compounds in both cell-based NF-κB and ISRE was prepared. These results provided preliminary SAR indicating the substituents on the two aryl rings necessary for activity and pointed to compound 1 as an advanced lead. Hence, further SAR studies on compound 1 were conducted by first identifying three areas (sites A, B, and C) of potential modification as shown in FIG. 1. To standardize the reaction, we began with synthesis of compound 1 by reaction of 4-ethoxysulfonyl chloride (3a) and 4-chloro-2,5-dimethoxy aniline (2a) in the presence of an organic base (Scheme 1). However, the reaction not only provided the desired compound 1 but also formed the bis-sulfonamide side-product in high yields. This undesired side-product was formed in situ by further reaction of compound 1 with another equivalent of 4-ethoxysulfonyl chloride (3a). We were able to isolate this bis-sulfonamide side-product but observed that it was somewhat unstable. Limited hydrolysis by lithium hydroxide facilitated the complete conversion of this bissulfonamide side-product to compound 1 without further hydrolysis of the monosulfonamide bond, thereby improving reaction yields for compound 1 (Scheme 1). This reaction strategy was utilized for synthesis of several site A and site B modified compounds for SAR analysis.

Scheme 1. Syntheses of compound 1 and its site A and B modified analogs.

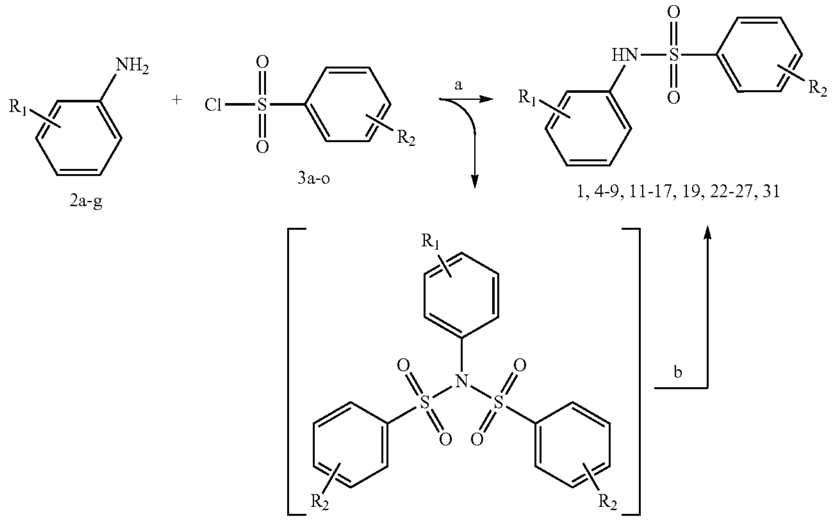

2a-g 3a-o 1, 4-9, 11-17, 19, 22-27, 31

Reagents and conditions: a) $Et_3N$, $CH_2Cl_2$; b) LiOH, MeOH, THF, $H_2O$.

SAR studies were initiated by modifying the substituents at site A (FIG. 1). These compounds were synthesized according to Scheme 1 using different anilines (2a-g). We probed the removal of one aryl substituent at a time to obtain compounds 4, 5, and 6 lacking the 2-methoxy, 3-methoxy, and 4-chloro substituents, respectively. Replacement of 4-chloro by a 4-bromo substituent gave compound 7, and migration of the 2-methoxy substituent to the 3-position gave compound 8. These compounds were evaluated for sustained activation of both NF-κB and ISRE pathways using LPS and IFN-α as primary stimuli, respectively. The SAR studies pointed to the importance of the methoxy substituents at the 2 and 5 positions of the aryl ring because either removal of any one of the substituents as in compound 4 and 5 or its displacement to another position on the ring as in 8 led to complete loss of activity. Removal of the 4-chloro as in compound 6 or its replacement with a spatially larger bromo substituent as in compound 7 retained activity (Table 1). Thus, to further explore position 4 on the phenyl ring, we synthesized analogs with 4-nitro (9) substitution and its 4-amino (10) derivative. However, both these analogs were inactive suggesting that only hydrophobic substituents at his site are tolerated (Table 1).

TABLE 1

Structure and bioactivity data for site A modified compounds.

| | | | NF-κB[b] | | ISRE[b] | | MTT[b] | |
|---|---|---|---|---|---|---|---|---|
| Compound | Reagent 2 | Site A Substitution[a] | % Activation | SEM | % Activation | SEM | % Viability | SEM |
| 1 | 2a | 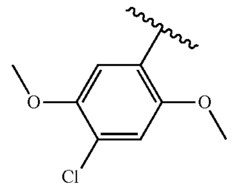 | 200 | — | 200 | — | 73.5 | 1.0 |
| 4 | 2b | 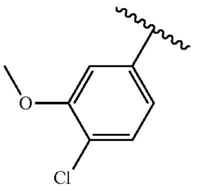 [SMILES: *c1ccc(Cl)c(OC)c1] | 126 | 2.4 | 99 | 1.1 | 83.7 | 1.8 |

TABLE 1-continued

Structure and bioactivity data for site A modified compounds.

| Compound | Reagent 2 | Site A Substitution[a] | NF-κB[b] % Activation | NF-κB[b] SEM | ISRE[b] % Activation | ISRE[b] SEM | MTT[b] % Viability | MTT[b] SEM |
|---|---|---|---|---|---|---|---|---|
| 5 | 2c | 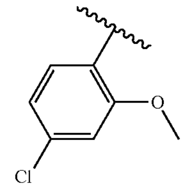 [SMILES: *c1ccc(Cl)cc1OC] | 141 | 7.8 | 109 | 3.1 | 78.3 | 1.5 |
| 6 | 2d | 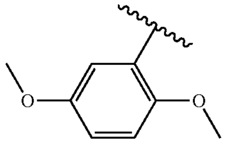 | 116 | 6.9 | 96 | 2.3 | 73.1 | 1.1 |
| 7 | 2e | 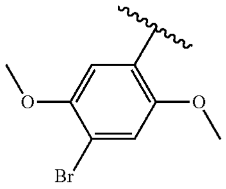 | 176 | 10.2 | 235 | 6.6 | 68.8 | 2.0 |
| 8 | 2f | 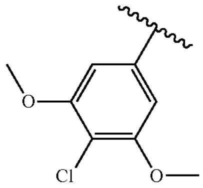 | 179 | 7.7 | 218 | 6.0 | 71.4 | 2.5 |
| 9 | 2g | 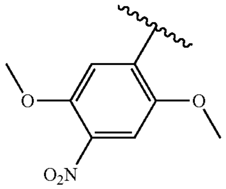 | 133 | 2.0 | 110 | 1.9 | 79.2 | 3.4 |
| 10 | —[c] | 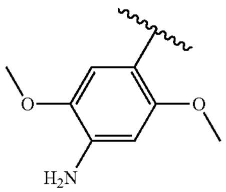 | 101 | 7.1 | 102 | 2.1 | 92.2 | 2.2 |

[a]Compounds 1, 4-9 were obtained by reaction of reagent 2 with 4-ethoxybenzenesulfonyl chloride (3a) as shown in Scheme 1.

[b]The % activation values in NF-κB and ISRE induction assays were two point normalized between compound 1 as 200% and LPS (10 ng/mL) for NF-κB or IFN-α (100 U/mL) for ISRE as 100%. The mean SEAP response in NF-κB assay for compound 1 + LPS and LPS alone was 3.44 ± 0.08 and 0.56 ± 0.06 μg/mL, respectively. The mean emission ratio in ISRE assay for compound 1 + IFN-α and IFN-α alone was 1.88 ± 0.04 and 0.69 ± 0.05 μg/mL, respectively. The % viability values for compounds in MTT assay were normalized to DMSO as 100%. The mean OD value at 405 nm for DMSO was 1.24 ± 0.03. All raw values used for normalization are represented as mean ± SEM.

[c]Compound 10 was derived from compound 9 as shown in Scheme 2.

Next, site B was modified (FIG. 1). The compounds were synthesized as discussed earlier (Scheme 1) using different aryl sulfonyl chlorides (3a-p) and 4-chloro-2,5-dimethoxyaniline (2a). Some of the arylsulfonyl chlorides were commercially available, while the others were synthesized. The homologous series of 4-O-alkylated compounds starting with 4-hydroxy analog 11, 4-methoxy analog 12, 4-propoxy analog 13, and 4-butoxy analog 14 compared to 4-ethoxy analog compound 1 was probed. Bioactivity evaluation of these compounds showed that only the smaller homolog as in 4-methoxy compound 12 was tolerated while the hydrophilic interaction with hydroxy group of 11 without any hydrophobic alkyl group was not tolerated. The higher 4-alkoxy chains showed gradual loss of activity (Table 2).

While the 4-propoxy substituted compound was weakly active, the 4-propargyloxy compound 15, designed to use the alkyne as a handle for click chemistry reactions, was found to be inactive. Removal of the ether oxygen to obtain 4-propyl substituted compound 16 also led to loss of activity, suggesting a crucial role of hydrogen bond interaction by the ether oxygen. Other functional groups that could be involved in such hydrogen bond interactions led to the syntheses of 4-nitro analog 17 and its amine bearing derivative 18 (Scheme 2) obtained by reduction of the nitro group. Also, the 4-nitrile analog 19, N-Boc methylamine derivative 20 obtained by in situ N-Boc protection during the reduction of the nitrile group, and its free methylamine derivative 21 (Scheme 2) were synthesized. All these compounds were also evaluated but found to be either weakly active or completely inactive. A prior report indicated that analogs bearing a 4-O-phenyl substitution exhibited ubiquitin ligase inhibition activity (Ramesh et al., 2005), so the 4-O-phenyl analog 22 was synthesized, but this compound was inactive. Encouraged by the activity of 4-methoxy substituted analog 12, 3-methoxy and 2-methoxy substituted compounds 23 and 24, respectively, were synthesized. However, none of these molecules were active. In order to find an additional handle for modification, bromine was introduced to obtain a 3-bromo-4-methoxy substituted compound 25, which was also found to be inactive. Learning from the requirement of a hydrogen bonding functional group at site B for activity, we probed the addition of another oxo-containing group to obtain the 4-methyl ester analog 26 and an amide analog 27, Ester hydrolysis of compound 26 yielded the 4-carboxyl derivative 28 (Scheme 2). While the methyl ester bearing analog 26 was active, the hydrolyzed carboxylic acid analog 28 and the amide linked compound 27 lost activity (Table 2), Hypothesizing that the lack of hydrophobic alkyl group interaction could be a cause for the loss of activity, compound 28 was further derivatized to obtain the ethyl ester analog 29 and the N-methylamide analog 30 (Scheme 2). While analog 29 retained partial activity, compound 30 was completely inactive suggesting that only hydrogen bond accepting substituents were tolerated (Table 2). An additional analog (compound 31, Scheme 1) was synthesized by inversing the sulfonamide bond obtained by reaction of 2-ethoxyaniline and 4-chloro-2,5-dimethoxybenzenesulfonyl chloride, but the inactivity of this analog suggested that the positioning of the sulfonamide functional group was also critical for activity.

Scheme 2. Syntheses of site A and B modified derivatives.

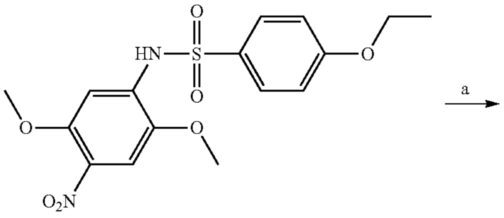

9

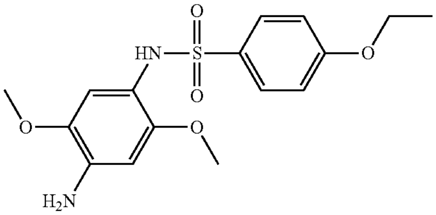

10

-continued

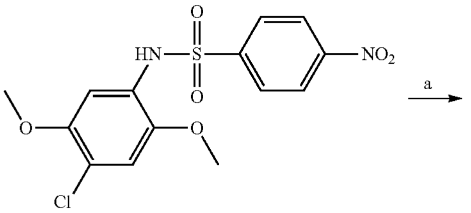

17

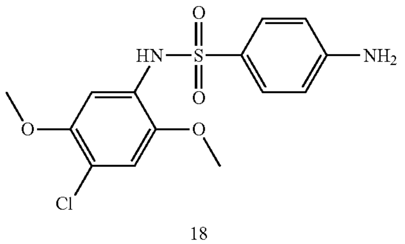

18

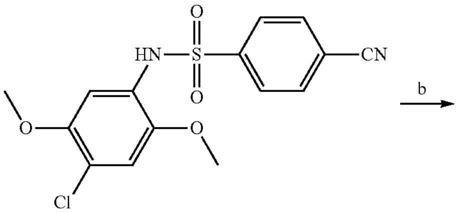

19

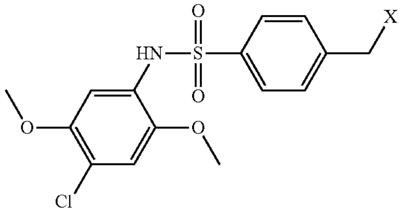

c

20, X = -NHBoc

21, X = -$NH_2$

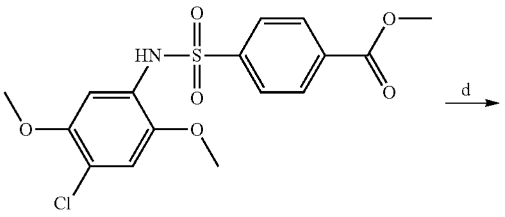

26

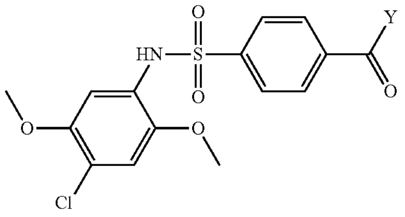

f e

28, X = -OH

29, Y = -$OCH_2CH_3$

30, Y = -$NHCH_3$

Reagents and conditions:

a) Pd/C, $H_2$ (50 psi), EtOAc b) $(Boc)_2O$, Pd/C, $H_2$ (50 psi), MeOH c) 4N HCl/dioxane d) LiOH, MeOH, THF, $H_2O$ e) TMSCl, EtOH f) $EtNH_2$, HATU, $Et_3N$, DMF.

TABLE 2
Structure and bioactivity data for site B modified compounds.
| Compound | Reagent 3 | Site B Substitution[a] | NF-κB[b] % Activation | NF-κB[b] SEM | ISRE[b] % Activation | ISRE[b] SEM | MTT[b] % Viability | MTT[b] SEM |
|---|---|---|---|---|---|---|---|---|
| 11 | 3b | 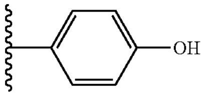 | 98 | 3.1 | 104 | 2.3 | 85.2 | 1.0 |
| 12 | 3c | 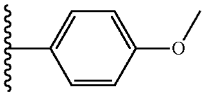 [SMILES: *c1ccc(OC)cc1] | 226 | 6.8 | 219 | 6.5 | 69.6 | 1.3 |
| 13 | 3d | 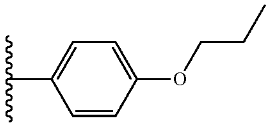 [SMILES: *c1ccc(OCCC)cc1] | 149 | 8.1 | 125 | 5.6 | 71.3 | 0.7 |
| 14 | 3e | 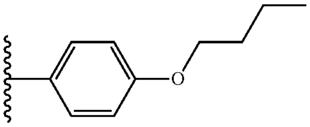 [SMILES: *c1ccc(OCCCC)cc1] | 101 | 2.3 | 106 | 1.3 | 95.3 | 1.5 |
| 15 | 3f | 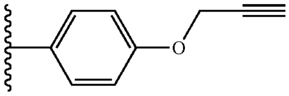 [SMILES: *c1ccc(OCC#C)cc1] | 97 | 2.6 | 99 | 1.6 | 80.9 | 0.9 |
| 16 | 3g | 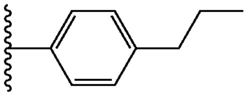 [SMILES: *c1ccc(CCC)cc1] | 102 | 2.3 | 103 | 5.1 | 85.7 | 4.3 |
| 17 | 3h | 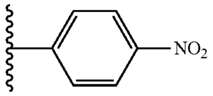 | 101 | 7.2 | 103 | 0.6 | 97.4 | 3.4 |
| 18 | —[c] | 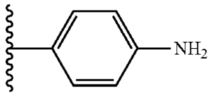 | 101 | 0.6 | 103 | 3.1 | 96.0 | 2.5 |
| 19 | 3i | 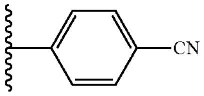 [SMILES: *c1ccc(C#N)cc1] | 97 | 2.2 | 106 | 1.5 | 102.9 | 3.7 |
| 20 | —[c] | 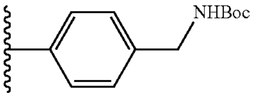 [SMILES: *c1ccc(CNC(=O)OC(C)(C)C)cc1] | 100 | 3.4 | 101 | 3.4 | 109.2 | 1.4 |
| 21 | —[c] | 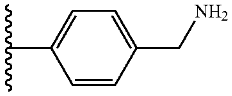 [SMILES: *c1ccc(CN)cc1] | 103 | 3.5 | 111 | 5.4 | 97.0 | 2.5 |
| 22 | 3j | 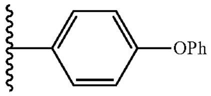 [SMILES: *c1ccc(Oc2ccccc2)cc1] | 98 | 4.4 | 95 | 4.8 | 91.3 | 1.6 |

TABLE 2-continued

Structure and bioactivity data for site B modified compounds.

| Compound | Reagent 3 | Site B Substitution[a] | NF-κB[b] % Activation | NF-κB[b] SEM | ISRE[b] % Activation | ISRE[b] SEM | MTT[b] % Viability | MTT[b] SEM |
|---|---|---|---|---|---|---|---|---|
| 23 | 3k | 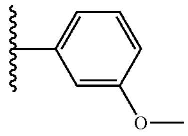 [SMILES: *c1cccc(OC)c1] | 116 | 7.3 | 104 | 0.9 | 79.6 | 1.4 |
| 24 | 31 | 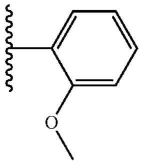 | 96 | 5.3 | 101 | 1.2 | 92.1 | 2.7 |
| 25 | 3m | 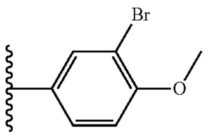 [SMILES: *c1ccc(OC)c(Br)c1] | 87 | 3.3 | 101 | 1.6 | 85.0 | 3.6 |
| 26 | 3n | 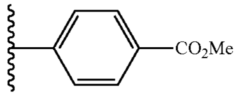 | 191 | 6.4 | 202 | 6.5 | 74.4 | 0.7 |
| 27 | 3o | 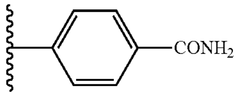 | 103 | 2.6 | 94 | 3.1 | 91.0 | 1.5 |
| 28 | —[c] | 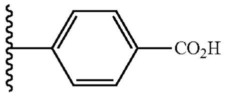 [SMILES: *c1ccc(C(=O)O)cc1] | 89 | 2.3 | 104 | 1.2 | 98.2 | 3.0 |
| 29 | —[c] | 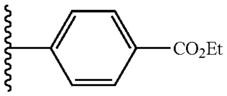 | 189 | 10.1 | 169 | 9.8 | 70.8 | 0.8 |
| 30 | —[c] | 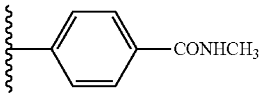 | 103 | 2.4 | 105 | 2.2 | 77.0 | 2.2 |

[a]Compounds 11-17, 19, 22-27 were obtained by reaction of reagent 3 with 4-chloro-2,5-dimethoxyaniline (2a) as shown in Scheme 1.

[b]The % activation values in NF-κB and ISRE induction assays were two point normalized between compound 1 as 200% and LPS (10 ng/mL) for NF-κB or IFN-α (100 U/mL) for ISRE as 100%. The mean SEAP response in NF-κB assay for compound 1 + LPS and LPS alone was 3.44 ± 0.08 and 0.56 ± 0.06 ug/mL, respectively. The mean emission ratio in ISRE assay for compound 1 + IFN-α and IFN-α alone was 1.88 ± 0.04 and 0.69 ± 0.05 μg/mL, respectively. The % viability values for compounds in MTT assay were normalized to DMSO as 100%. The mean OD value at 405 nm for DMSO was 1.24 ± 0.03. All raw values used for normalization are represented as mean ± SEM.

[c]The compounds were synthesized as shown in Scheme 2.

Moving forward, expansion at site C on the nitrogen of the sulfonamide function of compound 1 was examined. These compounds were synthesized by derivatization of compound 1 as shown in Scheme 3. The first extensive series of compounds were the N-alkylated derivatives including N-methyl (33), N-propyl (34), N-butyl (35), N-pentyl (36), N-hexyl (37), N-heptyl (38), and N-dodecyl (39), A clear correlation of bioactivity with the alkyl chain length was observed with potency gradually decreasing with increased alkyl chain length, and compounds bearing alkyl chain lengths greater than N-pentyl were completely inactive (Table 3), The effect of steric bulk around the core structure was probed by synthesizing N-isopropyl (40) and N-isobutyl (41) derivatives, Steric bulk closer to the core structure, as in compound 40, eliminated the NF-κB activity while retaining ISRE activity. In contrast, spacing the isopropyl group away by one methylene unit as in compound 41 regained the activity in both the NF-κB and ISRE assays. Encouraged by these results, alkyne bearing compounds were synthesized with an additional aim to utilize the functional group as a biorthogonal reactive site. A homologous series of alkyne bearing molecules including N-propargyl (42), N-butynyl (43), and N-pentynyl (44) were synthesized (Scheme 3). Activity data showed that while N-alkyl derivatization with increasing alkyl chain length led to dramatic loss of activity, the corresponding N-alkynyl derivatives retained activity almost equivalent to that of compound 1 (FIG. 2, Table 3) for the corresponding alkyl chain length. As shown in FIG. 2, the retention of activity for the N-alkynyl compounds compared to loss in activity for the analogous N-alkyl derivatives for the same carbon unit chain length suggested the possible involvement of π-π interactions in near proximity with the target receptor(s). of A triethylene glycol linked alkyne derivative (45) was investigated, placing the reactive functional group distant from the core. However, the 12-atom chain length equivalent to N-dodecyl compound 39 was too long to retain activity.

These results for the alkyne bearing compounds led to making compounds where substituents can form enhanced π-π interactions. Thus, N-benzyl (46) and N-phenethyl (47) derivatives were synthesized and were also found to be potent analogs (Table 3). Since the N-isopropyl analog 40 was inactive, it was determined if steric bulk was the only reason for its inactivity and if that could be mitigated by some hydrogen bonding functional group such as acetyl. Thus, the N-acetyl derivative (48) was synthesized and the bioactivity assays showed that the compound was active. However, before proceeding with syntheses of additional acylated analogs, its stability in stock solutions was evaluated since during the assay this compound could behave as a prodrug by undergoing deacetylation to release active compound 1. While the stock of compound 48 in DMSO was stable, incubation of compound with assay media showed release of compound 1 (data not shown), suggesting that the bioactivity could be due to a prodrug effect and not true interaction with the receptor. Thus, syntheses of additional acylated analogs were not pursued.

Scheme 3.
Syntheses of sulfonamdie N-substituted derivatives of compound 1.

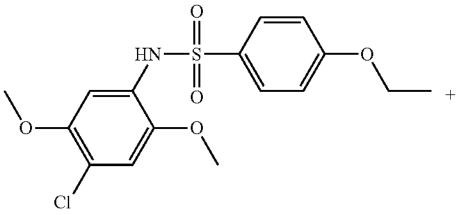
+

1

R—X a or b 32a-t

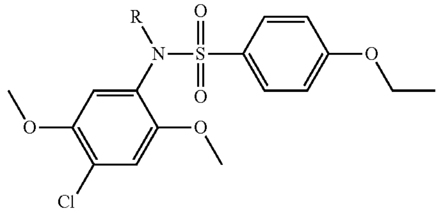

33-52

Reagents and conditions:
a) $K_2CO_3$, DMF, 45° C.
For compound 48:
b) $Et_3N$, $CH_2Cl_2$.

TABLE 3

Structure and bioactivity data for site C modified compounds.

| Compound | Reagent 32 | Site C Substitution Variable —R Group[a] | NF-κB[b] % Activation | NF-κB[b] SEM | ISRE[b] % Activation | ISRE[b] SEM | MTT[b] % Viability | MTT[b] SEM |
|---|---|---|---|---|---|---|---|---|
| 33 | 32a | 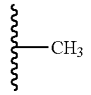 | 235 | 9.0 | 215 | 7.3 | 74.5 | 1.3 |
| 34 | 32b | 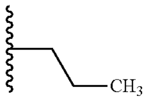 | 227 | 14.1 | 199 | 2.7 | 71.6 | 2.4 |
| 35 | 32c | 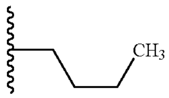 [SMILES: *CCCC] | 192 | 11.0 | 156 | 4.2 | 77.7 | 3.2 |
| 36 | 32d | 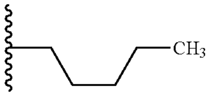 | 135 | 6.8 | 105 | 3.5 | 72.9 | 2.4 |
| 37 | 32e | 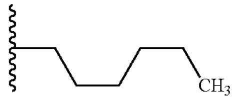 | 81 | 4.0 | 99 | 2.1 | 95.2 | 3.3 |
| 38 | 32f | 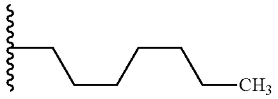 | 108 | 5 | 95 | 1.2 | 90.4 | 1.2 |

TABLE 3-continued
Structure and bioactivity data for site C modified compounds.
| Compound | Reagent 32 | Site C Substitution Variable —R Group[a] | NF-κB[b] % Activation | NF-κB[b] SEM | ISRE[b] % Activation | ISRE[b] SEM | MTT[b] % Viability | MTT[b] SEM |
|---|---|---|---|---|---|---|---|---|
| 39 | 32g | 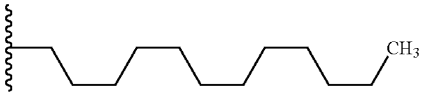 [SMILES: *CCCCCCCCCCCC] | 97 | 3.1 | 100 | 2.6 | 93.0 | 2.7 |
| 40 | 32h | 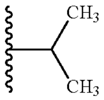 | 76 | 3.5 | 169 | 7.0 | 103.2 | 6.1 |
| 41 | 32i | 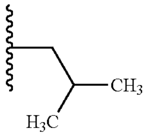 | 175 | 9.8 | 193 | 9.6 | 76.7 | 2.0 |
| 42 | 32j | 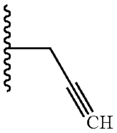 [SMILES: *CC#C] | 232 | 13.8 | 213 | 4.3 | 72.0 | 2.2 |
| 43 | 32k | 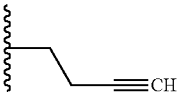 | 206 | 3.3 | 201 | 6.2 | 70.1 | 1.9 |
| 44 | 32l | 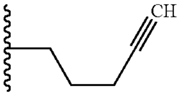 [SMILES: *CCCC#C] | 182 | 5.8 | 184 | 7.3 | 70.7 | 2.1 |
| 45 | 32m | 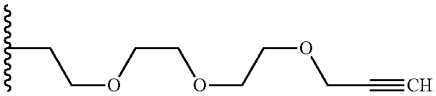 [SMILES: *CCOCCOCCOCC#C] | 107 | 2.9 | 130 | 4.4 | 73.7 | 1.6 |
| 46 | 32n | 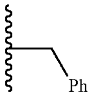 | 181 | 3.9 | 159 | 5.9 | 71.7 | 2.5 |
| 47 | 32o | 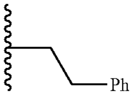 | 131 | 6.7 | 141 | 7.1 | 44.0 | 1.3 |
| 48 | 32p | 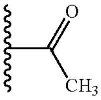 | 184 | 10.3 | 244 | 4.9 | 72.0 | 1.7 |
| 49 | 32q | 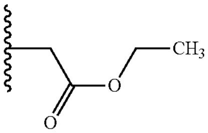 [SMILES: *CC(=O)OCC] | 202 | 10.6 | 184 | 7.5 | 81.4 | 2.5 |
| 50 | 32r | 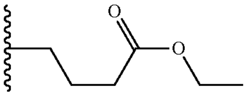 [SMILES: *CCCC(=O)OCC] | 199 | 4.7 | 199 | 2.5 | 80.1 | 2.2 |

TABLE 3-continued

Structure and bioactivity data for site C modified compounds.

| Compound | Reagent 32 | Site C Substitution Variable —R Group[a] | NF-κB[b] % Activation | NF-κB[b] SEM | ISRE[b] % Activation | ISRE[b] SEM | MTT[b] % Viability | MTT[b] SEM |
|---|---|---|---|---|---|---|---|---|
| 51 | 32s | 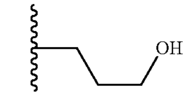 [SMILES: *CCCO] | 219 | 14.0 | 178 | 8.5 | 68.5 | 1.8 |
| 52 | 32t | 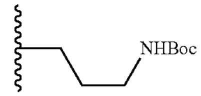 [SMILES: *CCCNC(=O)OC(C)(C)C] | 134 | 7.7 | 140 | 3.2 | 75.6 | 1.4 |
| 53 | —[c] | 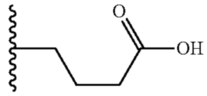 | 230 | 7.9 | 151 | 5.0 | 73.4 | 1.8 |
| 54 | —[c] | 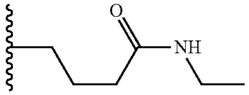 [SMILES: *CCCC(=O)NCC] | 206 | 4.4 | 137 | 7.3 | 78.2 | 1.8 |
| 55 | —[c] | 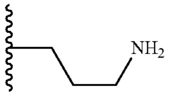 | 189 | 10.6 | 182 | 6.4 | 71.0 | 0.7 |

[a]Compounds 33-52 were obtained by reaction of reagent 32 with compound 1 as shown in Scheme 3.

[b]The % activation values in NF-κB and ISRE induction assays were two point normalized between compound 1 as 200% and LPS (10 ng/mL) for NF-κB or IFN-α (100 U/mL) for ISRE as 100%. The mean SEAP response in NF-κB assay for compound 1 + LPS and LPS alone was 3.44 ± 0.08 and 0.56 ± 0.06 μg/mL, respectively. The mean emission ratio in ISRE assay for compound 1 + IFN-α and IFN-α alone was 1.88 ± 0.04 and 0.69 ± 0.05 μg/mL, respectively. The % viability values for compounds in MTT assay were normalized to DMSO as 100%. The mean OD value at 405 nm for DMSO was 1.24 ± 0.03. All raw values used for normalization are represented as mean ± SEM.

[c]The compounds were derived from compounds 50 and 52 as shown in Scheme 4.

Since the hydrophobic alkyl and alkynyl groups were well tolerated at site C, it was examined if incorporating a hydrophilic group that could serve as a handle for further chemical modification would be acceptable for activity. A pair of compounds bearing a precursor to a reactive handle such as carboxylic esters were synthesized by alkylation of compound 1 to obtain the N-ethyl glycinate (49) and N-ethyl butanoate (50) analogs (Scheme 3). Attempts to make a stable propionate analog failed after several attempts likely due to retro Michael type reaction, and despite isolation of a few milligrams of the tert-butyl propionate ester derivative, activity studies were not pursued due to stability concerns. Both the ethyl ester substituted compounds 49 and 50 retained dual NF-κB and ISRE activities (Table 3). To avoid additional substitution closer to the core sulfonamide pharmacophore, a propylene spacer was selected for further analogs. A terminal hydroxy bearing analog as in N-propan-3-ol (51) and the N-Boc protected aminopropane analog (52) were then synthesized. The ethyl ester of compound 50 was de-esterified using lithium hydroxide to obtain its carboxylic acid analog 53, which was converted to the ethyl amide analog 54 (Scheme 4). Similarly, a free amine bearing molecule was obtained by N-Boc deprotection of 52 to obtain compound 55. Biological evaluation showed that the terminal hydroxy analog 51 retained activity in both assays while the N-Boc protected compound 52 showed reduction in activity, which was recovered when the N-Boc group was removed as in compound 55, Both the free carboxylic acid and ethyl amide derivatives retained activity, which was more skewed toward the NF-κB pathway (Table 3), Scheme 4.

Syntheses of chemically reactive handle bearing analogs of compound 1

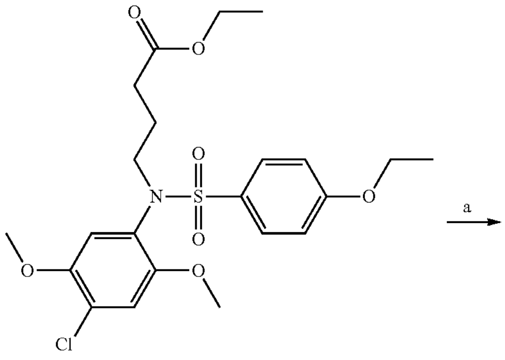

50

-continued

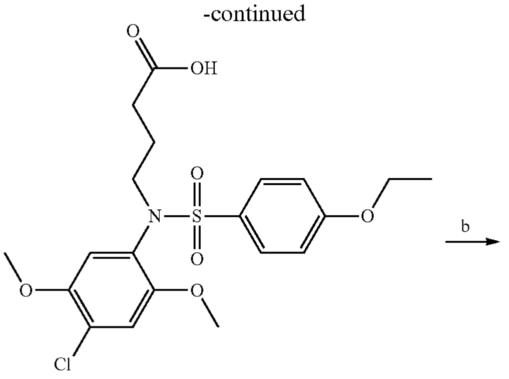

53

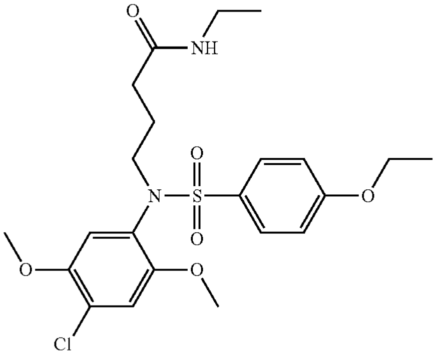

54

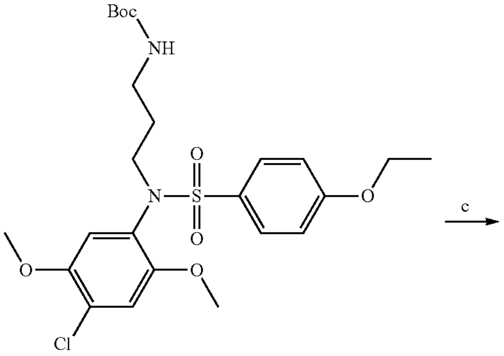

52

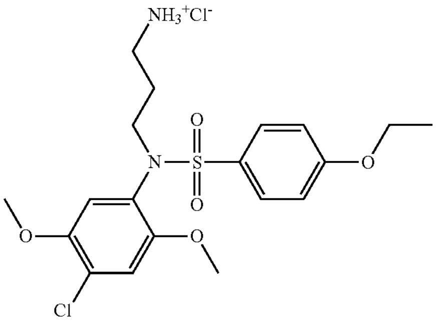

55

Reagents and conditions:
a) LiOH, MeOH, THF, $H_2O$
b) $EtNH_2$, HATU, $Et_3N$, DMF;
c) 4N HCl/dioxane.

All these compounds were evaluated for toxicity using 3-(4,5-dimethylthiazol-2-yl)-2,5-diphenyltetrazolium bromide (MTT) assays. All the active compounds showed viability between 69% and 81%. Some of the inactive compounds were completely nontoxic. Compound 47 with the N-phenethyl substitution was an exception showing somewhat higher toxicity (% viability=44%), suggesting that an aryl group connected by an ethylene unit near the core sulfonamide structure may lead to toxicity (Tables 1-23).

The bioactivity data from both the assays for all the compounds were plotted to verify the correlation between the chemical structure and bioactivity. Most of the compounds were active in both NF-κB and ISRE bioassays and showed a good correlation (Pearson two-tailed, R2=0.6812, P<0,0001, FIG. 3). The SAR trends however varied depending on the site of modification. Site A modifications involving removal of the methoxy substituent (compounds 4 and 5) led to significant loss of activity (FIG. 3), On the other hand, nonpolar modifications at position 4 of site A (compounds 7 and 8) showed slightly skewed ISRE activity compared to compound 1, while hydrogen bond forming substituents at this position led to loss of activity (compounds 9 and 10). Most of the site B modified compounds were inactive suggesting restricted SAR tolerance due to limited spatial availability in the target receptor. Only short alkyl groups connected via ether-linkage as in compounds 1, 12, and 13 or carboxyl (ester)-linkage as in compounds 26 and 29 retained activity. A good correlation was seen, however, between the two assays for these compounds. In contrast, most of the site C modified compounds were active in both bioassays suggesting that only a part of the substituent may be involved in receptor interaction and the rest of the group subtends out of the target receptor(s). A notable variation was observed in sterically hindered bulky groups close to the core structure as in compound 40 which led to a loss of NF-κB activity while still retaining ISRE activity. On the other hand, another subset of compounds bearing a reactive handle such as carboxylic acid analog 53 and its amidated derivative 54 showed reduction in ISRE activity while retaining the NF-κB activity (FIG. 3). This suggested that a negative charge on the compound may be a deterrent for ISRE activity.

Continuing with the focus on compounds that retain dual NF-κB and ISRE activity similar to original hit compound 1, site B modified compound 12, site C modified compound 33, and an aliphatic amine bearing compound 55 were selected for dose-response experiments and $EC_{50}$ determination as these compounds are nearly equipotent in both assays when evaluated at 5 μM concentration. As shown in FIG. 4, both compounds 12 and 33 showed relatively higher NF-κB activity at 5 μM concentration, but the activity of compound 12 decreased faster at lower concentrations which led to EC50 value of 1.85 μM. Compounds 1 and 33 were almost equipotent with EC50 values of 0.60 μM and 0.69 μM, respectively. Compound 55 was relatively weaker with $EC_{50}$ of 3.32 μM. The potency trends for these compounds remained the same in ISRE activity with compounds 1, 12, and 33 exhibiting EC50 of 0.66 μM, 1.4 μM, and 0.84 μM, respectively, and compound 55 with EC50=3.04 μM. Even though the activity of compound 55 was slightly attenuated, the amine handle can be utilized for derivatization to obtain affinity probes.

It was important to examine the adjuvanticity of the most potent compounds to verify if prolongation of immune stimulus by this chemotype leads to enhancement of in vivo antibody responses and if prolonged activation of the innate immune system could lead to systemic inflammation that may be harmful to the host (Cooks et al., 2013; Perez et al., 2015). In addition, it was also important to verify that the modifications on the scaffold that yielded potent compounds in vitro would retain the adjuvanticity in vivo as well. All the compounds administered to mice had low toxicity in the MTT assays. Since these vaccine coadjuvants are designed to be administered locally (mostly intramuscularly) and show negligible toxicity (based on MTT data), an excessive systemic inflammatory response was not anticipated. LPS is a widely recognized activator of the innate immune system and well characterized TLR-4 ligand to screen over 160 000 compounds for their ability to enhance APC activation (Chan et al., 2017; Shukla et al., 2018b). However, to test these compounds for potency as coadjuvants, TLR-4 adjuvant MPLA was employed for in vivo evaluation. Immunization experiments in mice (8 mice/group) were performed to evaluate the coadjuvanticity of the lead compounds 1, 12, or 33 using ovalbumin (OVA) as a model antigen and MPLA as an adjuvant. Amine handle bearing compound 55 was not used for designing affinity probes. The activity data led to the use of site C for the introduction of an identifiable tag by derivatizing compound 55. Although compound 55 was less potent than compound 1, the changes in the hydrophobic interaction after amine derivatization may improve the potency. Compound 55 was derivatized to obtain fluorescein labeled compound 56, rhodamine labeled compound 57, and biotin labeled compound 58 (Scheme 5). In primary screens, the biotin labeled compound 58 was equipotent to compound 1 and thus could serve as the affinity probe (FIG. 6, Table 4). The rhodamine analog 57 showed reduced activity compared to compound 1 in both the NF-κB and ISRE assays, likely due to the presence of a fixed charge on the molecule similar to the amine bearing compound 55. In contrast, the fluorescein analog 56 was completely inactive in both assays (FIG. 6, Table 4).

Scheme 5. Syntheses of fluroescent and biotin labeled derivatives of compound 1.

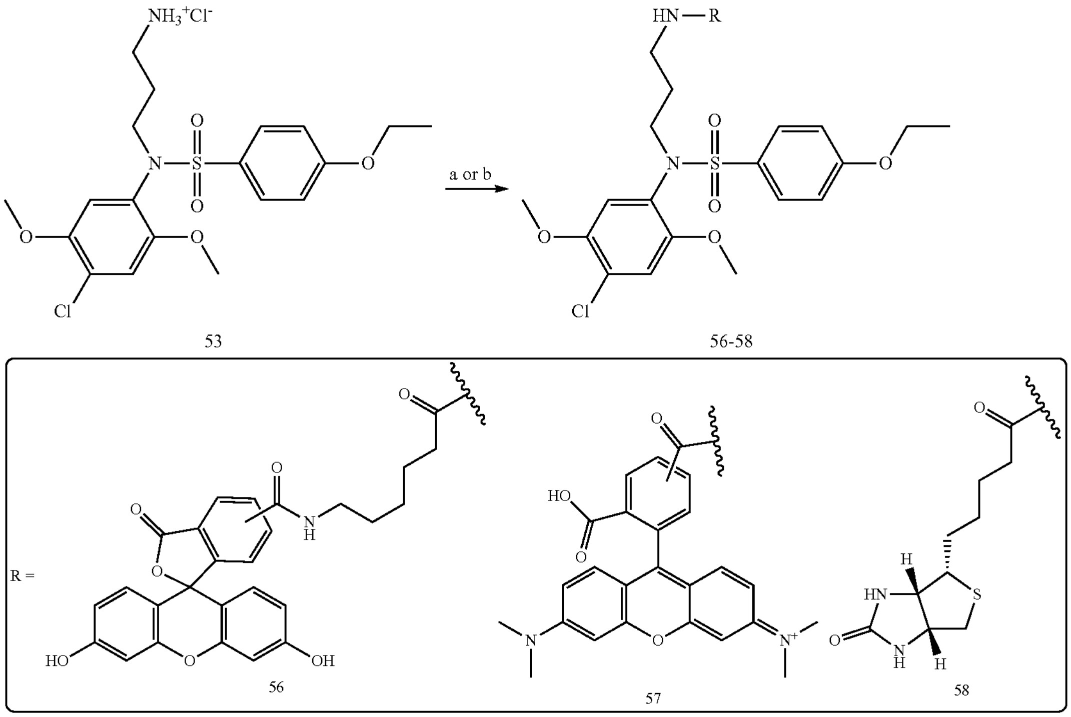

53

56-58

R =

56

57

58

Reagnets and conditions:
For compound 56: a) 5(6)-SFX SE, $Et_3N$, DMF;
For compound 57: b) NHS-Rhodamine, $Et_3N$, DMF;
For compound 58: b) biotin, HATU, $Et_3N$, DMF.

selected for immunization since it was designed for further derivatization as an intermediate to make probes as discussed below, Examination of OVA-specific IgG antibodies showed that coimmunization of MPLA with compounds 1 and 33 induced statistically significant increases in antigen-specific antibody titers when compared to mice immunized with MPLA alone (FIG. 5), without demonstrable systemic toxicity, as indicated by behavior change or weight loss. These results verified our approach that selected bis-aryl sulfonamide compounds that prolong immune stimulation could enhance the adjuvanticity of MPLA and that modified compounds that retained potency in vitro were equally potent in vivo as well.

In view of the confirmation of the in vitro and in vivo potency of selected active compounds, the SAR studies were Having validated specific site C modifications that tolerated the introduction of a trackable tag, for introduction of a photoreactive group such as aryl azide, useful to make photoaffinity probes, compounds 10 and 25 were derivatized, even though these were inactive but surmising that a change in the hydrogen bonding properties may have an opposite effect. The aromatic amine on position 4 at site A of compound 10 was converted to aryl azide using diazotization reaction to obtain compound 59 (Scheme 6). In parallel, the 3-bromo substitution at site B of compound 25 was reacted with sodium azide using copper catalyzed reaction. However, the major product of this reaction was aromatic amine analog 60, which was further converted to azide using the earlier described diazotization chemistry to obtain compound 61 (Scheme 6). The photoreactive aryl azide bearing compounds 59 and 61 and the aromatic amine analog 60 were then evaluated in the primary screens. While compound 61 was inactive just like its precursor bromo analog 25, the reversal of hydrogen bonding capacity in compound 60 led to resurgence of activity in both assays possibly due to hydrophilic interaction with the aromatic amine (FIG. 6, Table 4). In contrast, the reversal of hydrogen bonding capacity of compound 10 led us to a potent aryl azide bearing analog 59 which was then utilized for making photoaffinity probes (FIG. 6, Table 4).

Scheme 6. Syntheses of photoreactive analogs of compound 1.

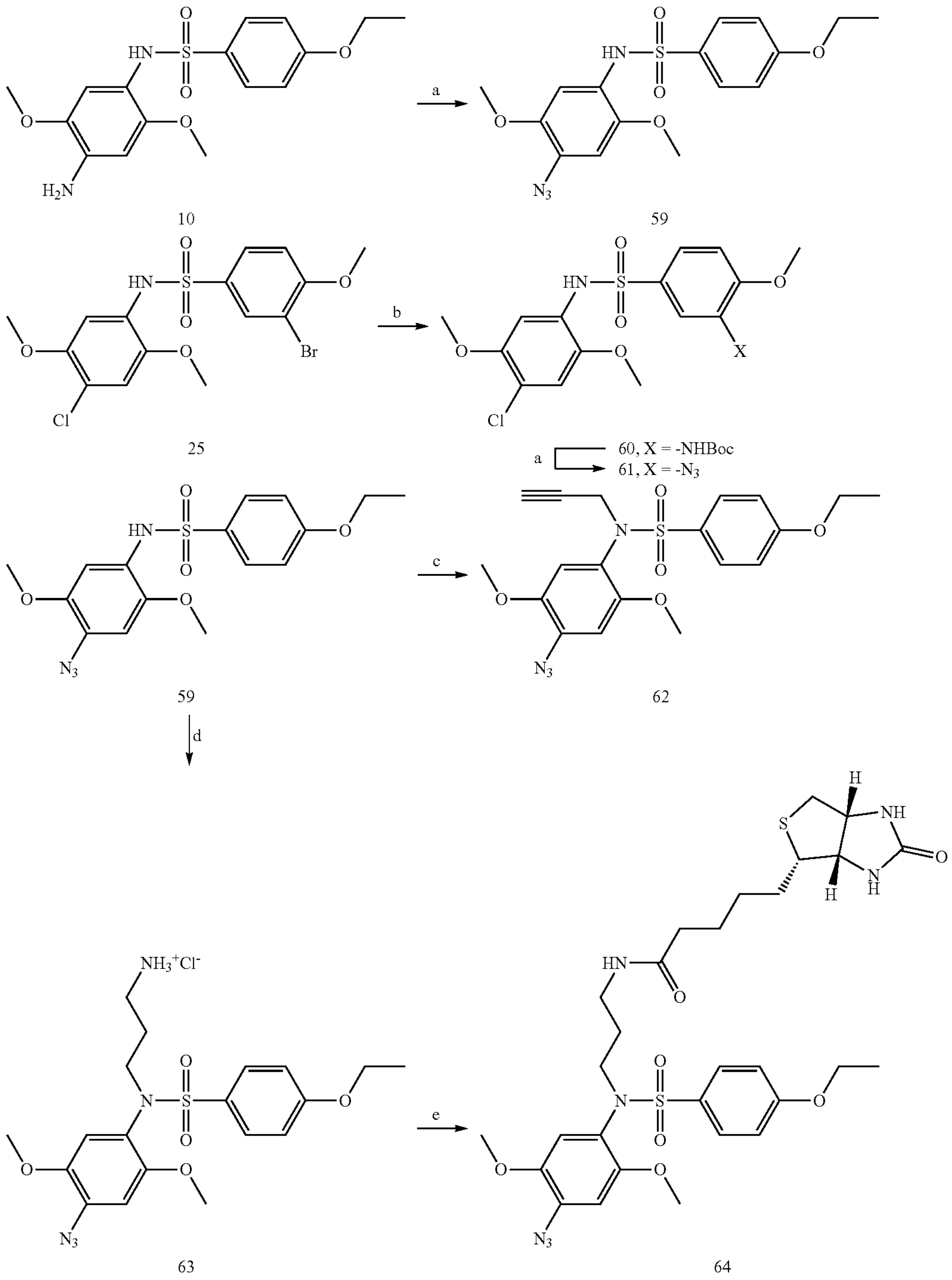

Reagents and conditions:
a) tert-butyl nitrite, trimethylsilyl azide, $CH_3CN$, 40° C.
b) CuI, $NaN_3$, N,N'-dimethylethane-1,2-diamine, sodium ascorbate, EtOH, $H_2O$
c) propargyl bromide, $K_2CO_3$, DMF
d) i. tert-butyl (3-bromopropyl)carbamate, $K_2CO_3$, DMF
ii. 4N HCl/dioxane
e) biotin, HATU, $Et_3N$, DMF.

By use of the methods utilized earlier, compound 59 was derivatized to obtain an alkyne analog 62, and a biotin analog 64 was obtained via an aliphatic amine derivative 63 (Scheme 6). Evaluation of these compounds in our primary screens showed that the alkyne probe 62 was very potent, while the biotin probe 64 showed relatively weak activity in both the NF-κB and ISRE assays (FIG. 5, Table 4). Also, all the affinity probes had viability in the same range as the potent compounds in this series.

TABLE 4

Bioactivity data for fluorescent, biotin and photoreactive analogs of compound 1.

| | NF-κB[a] | | ISRE[a] | | MTT[a] | |
|---|---|---|---|---|---|---|
| Compound | % Activation | SEM | % Activation | SEM | % Viability | SEM |
| 56 | 100 | 1.3 | 96 | 4.2 | 98.1 | 1.7 |
| 57 | 111 | 2.1 | 123 | 5.4 | 76.9 | 1.3 |
| 58 | 195 | 4.7 | 175 | 8.6 | 69.6 | 1.2 |
| 59 | 215 | 13.8 | 201 | 3.8 | 76.6 | 2.6 |
| 60 | 158 | 5.9 | 166 | 2.4 | 77.3 | 2.5 |
| 61 | 104 | 5.1 | 104 | 3.1 | 87.2 | 1.8 |
| 62 | 217 | 13.9 | 182 | 2.5 | 73.4 | 1.5 |
| 63 | 138 | 4.2 | 117 | 1.2 | 68.9 | 0.8 |
| 64 | 162 | 5.1 | 140 | 1.4 | 73.8 | 0.6 |

[a]The % activation values in NF-κB and ISRE induction assays were two point normalized between compound 1 as 200% and LPS (10 ng/mL) for NF-κB or IFN-α (100 U/mL) for ISRE as 100%. The mean SEAP response in NF-κB assay for compound 1 + LPS and LPS alone was 3.44 ± 0.08 and 0.56 ± 0.06 μg/mL, respectively. The mean emission ratio in ISRE assay for compound 1 + IFN-α and IFN-α alone was 1.88 ± 0.04 and 0.69 ± 0.05 μg/mL, respectively. The % viability values for compounds in MTT assay were normalized to DMSO as 100%. The mean OD value at 405 nm for DMSO was 1.24 ± 0.03. All raw values used for normalization are represented as mean ± SEM.

The systematic SAR studies on bis-aryl sulfonamides that sustain NF-κB and ISRE activation have led to the identification of not only rhodamine labeled affinity fluorescent probe 57 and biotin-tagged affinity probe 58, but also alkyne and biotin labeled photoaffinity probes 62 and 64, respectively. These affinity probes will be utilized in concert for target identification and cell trafficking experiments.

Conclusions

Compound 1 was identified from HTS campaigns that screened for agents capable of prolonging immune signaling and was shown to be a potent coadjuvant with MPLA in vivo. Here, we presented systematic SAR studies consisting of design, syntheses, and evaluation of analogs of compound 1 to identify sites on the scaffold that can tolerate modification while still retaining dual NF-κB and ISRE enhancing activities in order to obtain affinity and photoaffinity probes. SAR studies pointed to key substitutions at site B and site C that retain potency in vitro and in vivo, while site A allowed the introduction of photoreactive aryl azide functionality. In addition, observed SAR trends at site C allowed the introduction of trackable tags such as rhodamine or biotin. This led to syntheses of several affinity probes that will be utilized to determine the mechanism of action and receptor target for this bis-aryl sulfonamide series of compounds that sustain NF-κB and ISRE activation.

Experimental Section

Chemistry. Materials. Reagents were purchased as at least reagent grade from commercial vendors unless otherwise specified and used without further purification. Solvents were purchased from Fischer Scientific (Pittsburgh; PA) and were either used as purchased or redistilled with an appropriate drying agent. All the reagents 2a-g and 3g-o were purchased from commercially available vendors, while reagents 3a-f were synthesized from commercially available reagents. Compounds used for structure-activity studies were synthesized according to methods described below, and all the compounds were identified to be least 95% pure using HPLC.

Instrumentation. Analytical TLC was performed using precoated TLC silica gel 60 F254 aluminum sheets purchased from EMD (Gibbstown, N.J.) and visualized using UV light. Flash chromatography was carried out using with a Biotage Isolera One (Charlotte, N.C.) system using the specified solvent. Microwave reaction was performed using Biotage Initiator+ (Charlotte, N.C.). Reaction monitoring and purity analysis were done using an Agilent 1260 LC/6420 Triple Quad mass spectrometer (Santa Clara, Calif.) with Onyx Monolithic C18 (Phenomenex, Torrance, Calif.) column. All final compounds were analyzed by high resolution MS (HRMS) using an Agilent 6230 ESI-TOFMS (Santa Clara, Calif.). 1H and 13C NMR spectra were obtained on a Varian 500 with XSens probe (Varian, Inc., Palo Alto, Calif.). The chemical shifts are expressed in parts per million (ppm) using suitable deuterated NMR solvents.

General Procedure A for the Syntheses of Select Site A and Site B Modified Compounds. To a solution of a substituted phenylsulfonyl chloride (reagent 3, 1 equiv) in anhydrous CH2Cl2 were added triethylamine (2 equiv) and a solution of substituted aniline (reagent 2, 2 equiv) in CH2Cl2. The reaction mixture was stirred at room temperature overnight and then poured into water and acidified with 3 N HCl followed by extraction with EtOAc. The EtOAc fraction was then dried over MgSO4, and solvent was removed under vacuum. The resultant residue was dissolved in MeOH and THF, followed by the addition of lithium hydroxide monohydrate (15 equiv) in water and stirred at room temperature until bis-sulfonamide side product is converted to the desired product. The solvent was then removed, dissolved in EtOAc, washed with water and brine, dried under vacuum to obtain the residue which was purified by column chromatography to obtain the final product.

Compound 1 and site A modified compounds 4-9 were synthesized using general procedure A described above. N-(4-Chloro-2,5-dimethoxyphenyl)-4-ethoxybenzenesulfonamide (1). Compound 1 was synthesized using 4-chloro-2,5-dimethoxyaniline (2a, 1.7 g, 5.3 mmol) and 4-ethoxybenzenesulfonyl chloride (3a, 1 g, 4.5 mmol) after recrystallization in EtOH as pink crystals (1.2 g, yield=71%). 1H NMR (500 MHz, chloroform-d) δ 7.66 (d, J=8.80 Hz, 2H), 7.24 (5, 1H), 6.91 (s, 1H), 6.86 (d, J=8.80 Hz, 2H), 6.77 (s, 1H), 4.04 (q, J=6.93 Hz, 2H), 3.87 (s, 3H), 3.60 (s, 3H), 1.42 (t, J=6.97 Hz, 3H). 13C NMR (126 MHz, chloroformd) δ 162.6, 149.2, 143.6, 130.0, 129.4, 125.2, 117.8, 114.4, 113.1, 106.3, 64.0, 56.8, 56.4, 14.6. HRMS for C16H17ClNO5 [M−H−] calculated 370.0521, found 370.0523.

N-(4-Chloro-3-methoxyphenyl)-4-ethoxybenzenesulfonamide (4). Compound 4 was synthesized using 4-chloro-3-methoxyaniline (2b, 142.84 mg, 0.92 mmol) and 4-ethoxybenzenesulfonyl chloride (3a, 100 mg, 0.46 mmol) as off-white solid (83 mg, yield=54%). 1H NMR (500 MHz, chloroform-d) δ 7.70 (d, J=8.80 Hz, 2H), 7.17 (d, J=8.56 Hz, 1H), 7.01 (br s, 1H), 6.89 (d, J=9.05 Hz, 2H), 6.80 (d, J=2.20 Hz, 1H), 6.51 (dd, J=2.20, 8.56 Hz, 1H), 4.05 (q, J=7.09 Hz, 2H), 3.83 (s, 3H), 1.42 (t, J=6.97 Hz, 3H), 13C NMR (126 MHz, chloroform-d) δ 162.7, 155.3, 136.3, 130.4, 129.6, 129.4, 119.0, 114.6, 113.9, 105.8, 64.0, 56.2, 14.6. HRMS for C15H15ClNO4S [M−H]− calculated 340.0416, found 340.0416.

N-(4-Chloro-2-methoxyphenyl)-4-ethoxybenzenesulfonamide (5). Compound 5 was synthesized using 4-chloro-2-methoxyaniline (2c, 142.84 mg, 0.92 mmol) and 4-ethoxybenzenesulfonyl chloride (3a, 100 mg, 0.46 mmol) as tan solid (100 mg, yield=64%) 1H NMR (500 MHz, chloroform-d) δ 7.66 (d, J=8.80 Hz, 2H), 7.45 (d, J=8.56 Hz, 1H), 6.83-6.91 (m, 2H), 6.85 (d, J=8.80 Hz, 2H), 6.72 (d, J=1.96 Hz, 1H), 4.04 (q, J=7.09 Hz, 2H), 3.65 (s, 3H), 1.41 (t, J=6.97 Hz, 3H). 13C NMR (126 MHz, chloroform-d) δ 162.5, 150.0, 130.4, 130.2, 129.4, 124.8, 121.9, 121.0, 114.3, 111.3, 63.9, 55.9, 14.6, HRMS for C15H16ClNO4SNa [M+Na+] calculated 364.0381, found 364.0382.

N-(2,5-Dimethoxyphenyl)-4-ethoxybenzenesulfonamide (6). Compound 6 was synthesized using 2,5-dimethoxyaniline (2d, 138.8 mg, 0.92 mmol) and 4-ethoxybenzenesulfonyl chloride (3a, 100 mg, 0.46 mmol) as off-white solid (117 mg, yield=76%). 1H NMR (500 MHz, chloroform-d) δ 7.70 (d, J=8.80 Hz, 2H), 7.14 (d, J=2.93 Hz, 1H), 7.01 (s, 1H), 6.85 (d, J=8.80 Hz, 2H), 6.65 (d, J=8.80 Hz, 1H), 6.53 (dd, J=2.93, 9.05 Hz, 1H), 4.03 (q, J=6.85 Hz, 2H), 3.75 (s, 3H), 3.62 (s, 3H), 1.40 (t, J=7.09 Hz, 3H). 13C NMR (126 MHz, chloroform-d) δ 162.4, 153.8, 143.4, 130.4, 129.4, 126.8, 114.3, 111.4, 109.5, 106.8, 63.9, 56.2, 55.8, 14.6. HRMS for C16H19NO5SNa [M+Na+] calculated 360.0876, found 360.0877.

N-(4-Bromo-2,5-dimethoxyphenyl)-4-ethoxybenzenesulfonamide (7). Compound 7 was synthesized using 4-bromo-2,5-dimethoxyaniline (2e, 105.2 mg, 0.45 mmol) and 4-ethoxybenzenesulfonyl chloride (3a, 50 mg, 0.23 mmol) as purple solid (59 mg, yield=62%). 1H NMR (500 MHz, chloroform-d) δ 7.67 (d, J=8.80 Hz, 2H), 7.21 (s, 1H), 6.93 (s, 1H), 6.92 (s, 1H), 6.85 (d, J=9.05 Hz, 2H), 4.04 (q, J=7.09 Hz, 2H), 3.86 (5, 3H), 3.61 (5, 3H), 1.41 (t, J=6.97 Hz, 3H). 13C NMR (126 MHz, chloroform-d) δ 162.6, 150.2, 143.7, 130.0, 129.4, 126.0, 115.8, 114.4, 106.2, 105.8, 64.0, 56.9, 56.4, 14.6. HRMS for C16H18BrNO5SNa [M+Na+] calculated 437.9981, found 437.9979.

N-(4-Chloro-3,5-dimethoxyphenyl)-4-ethoxybenzenesulfonamide (8). Compound 8 was synthesized using 4-chloro-3,5-dimethoxyaniline (2f, 50 mg, 0.27 mmol) and 4-ethoxybenzenesulfonyl chloride (3a, 29 mg, 0.13 mmol) as white solid (30 mg, yield=61%). 1H NMR (500 MHz, chloroform-d) δ 7.71 (d, J=8.80 Hz, 2H), 6.89 (d, J=9.05 Hz, 2H), 6.76 (br s, 1H), 6.35 (s, 2H), 4.06 (q, J=7.01 Hz, 2H), 3.80 (s, 6H), 1.43 (t, J=6.97 Hz, 3H). 13C NMR (126 MHz, chloroform-d) δ 162.8, 156.3, 136.1, 129.7, 129.5, 114.6, 107.2, 98.2, 64.0, 56.4, 14.6. HRMS for C16H17ClNO5S [M−H]− calculated 370.0521, found 370.0519.

N-(2,5-Dimethoxy-4-nitrophenyl)-4-ethoxybenzenesulfonamide (9). Compound 9 was synthesized using 3,5-dimethoxy-4-nitroaniline (2 g, 50 mg, 0.27 mmol) and 4-ethoxybenzenesulfonyl chloride (3a, 29 mg, 0.13 mmol) as yellow solid (30 mg, yield=61%). 1H NMR (500 MHz, chloroform-d) δ 7.69-7.86 (m, J=8.80 Hz, 2H), 7.44 (s, 1H), 7.40 (s, 1H), 7.31 (s, 1H), 6.90-6.95 (m, 2H), 4.07 (q, J=6.93 Hz, 2H), 3.93 (s, 3H), 3.82 (s, 3H), 1.43 (t, J=6.97 Hz, 3H). 13C NMR (126 MHz, chloroform-d) δ 163.1, 149.4, 140.9, 133.1, 132.8, 129.5, 129.4, 114.8, 108.3, 103.2, 64.1, 57.0, 56.5, 14.5. HRMS for C16H19N2O7S [M+H+] calculated 383.0907, found 383.091.

N-(4-Amino-2,5-dimethoxyphenyl)-4-ethoxybenzenesulfonamide (10). To a solution of compound 9 (128 mg, 0.33 mmol) in EtOAc were added a catalytic amount of palladium on carbon and some sodium sulfate. The reaction was subjected to Parr hydrogenation apparatus using hydrogen gas at 50 psi pressure for 6 hours. The solvent was then removed, and the residue was purified using silica gel column chromatography (5% MeOH/CH2Cl2) to obtain 84 mg of compound 10 as tan solid (yield=72%), 1H NMR (500 MHz, methanol-d4) δ 7.55 (d, J=8.80 Hz, 2H), 6.91 (d, J=8.80 Hz, 2H), 6.87 (s, 1H), 6.26 (s, 1H), 4.06 (q, J=7.01 Hz, 2H), 3.78 (s, 3H), 3.33 (s, 3H), 1.38 (t, J=6.97 Hz, 3H). 13C NMR (126 MHz, methanol-d4) δ 162.2, 147.8, 140.9, 135.9, 131.2, 129.2, 114.4, 113.5, 110.3, 99.0, 63.6, 55.2, 54.7, 13.5. HRMS for C16H20N205SNa [M+Na+] calculated 375.0985, found 375.0988.

Site B modified compounds 11-17, 19, 22-27 were synthesized using general procedure A described above. N-(4-Chloro-2,5-dimethoxyphenyl)-4-hydroxybenzenesulfonamide (11). Compound 11 was synthesized using 4-chloro-2,5-dimethoxyaniline (2a, 383 mg, 2.03 mmol) and 4-hydroxybenzenesulfonyl chloride (3b, 195 mg, 1.02 mmol) as dark brown solid (237 mg, yield=68%). 1H NMR (500 MHz, DMSO-d6) δ 10.44 (s, 1H), 9.39 (s, 1H), 7.54 (d, J=8.80 Hz, 2H), 7.02 (s, 1H), 6.97 (s, 1H), 6.83 (d, J=8.80 Hz, 2H), 3.66-3.78 (m, 3H), 3.48 (s, 3H). 13C NMR (126 MHz, DMSO-d6) δ 161.2, 148.1, 146.0, 129.9, 129.2, 125.5, 117.3, 115.3, 113.9, 109.2, 56.5, 56.4. HRMS for C14H13ClNO5S [M−H]− calculated 342.0208, found 342.0205.

N-(4-Chloro-2,5-dimethoxyphenyl)-4-methoxybenzenesulfonamide (12). Compound 12 was synthesized using 4-chloro-2,5-dimethoxyaniline (2a, 450 mg, 2.40 mmol) and 4-methoxybenzenesulfonyl chloride (3c, 248 mg, 1.20 mmol) as light brown solid (189 mg, yield=44%). 1H NMR (500 MHz, chloroform-d) δ 7.68 (d, J=8.80 Hz, 2H), 7.24 (s, 1H), 6.92 (s, 1H), 6.88 (d, J=9.05 Hz, 2H), 6.77 (s, 1H), 3.87 (s, 3H), 3.83 (s, 3H), 3.61 (s, 3H). 13C NMR (126 MHz, chloroform-d) δ 163.1, 149.2, 143.6, 130.3, 129.4, 125.2, 117.9, 114.0, 113.1, 106.3, 56.8, 56.4, 55.6. HRMS for C15H16ClNO5SNa [M+Na+] calculated 380.033, found 380.0326.

N-(4-Chloro-2,5-dimethoxyphenyl)-4-propoxybenzenesulfonamide (13). Compound 13 was synthesized using 4-chloro-2,5-dimethoxyaniline (2a, 106 mg, 0.57 mmol) and 4-propoxybenzenesulfonyl chloride (3d, 66 mg, 0.28 mmol) as off-white solid (65 mg, yield=59%). 1H NMR (500 MHz, chloroform-d) δ 7.66 (d, J=8.80 Hz, 2H), 7.23 (5, 1H), 6.92 (s, 1H), 6.86 (d, J=9.05 Hz, 2H), 6.76 (s, 1H), 3.92 (t, J=6.60 Hz, 2H), 3.87 (s, 3H), 3.60 (5, 3H), 1.76-1.85 (m, 2H), 1.02 (t, J=7.46 Hz, 3H). 13C NMR (126 MHz, chloroform-d) δ 162.8, 149.2, 143.5, 130.0, 129.3, 125.2, 117.8, 114.4, 113.1, 106.2, 69.9, 56.8, 56.4, 22.3, 10.4. HRMS for C17H20ClNO5SNa [M+Na+] calculated 408.0643, found 408.0641.

4-Butoxy-N-(4-chloro-2,5-dimethoxyphenyl)benzenesulfonamide (14). Compound 14 was synthesized using 4-chloro-2,5-dimethoxyaniline (2a, 191 mg, 1.02 mmol) and 4-butoxybenzenesulfonyl chloride (3e, 127 mg, 0.51 mmol) as off-white solid (95 mg, yield=47%). 1H NMR (500 MHz, chloroform-d) δ 7.66 (d, J=8.80 Hz, 2H), 7.23 (s, 1H), 6.91 (s, 1H), 6.85 (d, J=8.80 Hz, 2H), 6.76 (s, 1H), 3.96 (t, J=6.48 Hz, 2H), 187 (s, 3H), 3.60 (s, 3H), 1.76 (quin, J=7.20 Hz, 2H), 1.47 (sxt, J=7.40 Hz, 2H), 0.97 (t, J=7.46 Hz, 3H). 13C NMR (126 MHz, chloroform-d) δ 162.8, 149.2, 143.5, 130.0, 129.3, 125.3, 117.8, 114.4, 113.1, 106.2, 68.1, 56.8, 56.4, 31.0, 19.1, 13.8. HRMS for C18H22ClNO5SNa [M+Na+] calculated 422.0799, found 422.0802.

N-(4-Chloro-2,5-dimethoxyphenyl)-4-(prop-2-yn-1-yloxy)-benzenesulfonamide (15). Compound 15 was synthesized using 4-chloro-2,5-dimethoxyaniline (2a, 66 mg, 0.35 mmol) and 4-(prop-2-yn-1-yloxy)benzenesulfonyl chloride (3f, 40.7 mg, 0.18 mmol) as off-white solid (24 mg, yield=32%). 1H NMR (500 MHz, chloroform-d) δ 7.69 (d, J=9.05 Hz, 2H), 7.23 (s, 1H), 6.96 (d, J=8.80 Hz, 2H), 6.90 (s, 1H), 6.76 (s, 1H), 4.72 (d, J=2.20 Hz, 2H), 3.87 (s, 3H), 3.59 (s, 3H), 2.55 (t, J=2.45 Hz, 1H). 13C NMR (126 MHz, DMSOd6) δ 160.2, 148.1, 146.4, 132.5, 128.9, 125.1, 117.7, 114.9, 113.9, 109.9, 78.8, 78.5, 56.4, 55.8, HRMS for C17H15ClNO5S [M−H]− calculated 380.0365, found 380.0365.

N-(4-Chloro-2,5-dimethoxyphenyl)-4-propylbenzenesulfonamide (16). Compound 16 was synthesized using 4-chloro-2,5-dimethoxyaniline (2a, 210 mg, 1.12 mmol) and 4-propylbenzenesulfonyl chloride (3 g, 100 μL, 0.56 mmol) as white solid (121 mg, yield=59%). 1H NMR (500 MHz, chloroform-d) δ 7.64 (d, J=8.31 Hz, 2H), 7.23 (s, 1H), 7.21 (d, J=8.31 Hz, 2H), 6.92 (s, 1H), 6.76 (s, 1H), 3.87 (5, 3H), 3.53-3.58 (m, 3H), 2.60 (t, J=7.70 Hz, 2H), 1.61 (sxt, J=7.60 Hz, 2H), 0.91 (t, J=7.34 Hz, 3H). 13C NMR (126 MHz, chloroform-d) δ 149.2, 148.6, 143.6, 136.0, 128.9, 127.2, 125.1, 117.9, 113.1, 106.4, 56.8, 56.3, 37.8, 24.1, 13.7. HRMS for C17H20ClNO4SNa [M+Na+] calculated 392.0694, found 392.0695.

N-(4-Chloro-2,5-dimethoxyphenyl)-4-nitrobenzenesulfonamide (17). Compound 17 was synthesized using 4-chloro-2,5-dimethoxyaniline (2a, 847 mg, 4.51 mmol) and 4-nitrobenzenesulfonyl chloride (3h, 500 mg, 2.25 mmol) as yellow solid (182 mg, yield=22%). 1H NMR (500 MHz, DMSO-d6) δ 10.15 (s, 1H), 8.37 (d, J=8.80 Hz, 2H), 7.93 (d, J=8.80 Hz, 2H), 7.04 (s, 1H), 7.01 (s, 1H), 3.76 (s, 3H), 3.35 (s, 3H). 13C NMR (126 MHz, chloroform-d) δ 150.2, 149.4, 144.5, 144.0, 128.4, 124.1, 123.5, 119.6, 113.2, 107.4, 56.9, 56.3. HRMS for C14H12ClN2O6S [M−H]− calculated 371.011, found 371.0104.

4-Amino-N-(4-chloro-2,5-dimethoxyphenyl)benzenesulfonamide (18). To a solution of compound 17 (150 mg, 0.4 mmol) in EtOAc were added a catalytic amount of palladium on carbon and some sodium sulfate. The reaction was subjected to hydrogenation on a Parr hydrogenation apparatus using hydrogen gas at 50 psi pressure for 6 hours. The solvent was then removed, and the residue was purified using silica gel column chromatography (9% MeOH/CH2Cl2) to obtain 79 mg of compound 18 as tan solid (yield=58%). 1H NMR (500 MHz, DMSO-d6) δ 9.07 (s, 1H), 7.31-7.41 (m, J=8.56 Hz, 2H), 6.97 (s, 1H), 7.01 (s, 1H), 6.47-6.56 (m, J=8.80 Hz, 2H), 5.98 (s, 2H), 3.70 (s, 3H), 3.54 (s, 3H). 13C NMR (126 MHz, DMSO-d6) δ 152.9, 148.1, 145.5, 128.9, 126.1, 124.6, 116.4, 113.9, 112.4, 108.0, 56.6, 56.4. HRMS for C14H15ClN204SNa [M+Na+] calculated 365.0333, found 365.0335.

N-(4-Chloro-2,5-dimethoxyphenyl)-4-cyanobenzenesulfonamide (19), Compound 19 was synthesized using 4-chloro-2,5-dimethoxyaniline (2a, 372 mg, 1.98 mmol) and 4-cyanobenzenesulfonyl chloride (3i, 100 mg, 0.50 mmol) as white solid (40 mg, yield=23%). 1H NMR (500 MHz, chloroform-d) δ 7.83 (d, J=8.56 Hz, 2H), 7.73 (d, J=8.31 Hz, 2H), 7.25 (s, 1H), 6.92 (s, 1H), 6.79 (s, 1H), 3.90 (5, 3H), 3.57 (s, 3H). 13C NMR (126 MHz, chloroform-d) δ 149.4, 144.0, 142.9, 132.6, 127.8, 123.5, 119.5, 117.1, 116.7, 113.1, 107.4, 56.8, 56.2. HRMS for C15H12ClN2O4S [M−H]− calculated 351.0212, found 351.021.

test-Butyl (4-(N-(4-Chloro-2,5-dimethoxyphenyl)sulfamoyl)-benzyl)carbamate (20). To a crude solution of compound 19 (280 mg, 0.75 mmol) in methanol was added a catalytic amount of palladium on carbon and di-tert-butyl dicarbonate (326 mg, 1.5 mmol). The reaction was subjected to hydrogenation on Parr hydrogenation apparatus using hydrogen gas at 50 psi pressure overnight. The solvent was then removed, and the residue was purified using silica gel column chromatography (40% EtOAc/hexanes) to obtain 65 mg of compound 20 as white solid (yield=20%). 1H NMR (500 MHz, chloroform-d) δ 7.70 (d, J=8.07 Hz, 2H), 7.33 (d, J=8.07 Hz, 2H), 7.25 (s, 1H), 6.93 (br s, 1H), 6.76 (s, 1H), 4.94 (br s, 1H), 4.34 (d, J=5.87 Hz, 2H), 3.87 (s, 3H), 3.57 (s, 3H), 1.46 (s, 9H). 13C NMR (126 MHz, chloroform-d) δ 155.8, 149.3, 144.9, 143.7, 137.5, 127.5, 127.5, 124.8, 118.2, 113.1, 106.5, 80.0, 56.8, 56.3, 44.0, 28.3. HRMS for C20H25ClN2O6SNa [M+Na+] calculated 479.1014, found 479.1018.

4-(Aminomethyl)-N-(4-chloro-2,5-dimethoxyphenyl)-benzenesulfonamide (21). Compound 20 (11 mg, mmol) was stirred in a solution of 4 N HCl in dioxane for 1 h. The solvent was then removed to obtain compound 21 in quantitative yield as hydrochloride salt (gray solid). 1H NMR (500 MHz, methanol-d4) δ 7.71-7.88 (m, J=8.31 Hz, 2H), 7.51-7.67 (m, J=8.31 Hz, 2H), 7.23 (s, 1H), 6.87 (s, 1H), 4.17 (s, 2H), 3.82 (s, 3H), 3.51 (s, 3H). 13C NMR (126 MHz, methanol-d4) δ 150.5, 147.2, 142.1, 139.5, 130.5, 129.3, 126.3, 120.3, 114.7, 110.4, 57.3, 57.0, 43.7. HRMS for C15H18ClN2O4S [M+H+] calculated 357.067, found 357.0674.

N-(4-Chloro-2,5-dimethoxyphenyl)-4-phenoxybenzenesulfonamide (22). Compound 22 was synthesized using 4-chloro-2,5-dimethoxyaniline (2a, 140 mg, 0.74 mmol) and 4-phenoxybenzenesulfonyl chloride (3j, 100 mg, 0.37 mmol) as light yellow solid (51 mg, yield=33%). 1H NMR (500 MHz, chloroform-d) δ 7.69 (d, J=8.80 Hz, 1H), 7.41 (t. J=7.95 Hz, 1H), 7.25 (s, 2H), 7.23 (t, J=7.60 Hz, 2H), 7.03 (d, J=7.58 Hz, 2H), 6.95 (s, 1H), 6.94 (d, J=8.80 Hz, 2H), 6.80 (s, 1H), 3.87 (s, 3H), 3.64 (s, 3H). 13C NMR (126 MHz, chloroform-d) δ 161.9, 154.8, 149.3, 143.6, 132.2, 130.2, 129.4, 125.1, 125.0, 120.3, 118.0, 117.2, 113.1, 106.3, 56.8, 56.4. HRMS for C20H18ClNO5SNa [M+Na+] calculated 442.0486, found 442.0489.

N-(4-Chloro-2,5-dimethoxyphenyl)-3-methoxybenzenesulfonamide (23). Compound 23 was synthesized using 4-chloro-2,5-dimethoxyaniline (2a, 182 mg, 0.97 mmol) and 3-methoxybenzenesulfonyl chloride (3k, 100 mg, 0.48 mmol) as brown solid (189 mg, yield=54%). 1H NMR (500 MHz, chloroform-d) δ 7.29-7.35 (n, 2H), 7.21-7.26 (m, 2H), 7.00-7.09 (m, 1H), 6.94 (s, 1H), 6.78 (s, 1H), 3.87 (s, 3H), 3.77 (s, 3H), 3.58 (s, 3H), 13C NMR (126 MHz, chloroform-d) δ 159.6, 149.3, 143.7, 139.8, 129.9, 124.9, 119.5, 119.3, 118.2, 113.1, 111.7, 106.5, 56.8, 56.4, 55.6. HRMS for C15H16ClNO5SNa [M+Na+] calculated 380.033, found 380.0329.

N-(4-Chloro-2,5-dimethoxyphenyl)-2-methoxybenzenesulfonamide (24). Compound 24 was synthesized using 4-chloro-2,5-dimethoxyaniline (2a, 182 mg, 0.97 mmol) and 2-methoxybenzenesulfonyl chloride (3l, 100 mg, 0.48 mmol) as tan solid (121 mg, yield=70%). 1H NMR (500 MHz, chloroform-d) δ 7.87 (td, J=1.70, 7.70 Hz, 1H), 7.58 (s, 1H), 7.49 (tt, J=1.50, 7.70 Hz, 1H), 7.22 (s, 1H), 6.99 (t, J=7.70 Hz, 1H), 6.95 (d, J=8.31 Hz, 1H), 6.78 (s, 1H), 3.95 (s, 3H), 3.80 (s, 3H), 3.73 (s, 3H). 13C NMR (126 MHz, chloroform-d) δ 156.4, 149.2, 142.9, 135.1, 130.9, 126.1, 125.7, 120.3, 116.8, 113.0, 111.8, 104.9, 56.7, 56.6, 56.1. HRMS for C15H16ClNO5SNa [M+Na+] calculated 380.033, found 380.0329.

3-Bromo-N-(4-chloro-2,5-dimethoxyphenyl)-4-ethoxy-benzenesulfonamide (25). Compound 25 was synthesized using 4-chloro-2,5-dimethoxyaniline (2a, 180 mg, 0.70 mmol) and 3-bromo-4-methoxybenzenesulfonyl chloride (3m, 100 mg, 0.35 mmol) as brown solid (68 mg, yield=58%). 1H NMR (500 MHz, chloroform-d) δ 7.99 (d, J=2.20 Hz, 1H), 7.64 (dd, J=1.96, 8.56 Hz, 1H), 7.22 (s, 1H), 6.93 (s, 1H), 6.85 (d, J=8.56 Hz, 1H), 6.79 (s, 1H), 3.93 (s, 3H), 3.89 (s, 3H), 3.65 (s, 3H). 13C NMR (126 MHz, chloroform-d) δ 159.4, 149.3, 143.7, 132.4, 131.4, 128.5, 124.6, 118.4, 113.1, 112.0, 111.0, 106.6, 56.8, 56.6, 56.4. HRMS for C15H14BrClNO5S [M−H]− calculated 433.947, found 433.9469.

Methyl 4-(N-(4-Chloro-2,5-dimethoxyphenyl)sulfamoyl)-benzoate (26). Compound 26 was synthesized using 4-chloro-2,5-dimethoxyaniline (2a, 80 mg, 0.42 mmol) and methyl 4-(chlorosulfonyl)benzoate (3n, 50 mg, 0.21 mmol) as tan solid (31 mg, yield=38%). 1H NMR (500 MHz, chloroform-d) δ 8.08 (d, J=8.31 Hz, 2H), 7.80 (d, J=8.31 Hz, 2H), 7.25 (s, 1H), 6.94 (s, 1H), 6.76 (s, 1H), 3.94 (s, 3H), 3.89 (s, 3H), 3.55 (s, 3H). 13C NMR (126 MHz, chloroform-d) δ 165.5, 149.3, 143.8, 142.5, 134.1, 130.0, 127.2, 124.1, 118.9, 113.1, 107.0, 56.8, 56.2, 52.7. HRMS for C16H15ClNO6S [M−H]− calculated 384.0314, found 384.0308.

4-(N-(4-Chloro-2,5-dimethoxyphenyl)sulfamoyl)benzamide (27). Compound 27 was synthesized using 4-chloro-2,5-dimethoxyaniline (2a, 171 mg, 0.77 mmol) and 4-carbamoylbenzenesulfonyl chloride (3o, 100 mg, 0.46 mmol) as white solid (14 mg, yield=8%). 1H NMR (500 MHz, DMSO-d6) δ 9.83 (br s, 1H), 8.13 (br s, 1H), 7.96 (d, J=8.31 Hz, 2H), 7.76 (d, J=8.31 Hz, 2H), 7.60 (br s, 1H), 7.02 (s, 1H), 6.99 (s, 1H), 3.74 (s, 3H), 3.38 (br s, 3H). 13C NMR (126 MHz, DMSO-d6) δ 166.7, 148.2, 146.7, 142.4, 138.0, 128.0, 126.7, 124.5, 118.3, 114.0, 110.7, 56.5, 56.3. HRMS for C15H14ClN2O5S [M−H]− calculated 369.0317, found 369.0315, 4-(N-(4-Chloro-2,5-dimethoxyphenyl)sulfamoyl) benzoic Acid (28). To a solution of compound 26 (25.0 mg, 0.06 mmol) in MeOH and THF was added a solution of LiOH (40.1 mg, 0.97 mmol) in water. The reaction was stirred overnight and the solvent was then removed under vacuum. The residue was mixed with acidified water (3 N aq HCl), extracted with EtOAc, dried over MgSO4, and concentrated to dryness under vacuum to obtain compounds 28 as white solid (21 mg, yield=87%). 1H NMR (500 MHz, DMSO-d6) δ 10.44 (s, 1H), 9.39 (s, 1H), 7.54 (d, J=8.80 Hz, 2H), 7.02 (s, 1H), 6.97 (s, 1H), 6.83 (d, J=8.80 Hz, 2H), 3.66-3.78 (m, 3H), 3.48 (s, 3H). 13C NMR (126 MHz, DMSO-d6) δ 166.4, 148.3, 147.0, 143.9, 134.5, 129.9, 127.1, 124.4, 118.7, 114.0, 111.1, 56.6, 56.3, HRMS for C15H13ClNO6S [M−H]− calculated 370.0158, found 370.0152.

Ethyl 4-(N-(4-Chloro-2,5-dimethoxyphenyl)sulfamoyl)-benzoate (29). To a solution of compound 28 (20 mg, 0.05 mmol) in anhydrous EtOH was added trimethylsilyl chloride (68.3 μL, 0.54 mmol), and the reaction was stirred at room temperature until completion. The reaction mixture was poured into water and extracted with EtOAc. The organic layer was dried over MgSO4 and concentrated under vacuum to obtain the residue which was purified by silica gel column chromatography (25% EtOAc/hexanes) to obtain compound 29 as white solid. (17.6 mg, yield=82%). 1H NMR (500 MHz, chloroform-d) δ 8.09 (d, J=8.31 Hz, 2H), 7.80 (d, J=8.31 Hz, 2H), 7.26 (s, 1H), 6.95 (s, 1H), 6.76 (s, 1H), 4.39 (q, J=7.17 Hz, 2H), 3.89 (s, 3H), 3.56 (s, 3H), 1.40 (t, J=7.09 Hz, 3H). 13C NMR (126 MHz, chloroform-d) δ 165.0, 149.3, 143.8, 142.4, 134.5, 130.0, 127.2, 124.2, 118.8, 113.1, 106.9, 61.8, 56.8, 56.3, 14.2. HRMS for C17H17ClNO6S [M−H]− calculated 398.0471, found 398.0467.

4-(N-(4-Chloro-2,5-dimethoxyphenyl)sulfamoyl)-N-methylbenzamide (30). To a solution of compound 23 (25 mg, 0.07 mmol) in anhydrous DMF were added 2 M methyl amine solution in THF (67 μL, 0.13 mmol), triethylamine (38 μL, 0.27 mmol), and HATU (31 mg, 0.08 mmol). The reaction was stirred at room temperature until completion. The reaction mixture was poured into water and extracted with EtOAc. The organic layer was dried over MgSO4 and concentrated under vacuum to obtain the residue which was purified by reverse-phase C18 column chromatography (56% MeOH/1-120 with 0.1% CF3CO2H) to yield compound 30 as white solid (3 mg, yield=12%). 1H NMR (500 MHz, chloroform-d) δ 7.79 (s, 4H), 7.26 (s, 1H), 6.94 (s, 1H), 6.76 (s, 1H), 6.14 (5, 1H), 3.89 (5, 3H), 3.56 (s, 3H), 3.03 (d, J=4.89 Hz, 3H). 13C NMR (126 MHz, chloroform-d) δ 166.4, 149.3, 143.8, 141.2, 138.8, 127.5, 127.4, 124.2, 118.8, 113.1, 106.9, 56.8, 56.3, 27.0. HRMS for C16H16ClN2O5S [M−H]− calculated 383.0474, found 383.0468.

4-Chloro-N-(4-ethoxyphenyl)-2,5-dimethoxybenzene-sulfonamide (31). Compound 31 was synthesized using the general procedure A using p-phenetidine (2h, 166.04 μL, 1.21 mmol) and 4-Cl-2,5-dimethoxybenzenesulfonyl chloride (3p, 100 mg, 0.61 mmol) as brown solid (98 mg, yield=43.6%), 1H NMR (500 MHz, DMSOd6) δ 9.74 (br s, 1H), 7.35 (s, 1H), 7.28 (s, 1H), 6.97 (d, J=8.80 Hz, 2H), 6.75 (d, J=9.05 Hz, 2H), 3.88 (q, J=7.10 Hz, 2H), 3.86 (s, 3H), 3.77 (s, 3H), 1.24 (t, J=6.85 Hz, 3H), 13C NMR (126 MHz, chloroform-d) δ 157.5, 149.7, 149.0, 128.4, 128.4, 125.4, 125.1, 114.9, 114.9, 113.7, 63.6, 57.3, 56.8, 14.8, HRMS for C16H18ClNO5SNa [M+Na+] calculated 394.0486, found 394.0489.

General Procedure B for the Syntheses of Site C Modified Compounds 33-47 and 49-52. To a solution of compound 1 (1 equiv) in anhydrous DMF were added, potassium carbonate (2 equiv), and reagent 32 (1.1 equiv). The reaction was then heated at 45° C. with stirring until completion. The suspension was extracted with EtOAc and brine. Then the organic layer was isolated, dried over MgSO4, and concentrated in vacuo. The crude material was purified by chromatography to obtain the final compounds.

N-(4-Chloro-2,5-dimethoxyphenyl)-4-ethoxy-Nmethyl-benzenesulfonamide (33). Compound 33 was synthesized using compound 1 (10 mg, 0.03 mmol) and iodomethane (32a, 1.85 μL, 0.03 mmol) as white solid (10 mg, yield=95%). 1H NMR (500 MHz, chloroform-d) δ 7.61 (d, J=8.80 Hz, 2H), 6.96 (s, 1H), 6.92 (d, J=8.80 Hz, 2H), 6.83 (s, 1H), 4.09 (d, J=6.85 Hz, 2H), 3.85 (5, 3H), 3.39 (s, 3H), 3.19 (s, 3H), 1.45 (t, J=6.97 Hz, 3H). 13C NMR (126 MHz, dichloroethane) δ 162.1, 150.4, 148.6, 130.6, 129.7, 128.0, 122.5, 116.1, 114.0, 113.8, 63.9, 56.7, 55.6, 37.8, 14.6. HRMS for C17H29ClNO5SNa [M+Na+] calculated 408.0643, found 408.0641.

N-(4-Chloro-2,5-dimethoxyphenyl)-4-ethoxy-Npropyl-benzenesulfonamide (34). Compound 34 was synthesized using compound 1 (10 mg, 0.03 mmol) and 1-iodopropane (32b, 2.9 μL, 0.03 mmol) as tan solid (11 mg, yield=96%). 1H NMR (500 MHz, chloroform-d) δ 7.59 (d, J=8.80 Hz, 2H), 6.86-6.92 (m, 3H), 6.81 (s, 1H), 4.07 (q, J=7.09 Hz, 2H), 3.84 (s, 3H), 3.51 (br s, 2H), 3.36 (5, 3H), 1.44 (sxt, J=7.30 Hz, 5H), 0.89 (t, J=7.34 Hz, 3H). 13C NMR (126 MHz, chloroform-d) δ 162.0, 150.7, 148.6, 131.7, 129.6, 125.7, 122.6, 117.4, 113.9, 113.7, 63.9, 56.8, 55.6, 51.4, 22.2, 14.6, 11.2. HRMS for C19H24ClNO5SNa [M+Na+] calculated 436.0956, found 436.0954.

N-(4-Chloro-2,5-dimethoxyphenyl)-4-ethoxy-Nbutyl-benzenesulfonamide (35). Compound 35 was synthesized using compound 1 (10 mg, 0.03 mmol) and 1-iodobutane (32c, 2.9 μL, 0.03 mmol) as white solid (11 mg, yield=96%). 1H NMR (500 MHz, chloroform-d) δ 7.60 (d, J=8.80 Hz, 2H), 6.87-6.93 (m, 3H), 6.82 (s, 1H), 4.08 (q, J=6.93 Hz, 2H), 3.85 (s, 3H), 3.48-3.61 (m, 2H), 3.37 (s, 3H), 1.45 (t, J=6.85 Hz, 3H), 1.39 (dd, J=7.46, 14.79 Hz, 2H), 1.29-1.35 (in, 2H), 0.87 (t, J=7.09 Hz, 3H). 13C NMR (126 MHz, chloroform-d) δ 162.0, 150.8, 148.6, 131.7, 129.6, 125.6, 122.6, 117.4, 113.9, 113.7, 63.9, 56.8, 55.6, 49.4, 31.0, 19.8, 14.6, 13.7. HRMS for C20H26ClNO5SNa [M+Na+] calculated 450.1112, found 450.1106.

N-(4-Chloro-2,5-dimethoxyphenyl)-4-ethoxy-Npentyl-benzenesulfonamide (36), Compound 36 was synthesized using compound 1 (10 mg, 0.03 mmol) and 1-iodopentane (32d, 3.9 μL, 0.03 mmol) as off-white solid (12 mg, yield=98%), 1H NMR (500 MHz, chloroform-d) δ 7.59 (d, J=8.80 Hz, 2H), 6.87-6.92 (m, 3H), 6.82 (s, 1H), 4.08 (q, J=7.09 Hz, 2H), 3.85 (s, 3H), 3.54 (br s, 2H), 3.36 (s, 3H), 1.45 (t, J=6.97 Hz, 3H), 1.37-1.42 (m, 2H), 1.26-1.30 (m, J=3.70 Hz, 4H), 0.85 (t, J=6.85 Hz, 3H). 13C NMR (126 MHz, chloroform-d) δ 162.0, 150.8, 148.6, 131.7, 129.6, 125.6, 122.6, 117.4, 113.9, 113.7, 63.9, 56.8, 55.5, 49.7, 28.7, 28.5, 22.3, 14.6, 14.0. HRMS for C21H28ClNO5SNa [M+Na+] calculated 464.1269, found 464.1265.

N-(4-Chloro-2,5-dimethoxyphenyl)-4-ethoxy-Nhexyl-benzenesulfonamide (37). Compound 37 was synthesized using compound 1 (10 mg, 0.03 mmol) and 1-iodohexane (32e, 4.4 μL, 0.03 mmol) as off-white solid (8 mg, yield=65%). 1H NMR (500 MHz, chloroform-d) δ 7.59 (d, J=8.80 Hz, 2H), 6.86-6.91 (m, 3H), 6.81 (s, 1H), 4.07 (q, J=7.09 Hz, 2H), 3.84 (s, 3H), 3.47-3.62 (m, 2H), 3.36 (s, 3H), 1.44 (t, J=7.10 Hz, 3H), 1.39 (quin, J=7.60 Hz, 2H), 1.16-1.34 (m, 6H), 0.85 (t, J=6.85 Hz, 3H). 13C NMR (126 MHz, chloroform-d) δ 162.0, 150.8, 148.6, 131.7, 129.6, 125.6, 122.6, 117.4, 113.9, 113.7, 63.9, 56.8, 55.5, 49.7, 31.4, 28.8, 26.2, 22.6, 14.6, 14.0. HRMS for C22H30ClNO5SNa [M+Na+] calculated 478.1425, found 478.1422.

N-(4-Chloro-2,5-dimethoxyphenyl)-4-ethoxy-Nheptyl-benzenesulfonamide (38). Compound 38 was synthesized using compound 1 (10 mg, 0.03 mmol) and 1-iodoheptane (32f, 4.9 μL, 0.03 mmol) as white solid (12 mg, yield=95%). 1H NMR (500 MHz, chloroform-d) δ 7.59 (d, J=8.80 Hz, 2H), 6.87-6.91 (m, 3H), 6.81 (s, 1H), 4.07 (q, J=6.85 Hz, 2H), 3.84 (s, 3H), 3.45-3.63 (m, 2H), 3.36 (s, 3H), 1.44 (t, J=7.10 Hz, 6H), 1.39 (quin, J=7.40 Hz, 1H), 1.14-1.33 (m, 10H), 0.85 (t, J=6.97 Hz, 3H). 13C NMR (126 MHz, chloroform-d) δ 161.9, 150.7, 148.5, 131.6, 129.5, 125.6, 122.6, 117.3, 113.9, 113.6, 63.9, 56.7, 55.5, 49.6, 31.7, 28.9, 28.9, 26.5, 22.6, 14.6, 14.1. HRMS for C23H32ClNO5SNa [M Na+] calculated 492.1582, found 492.1578.

N-(4-Chloro-2,5-dimethoxyphenyl)-4-ethoxy-Ndodecyl-benzenesulfonamide (39). Compound 39 was synthesized using compound 1 (10 mg, 0.03 mmol) and 1-bromododecane (32g, 7.1 μL, 0.03 mmol) as white solid (14 mg, yield=96%). 1H NMR (500 MHz, chloroform-d) δ 7.59 (d, J=8.80 Hz, 2H), 6.86-6.92 (m, 3H), 6.81 (s, 1H), 4.07 (q, J=7.09 Hz, 2H), 3.84 (s, 3H), 3.45-3.63 (m, 2H), 3.36 (s, 3H), 1.44 (t, J=6.97 Hz, 3H), 1.38 (quin, J=7.30 Hz, 2H), 1.23-1.30 (m, 10H), 0.88 (t, J=6.97 Hz, 3H). 13C NMR (126 MHz, chloroform-d) δ 161.9, 150.7, 148.5, 131.6, 129.6, 125.6, 122.6, 117.3, 113.9, 113.6, 63.9, 56.7, 55.5, 49.7, 31.9, 29.7, 29.6, 29.6, 29.6, 29.4, 29.2, 28.9, 26.6, 22.7, 14.6, 14.1, HRMS for C28H43ClNO5S [M+H+] calculated 540.2545, found 540.2549.

N-(4-Chloro-2,5-dimethoxyphenyl)-4-ethoxy-Nisopropylbenzenesulfonamide (40). Compound 40 was synthesized using compound 1 (10 mg, 0.03 mmol) and 2-iodopropane (32h, 2.96 μL, 0.03 mmol) as white solid (5 mg, yield=48%). 1H NMR (500 MHz, chloroform-d) δ 7.76 (d, J=8.80 Hz, 2H), 6.94 (s, 1H), 6.92 (d, J=8.80 Hz, 2H), 6.70 (s, 1H), 4.39 (spt, J=6.70 Hz, 1H), 4.09 (q, J=7.09 Hz, 2H), 3.81 (s, 3H), 3.61 (s, 3H), 1.46 (t, J=6.97 Hz, 3H), 1.13 (d, J=6.60 Hz, 3H), 0.99 (d, J=6.60 Hz, 3H). 13C NMR (126 MHz, chloroform-d) δ 161.9, 152.9, 148.3, 132.9, 129.8, 123.3, 122.6, 118.5, 114.0, 113.9, 63.9, 56.8, 55.8, 51.9, 22.2, 20.9, 14.6. HRMS for C19H24ClNO5SNa [M+Na+] calculated 436.0956, found 436.0957.

N-(4-Chloro-2,5-dimethoxyphenyl)-4-ethoxy-Nisobutyl-benzenesulfonamide (41), Compound 41 was synthesized using compound 1 (10 mg, 0.03 mmol) and 1-iodo-2-methylpropane (32i, 3.4 μL, 0.03 mmol) as white solid (9 mg, yield=77%). 1H NMR (500 MHz, chloroform-d) δ 7.56 (d, J=8.80 Hz, 2H), 6.92 (5, 1H), 6.89 (d, J=8.80 Hz, 2H), 6.80 (s, 1H), 4.07 (q, J=7.09 Hz, 2H), 3.85 (s, 3H), 3.29-3.51 (m, 2H), 3.33 (s, 3H), 1.59 (spt, J=7.00 Hz, 2H), 1.44 (t, J=6.97 Hz, 3H), 0.91 (br s, 6H). 13C NMR (126 MHz, chloroform-d) δ 161.9, 150.6, 148.5, 131.5, 129.6, 126.0, 122.5, 117.2, 113.9, 113.7, 63.9, 57.1, 56.8, 55.5, 27.6, 20.1, 14.6. HRMS for C20H26ClNO5SNa [M+Na+] calculated 450.1112, found 450.1109.

N-(4-Chloro-2,5-dimethoxyphenyl)-4-ethoxy-N-(prop-2-yn-1-yl)benzenesulfonamide (42). Compound 42 was synthesized using compound 1 (10 mg, 0.03 mmol) and propargyl bromide solution in toluene (32j, 2.8 μL, 0.03 mmol) as white solid (9 mg, yield=81%). 1H NMR (500 MHz, chloroform-d) δ 7.62 (d, J=8.80 Hz, 2H), 6.96 (s, 1H), 6.90 (d, J=8.80 Hz, 2H), 6.85 (s, 1H), 4.44 (br s, 2H), 4.08 (q, J=7.09 Hz, 2H), 3.82 (s, 3H), 3.44 (s, 3H), 2.12-2.23 (m, 1H), 1.45 (t, J=6.85 Hz, 3H). 13C NMR (126 MHz, chloroform-d) δ 162.3, 150.5, 148.6, 131.1, 129.8, 125.0, 123.1, 117.2, 114.1, 113.7, 78.4, 73.2, 64.0, 56.7, 55.8, 39.6, 14.6. HRMS for C19H20ClNO5SNa [M+Na+] calculated 432.0643, found 432.0639.

N-(But-3-yn-1-yl)-N-(4-chloro-2,5-dimethoxyphenyl)-4-ethoxybenzenesulfonamide (43). Compound 43 was synthesized using compound 1 (40 mg, 0.11 mmol) and 4-bromo-1-butyne (32k, 11.1 μL, 0.11 mmol) as white solid (3 mg, yield=7%). 1H NMR (500 MHz, chloroform-d) δ 7.59 (d, J=8.80 Hz, 2H), 6.98 (s, 1H), 6.90 (d, J=8.80 Hz, 2H), 6.81 (s, 1H), 4.08 (q, J=7.09 Hz, 2H), 3.85 (s, 3H), 3.72 (br s, 2H), 3.35 (s, 3H), 2.42 (dt, J=2.57, 7.40 Hz, 2H), 1.95 (t, J=2.57 Hz, 1H), 1.45 (t, J=6.97 Hz, 3H). 13C NMR (126 MHz, chloroform-d) δ 162.1, 150.3, 148.6, 131.4, 129.6, 125.2, 123.0, 117.6, 114.0, 113.6, 81.0, 70.0, 63.9, 56.7, 55.5, 48.6, 19.7, 14.6. HRMS for C20H22ClNO5SNa [M+Na+] calculated 446.0799, found 446.0798.

N-(4-Chloro-2,5-dimethoxyphenyl)-4-ethoxy-N-(pent-4-yn-1-yl)benzenesulfonamide (44). Compound 44 was synthesized using compound 1 (40 mg, 0.11 mmol) and 5-iodopent-1-yne (32l, 13.5 μL, 0.12 mmol) as off-white solid (40 mg, yield=84%). 1H NMR (500 MHz, chloroform-d) δ

7.59 (d, J=8.80 Hz, 2H), 6.90 (d, J=8.80 Hz, 2H), 6.87 (s, 1H), 6.83 (s, 1H), 4.08 (q, J=7.09 Hz, 2H), 3.84 (s, 3H), 3.64 (br s, 2H), 3.38 (s, 3H), 2.26 (dt, J=2.45, 7.21 Hz, 2H), 1.91 (t, J=2.57 Hz, 1H), 1.67 (quin, J=7.09 Hz, 2H), 1.44 (t, J=6.97 Hz, 3H), 13C NMR (126 MHz, chloroform-d) δ 162.1, 150.7, 148.6, 131.3, 129.6, 125.5, 122.8, 117.0, 114.0, 113.7, 83.4, 68.7, 63.9, 56.8, 55.6, 48.9, 27.8, 15.8, 14.6. HRMS for C21H24ClNO5SNa [M+Na+] calculated 460.0956, found 460.0954.

N-(4-Chloro-2,5-dimethoxyphenyl)-4-ethoxy-N-(2-(2-(2-(prop-2-yn-1-yloxy)ethoxy)ethoxy)ethyl)benzenesulfonamide (45). Compound 45 was synthesized using compound 1 (40 mg, 0.11 mmol) and propargyl-PEG3-bromide (32m, 29.7 μL, 0.12 mmol) as clear oil (48 mg, yield=82%). 1H NMR (500 MHz, methanol-d4) δ 7.59 (d, J=8.80 Hz, 2H), 7.02 (d, J=8.80 Hz, 2H), 6.97 (s, 1H), 6.96 (s, 1H), 4.16 (d, J=2.20 Hz, 2H), 4.11 (q, J=7.09 Hz, 2H), 3.72-3.85 (m, 5H), 3.61-3.65 (m, 2H), 3.57-3.60 (m, 2H), 3.48-3.54 (m, 6H), 3.38 (5, 3H), 2.85 (t, J=2.32 Hz, 1H), 1.41 (t, J=6.97 Hz, 3H). 13C NMR (126 MHz, methanol-d4) δ 164.0, 152.4, 150.1, 132.9, 131.0, 127.1, 124.3, 119.1, 115.5, 115.0, 80.7, 76.1, 71.7, 71.5, 71.3, 70.5, 70.2, 65.3, 59.2, 57.4, 56.4, 50.4, 15.1. HRMS for C25H32ClNO8SNa [M+Na+] calculated 564.1429, found 564.1431.

Benzyl-N-(4-chloro-2,5-dimethoxyphenyl)-4-ethoxybenzenesulfonamide (46). Compound 46 was synthesized using compound 1 (10 mg, 0.03 mmol) and benzyl chloride (32n, 3.4 μL, 0.03 mmol) as white solid (12 mg, yield=94%). 1H NMR (500 MHz, chloroform-d) δ 7.65 (d, J=8.80 Hz, 2H), 7.10-7.25 (m, 5H), 6.92 (d, J=8.80 Hz, 2H), 6.75 (s, 1H), 6.63 (5, 1H), 4.74 (br s, 2H), 4.09 (q, J=6.85 Hz, 2H), 3.67 (5, 3H), 3.35 (s, 3H), 1.46 (t, J=6.85 Hz, 3H). 13C NMR (126 MHz, chloroform-d) δ 162.1, 150.5, 148.4, 136.5, 131.7, 129.6, 128.8, 128.2, 127.6, 125.1, 122.6, 117.9, 114.0, 113.5, 63.9, 56.6, 55.5, 53.4, 14.6. HRMS for C23H24ClNO5SNa [M+Na+] calculated 484.0956, found 484.0952.

N-(4-Chloro-2,5-dimethoxyphenyl)-4-ethoxy-Nphenethylbenzenesulfonamide (47). Compound 47 was synthesized using compound 1 (10 mg, 0.03 mmol) and (2-iodoethyl)-benzene (320, 3.4 μL, 0.03 mmol) as off-white solid (12 mg, yield=95%). 1H NMR (500 MHz, chloroform-d) δ 7.45-7.52 (m, 2H), 7.18 (d, J=7.60 Hz, 2H), 7.12 (t, J=7.30 Hz, 1H), 7.06 (d, J=7.60 Hz, 2H), 6.76-6.83 (m, J=8.80 Hz, 2H), 6.72 (5, 1H), 6.66 (s, 1H), 3.99 (q, J=6.85 Hz, 2H), 3.61-3.85 (m, 5H), 3.25 (s, 3H), 2.74 (t, J=7.70 Hz, 2H), 1.37 (t, J=6.97 Hz, 3H). 13C NMR (126 MHz, chloroform-d) δ 162.0, 150.4, 148.5, 138.4, 131.4, 129.5, 128.9, 128.3, 126.4, 125.6, 122.6, 117.5, 113.9, 113.4, 63.9, 56.6, 55.5, 51.2, 35.8, 14.6. HRMS for C24H26ClNO5SNa [M+Na+] calculated 498.1112, found 498.111.

N-(4-Chloro-2,5-dimethoxyphenyl)-N4(4-ethoxyphenyl)-sulfonyl)acetamide (48). To a solution of compound 1 (10 mg, 0.03 mmol) in anhydrous CH2Cl2 were added, acetyl chloride (32p, 3.8 μL, 0.03 mmol) and triethylamine (15 μL, 0.12 mmol) and the reaction was heated at 45° C. with stirring for 20 h upon which more acetyl chloride (3.8 μL, 0.03 mmol) was added to drive the reaction to completion. The solvent was then removed, and the residue was dissolved in EtOAc, washed with water and brine, dried over $MgSO_4$, and concentrated under vacuum to obtain the residue which was purified by silica gel column chromatography (30% EtOAc/hexanes) to obtain compound 48 as white solid (5 mg, yield=45%). 1H NMR (500 MHz, chloroform-d) δ 7.98 (d, J=8.80 Hz, 2H), 7.05 (s, 1H), 6.85-7.01 (m, 3H), 4.12 (q, J=7.10 Hz, 2H), 3.91 (s, 3H), 3.67-3.76 (m, 3H), 1.86 (s, 3H), 1.46 (t, J=6.97 Hz, 3H), 13C NMR (126 MHz, chloroform-d) δ 170.1, 163.2, 149.8, 149.3, 131.8, 130.0, 124.9, 123.9, 115.7, 114.1, 113.8, 64.0, 56.9, 56.0, 24.0, 14.6. HRMS for C18H20ClNO6SNa [M+Na+] calculated 436.0592, found 436.0592.

Ethyl N-(4-Chloro-2,5-dimethoxyphenyl)-N-((4-ethoxyphenyl)sulfonyl)glycinate (49). Compound 49 was synthesized using compound 1 (10 mg, 0.03 mmol) and ethyl bromoacetate (32q, 3.3 μL, 0.03 mmol) as off-white solid (12 mg, yield=97%). 1H NMR (500 MHz, chloroform-d) δ 7.60 (d, J=8.80 Hz, 2H), 7.18 (s, 1H), 6.89 (d, J=8.80 Hz, 2H), 6.80 (5, 1H), 4.38 (5, 2H), 4.16 (d, J=7.09 Hz, 2H), 4.07 (d, J=7.09 Hz, 2H), 3.83 (s, 3H), 3.39 (5, 3H), 1.44 (t, J=6.97 Hz, 3H), 1.25 (t, J=7.09 Hz, 3H). 13C NMR (126 MHz, chloroform-d) δ 169.4, 162.3, 149.8, 148.6, 131.3, 129.7, 125.6, 123.0, 117.8, 114.0, 113.5, 63.9, 61.3, 56.7, 55.7, 51.0, 14.6, 14.2. HRMS for C20H25ClNO7S [M+H+] calculated 458.1035, found 458.1035.

Ethyl 4-((N-(4-Chloro-2,5-dimethoxyphenyl)-4-ethoxyphenyl)sulfonamido)butanoate (50). Compound 50 was synthesized using compound 1 (40 mg, 0.11 mmol) and ethyl 4-bromobutyrate (32r, 16.9 μL, 0.12 mmol) as white solid (47 mg, yield=91%). 1H NMR (500 MHz, chloroform-d) δ 7.58 (d, J=8.80 Hz, 2H), 6.89 (d, J=8.80 Hz, 2H), 6.87 (s, 1H), 6.82 (s, 1H), 4.09 (q, J=7.20 Hz, 2H), 4.07 (q, J=7.00 Hz, 2H), 3.84 (s, 3H), 3.60 (br s, 2H), 3.37 (s, 3H), 2.41 (t, J=7.46 Hz, 2H), 1.74 (quin, J=7.09 Hz, 2H), 1.44 (t, J=6.97 Hz, 3H), 1.23 (t, J=7.21 Hz, 3H). 13C NMR (126 MHz, chloroform-d) δ 173.1, 162.1, 150.7, 148.6, 131.3, 129.6, 125.3, 122.9, 117.0, 114.0, 113.7, 63.9, 60.4, 56.8, 55.6, 49.0, 31.1, 24.1, 14.6, 14.2. HRMS for C22H28ClNO7SNa [M+Na+] calculated 508.1167, found 508.117.

N-(4-Chloro-2,5-dimethoxyphenyl)-4-ethoxy-N-(3-hydroxypropyl)benzenesulfonamide (51). Compound 51 was synthesized using compound 1 (10 mg, 0.03 mmol) and 3-bromo-1-propanol (32s, 2.7 μL, 0.03 mmol) as off-white solid (5 mg, yield=42%). 1H NMR (500 MHz, DMSO-d6) δ 7.55 (d, J=8.80 Hz, 2H), 7.14 (s, 1H), 7.08 (d, J=8.80 Hz, 2H), 6.76 (s, 1H), 4.43 (t, J=4.89 Hz, 1H), 4.11 (q, J=6.85 Hz, 2H), 3.72 (s, 3H), 3.50 (br s, 2H), 3.42 (s, 3H), 3.33-3.36 (m, 2H), 1.46 (quin, J=6.80 Hz, 2H), 1.34 (t, J=6.85 Hz, 3H). 13C NMR (126 MHz, DMSO-d6) δ 161.8, 151.1, 147.9, 130.8, 129.5, 125.9, 121.5, 116.4, 114.5, 114.3, 63.8, 58.1, 56.5, 56.1, 47.0, 31.7, 14.5. HRMS for C19H24ClNO6SNa [M+Na+] calculated 452.0905, found 452.0907.

tert-Butyl (3-((N-(4-Chloro-2,5-dimethoxyphenyl)-4-ethoxyphenyl)sulfonamido)propyl)carbamate (52). Compound 52 was synthesized using compound 1 (50 mg, 0.13 mmol) and tertbutyl (3-bromopropyl)carbamate (32t, 35.2 μL, 0.15 mmol) as off-white solid (60 mg, yield=84%). 1H NMR (500 MHz, chloroform-d) δ 7.59 (d, J=8.80 Hz, 2H), 6.91 (d, J=8.80 Hz, 2H), 6.84 (s, 1H), 6.84 (s, 1H), 5.00 (br s, 1H), 4.08 (q, J=6.85 Hz, 2H), 3.84 (s, 3H), 3.61 (br s, 2H), 3.38 (s, 3H), 3.27 (br s, 2H), 1.56 (quin, J=6.40 Hz, 2H), 1.40-1.50 (m, 12H). 13C NMR (126 MHz, chloroform-d) δ 162.1, 156.0, 150.7, 148.7, 131.2, 129.6, 125.2, 123.0, 117.0, 114.0, 113.8, 79.1, 63.9, 56.8, 55.6, 47.0, 37.1, 28.8, 28.4, 14.6. HRMS for C24H33ClN2O7SNa [M+Na+] calculated 551.1589, found 551.1587.

4-((N-(4-Chloro-2,5-dimethoxyphenyl)-4-ethoxyphenyl)-sulfonamido)butanoic Acid (53). To a solution 01 compound 50 (38 mg, 0.08 mmol) in MeOH (0.5 mL) was added a solution of lithium hydroxide monohydrate (16.4 mg, 0.39 mmol) in water (0.5 mL), and the reaction was stirred overnight. The solvent was then removed and the residue was dissolved in acidified water (3 N aq HCl) and extracted with EtOAc. The organic layer was dried over $MgSO_4$ and concentrated under vacuum to obtain the residue which was purified by silica gel column chromatography (8% MeOH/CH2Cl2) to obtain compounds 53 as white solid (26 mg, yield=73%). 1H NMR (500 MHz, DMSO-d6) δ 11.74-12.24 (m, 1H), 7.54 (d, J=9.05 Hz, 2H), 7.14 (s, 1H), 7.07 (d, J=9.05 Hz, 2H), 6.75 (s, 1H), 4.11 (q, J=7.09 Hz, 2H), 3.70 (s, 3H), 3.45-3.47 (m, 2H), 3.41 (s, 3H), 2.26 (t, J=7.34 Hz, 2H), 1.50 (quin, J=7.03 Hz, 2H), 1.34 (t, J=6.85 Hz, 3H). 13C NMR (126 MHz, DMSO-d6) δ 174.1, 161.8, 151.1, 148.0, 130.7, 129.5, 125.8, 121.6, 116.2, 114.5, 114.3, 63.8, 56.5, 56.1, 48.9, 30.4, 23.5, 14.5. HRMS for C20H23ClNO7S [M−H]− calculated 456.0889, found 456.0889.

4-((N-(4-Chloro-2,5-dimethoxyphenyl)-4-ethoxyphenyl)-sulfonamido)-N-ethylbutanamide (54). To a solution of compound 53 (7 mg, 0.02 mmol) in anhydrous DMF were added HATU (6.4 mg, 0.02), 2 M ethylamine solution in THF (8.36 μL, 0.02 mmol), and triethylamine (4.3 μL, 0.03 mmol), and the reaction was stirred until completion. The solvent was then removed under vacuum and the residue was purified by silica gel column chromatography (5% MeOH/CH2Cl2) to obtain compound 54 as white solid (6 mg, yield=81%). 1H NMR (500 MHz, chloroform-d) δ 7.56 (d, J=8.80 Hz, 2H), 6.91 (d, J=8.80 Hz, 2H), 6.85 (s, 1H), 6.79 (5, 1H), 5.90 (br s, 1H), 4.08 (q, J=7.09 Hz, 2H), 3.83 (5, 3H), 3.58 (br s, 2H), 3.40 (s, 3H), 3.32 (quin, J=6.85 Hz, 2H), 2.33 (t, J=6.85 Hz, 2H), 1.73 (quin, J=6.48 Hz, 2H), 1.45 (t, J=6.97 Hz, 3H), 1.18 (t, J=7.34 Hz, 3H). 13C NMR (126 MHz, chloroform-d) δ 172.3, 162.2, 150.7, 148.7, 131.1, 129.6, 125.2, 123.1, 116.8, 114.1, 114.0, 63.9, 56.8, 55.7, 48.9, 34.4, 33.3, 24.6, 14.8, 14.6. HRMS for C22H30ClN2O6S [M+H+] calculated 485.1508, found 485.1511.

N-(3-Aminopropyl)-N-(4-chloro-2,5-dimethoxyphenyl)-4-ethoxybenzenesulfonamide Hydrochloride (55). Compound 52 (48 mg, 0.09 mmol) was dissolved in 4 N HCl solution in dioxane (1 mL) and stirred at room temperature for 20 h, Solvent was then removed under vacuum, reside was suspended in CH2Cl2 followed by removal of the solvent under vacuum to obtain compound 55 as white solid (37.1 mg, yield=95%). 1H NMR (500 MHz, DMSO-d6) δ 7.85 (br s, 3H), 7.56 (d, J=8.80 Hz, 2H), 7.17 (s, 1H), 7.09 (d, J=8.80 Hz, 2H), 6.78 (s, 1H), 4.11 (q, J=6.85 Hz, 2H), 3.71-3.75 (m, 3H), 3.53 (br s, 2H), 3.42 (s, 3H), 2.83 (t, J=8.10 Hz, 2H), 1.61 (Ed, J=7.00, 14.61 Hz, 2H), 1.34 (t, J=6.97 Hz, 3H). 13C NMR (126 MHz, DMSO-d6) δ 161.9, 151.0, 148.0, 130.5, 129.5, 125.5, 121.8, 116.3, 114.6, 114.4, 63.8, 56.6, 56.2, 47.1, 36.6, 26.4, 14.5. HRMS for C19H26ClN2O5S [M+H+] calculated 429.1245, found 429.1246.

N-(6-((3-((N-(4-Chloro-2,5-dimethoxyphenyl)-4-ethoxyphenyl)sulfonamido)propyl)amino)-6-oxohexyl)-3',6'-dihydroxy-3-oxo-3H-spiro[isobenzofuran-1,9'-xanthene]-5-carboxamide (56). To a solution of compound 55 (4 mg, 0.01 mmol) in anhydrous DMF were added triethylamine (3.6 μL, 0.03 mmol) and fluorescein-5(6)-carboxamidocaproic acid N-succinimidyl ester (5(6)-SFX SE, Chemodex, no. F0044) (5 mg, 0.01 mmol). After completion of the reaction, solvent was removed, and the residue was purified using silica gel column chromatography (10% MeOH/CH2Cl2) to obtain compound 56 as bright yellow solid (5.4 mg, yield=70%). 1H NMR (500 MHz, methanol-d4) δ 8.12 (d, J=8.07 Hz, 1H), 8.06 (d, J=8.10 Hz, 1H), 7.60 (5, 1H), 7.55 (d, J=8.80 Hz, 2H), 6.99-7.03 (m, 2H), 6.97 (s, 1H), 6.87 (5, 1H), 6.65-6.73 (m, 2H), 6.60 (br s, 2H), 6.54 (s, 2H), 4.10 (q, J=7.09 Hz, 2H), 3.78 (s, 3H), 3.54-3.64 (m, 2H), 3.35-3.37 (m, 3H), 3.12-3.28 (m, 4H), 2.12 (s, 2H), 1.48-1.69 (m, 8H), 1.40 (t, J=6.97 Hz, 3H). HRMS for C46H47ClN3O12S [M+H+] calculated 900.2563, found 900.2563.

N-(9-(2-Carboxy-4-((3-((N-(4-chloro-2,5-dimethoxyphenyl)-4-ethoxyphenyl)sulfonamido)propyl)carbamoyl)phenyl)-6-(diethylamino)-3H-xanthen-3-(57). To a solution of compound 55 (5 mg, 0.01 mmol) in anhydrous DMF were added triethylamine (4.5 μL, 0.03 mmol) and 5(6)-carboxytetramethylrhodamine succinimidyl ester (NHS-rhodamine, 6 mg, 0.01 mmol). After completion of the reaction, solvent was removed, and the residue was purified using silica gel column chromatography (20% MeOH/CH2Cl2) to obtain compound 57 as dark purple solid (8.5 mg, yield=94%). 1H NMR (500 MHz, acetone) δ 8.38 (s, 1H), 7.99-827 (m, 2H), 7.58-7.73 (m, 2H), 7.55 (d, J=8.80 Hz, 1H), 7.33 (d, J=7.83 Hz, 1H), 6.93-7.11 (m, 4H), 6.52-6.69 (m, 5H), 4.11-4.19 (m, 2H), 3.86 (s, 2H), 3.68-3.83 (m, 3H), 3.59 (s, 2H), 3.47 (s, 2H), 3.37 (s, 1H), 2.97-3.12 (m, 12H), 1.78 (quin, J=6.80 Hz, 1H), 1.59-1.68 (m, J=6.85, 6.85, 6.85, 6.85 Hz, 1H), 1.37-1.42 (m, 3H). HRMS for C44H46ClN4O9S [M+] calculated 841.2669, found 841.2659.

N-(3-((N-(4-Chloro-2,5-dimethoxyphenyl)-4-ethoxyphenyl)-sulfonamido)propyl)-5-((3aR,4R,6aS)-2-oxohexahydro-1Hthieno[3,4-d]imidazol-4-yl)pentanamide (58). To a solution of compound 55 (10 mg, 0.02 mmol) in anhydrous DMF were added HATU (14.9 mg, 0.04 mmol), biotin (5.8 mg, 0.02 mmol), and triethylamine (11 μL, 0.08 mmol). After stirring overnight, the solvent was removed and the residue was purified using silica gel column chromatography (10% MeOH/CH2Cl2) to obtain compound 58 as off-white solid (14 mg, quantitative yield). 1H NMR (500 MHz, methanol-d4) δ 7.57 (d, J=8.80 Hz, 2H), 7.03 (d, J=8.80 Hz, 2H), 6.99 (s, 1H), 6.89 (s, 1H), 4.48 (dd, J=4.89, 7.83 Hz, 1H), 4.30 (dd, J=4.40, 7.83 Hz, 1H), 4.12 (q, J=7.09 Hz, 2H), 3.80 (5, 3H), 3.63 (br s, 2H), 3.39 (s, 3H), 3.17-3.29 (m, 3H), 2.92 (dd, J=4, 89, 12.72 Hz, 1H), 2.70 (d, J=12.72 Hz, 1H), 2.17 (t, J=7.34 Hz, 2H), 1.57-1.75 (m, 6H), 1.36-1.48 (m, 5H). 13C NMR (126 MHz, methanol d4) δ 176.2, 166.3, 164.1, 152.6, 150.2, 132.4, 131.0, 126.8, 124.4, 118.5, 115.5, 115.2, 65.3, 63.5, 61.8, 57.3, 57.1, 56.5, 41.2, 37.8, 37.0, 29.9, 29.8, 29.6, 27.1, 15.1, HRMS for C29H40ClN4O7S2 [M+H+] calculated 655.2021, found 655.2025.

N-(4-Azido-2,5-dimethoxyphenyl)-4-ethoxybenzenesulfonamide (59). To a solution of compound 10 (84 mg, 0.24 mmol) in anhydrous acetonitrile were added tert-butyl nitrite (37 mg, 0.36 mmol) and azidotrimethylsilane (33 mg, 0.29 mmol), and the reaction was heated at 45° C. for 1 h. The solvent was then removed, and the residue was purified using silica gel column chromatography (20% EtOAc/hexanes) under low-light conditions to obtain compound 59 as white solid (52 mg, yield=57%). 1H NMR (500 MHz, chloroform-d) δ 7.64 (d, J=8.80 Hz, 2H), 7.19 (s, 1H), 6.81-6.89 (m, 3H), 6.36 (s, 1H), 4.04 (q, J=6.85 Hz, 2H), 3.86 (5, 3H), 3.56 (s, 3H), 1.42 (t, J=6.97 Hz, 3H). 13C NMR (126 MHz, chloroform-d) δ 162.5, 146.3, 144.2, 130.1, 129.3, 124.7, 122.9, 114.3, 107.3, 103.8, 63.9, 56.7, 56.3, 14.6. HRMS for C16H18N4O5SNa [M+Na+] calculated 401.089, found 401.0894.

3-Amino-N-(4-chloro-2,5-dimethoxyphenyl)-4-methoxybenzenesulfonamide (60). Combine 1,2-dimethylethylenediamine (7.2 μL, 0.069 mmol), CuI (9.2 mg, 0.057 mmol) and sodium ascorbate (8.7 mg, 0.057 mmol) in a microwave reaction vial. Seal and evacuate the vial and add $H_2O$ (300 μL). Separately combine compound 25 (50 mg, 0.11 mmol) and NaN3 (41.6 mg, 0.23 mmol) in EtOH (350 μL) and DMF (350 μL) and add to the reaction vial. Fill vial with argon gas and irradiate reaction using microwave at 100° C. for 1 h. Water was poured into the reaction mixture and extracted with EtOAc. The organic layer was collected, solvent was removed to obtain the residue which was purified using silica gel column chromatography (30% EtOAc/hexanes) to obtain compound 60 as a tan solid (28 mg, yield=63%). 1H NMR (500 MHz, methanol-d4) δ 7.16 (s, 1H), 7.02-7.10 (m, 2H), 6.89 (s, 1H), 6.84 (d, J=8.56 Hz, 1H), 3.86 (s, 3H), 3.80 (s, 3H), 3.55 (s, 3H). 13C NMR (126 MHz, ethanol-d4) δ 152.1, 150.5, 147.1, 138.9, 132.7, 127.1, 119.6, 119.0, 114.7, 113.7, 110.4, 109.8, 57.2, 57.2, 56.4. HRMS for C15H18ClN2O5S [M+H+] calculated 373.0619, found 373.062.

3-Azido-N-(4-chloro-2,5-dimethoxyphenyl)-4-methoxybenzenesulfonamide (61), To a solution of compound 60 (23 mg, 0.06 mmol) in anhydrous acetonitrile were added tert-butyl nitrite (10 mg, 0.09 mmol) and azidotrimethylsilane (9 mg, 0.07 mmol), and the reaction was heated at 45° C. for 1 hour. The solvent was then removed, and the residue was purified using silica gel column chromatography (25% EtOAc/hexanes) under low-light conditions to obtain compound 61 as light yellow solid (22 mg, yield=88%). 1H NMR (500 MHz, chloroform-d) δ 7.49 (dd, J=1.96, 8.56 Hz, 1H), 7.38 (d, J=1.71 Hz, 1H), 7.24 (s, 1H), 6.95 (5, 1H), 6.85 (d, J=8.56 Hz, 1H), 6.80 (s, 1H), 3.91 (5, 3H), 3.88 (5, 3H), 3.66 (s, 3H). 13C NMR (126 MHz, chloroform-d) δ 155.4, 149.3, 143.5, 131.2, 129.2, 125.4, 124.8, 119.2, 118.2, 113.1, 111.2, 106.2, 56.8, 56.4, 56.3. HRMS for C15H15ClN4O5SNa [M+Na+] calculated 421.0344, found 421.0348.

N-(4-Azido-2,5-dimethoxyphenyl)-4-ethoxy-N-(prop-2-yn-1-yl)benzenesulfonamide (62). To a solution of compound 61 (10 mg, 0.03 mmol) in anhydrous DMF were added potassium carbonate (7.0 mg, 0.06 mmol) and propargyl bromide solution in toluene (32j, 3.23 μL, 0.03 mmol). The reaction was heated at 45° C. for 2 hours, followed by removal of the solvent. The residue was then dissolved in EtOAc and washed by water and brine, dried over sodium sulfate, concentrated under vacuum to obtain the residue which was purified by silica gel column chromatography (28% EtOAc/hexanes) to obtain compound 62 as off-white solid (10 mg, yield=89%). 1H NMR (500 MHz, chloroform-d) δ 7.62 (d, J=8.80 Hz, 2H), 6.81-6.97 (m, 3H), 6.41 (s, 1H), 4.43 (br s, 2H), 4.08 (q, J=7.10 Hz, 2H), 3.80 (s, 3H), 3.42 (s, 3H), 2.17 (t, J=2.40 Hz, 1H), 1.44 (t, J=6.97 Hz, 3H). 13C NMR (126 MHz, chloroform-d) δ 162.3, 151.0, 145.6, 131.2, 129.8, 129.2, 122.6, 117.4, 114.1, 104.2, 78.6, 73.1, 63.9, 56.6, 55.7, 39.7, 14.6. HRMS for C19H20N4O5SNa [M+Na+] calculated 439.1047, found 439.105.

N-(3-Aminopropyl)-N-(4-azido-2,5-dimethoxyphenyl)-4-ethoxybenzenesulfonamide (63). To a solution of compound 61 (27 mg, 0.07 mmol) in anhydrous DMF were added potassium carbonate (19.5 mg, 0.14 mmol) and tert-butyl (3-bromopropyl)-carbamate (32t, 22 mg, 0.09 mmol). The reaction was heated at 45° C. for 2 hours, followed by removal of the solvent. The residue was then dissolved in EtOAc and washed by water and brine, dried over sodium sulfate, concentrated under vacuum to obtain the residue which was purified by silica gel column chromatography (35% EtOAc/hexanes) to obtain N-Boc protected intermediate (14 mg) which was stirred in a solution of 4 N HCl in dioxane for 1 h. The solvent was then removed to obtain the compound 63 as tan solid (12 mg, yield=36%). 1H NMR (500 MHz, methanol-d4) δ 7.58 (d, J=8.80 Hz, 2H), 7.04 (d, J=8.80 Hz, 2H), 6.79 (s, 1H), 6.56 (s, 1H), 4.12 (q, J=7.09 Hz, 2H), 3.79 (s, 3H), 3.67-312 (m, 2H), 3.40 (s, 3H), 3.13 (t, J=7.58 Hz, 2H), 1.77 (quin, J=7.00 Hz, 2H), 1.42 (t, J=6.97 Hz, 3H). 13C NMR (126 MHz, methanol-d4) δ 164.3, 153.1, 147.8, 132.1, 131.2, 131.0, 124.2, 118.3, 115.6, 106.5, 65.3, 57.5, 56.4, 38.6, 28.0, 15.1. HRMS for C19H26N5O5S [M+H+] calculated 436.1649, found 436.1652.

N-(3-((N-(4-Azido-2,5-dimethoxyphenyl)-4-ethoxyphenyl)-sulfonamido)propyl)-5-((3aR,4R,6aS)-2-oxohexahydro-1Hthieno[3,4-d]imidazol-4-yl)pentanamide (64). To a solution of compound 63 (9 mg, 0.02 mmol) in anhydrous DMF were added HATU (8.6 mg, 0.02 mmol), biotin (4.3 mg, 0.02 mmol), and triethylamine (6.6 μL, 0.05 mmol). The reaction was stirred overnight, followed by removal of the solvent to obtain the residue which was purified using silica gel column chromatography (10% MeOH/CH2Cl2) to obtain compound 64 as off-white solid (8.4 mg, 67%). 1H NMR (500 MHz, methanol-d4) δ 7.91 (br s, 1H), 7.57 (d, J=8.80 Hz, 2H), 7.02 (d, J=8.80 Hz, 2H), 6.84 (s, 1H), 6.51 (s, 1H), 4.48 (dd, J=5.01, 7.70 Hz, 1H), 4.30 (dd, J=4.40, 7.83 Hz, 1H), 4.12 (q, J=6.85 Hz, 2H), 3.80 (s, 3H), 3.61 (br s, 2H), 3.36 (s, 3H), 3.16-3.29 (m, 3H), 2.92 (dd, J=5.14, 12.72 Hz, 1H), 2.70 (d, J=12.72 Hz, 1H), 2.17 (t, J=7.34 Hz, 2H), 1.51-1.80 (m, 6H), 1.36-1.49 (m, 5H). 13C NMR (126 MHz, methanol-d4) δ 176.3, 176.2, 166.3, 164.1, 153.0, 147.6, 132.5, 131.0, 130.7, 124.3, 118.8, 115.5, 106.2, 65.3, 63.5, 61.8, 57.5, 57.1, 56.3, 41.2, 37.8, 37.0, 29.9, 29.7, 29.6, 27.1, 15.1. HRMS for C29H39N7O7S2Na [M+Na+] calculated 684.2245, found 684.2241.

Biology: Cell Lines and Reagents. The THP1-Blue NF-κB cell line was purchased from Invivogen (San Diego, Calif.) which contains a stably integrated NF-κB-inducible secreted embryonic alkaline phosphatase (SEAP). ISRE-bla THP-1 cell line was generated by us as described earlier.42 QuantiBlue was purchased from Invivogen, MTT (3-[4,5-dimethylthiazol-2-yl]-2,5-diphenyltetrazolium bromide) was purchased from Acros Organics, LPS (lps-eb) from Invivogen, and IFN-α was from R&D Systems (no. 11200-2).

Measurement of NF-κB Activation Using THP1-Blue NF-κB Cells. THP1-Blue NF-κB cells were plated in 96-well plates at 105 cells/well in 100 μL of RPMI supplemented with 10% fetal bovine serum (FBS, Omega Scientific, Inc., Tarzana, Calif.), 100 U/mL penicillin, 100 μg/mL streptomycin (Thermo Fisher Scientific), and Normocin (Invivogen). LPS was prepared in assay medium at a concentration of 20 μg/mL. Tested compounds were dissolved in DMSO at 1 mM as a stock solution and were further diluted in the LPS solution to a final concentration of 10 μM. 100 μL of this solution was then transferred to the plated cells to obtain a final concentration of LPS at 10 μg/mL and compound at 5 μM (0.05% DMSO). The culture supernatants were harvested after a 20 hours incubation period. SEAP activity in the culture supernatants was determined by a colorimetric assay using QuantiBlue (Invivogen). Plate absorbance was read at 630 nm using a Tecan Infinite M200 plate reader (Mannedorf, Switzerland). The SEAP concentration was directly proportional to NF-κB activity, which was two-point normalized to yield activity of compound 1+LPS as 200% and activity for LPS as 100%.

Measurement of ISRE Activity in ISRE-bla THP-1 Cells. ISREbla THP-1 cells were plated in 96-well plates at 5×104 cells/well in 50 μL of RPMI supplemented with 10% dialyzed FBS (Atlanta Biologicals, Inc., GA), 0.1 mM nonessential amino acids, 1 mM sodium pyruvate, 100 U/mL penicillin, and 100 μg/mL streptomycin. Type I IFN-α (R&D Systems, no. 11200-2) solution was prepared in assay medium at a concentration of 200 U/mL. Tested compounds were dissolved in DMSO at 1 mM and were further diluted in the IFN-α solution to a final concentration of 10 μM. 50 μL of this solution was then transferred to the plated cells to obtain a final concentration of IFN-α at 100 U/mL and compound at 5 μM (0.05% DMSO). The cells were incubated for 16 hours, after which 20 μL of 6×LiveBLAzer FRET B/G substrate (CCF4-AM) mixture (prepared according to the manufacturer's instructions) was added to each well. Plates were incubated at room temperature in the dark for 3 hours. Fluorescence was measured on a Tecan Infinite M200 plate reader at an excitation wavelength of 405 nm and emission wavelengths of 465 and 535 nm. Background values (cell free wells at the same fluorescence wavelength) were subtracted from the raw fluorescence intensity values and the emission ratios were calculated as the ratio of background subtracted fluorescence intensities at 465 nm to background subtracted fluorescence intensities at 535 nm. The ISRE activity values for these compounds were two-point normalized to yield activity of compound 1+IFN-α as 200% and activity for IFN-α as 100%.

Cell Viability Assay. THP-1 cells were plated in 96-well plates (105 cells/well) in 100 μL RPMI supplemented with 10% FBS, 100 U/mL penicillin, and 100 μg/mL streptomycin. Compounds were dissolved in DMSO at 1 mM stock solution and were further diluted to 10 μM in the assay medium. 100 μL of this solution was added to the cells to obtain a final compound concentration of 5 μM (0.05% DMSO). After 18 h incubation, a solution of MTT in assay media (0.5 mg/mL) was added to each well and further incubated for 4-6 hours, followed by addition of cell lysis buffer (15% w/v SDS and 0.12% v/v 12 N HCl aqueous solution), incubation overnight, and then absorbance was measured at 570 nm using 650 nm as reference using Tecan Infinite M200 plate reader.

Animals. Seven- to nine-week-old C57BL/6 (wild-type, WT) mice were purchased from The Jackson Laboratories (Bar Harbor, Me.). All animal experiments received prior approval from the UCSD Institutional Animal Care and Use Committee.

In Vivo Adjuvant Activity Study. WT mice (n=8 per group) were immunized in the gastronemius muscle with ovalbumin (20 μg/animal) mixed with MPLA (10 ng/animal) and compound 1 or 12 or 33 (50 nmol/animal) on days 0 and 21. On day 28, immunized mice were bled and OVA-specific IgG titers were measured by ELISA as previously described (Chan et al., 2009).

Statistical Analysis. Data are represented as the mean±standard error of the mean (SEM). Origin 7 (Origin Lab, Northampton, Mass.) graphing software was used for figure preparation, while Prism 4 (GraphPad, San Diego, Calif.) software was used for statistical calculations.

Example 3

In addition, the amine bearing handle was further utilized to introduce chemically reactive electrophilic functional groups to obtain derivatives that can react with proteins and peptides to form self-adjuvanting vaccine constructs. These include isothiocyanate bearing analog 65, maleimide bearing analog 66, and NHS ester 67 as shown in Scheme 7. These compounds can be utilized to make protein and peptide conjugates to evaluate the self-adjuvanting constructs. To test their activity, they were covalently conjugated with ovalbumin.

Scheme 7. Syntheses of reactive electrophilic derivatives of compound 55.

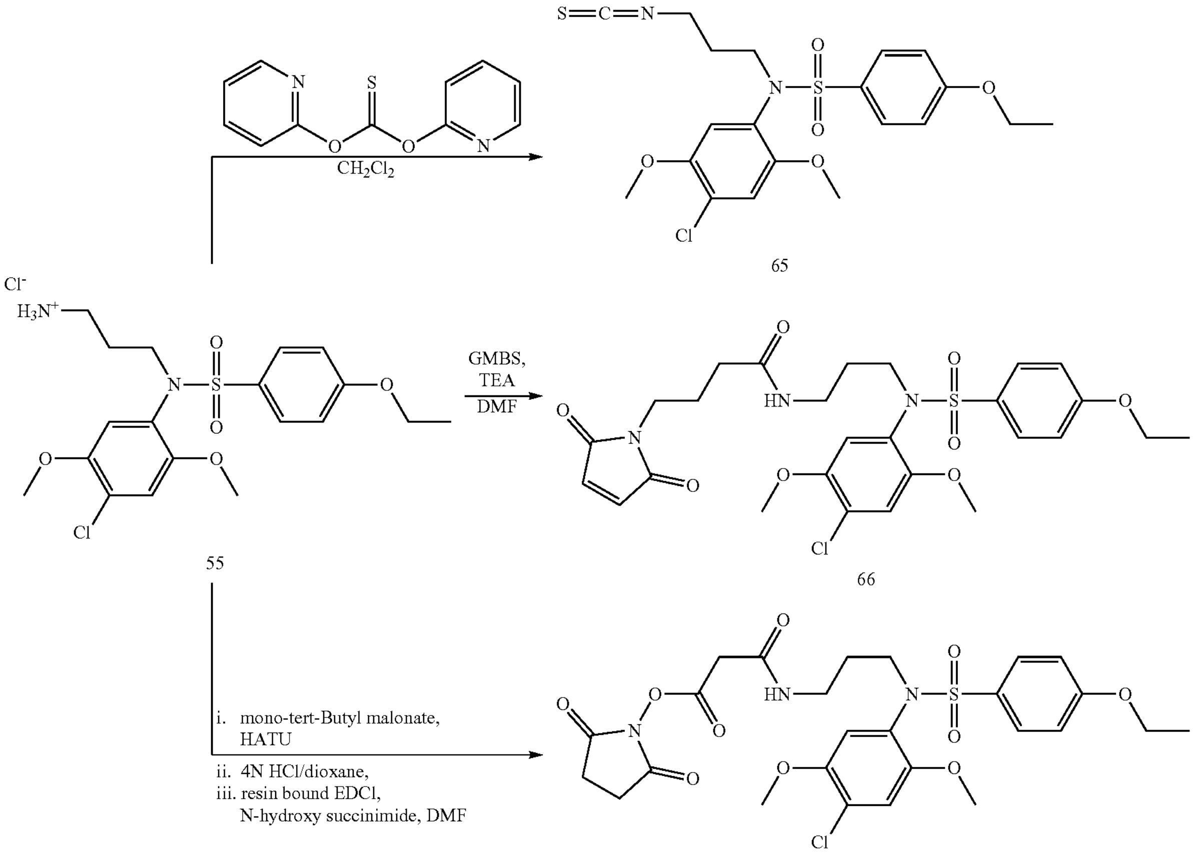

65

55

66

67

Conjugate with other immunopotentiators: The amine handle allows conjugation to other immune potentiators such as 8-oxoadenine analogs TLR-7 agonist 1V209 as shown in Scheme 8.
The conjugated compound 68 retained the activity of both compound 1 and TLR-7 agonistic acitivity of 1V209.
Scheme 8.
Synthesis of conjugate with TLR-7 agonist 1V209.

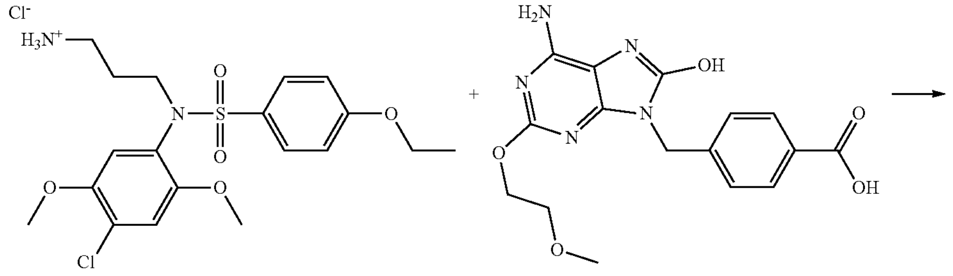

55 1V209

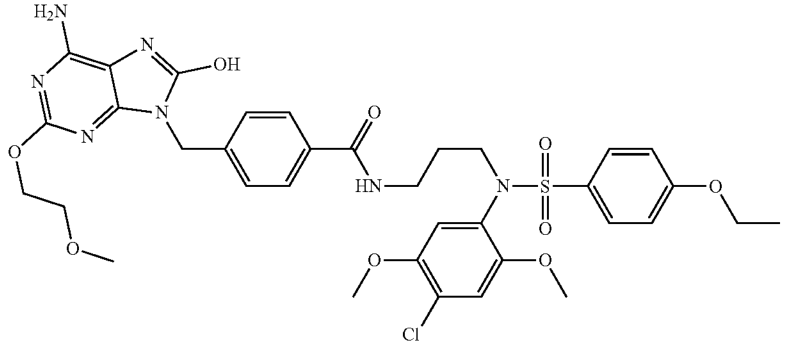

68

Prodrug syntheses: The bioactivity profile of compound 48 suggested that the acetyl bond may be reversible under enzymatic conditions and we found that the THP-1 cells could hydrolyze the amide bond to regenerate compound 1, Amide and carbamate linked prodrugs of compound 1 were generated including amide linked compounds consisting of electrophilic reactive NHS handle bearing compound 69 as well as alkyne bearing compound 70 which can be used for linking with azides using biorthogonal Click chemistry reaction. The syntheses of these compounds including carbamate linked compound 72 is shown in Scheme 9.

Scheme 9. Synthesis of prodrugs of compound 1.
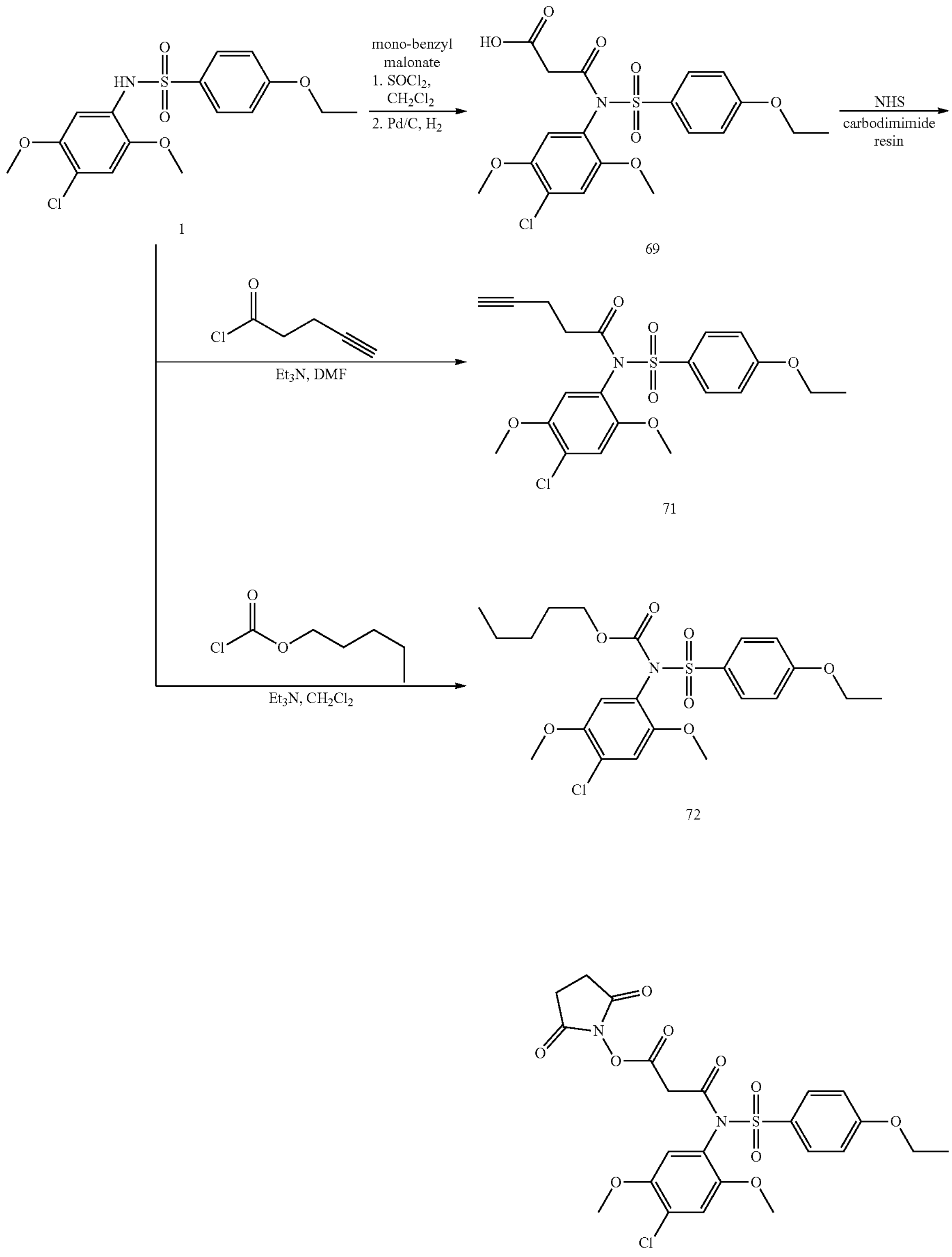
1
69
71
72
70
Other synthesized compounds include the following as shown below.

73

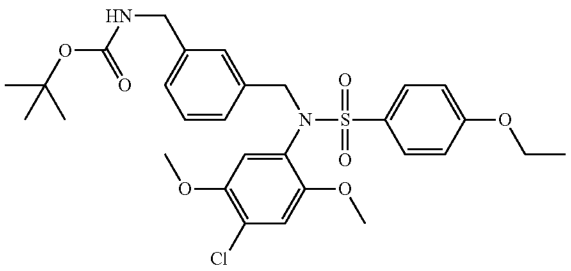

74

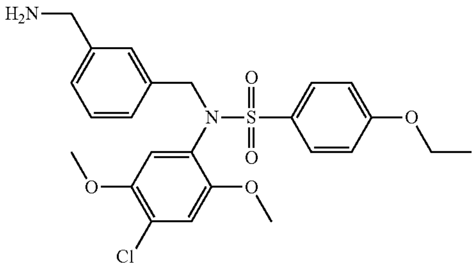

75

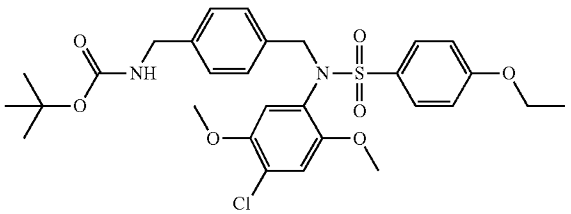

76

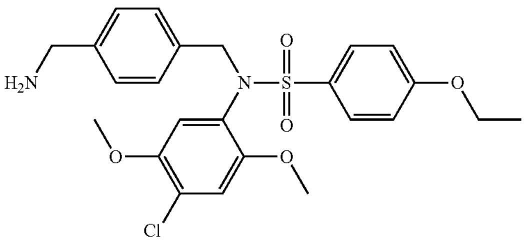

Example 4

Scheme S1. Syntheses of Compound 3a-f

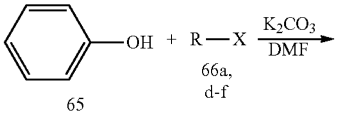

65 66a, d-f

-continued

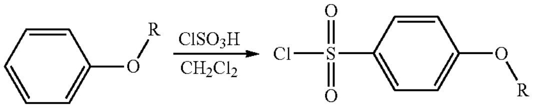

67a, c-f 3a, c-f

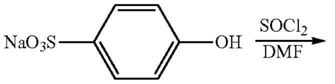

68

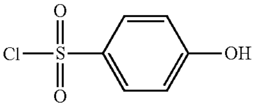

3b

General procedure A for the synthesis of intermediate 67a, d, e, f. To a suspension of K2CO3 (1.5 eq) in DMF was added liquified phenol (90%) (1 eq) and bromoethane (1.5 eq). The reaction mixture was heated at 70° C. for 5 hours. Solids were filtered, and the filtrate was extracted with brine and EtOAc. The organic layer was dried over $MgSO_4$ and concentrated in vacuo. The resultant residue was purified by column chromatography.

Compound 67c (Anisole) was commercially available.

General Procedure B for the Synthesis of Compounds 3a, c, d e, f.

Dissolve Intermediate 67 (1 eq) in CH2Cl2 and cool to −5° C. Separately dilute chlorosulfonic acid (1.5 eq) with CH2Cl2 and cool to −5° C. Add chlorosulfonic acid solution to 67 solution dropwise with vigorous stirring over 60 m at −5° C. Allow mixture to warm to room temperature and stir for an additional 60 minutes. Pour entire reaction mixture into ice water and extract with CH2Cl2. Dry organic layer over $MgSO_4$ and concentrate in vacuo. Add ether and concentrate in vacuo two times to remove remaining moisture. The solid was stored under argon at −20° C. or used immediately without further purification.

Synthesis of Compound 3b.

Sodium 4-hydroxybenzenesulfonate (200 mg, 1.0 mmol), thionyl chloride (800 μL, excess) and DMF (1 mL) were combined in a round bottom flask and stirred at 45° C. for 1 hour. The reaction mixture was concentrated in vacuo and then ethyl ether was added and concentrated in vacuo again. The resultant residue was used without further purification.

TABLE 5

Syntheses of Compounds 3a, c-f

| Compound 3 | Reagent 66 | Volume of 65 used (mL) | Amount of intermediate 67 obtained (g) | Amount of intermediate 67 used (mg or mL) | Amount of compound 3 obtained (mg) |
|---|---|---|---|---|---|
| 3a | 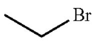 | 5 mL | 4.12 g | 3000 mg | 2570 mg |

TABLE 5-continued

| Syntheses of Compounds 3a, c-f | | | | | |
|---|---|---|---|---|---|
| Compound 3 | Reagent 66 | Volume of 65 used (mL) | Amount of intermediate 67 obtained (g) | Amount of intermediate 67 used (mg or mL) | Amount of compound 3 obtained (mg) |
| 3d | 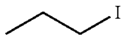 | 0.2 mL | 1.29 g | 121.5 mg | Quantitative[a] |
| 3e | 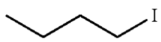 | 1 mL | 1.32 g | 304.6 mg | Quantitative[a] |
| 3f | 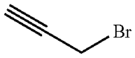 | 1 mL | 1.23 g | 152.67 mg | Quantitative[a] |
| 3c | — | — | — | 1 mL | Quantitative[a] |

[a]The crude material was used for next reaction without purification.

REFERENCES

Alving et al., *Curr. Opin. Immunol.,* 24:310 (2012),
An et al., *Immunity,* 25:919 (2006).
Ban et al., *Bioconjugate Chem.,* 27:1911 (2016).
Basto & Leitao, *J. Immunol. Res.,* 2014:619410 (2014),
Beran, *Expert Opin. Biol. Ther,* 8:235 (2008).
Brady et al., *Vaccine,* 27:5091 (2009).
Campbell, *Methods Mol, Biol.,* 1494:15 (2017).
Chan et al., *ACS Comb. Sol.,* 19:533 (2017).
Chan et al., *Bioconjugate Chem.,* 20:1194 (2009).
Chan et al., *J. Med. Chem.,* 56:4206 (2013).
Cooks et al., *Cancer Cell,* 23:634 (2013).
Ebensen et al., *Front. Cell. Infect. Microbiol.,* 9:31 (2019).
Fabrizi et al., *Clin. Res. Hepatol. Gastroenterol.,* _:_ (2019) DOI: 10.1016/j.clinre.2019.06.010.
Fagan et al., *ChemBioChem,* 18:545 (2017).
Forster et al., *Trends Immunol.,* 33:271 (2012).
Fraser et al., *Expert Rev. Vaccines,* 6:559 (2007).
Gential et al., *Bioorg. Med. Chem. Lett.,* 29:1340 (2019).
Gurser & Gregoriadis, In Vaccines: New Generation Immunological Adjuvants: Gregoriadis, G., McCormack, B., Allison, A. C., Eds.; Springer US: Boston, Mass., p. 45 (1995).
Ho et al., *Front. Immunol.,* 9:2874 (2018.
Ho et al., *Nat. Immunol.,* 13:379 (2012).
Hyer & Janssen, *Open Forum Infect. Dis.,* 5:S677 (2018).
Ignacio et al., *Bioconjugate Chem.,* 29:587 (2018).
Kan et al., *Org. Lett.,* 9:2055 (2007).
Kawada et al., *J. Med. Chem.,* 32:256 (1989).
Kim et al., *J. Immunol.,* 175:847 (2005).
Kobayashi et al., *Cell.* 110:191 (2002).
Kondo et al., *Trends Immunol.,* 33:449 (2012).
Levast et al., *Vaccines* (Basel, Switz.), 2:297 (2014).
Li & Guo, *Molecules,* 23:1583 (2018).
Liao et al., *Eur. J. Med. Chem.,* 173:250 (2019).
Lin et al., *Pediatr. Infect. Dis. J.,* 37:e93 (2018).
Liu et al., *J. Immunol.,* 185:7244 (2010).
Ma et al., *J. Immunol.,* 184:6053 (2010).
Maisonneuve et al., *Proc. Natl. Acad. Sci. USA,* 111:12294 (2014).
Martin-Fontecha et al., *Handb. Exp. Pharmacol.,* 188:31 (2009).
Mori et al.. *Eur. J. Immunol.,* 42:2709 (2012).
Mutwiri et al., *Expert Rev. Vaccines,* 10:95 (2011).
Nevagi et al., *Eur. J, Med. Chem.,* 179:100 (2019).
Pan et al., *Nat. Prod. Rep.,* 33:612 (2016).
Pavot et al., *Biomaterials,* 75:327 (2016).
Perez et al., *Cell Rep.,* 12:537 (2015).
Probst et al., *Vaccine,* 35:1964 (2017),
Proietti et al *J, Immunol.,* 169:375 (2002).
Qian & Cao, *Ann. N. Y. Acad. Sci.,* 1283:67 (2013).
Ramesh et al., 20050009871 A1, 2005.
Reed et al., *Nat. Med.,* 19:1597 (2013).
Schenone et al., *Nat. Chem. Biol.,* 9:232 (2013).
Schwarz et al., *BJOG,* 122:107 (2015).
Shukla et al., *ACS Med. Chem. Lett.,* 9:1156 (2018a).
Shukla et al., *Bioorg. Med. Chem. Lett.,* 20:6384 (2010).
Shukla et al., *Bioorg. Med. Chem. Lett.,* 21:3232 (2011).
Shukla et al., *PLoS One,* 7:e43612 (2012).
Shukla et al., *SLAS Discov.,* 23:960 (2018b).
Smith & Collins; *Future Med. Chem.,* 7:159 (2015).
Sumranjit & Chung, *Molecules,* 18:10425 (2013).
Tovey & Lallemand, *Methods Mol. Biol.,* 626:287 (2010).
Turnis et al., *J. Immunol.,* 185:4223 (2010).
Vasilakos et al., *Expert Rev. Vaccines,* 12:809 (2013).
Wheeler et al., *Lancet Infect. Dis.,* 16:1154 (2016).
Yuk et al., *Nat. Immunol.,* 12:742 (2011).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A compound of formula (II)

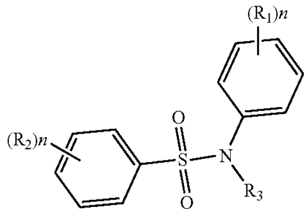

wherein each n is an integer from 1 to 4;

wherein $R_1$ is independently selected from the group consisting of halogen, nitro, azido, hydroxyl, amino, $C_{1-10}$-alkylamino, $—CF_3$, carboxylic acid, and $—O(C_1-C_6$ alkyl); and wherein $R_2$ is independently selected from the group consisting of halogen, nitro, azido, hydroxyl, amino, $C_{1-10}$-alkylamino, $—CF_3$, carboxylic acid, and $—O(C_2-C_6$ alkyl);

wherein $R_3$ is -L1-G,

L1 is a divalent linker consisting of $C_1$-$C_6$ alkylene, $C_{6-10}$-arylene, $C_1$-$C_6$ alkylene-amino, $C_1$-$C_6$ alkylene-amido, $C_1$-$C_6$ alkylene-ether, $C_1$-$C_6$ alkylene-ester, and combinations thereof, and G is

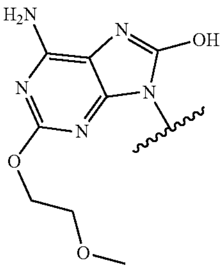 [SMILES: *n1c(O)nc2c(N)nc(OCCOC)nc21]

or a salt thereof.

2. The compound of claim 1 wherein L1 is selected from a $C_1$-$C_6$ alkylene, a $C_6$-arylene, and combinations thereof.

3. A compound having the structure:

65

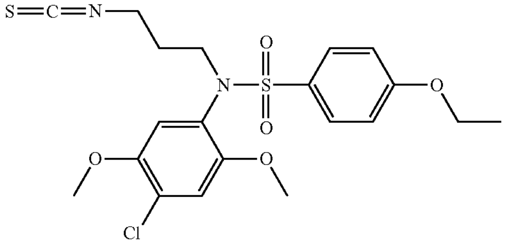

66

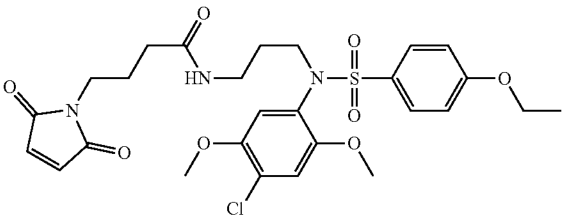

67

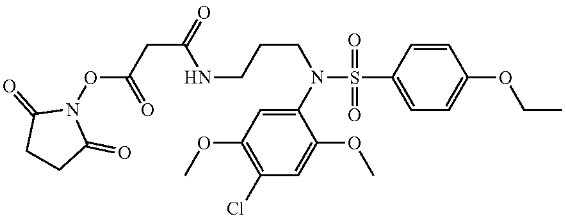

68

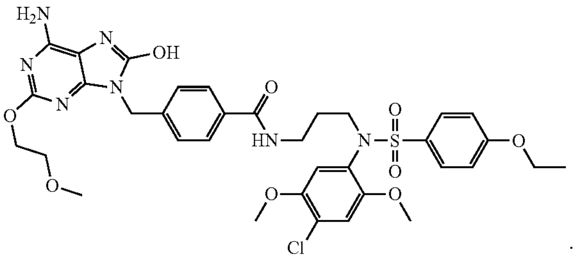

.

-continued

69

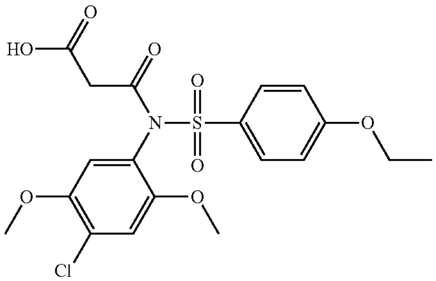

70

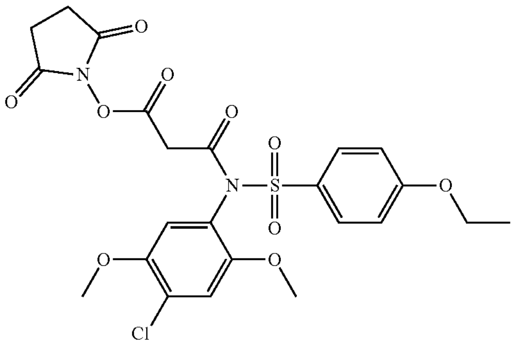

71

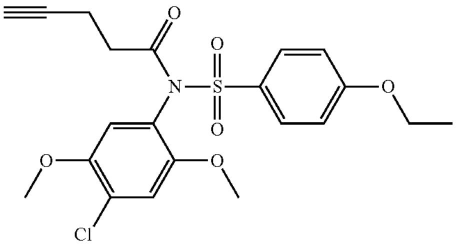

72

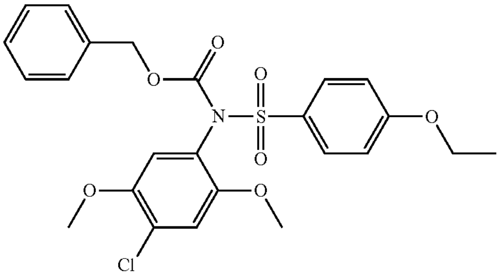

73

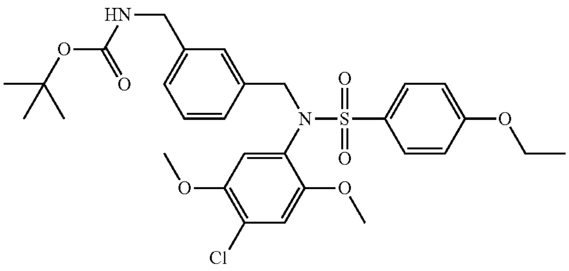

-continued
74
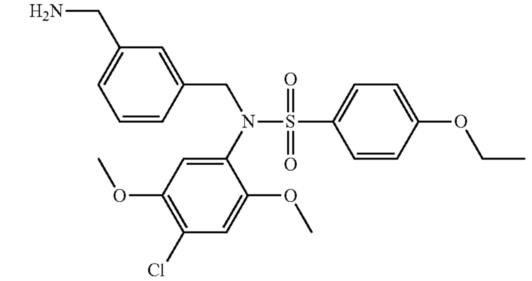
75
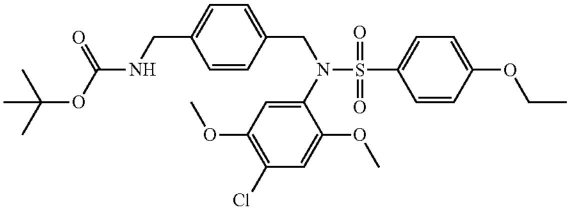
-continued
76
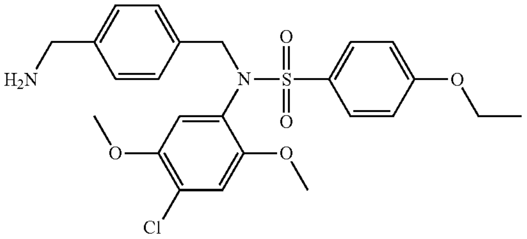
or
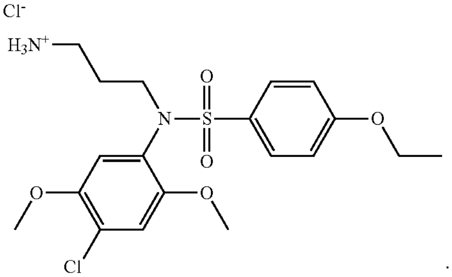
.
* * * * *